US008182813B2

(12) United States Patent
Brasel et al.

(10) Patent No.: US 8,182,813 B2
(45) Date of Patent: May 22, 2012

(54) HUMAN C-FMS ANTIGEN BINDING PROTEINS

(75) Inventors: Kenneth Allan Brasel, Seattle, WA (US); James F. Smothers, Quincy, MA (US); Douglas Pat Cerretti, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 798 days.

(21) Appl. No.: 12/195,169

(22) Filed: Aug. 20, 2008

(65) Prior Publication Data

US 2009/0155164 A1    Jun. 18, 2009

Related U.S. Application Data

(60) Provisional application No. 61/084,588, filed on Jul. 29, 2008, provisional application No. 60/957,148, filed on Aug. 21, 2007.

(51) Int. Cl.
*A61K 39/00* (2006.01)
*A61K 39/395* (2006.01)
*C12N 5/16* (2006.01)
*C07K 16/00* (2006.01)
*C12P 21/08* (2006.01)

(52) U.S. Cl. ............... 424/139.1; 424/141.1; 424/142.1; 424/143.1; 435/328; 530/387.1; 530/387.9; 530/391.3

(58) Field of Classification Search .................. None
See application file for complete search history.

(56) References Cited

U.S. PATENT DOCUMENTS

2009/0317403 A1   12/2009   Aharinejad et al.

FOREIGN PATENT DOCUMENTS

| EP | 1223980 | 5/2003 |
| WO | 99/17798 A | 4/1999 |
| WO | 2004/045532 A | 6/2004 |

OTHER PUBLICATIONS

Aharinejad et al., "Colony-stimulating factor-1 antisense treatment suppresses growth of human tumor xenografts in mice," Cancer Res 62:5317-5324 (2002).
Aharinejad et al., "Colony-stimulating factor-1 blockade by antisense oligonucleotides and small interfering RNAs suppresses growth of human mammary tumor xenografts in mice," Cancer Res 64:5378-5384 (2004).
Aharinejad et al., "Target validation using RNA interference in solid tumors,"(ed. M. Sioud) In Methods in Molecular Biology 361 (2):227-238 (2007).
Anderson et al., "Ovarian adenocarcinomas express fms-complementary transcripts and fms antigen, often with coexpression of CSF-1," Gynecol Oncol 74:202-207 (1999).
Ashmun et al., "Expression of CSF-1 receptors on human leukemic blasts," UCLA Symposia on Molecular and Cellular Biology, New Series 100 (Mech Action Ther Appl Biol Cancer Immune Defic Disord) 39:55 (1989).

Baiocchi et al., "Expression of the macrophage colony-stimulating factor and its receptor in gynecologic malignancies," Cancer 67(4):990-996 (1991).
Borycki et al., "Colony-stimulating factor 1 (CSF-1) is involved in an autocrine growth control of rat myogenic cells," Exp Cell Res 218:213-222 (1995).
Borycki et al., "Repression of the CSF-1 receptor (c-fms protooncogene product) by antisense transfection induces G1-growth arrest in L6a1 rat myoblasts," Oncogene 10:1799-1811 (1995).
Chambers et al., "Overexpression of epithelial macrophage colony-stimulating factor (CSF-1) and CSF-1 receptor: a poor prognostic factor in epithelial ovarian cancer, contrasted with a protective effect of stromal CSF-1," Clin Cancer Res 3:999-1007 (1997).
Database UNIPROT Accession No. P09603, "Macrophage colony-stimulating factor 1 (Human)," Jul. 1, 1989.
Database UNIPROT Accession No. Q6ZMJ4, "Interleukin-34 (Human)," Jul. 5, 2004.
Dewar et al., "Macrohage colony stimulating factor receptor, c-fms, is a noval target of imatinib," Blood 105(8):3127-3132 (2005).
Filderman et al., "Macrophage colony-stimulating factor (CSF-1) enhances invasiveness in CSF-1 receptor-positive carcinoma cell lines," Cancer Res 52:3661-3666 (1992).
Flick et al., "Recognition of activated CSF-1 receptor in breast carcinomas by a tyrosine 723 phosphospecific antibody," Oncogene 14:2553-2561 (1997).
Garceau et al., "Pivotal advance: avian colony-stimulating factor 1 (CSF-1), interleukin-34 (IL-34), and CSF-1 receptor genes and gene products," J Leukoc Biol 87:753-764 (2010).
Gill etal., "Regulation of colony stimulating factor-1 (CSF-1) in endometrial cells: glucocorticoids and oxidative stress regulate the expression of CSF-1 and its receptor *c-fms* in endometrial cells," Fertil Steril 76:1005-1011 (2001).
Hakala et al., "Macrophage colony-stimulating factor 1, a clinically useful tumor marker in endometrial adenocarcinoma: comparison with CA 125 and the aminoterminal propeptide of type III procollagen," Am J Obstet Gynecol 173:112-119 (1995).
Haran-Ghera et al., "Increased circulating colony-stimulating factor-1 (CSF-1) in SJL/J mice with radiation-induced acute myeloid leukemia (AML) is associated with autocrine regulation of AML cells by CSF-1," Blood 89:2537-2545 (1997).
Ide, "Expression of colony-stimulating factor 1 receptor during prostate development and prostate cancer progression," PNAS 99(22):14404-14409 (2002).
Kacinski et al., "FMS (CSF-1 receptor) and CSF-1 transcripts and protein are expressed by human breast carcinomas in vivo and in vitro," Oncogene 6(6):941-952 (1991).
Kacinski et al., "Ovarian adenocarcinomas express fms-complementary transcripts and fms antigen, often with coexpression of CSF-1," Am J Pathol 137(1):134-147 (1990).
Kacinski et al., "The cytokine CSF-1 (M-CSF) expressed by endometrial carcinomas in vivo and in vitro, may also be a circulating tumor marker of neoplastic disease activity in endometrial carcinoma patients," Int J Radiat Oncol Biol Phys 19(3):619-626 (1990).

(Continued)

*Primary Examiner* — Elly-Gerald Stoica
(74) *Attorney, Agent, or Firm* — Scott L. Ausenhus

(57) ABSTRACT

Antigen binding proteins that bind to human c-fms protein are provided. Nucleic acids encoding the antigen binding protein, vectors, and cells encoding the same are also provided. The antigen binding proteins can inhibit binding of c-fms to CSF-1, reduce monocyte migration into tumors, and reduce the accumulation of tumor-associated macrophages.

10 Claims, 20 Drawing Sheets

OTHER PUBLICATIONS

Kacinski, "CSF-1 and its receptor in breast carcinomas and neoplasms of the female reproductive tract," Mol Reprod Dev 46:71-74 (1997).

Kacinski, "CSF-1 and its receptor in ovarian, endometrial and breast cancer," Ann Med 27:79-85 (1995).

Kascinski, "Expression of CSF-1 and its receptor CSF-1R in non-hematopoietic neoplasms," Cancer Treat Res 107:285-292 (2002).

Keshava et al., "Blocking of colony stimulating factor expression with antisense RNA in breast and ovarian cancer epithelial cells leads to programmed cell death," Proceedings of the Annual Meeting of the American Association for Cancer Research, New York, NY, US, vol. 38, p. 500 (Mar. 1997).

Keshava et al., "Overexpression of macrophage colony-stimulating factor (CSF-1) and its receptor, c-fms, in normal ovarian granulose cells leads to cell proliferation and tumorigenesis," J Soc Gynecol Investig 6:41-49 (1999).

Kitaura et al., "M-CSF mediates TNF-induced inflammatory osteolysis," J Clin Invest 115(12):3418-3427 (2005).

Lee et al., "CSF-1 activates MAPK-dependent and p53-independent pathways to induce growth arrestof hormone-dependent human breast cancer cells," Oncogene 18:7477-7494 (1999).

Lin et al. "Regulation of myeloid growth and differentiation by a novel cytokine, interleukin-34 (IL-34), via the CSF-1 receptor," Cytokine 39(1):24 (2007) and 15th Annual Meeting of the International-Cytokine-Society, San Francisco, CA USA, Oct. 26-30, 2007.

Lin et al., "Discovery of a cytokine and its receptor by functional screening of the extracellular proteome," Science 320(5877):807-811 (2008).

Lin et al., "The macrophage growth factor CSF-1 in mammary gland development and tumor progression," Mammary Gland Biol Neoplasia 7(2):147-162 (2002).

Maher et al., "Prognostic significance of colony-stimulating factor receptor expression in ipsilateral breast cancer recurrence," Clin Cancer Res 4:1851-1856 (1998).

Menetrier-Caux et al., "Inhibition of the differentiation of dendritic cells from CD34+* progenitors by tumor cells: role of interleukin-6 and macrophage colony-stimulating factor," Blood 92:4778-4791 (1998).

Nowicki et al., "Impaired tumor growth in colony-stimulating factor 1 (CSF-1)-deficient, macrophage-deficient *op/op* mouse: evidence for a role of CSF-1-dependent macrophages in formation of tumor stroma," Int J Cancer 65:112-119 (1996).

Paulus et al., "Colony-stimulating factor-1 antibody reverses chemoresistance in human MCF-7 breast cancer xenografts," Cancer Res 66(8):4349-4356 (2006).

Pollard, "Tumour-educated macrophages promote tumour progression and metastasis," Nat Rev Cancer 4:71-78 (2004).

Rao et al., "Membrane-bound macrophage colony-stimulating factor mediated auto-juxtacrine downregulates matrix metalloproteinase-9 release on J6-1 leukemic cell," Exp Biol Med (Maywood) 229(9):946-953 (2004).

Rettenmier et al., "The colony-stimulating factor 1(CSF-1) receptor (c-fms proto-oncogene product) and its ligand," J Cell Sci Suppl 9:27-44 (1988).

Roussel et al., "Transforming potential of the c-fms proto-oncogene (CSF-1 receptor), "Nature 325:549-552 (1987).

Sapi et al., "The role of CSF-1 in normal and neoplastic breast physiology," Proc Soc Exp Biol Med 220:1-8 (1999).

Sapi et al., "Transcriptional regulation of the *c-fms* (CSF-1R) proto-oncogene in human breast carcinoma cells by glucocorticoids," Oncogene 10:529-542 (1995).

Scholl et al., "Anti-colony-stimulating factor-1 antibody staining in primary breast adenocarcinomas correlates with marked inflammatory cell infiltrates and prognosis," J Natl Cancer Inst 86(2):120-126 (1994).

Scholl et al., "Is colony-stimulating factor-1 a key mediator of breast cancer invasion and metastasis?" Mol Carcinog 7:207-211 (1993).

Shadduck et al., "Paradoxical stimulation of normal and leukemic rat hematopoiesis by monoclonal by monoclonal antibody to CSF-1 receptor," Exp Hematol 24(2):314-317 (1996).

Shadduck et al., "Preparation of a monoclonal antibody directed against the receptor for murine colony-stimulating factor-1," Exp Hematol 21(4):515-520 (1993).

Sherr CJ et al , "Inhibition of colony-stimulating factor-1 activity by monoclonal antibodies to the human CSF-1 receptor," Blood 73(7):1786-1793 (1989).

Sherr and Rettenmier, "The fms gene and the CSF-1 receptor," Cancer Surv 5(2):221-232 (1986).

Sherr CJ, "Regulation of mononuclear phagocyte proliferation by colony-stimulating factor-1," Int J Cell Cloning 8(Suppl.1):46-62 (1990).

Sherr et al., "Colony-stimulating factor-1 receptor (c-fms)," J Cell Biochem 38(3):179-187 (1988).

Smith et al., "The role of colony-stimulating factor 1 and its receptor in the etiopathogenesis of endometrial adenocarcinoma," Clin Cancer Res 1(3):313-325 (1995).

Tang et al., "M-CSF (monocyte colony stimulating factor) and M-CSF receptor expression by breast tumour cells: M-CSF mediated recruitment of tumour infiltrating monocytes?" J Cell Biochem 50(4):350356 (1992).

Wang et al., "Identification of the ligand-binding regions in the macrophage colony-stimulating factor receptor extracellular domain," Mol Cell Biol 13:5348-5359 (1993).

Zheng G et al., "Membrane-bound macrophage colony-stimulating factor and its receptor play adhesion molecule-like roles in leukemic cells," Leukemia Res 24(5):375-383 (2000).

|  | 1 | 20 |  | | 40 | | | 60 | |
|---|---|---|---|---|---|---|---|---|---|
| V_H1 | QVQLVQSGAE | VKKPGASVKV | SCKASGYTFT | A..YYMH | WVR | QAPGQGLEWM | GWIN.PNSGG | TN.YAQKFQG |
| V_H2 | QVQLQESGPG | LVKPSETLSL | TCTVSGGSVS | SGGYYWS | WIR | QPPGQGLEWI | GYIY...YSGS | TN.YNPSLKS |
| V_H3 | QVQLVQSGAE | VKKPGASVKV | SCKASGYTFT | G..YYIH | WVR | QAPGQGLEWM | GWIN.PNSGG | TN.YAQKFQG |
| V_H4 | EVQLVESGGG | VVQPGRSLRL | SCAASGFTFS | S..YGMH | WVR | QAPGKGLEWV | AVIW.YDGSN | KY.YADSVKG |
| V_H5 | EVQLVESGGG | LVKPGGSLRL | SCAASGFTFS | N..AWMS | WVR | QAPGKGLEWV | GRIKSKTDGG | TTDNAAPVKG |
| V_H6 | EVQLVESGGG | LVKPGGSLRL | SCAASGFTFS | N..AWMS | WVR | QAPGKGLEWV | GRIKSKTDGG | TTDYAAPVKG |
| V_H7 | EVQLVESGGG | LVKPGGSLRL | SCAASGFTFS | N..AWMS | WVR | QAPGKGLEWV | GRIKSKTDGW | TTDYAAPVKG |
| V_H8 | QVQLVQSGAE | VKKPGASVKV | SCKASGYTFT | S..YGIS | WVR | QAPGQGLEWM | GWIS.AYNGN | TN.YAQKLQG |
| V_H9 | EVQLVESGGG | LVKPGGSLRL | SCAASGFTFS | N..AWMS | WVR | QAPGKGLEWV | GRIKSKTDGG | TTDYAAPVKG |
| V_H10 | EVQLVESGGG | LVKPGGSLRL | SCAASGFTFS | N..AWMS | WVR | QAPGKGLEWV | GRIKSKTDGG | TTDYAAPVKG |
| V_H11 | QVQLVQSGAE | VKKPGASVKV | SCKASGYTFT | S..YGIS | WVR | QAPGQGLEWM | GWIS.AYNGN | TN.YAQKLQG |
| V_H12 | QVQLVQSGAE | VKKPGASVKV | SCKASGYTFT | G..YYMH | WVR | QAPGQGLEWM | GWIN.PNSGG | TN.YAQKFQG |
| V_H13 | QVQLVQSGAE | VKKPGASVKV | SCKASGYTFT | G..YYMH | WVR | QAPGQGLEWM | GWIN.PNSGG | TN.YAQKFQG |
| V_H14 | EVQLVESGGG | LVKPGGSLRL | SCAASGFTFS | N..AWMS | WVR | QAPGKGLEWV | GRIKSKTDGG | TTDYAAPVKG |
| V_H15 | EVQLVESGGG | LVKPGGSLRL | SCAASGFTFS | N..AWMS | WVR | QAPGKGLEWV | GRIKSKTDGG | TADYAAPVKG |
| V_H16 | QVQLVQSGAE | VKKPGASVKV | SCKASGYTFT | S..YGIS | WVR | QAPGQGLEWM | GWIS.AYNGN | TN.YAQKLQG |
| V_H17 | EVQLVESGGG | LVQPGGSLRL | SCAASGFTFS | S..YDMH | WVR | QATGKGLEWV | SGIG..TAGD | T.YYPGSVKG |
| V_H18 | EVQLVESGGG | VVQPGRSLRL | SCAASGFTFS | S..YGMH | WVR | QAPGKGLEWV | AVIW..YDGS | NEYYADSVKG |
| V_H19 | EVQLVESGGG | LVEPGGSLRL | SCAASGFTFS | T..AWMS | WVR | QAPGKGLEWV | GRIKSKTDGG | TTDYAAPVKG |
| V_H20 | EVQLVESGGG | LVKPGGSLTL | SCAASGFTEN | N..AWMS | WVR | QAPGKGLEWV | GRIKSKTDGG | TTDYAAPVKG |
| V_H21 | QVQLVESGGG | VVQPGRSLRL | SCAASGFTFS | S..YGMH | WVR | QSAGKGLEWI | AVIW..YDGS | NKYYADSVKG |
| V_H22 | QVQLVESGPG | LVKPSETLSL | TCTVSGGSIS | N..YYWS | WIR | QSAGKGLEWI | GRIY..TSGS | TH.YNPSLKS |
| V_H23 | QVQLVESGGG | VVQPGRSLRL | SCAASGFTFS | S..YGMH | WVR | QAPGKGLEWV | AVIW..YDGS | YKYYADSVKG |
| V_H24 | QVQLVQSGAE | VKKPGASVKV | SCKVSGYTLT | E..LSMH | WVR | QAPGKGLEWM | GGFD...PEDG | ETIYAQKFQG |
| V_H25 | QVQLVQSGAE | VKKPGASVKV | SCKVSGYTLT | E..LSMH | WVR | QAPGKGLEWM | GGFD...PEDG | ETIYAQKFQG |
| V_H26 | QVQLVQSGAE | VKKPGASVKV | SCKVSGYTLT | E..LSMH | WVR | QAPGKGLEWM | GGFD...PEDG | ETIYAQKFQG |
| V_H27 | QVQLQESGPG | LVKPSETLSL | TCTVSGGSIS | S..YYWS | WIR | QPPGKGLEWI | GYIY..YSGN | TNYNPSLKSR |
| V_H28 | QVQLVESGPG | LVKPSETLSL | TCTVSGGSIS | S..YYWS | WIR | QPPGKGLEWI | GYIY..YSGN | TNYNPSLKSR |
| V_H29 | QVQLVESGGG | VVQPGRSLRL | SCAASGFTFS | S..YGMH | WVR | QAPGKGLEWV | AVIW..YDGS | NKYYADSVKG |
| V_H30 | QVQLQESGPG | LVKPSQTLSL | TCTVSGGSIS | S..YGIS | WVR | QHPGKGLEWI | GYIS..YSGD | T.YYNPSLKS |
| V_H31 | QVQLVQSGAE | VKKPGASVKV | SCKASGYTFT | S..YGIS | WVR | QAPGQGLEWM | GWIS..AYNG | NPNYAQKFQG |
| V_H32 | EVQLVESGGG | LVKPGGSLRL | SCAASGFTFS | N..AWMS | WVR | QAPGKGLEWV | GRIKTKTDGG | TTDYAAPVKG |
|  | FR1 | | | CDR1 | | FR2 | | CDR2 |

FIGURE 1A-1

| | 80 | | | 100 | | 120 | | 133 | |
|---|---|---|---|---|---|---|---|---|---|
| V$_H$1 | RVTMTRDTSI | STAYMELSRL | RSDDTAVYYC | ARGGYSGYDL | G.....YYYGM | DVWGQGTTVT | VSS | (SEQ ID NO:70) |
| V$_H$2 | RVTISVDTSK | NQFSLKLSSV | TAADTAVYYC | AAGIAATGT. | .........LF | DCWGQGTTVT | VSS | (SEQ ID NO:71) |
| V$_H$3 | RVTMTRDTSI | STAYMELSRL | RSDDTAVYYC | ARDRGQLWLW | ...YYYYGM | DVWGQGTTVT | VSS | (SEQ ID NO:72) |
| V$_H$4 | RFTISRDNSK | NTLYLQMNSL | RAEDTAVYYC | ASSSWS.... | ........YYGM | DVWGQGTTVT | VSS | (SEQ ID NO:73) |
| V$_H$5 | RFTISRDDSK | NTLYLQMNSL | KTEDTAVYYC | TTGGSLLWTG | PN..YYYYGM | DVWGQGTTVT | VSS | (SEQ ID NO:74) |
| V$_H$6 | RFTISRDDSK | NTLYLQMNSL | KTEDTAVYYC | TTEYYGSGGV | W.....YYGM | DVWGQGTTVT | VSS | (SEQ ID NO:75) |
| V$_H$7 | RFTISRDDSK | NTLYLQMNSL | KTEDTAVYYC | TTDLRITGTT | ..YYYYYGM | DVWGQGTTVT | VSS | (SEQ ID NO:76) |
| V$_H$8 | RFTMTTDTST | STAYMELRSL | RSDDTAVYYC | ARES..W... | ......FGEVFF | DYWGQGTTVT | VSS | (SEQ ID NO:77) |
| V$_H$9 | RFTISRDDSK | NTLYLQMNSL | KTEDTAVYYC | TTEYYGSGGV | W.....YYGM | DVWGQGTTVT | VSS | (SEQ ID NO:78) |
| V$_H$10 | RFTMTTDTST | STAYMELSRL | RSDDTAVYYC | TTDGATVVTP | G...YYYYGT | DVWGQGTLVT | VSS | (SEQ ID NO:79) |
| V$_H$11 | RVTMTRDTSI | STAYMELSRL | RSDDTAFYYC | ARES..W... | ......FGEVFF | DPWGQGTLVT | VSS | (SEQ ID NO:80) |
| V$_H$12 | RVTMTRDTST | STAYMELSRL | RSDDTAFYYC | ARDSNW.... | ......YHNWF | DVWGQGTLVT | VSS | (SEQ ID NO:81) |
| V$_H$13 | RVTMTRDTSI | STAYMELSRL | RSDDTAVYYC | ARDSNWYH.. | ........NWF | DEWGQGTLVT | VSS | (SEQ ID NO:82) |
| V$_H$14 | RFTISRDDSK | NTLYLQMNSL | KTEDTAVYYC | TTDGATVVTP | G...YYYYGT | DVWGQGTLVT | VSS | (SEQ ID NO:83) |
| V$_H$15 | RFTISRDDSK | NTLYLQMNSL | KTEDTAVYYC | TTEGPYSDY. | G...YYYYGM | DVWGQGTTVT | VSS | (SEQ ID NO:84) |
| V$_H$16 | RFTMTTDTST | STAYMELRSL | RSDDTAVYYC | ARESWFGEV. | .........FF | DYWGQGTLVT | VSS | (SEQ ID NO:85) |
| V$_H$17 | RFNISRENAK | NSLYLQMNSL | RAGDTAVYYC | AREGSW.... | .........YGF | DYWGQGTLVT | VSS | (SEQ ID NO:86) |
| V$_H$18 | RFTISRDNSK | STLYLQMNSL | RAEDTAVYYC | AHSSGN.... | .........YDM | DVWGQGTTVT | VSS | (SEQ ID NO:87) |
| V$_H$19 | RFTISRDDSK | NTLYLQMNSL | KNEDTAVYYC | TTEGPYSNYG | ...YYYYGV | DVWGQGTLVT | VSS | (SEQ ID NO:88) |
| V$_H$20 | RFTISRDDSK | NTLYLQMNSL | KTEDTAVYYC | TTEYYHILTG | .SFYYSYYGM | DVWGQGTTVT | VSS | (SEQ ID NO:89) |
| V$_H$21 | RFTISRDNSK | NTLYLQMNSL | RAEDTAVYYC | ASSSSN.... | ........FYDM | DVWGQGTTVT | VSS | (SEQ ID NO:90) |
| V$_H$22 | RIIMSVDTSK | NQFSLKLSSV | TAADTAVYYC | ARDRVF.... | .........YGM | DVWGQGTTVT | VSS | (SEQ ID NO:91) |
| V$_H$23 | RFTISRDNSK | NTLYLQMNSL | RAEDTAVYYC | ARE....GD | ...YSDYYGM | DEWGQGTTVT | VSS | (SEQ ID NO:92) |
| V$_H$24 | RVTMTEDTST | DTVYMELSSL | RSEDTAVYYC | ATGVMITFGG | VIVGHSYYGM | DYWGQGTTVT | VSS | (SEQ ID NO:93) |
| V$_H$25 | RVTMTEDTST | DTAYMELSSL | RSEDTAVYYC | ATGVMITFGG | VIVGHSYYGM | DYWGQGTTVT | VSS | (SEQ ID NO:94) |
| V$_H$26 | RVTMTEDTST | DTAYMELSSL | RSEDTAVYYC | ATRAGTT.LA | ...YYYYAM | DVWGQGTTVT | VSS | (SEQ ID NO:95) |
| V$_H$27 | FTLSIDTSKN | QFSLRLSSVT | AADTAVYYCA | C.IATR.... | ..........PF | DYWGQGTLVT | VSS | (SEQ ID NO:96) |
| V$_H$28 | RFTISRDNSK | NTLYLQMNSL | RAEDTAVYYC | ADSSG..... | ......DYYGM | DVWGQGTTVT | VSS | (SEQ ID NO:97) |
| V$_H$29 | RVTMTEDTST | DTAYMELSSL | RSEDTAVYYC | ATAGLEIR.. | ..........WF | DFWGQGTTVT | VSS | (SEQ ID NO:98) |
| V$_H$30 | RLTISVDTSK | HQFSLRLSSV | TSADTAVYYC | ASLDL..... | ......YG.DY.F | DYWGQGTLVT | VSS | (SEQ ID NO:99) |
| V$_H$31 | RVTMTTDTST | STAYMELRSL | RSDDTAVYYC | ARDQGLLGFG | ELEG....LF | DYWGQGTLVT | VSS | (SEQ ID NO:100) |
| V$_H$32 | RFTISRDDSQ | NTLYLQMNSL | KTEDTAVYYC | TTEYYGIVTG | SF.YYYYGM | DVWGQGTTVT | VSS | (SEQ ID NO:101) |

FR3 | CDR3 | J/Fr4

FIGURE 1A-2

| | FR1 | | CDR1 | | FR2 | CDR2 | |
|---|---|---|---|---|---|---|---|
| | 1 | 20 | | 40 | | | 62 |
| V_L1 | DIQMTQSPSS | LSASVGDRVT | ITC...QASQ | NISN...FLD | WYQQKPGKAP | NLLIY DASDL | DP |
| V_L2 | DIQMTQSPSS | LSASVGDRVT | ITC...QASQ | DISN...FLD | WYQQKPGKAP | KLLIY DASDL | DP |
| V_L3 | DNVMTQTPLS | LSVTPGQPAS | ISCKSSQSLL | HSDGKTYLY. | WYLQKPGQPP | QLLIY EASNR | FS |
| V_L4 | DIQMTQSPSS | LSASVGDRVT | ITC...QASQ | DINN...YLN | WYQQKPGKAP | KLLIY DASNL | EI |
| V_L5 | DIQMTQSPSS | LSASVGDRVT | ITC...QASQ | DINN...YLN | WYQHKPGKAP | KLLIY DTSNL | EP |
| V_L6 | DIQMTQSPSS | LSASVGDRVT | ITC...QASQ | DISN...YLN | WYQQKPGKAP | KLLIY DASNL | ET |
| V_L7 | DIQMTQSPSS | LSASVGDRVT | ITC...QASQ | DISN...YLN | WYQHKPGKAP | KFLIY DASNL | ET |
| V_L8 | DIVMTQSPDS | LAVSLGERAT | INCKSSQSVL | DSSDNKNYLA | WYQQKPGQPP | KLLIY WASNR | ES |
| V_L9 | DIVMTQSPDS | LAVSLGERAT | INCKSSQSVL | DSSDNKNYLA | WYQQKPGQPP | KLLIY WASNR | ES |
| V_L10 | DIQMTQSPSS | LSASVGDRVT | ITC...QASQ | DISN...YLN | WYQQKPGKAP | KLLIY DASNL | ET |
| V_L11 | DIVMTQSPDS | LAVSLGERAT | IDCKSSQGVL | DSSNNKNFLA | WYQQKPGQPP | NLLIY AASSL | QS |
| V_L12 | DIVMTQSPSS | LSASVGDRVT | ITCRASQSIS | D......YLN | WYQQKPGKAP | KLLIY DASNL | ET |
| V_L13 | DIVMTQSPSS | LSASVGDRVT | ITC...QASQ | DISN...YLN | WYQQKPGKAP | KLLIY DASNL | ET |
| V_L14 | DIVMTQSPSS | LSASVGDRVT | ITC...QASQ | DISN...YLN | WYQQKPGKAP | KVLIY DASNR | ES |
| V_L15 | DIVMTQSPDS | LAVSLGERAT | IDCKSSQSVL | DSSNNKNFLA | WYQQKPGQPP | KLLIY WASNR | ES |
| V_L16 | EIVLTQSPGT | LSLSPGERAT | LSCRASQSVS | SG...YLAYLA | WYQQRPGQAP | RLLIY GASST | AT |
| V_L17 | DIQMTQSPSS | LSASVGDRVT | ITC...QASQ | DISN...FLN | WYQQRPGKAP | KLLIY DASNL | ET |
| V_L18 | DIQMTQSPSS | LSASVGDRVT | ITC...QASQ | DISN...YLN | WYQQKPGKAP | KLLIY DASNL | ET |
| V_L19 | DIQMTQSPSS | LSASVGDRVT | ITC...QASQ | DISN...YLN | WYQQRPGKAP | KLLIY DASNL | ET |
| V_L20 | DIQMTQSPSS | LSASVGDRVT | ITC...QASQ | ....N..YLA | WYQQRPGKAP | KLLIY AASTL | QS |
| V_L21 | DIQMTQSPSS | LSASVGDRVT | ITCRASQGFS | ....N..YLA | WYQQKPGKVP | KLLIY VASTL | QS |
| V_L22 | DIQMTQSPSS | LSASVGDRVT | ITCRASQGIN | ....N..YLA | WYQQKPGKVP | QLLIY VASTL | QS |
| V_L23 | DIQMTQSPSS | LSASVGDRVT | ITCRASQGIN | ......RYLN | WYQQKPGKVP | KLLIY VASTL | QS |
| V_L24 | DIQMTQSPSS | LSASVGDRVT | ITCRASQSIS | ......ND..LD | WYQQKPGKAP | NLLIH AASSL | QS |
| V_L25 | EIVLTQSPGT | LSLSPGERAT | ITCRASQGIR | DISN...YLN | WYQQRPGKAP | KRLIY AASSL | ET |
| V_L26 | DIQMTQSPLS | LPVTPGEPAS | ISCRSSQSLL | DISN...YLN | WYLQKPGQSP | KFLIS DASNL | ET |
| V_L27 | QSVTLTQSPDF | QSVTPKEKVT | ITCRASQYIG | HSNGYNYLD | WYQQTPDQSP | QFLIY LGSIR | AS |
| V_L28 | EIVLTQSPDF | LAVSLGARAT | ISCKSSQSVL | SS......LH | WYQQKPGQPP | KLLIN VYSQS | FS |
| V_L29 | DIVMTQSPDS | LSASVGDRVT | ITCKSSQSVL | YSSNNKNYLA | WYQQKPGQPP | KLLIY WASTR | ES |
| V_L30 | DIQMTQSPSS | LSASVGDRVT | ITC...QASQ | DI.NN..YLN | WYQHKPGKAP | KLLIY DASNL | ET |
| V_L31 | DIQMTQSPSS | LSASVGDRVT | ITC...QASQ | DISN...YLN | WYQQKPGKAP | KLLIY DASNL | ET |
| V_L32 | DIQMTQSPSS | LSASVGDRVT | ITC...QASQ | DISN...YLN | WYQHKPGKAP | KLLIY DASNL | ET |
| V_L33 | DVVMTQSPLS | LPVTLGQPAS | ISCRSSQSLV | YSDGNT.YLN | WFQQRPGQSP | RRLIY KVSNW | DS |
| V_L34 | DVVMTQSPLS | LPVTLGQPAS | ISCRSSQSLV | YSDGNT.YLN | WFQQRPGQSP | RRLIY KVSNW | DS |

FIGURE 1B-1

|  | 63 | 80 | | | 100 | | J/FR4 | |
|---|---|---|---|---|---|---|---|---|
| | | FR3 | | | | CDR3 | | |
| V_L1 | GVPSRFSG | SGSGTDFTFT | ISSLQPEDIA | TYYC | QQYVSL | ....PLT | FGGG TKVEIK | (SEQ ID NO:102) |
| V_L2 | GVPSRFSG | SGSGTDFTFT | ISSLQPEDIA | TYYC | QQYVSL | ....PLT | FGGG TKVEIK | (SEQ ID NO:103) |
| V_L3 | GVPDRFSG | SGSGTDFTLK | ISRVEAEDVG | VYYC | MQSIQL | ....PLT | FGGG TKVEIK | (SEQ ID NO:104) |
| V_L4 | GVPSRFSG | SGSGTDFIFT | ISSLQPEDIA | TYYC | QQYDNF | ....PFT | FGGG TKVEIK | (SEQ ID NO:105) |
| V_L5 | GVPSRFSG | SGSGTDFTFT | ISSLQPEDIA | TYYC | QQYDNL | ....LTF | GGGQ TRLEIK | (SEQ ID NO:106) |
| V_L6 | GVPSRFSG | SGSGTDFTFT | ISSLQPEDIA | TYYC | QQYDNL | ....LTF | GQGQ TKVEIK | (SEQ ID NO:107) |
| V_L7 | GVPSRFSG | SGSGTDFTFT | ISSLQPEDIA | TYYC | QQYDNL | ....ITF | GQGQ TRLEIK | (SEQ ID NO:108) |
| V_L8 | GVPSRFSG | SGSGTDFSLT | ISSLQAEDVA | VYYC | QQYYSD | ....PFT | FGPG TKVDIK | (SEQ ID NO:109) |
| V_L9 | GVPDRFSG | SGSGTDFTLT | ISSLQAEDVA | VYYC | QQYYSD | ....PFT | FGPG TKVDIK | (SEQ ID NO:110) |
| V_L10 | GVPSRFSG | SGSGTDFTFT | ISSLQPEDIA | TYYC | QQYDNL | ....LTF | GGGQ TKVEIK | (SEQ ID NO:111) |
| V_L11 | GVPVRFSG | SGSGTDFTLI | ISSLQAEDVA | LYYC | QQYYSD | ....PFT | FGPG TKVDIK | (SEQ ID NO:112) |
| V_L12 | GVPSRFSG | SGSGTDFTLI | ISSLQPEDFA | TYFC | QQTYSD | ....PFT | FGPG TKVDIK | (SEQ ID NO:113) |
| V_L13 | GVPSRFSG | SGSGTDFTFT | ISSLQPEDIA | TYYC | QQYDNL | ....LTF | GGGQ TKVEIK | (SEQ ID NO:114) |
| V_L14 | GVPSRFSG | SGSGTDFTLT | ISSLQAEDVA | VYYC | QQYYSD | ....PFT | FGPG TKVDIK | (SEQ ID NO:115) |
| V_L15 | GVPSRFSG | SGSGTDFTLT | ISRLEPEDFA | VYYC | QQYGSS | ....PIT | FGQG TRLEIK | (SEQ ID NO:116) |
| V_L16 | GIPDRFSG | SGSGTDFTLT | ISSLQAEDVA | VYYC | QQYYSD | ....PFT | FGQG TKVDIK | (SEQ ID NO:117) |
| V_L17 | GVPSRFSG | SGSGTDFTFT | ISSLQPEDFA | TYYC | QQYDNL | ....PFT | FGPG TKVEIK | (SEQ ID NO:118) |
| V_L18 | GVPSRFSG | SGSGTDFTFT | ISSLQPEDFA | TYYC | QQYDNL | ....LTF | GGGQ TRLEIK | (SEQ ID NO:119) |
| V_L19 | GVPSRFSG | SGSGTDFTFT | INSLQPEDIA | TYYC | QQRYDDL | ....PIT | FGPG TKVEIK | (SEQ ID NO:120) |
| V_L20 | GVPSRFSG | SGSGTDFTFT | ISSLQPEDIA | TYYC | QQYDNL | ....LTF | GGGQ TRLEIK | (SEQ ID NO:121) |
| V_L21 | GVPSRFSG | SGSGTDFTLI | ISSLQPEDVA | TYYC | QQKYNSA | ....LTF | GGGQ TKVEIK | (SEQ ID NO:122) |
| V_L22 | GVPSRFSG | SGSGTDFTLI | ISSLQPEDVA | TYYC | QQKYNSG | ....PFT | FGPG TKVDIK | (SEQ ID NO:123) |
| V_L23 | GVPSRFSG | SGSGTDFTLT | ISSLQPEDVA | TYYC | QQKYNSG | ....PFT | FGPG TKVDIK | (SEQ ID NO:124) |
| V_L24 | GVPDRFSG | SGSGTDFTLT | ISSLQPEDFA | TYYC | QQSYIT | ....PPS | FGQG TKLEIK | (SEQ ID NO:125) |
| V_L25 | GVPSRFSG | SGSGTEFTLT | ISSLQPEDFA | TYYC | QQYNSY | ....PIT | FGGG TRLEIK | (SEQ ID NO:126) |
| V_L26 | GVPSRFSG | SGSGTDFTFT | INSLQPEDFA | TYYC | QLQYNSY | ....PIT | FGPG TKVEIK | (SEQ ID NO:127) |
| V_L27 | GVPSRFSG | SGSGTDFALT | ISRVEAEDVG | VYYC | MQALQT | ....PRT | FGQG TKVDIK | (SEQ ID NO:128) |
| V_L28 | GVPSRFSG | SGSGTDFTLI | INSLEAEDAA | TYYC | HQSSSL | ....PFT | FGQG TKVDIK | (SEQ ID NO:129) |
| V_L29 | GVPSRFSG | SGSGTDFTLT | ISTLQAEDVA | VYYC | QQYYTT | ....PPT | FGQG TKVEIK | (SEQ ID NO:130) |
| V_L30 | GVPSRFSG | SGSGTDFTFT | ISSLQPEDIA | TYYC | QQYDDL | ....LTF | GGGQ TKVEIK | (SEQ ID NO:131) |
| V_L31 | GVPSRFSG | SGSGTDFTFI | ISSLQPEDIA | TYYC | QQYDNL | ....PPT | FGGG TKVEIK | (SEQ ID NO:132) |
| V_L32 | GVPSRFSG | SGSGTDFTFT | ISSLQPEDIA | TYYC | QQYDNL | ....LTF | GGGQ TKVEIK | (SEQ ID NO:133) |
| V_L33 | GVPDRFSG | SGSGTDFTLK | ISRVEAEDVG | VYYC | MQGTHW | PRGLFT | FGPG TKVDIK | (SEQ ID NO:134) |
| V_L34 | GVPDRFNG | SGSGTDFTLK | ISRVEAEDVG | VYYC | MQGTHW | ....PIT | FGQG TGLEIK | (SEQ ID NO:135) |

FIGURE 1B-2

Human cfms ECD

```
  1  MGPGVLLLLL  VATAWHGQGI  PVIEPSVPEL  VVKPGATVTL  RCVGNGSVEW
 51  DGPPSPHWTL  YSDGSSSILS  TNNATFQNTG  TYRCTEPGDP  LGGSAAIHLY
101  VKDPARPWNV  LAQEVVVFED  QDALLPCLLT  DPVLEAGVSL  VRVRGRPLMR
151  HTNYSFSPWH  GFTIHRAKFI  QSQDYQCSAL  MGGRKVMSIS  IRLKVQKVIP
201  GPPALTLVPA  ELVRIRGEAA  QIVCSASSVD  VNFDVFLQHN  NTKLAIPQQS
251  DFHNNRYQKV  LTLNLDQVDF  QHAGNYSCVA  SNVQGKHSTS  MFFRVVESAY
301  LNLSSEQNLI  QEVTVGEGLN  LKVMVEAYPG  LQGFNWTYLG  PFSDHQPEPK
351  LANATTKDTY  RHTFTLSLPR  LKPSEAGRYS  FLARNPGGWR  ALTFELTLRY
401  PPEVSVIWTF  INGSGTLLCA  ASGYPQPNVT  WLQCSGHTDR  CDEAQVLQVW
451  DDPYPEVLSQ  EPFHKVTVQS  LLTVETLEHN  QTYECRAHNS  VGSGSWAFIP
501  ISAGAHTHPP  DE
```

<u>Underline</u> - signal sequence
Bold - Ig-like loop1 and 2 sequence
*Italic* - Ig-like loop3 to 5 sequence

FIGURE 8

SEQUENCE LISTING

<160> NUMBER OF SEQ ID NOS: 326

<210> SEQ ID NO 1
<211> LENGTH: 512
<212> TYPE: PRT
<213> ORGANISM: Homo Sapiens

<400> SEQUENCE: 1

```
Met Gly Pro Gly Val Leu Leu Leu Leu Val Ala Thr Ala Trp His
 1               5                  10                  15

Gly Gln Gly Ile Pro Val Ile Glu Pro Ser Val Pro Glu Leu Val Val
             20                  25                  30

Lys Pro Gly Ala Thr Val Thr Leu Arg Cys Val Gly Asn Gly Ser Val
         35                  40                  45

Glu Trp Asp Gly Pro Pro Ser Pro His Trp Thr Leu Tyr Ser Asp Gly
     50                  55                  60

Ser Ser Ser Ile Leu Ser Thr Asn Asn Ala Thr Phe Gln Asn Thr Gly
 65                 70                  75                  80

Thr Tyr Arg Cys Thr Glu Pro Gly Asp Pro Leu Gly Gly Ser Ala Ala
                 85                  90                  95

Ile His Leu Tyr Val Lys Asp Pro Ala Arg Pro Trp Asn Val Leu Ala
             100                 105                 110

Gln Glu Val Val Val Phe Glu Asp Gln Asp Ala Leu Leu Pro Cys Leu
         115                 120                 125

Leu Thr Asp Pro Val Leu Glu Ala Gly Val Ser Leu Val Arg Val Arg
 130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                 165                 170                 175

Cys Ser Ala Leu Met Gly Gly Arg Lys Val Met Ser Ile Ser Ile Arg
             180                 185                 190

Leu Lys Val Gln Lys Val Ile Pro Gly Pro Pro Ala Leu Thr Leu Val
         195                 200                 205

Pro Ala Glu Leu Val Arg Ile Arg Gly Glu Ala Ala Gln Ile Val Cys
 210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                 245                 250                 255

Tyr Gln Lys Val Leu Thr Leu Asn Leu Asp Gln Val Asp Phe Gln His
             260                 265                 270

Ala Gly Asn Tyr Ser Cys Val Ala Ser Asn Val Gln Gly Lys His Ser
         275                 280                 285

Thr Ser Met Phe Phe Arg Val Val Glu Ser Ala Tyr Leu Asn Leu Ser
 290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                 325                 330                 335

Thr Tyr Leu Gly Pro Phe Ser Asp His Gln Pro Glu Pro Lys Leu Ala
             340                 345                 350

Asn Ala Thr Thr Lys Asp Thr Tyr Arg His Thr Phe Thr Leu Ser Leu
         355                 360                 365

Pro Arg Leu Lys Pro Ser Glu Ala Gly Arg Tyr Ser Phe Leu Ala Arg
 370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                 405                 410                 415
```

```
Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
            485                 490                 495

Ala Phe Ile Pro Ile Ser Ala Gly Ala His Thr His Pro Asp Glu
            500                 505                 510

<210> SEQ ID NO 2
<211> LENGTH: 326
<212> TYPE: PRT
<213> ORGANISM: Homo Sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285
```

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 3
<211> LENGTH: 107
<212> TYPE: PRT
<213> ORGANISM: Homo Sapiens

<400> SEQUENCE: 3

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 4
<211> LENGTH: 451
<212> TYPE: PRT
<213> ORGANISM: Homo Sapiens

<400> SEQUENCE: 4

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ala Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                 85                  90                  95

Ala Arg Gly Gly Tyr Ser Gly Tyr Asp Leu Gly Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser

```
                 180                 185                 190
Val Val Thr Val Pro Ser Ser Asn Phe Gly Thr Gln Thr Tyr Thr Cys
                195                 200                 205

Asn Val Asp His Lys Pro Ser Asn Thr Lys Val Asp Lys Thr Val Glu
                210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Gln Phe Asn Trp Tyr Val Asp Gly Val Glu Val
                275                 280                 285

His Asn Ala Lys Thr Lys Pro Arg Glu Glu Gln Phe Asn Ser Thr Phe
                290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 5
<211> LENGTH: 447
<212> TYPE: PRT
<213> ORGANISM: Homo Sapiens

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Gly Tyr Tyr Trp Ser Trp Ile Arg Gln Pro Pro Gly Lys Gly Leu Glu
                35                  40                  45

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ala Gly Ile Ala Ala Thr Gly Thr Leu Phe Asp Cys Trp Gly
```

```
               100                 105                 110
Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
            210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 6
<211> LENGTH: 452
<212> TYPE: PRT
<213> ORGANISM: Homo Sapiens

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
```

```
              35                  40                  45
Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Arg Gly Gln Leu Trp Leu Trp Tyr Tyr Tyr Tyr Tyr Gly
                100                 105                 110

Met Asp Val Trp Gly Gln Gly Thr Thr Val Thr Val Ser Ser Ala Ser
                115                 120                 125

Thr Lys Gly Pro Ser Val Phe Pro Leu Ala Pro Cys Ser Arg Ser Thr
            130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Asn Phe Gly Thr Gln Thr Tyr Thr
            195                 200                 205

Cys Asn Val Asp His Lys Pro Ser Asn Thr Lys Val Asp Lys Thr Val
            210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
            450
```

```
<210> SEQ ID NO 7
<211> LENGTH: 445
<212> TYPE: PRT
<213> ORGANISM: Homo Sapiens

<400> SEQUENCE: 7

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Ser Ser Trp Ser Tyr Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

```
Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 8
<211> LENGTH: 455
<212> TYPE: PRT
<213> ORGANISM: Homo Sapiens

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Asn Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Thr Thr Gly Gly Ser Leu Leu Trp Thr Gly Pro Asn Tyr Tyr
        100                 105                 110

Tyr Tyr Gly Met Asp Val Trp Gly Gln Gly Thr Thr Val Thr Val Ser
    115                 120                 125

Ser Ala Ser Thr Lys Gly Pro Ser Val Phe Pro Leu Ala Pro Cys Ser
130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
            165                 170                 175

Ser Gly Val His Thr Phe Pro Ala Val Leu Gln Ser Ser Gly Leu Tyr
        180                 185                 190

Ser Leu Ser Ser Val Val Thr Val Pro Ser Ser Asn Phe Gly Thr Gln
    195                 200                 205

Thr Tyr Thr Cys Asn Val Asp His Lys Pro Ser Asn Thr Lys Val Asp
210                 215                 220

Lys Thr Val Glu Arg Lys Cys Cys Val Glu Cys Pro Pro Cys Pro Ala
225                 230                 235                 240

Pro Pro Val Ala Gly Pro Ser Val Phe Leu Phe Pro Pro Lys Pro Lys
            245                 250                 255

Asp Thr Leu Met Ile Ser Arg Thr Pro Glu Val Thr Cys Val Val Val
        260                 265                 270

Asp Val Ser His Glu Asp Pro Glu Val Gln Phe Asn Trp Tyr Val Asp
    275                 280                 285

Gly Val Glu Val His Asn Ala Lys Thr Lys Pro Arg Glu Glu Gln Phe
290                 295                 300

Asn Ser Thr Phe Arg Val Val Ser Val Leu Thr Val His Gln Asp
305                 310                 315                 320
```

```
Trp Leu Asn Gly Lys Glu Tyr Lys Cys Lys Val Ser Asn Lys Gly Leu
            325                 330                 335

Pro Ala Pro Ile Glu Lys Thr Ile Ser Lys Thr Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Met Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
            450                 455

<210> SEQ ID NO 9
<211> LENGTH: 452
<212> TYPE: PRT
<213> ORGANISM: Homo Sapiens

<400> SEQUENCE: 9

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
             35                  40                  45

Gly Arg Ile Lys Ser Lys Thr Asp Gly Gly Thr Thr Asp Tyr Ala Ala
             50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
             85                  90                  95

Tyr Cys Thr Thr Glu Tyr Gly Ser Gly Gly Val Trp Tyr Tyr Gly
            100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Cys Ser Arg Ser Thr
            130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
            195                 200                 205

Cys Asn Val Asp His Lys Pro Ser Asn Thr Lys Val Asp Lys Thr Val
            210                 215                 220

Glu Arg Lys Cys Cys Val Glu Cys Pro Pro Cys Pro Ala Pro Pro Val
225                 230                 235                 240
```

```
Ala Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 10
<211> LENGTH: 455
<212> TYPE: PRT
<213> ORGANISM: Homo Sapiens

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Trp Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Leu Arg Ile Thr Gly Thr Thr Tyr Tyr Tyr Tyr
            100                 105                 110

Tyr Tyr Gly Met Asp Val Trp Gly Gln Gly Thr Thr Val Thr Val Ser
        115                 120                 125

Ser Ala Ser Thr Lys Gly Pro Ser Val Phe Pro Leu Ala Pro Cys Ser
    130                 135                 140

Arg Ser Thr Ser Glu Ser Thr Ala Ala Leu Gly Cys Leu Val Lys Asp
145                 150                 155                 160
```

-continued

```
Tyr Phe Pro Glu Pro Val Thr Val Ser Trp Asn Ser Gly Ala Leu Thr
            165                 170                 175

Ser Gly Val His Thr Phe Pro Ala Val Leu Gln Ser Ser Gly Leu Tyr
        180                 185                 190

Ser Leu Ser Ser Val Val Thr Val Pro Ser Ser Asn Phe Gly Thr Gln
            195                 200                 205

Thr Tyr Thr Cys Asn Val Asp His Lys Pro Ser Asn Thr Lys Val Asp
210                 215                 220

Lys Thr Val Glu Arg Lys Cys Cys Val Glu Cys Pro Pro Cys Pro Ala
225                 230                 235                 240

Pro Pro Val Ala Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Gln Phe Asn Trp Tyr Val Asp
            275                 280                 285

Gly Val Glu Val His Asn Ala Lys Thr Lys Pro Arg Glu Glu Gln Phe
        290                 295                 300

Asn Ser Thr Phe Arg Val Val Ser Val Leu Thr Val Val His Gln Asp
305                 310                 315                 320

Trp Leu Asn Gly Lys Glu Tyr Lys Cys Lys Val Ser Asn Lys Gly Leu
                325                 330                 335

Pro Ala Pro Ile Glu Lys Thr Ile Ser Lys Thr Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Met Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 11
<211> LENGTH: 446
<212> TYPE: PRT
<213> ORGANISM: Homo Sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
             85                  90                  95

Ala Arg Glu Ser Trp Phe Gly Glu Val Phe Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 12
<211> LENGTH: 452
<212> TYPE: PRT
<213> ORGANISM: Homo Sapiens

<400> SEQUENCE: 12

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                    85                  90                  95

Tyr Cys Thr Thr Glu Tyr Tyr Gly Ser Gly Val Tyr Tyr Gly
                100                 105                 110

Met Asp Val Trp Gly Gln Gly Thr Thr Val Thr Val Ser Ser Ala Ser
                115                 120                 125

Thr Lys Gly Pro Ser Val Phe Pro Leu Ala Pro Cys Ser Arg Ser Thr
        130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Asn Phe Gly Thr Gln Thr Tyr Thr
            195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445
```

-continued

```
Ser Pro Gly Lys
    450

<210> SEQ ID NO 13
<211> LENGTH: 454
<212> TYPE: PRT
<213> ORGANISM: Homo Sapiens

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gly Ala Thr Val Val Thr Pro Gly Tyr Tyr Tyr
            100                 105                 110

Tyr Gly Thr Asp Val Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Asn Phe Gly Thr Gln Thr
        195                 200                 205

Tyr Thr Cys Asn Val Asp His Lys Pro Ser Asn Thr Lys Val Asp Lys
    210                 215                 220

Thr Val Glu Arg Lys Cys Cys Val Glu Cys Pro Pro Cys Pro Ala Pro
225                 230                 235                 240

Pro Val Ala Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Phe Arg Val Val Ser Val Leu Thr Val Val His Gln Asp Trp
305                 310                 315                 320

Leu Asn Gly Lys Glu Tyr Lys Cys Lys Val Ser Asn Lys Gly Leu Pro
                325                 330                 335

Ala Pro Ile Glu Lys Thr Ile Ser Lys Thr Lys Gly Gln Pro Arg Glu
            340                 345                 350

Pro Gln Val Tyr Thr Leu Pro Pro Ser Arg Glu Glu Met Thr Lys Asn
        355                 360                 365
```

```
Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Met Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 14
<211> LENGTH: 446
<212> TYPE: PRT
<213> ORGANISM: Homo Sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ser Trp Phe Gly Glu Val Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285
```

-continued

```
Lys Pro Arg Glu Glu Gln Phe Asn Ser Thr Phe Arg Val Val Ser Val
    290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 15
<211> LENGTH: 446
<212> TYPE: PRT
<213> ORGANISM: Homo Sapiens

<400> SEQUENCE: 15

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Phe Tyr Tyr Cys
                85                  90                  95
Ala Arg Asp Ser Asn Trp Tyr His Asn Trp Phe Asp Pro Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Asn Phe Gly Thr Gln Thr Tyr Thr Cys Asn Val Asp His Lys
        195                 200                 205
Pro Ser Asn Thr Lys Val Asp Lys Thr Val Glu Arg Lys Cys Cys Val
    210                 215                 220
```

```
Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 16
<211> LENGTH: 446
<212> TYPE: PRT
<213> ORGANISM: Homo Sapiens

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Phe Tyr Tyr Cys
                85                  90                  95

Ala Arg Asp Ser Asn Trp Tyr His Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Asn Phe Gly Thr Gln Thr Tyr Thr Cys Asn Val Asp His Lys
        195                 200                 205
Pro Ser Asn Thr Lys Val Asp Lys Thr Val Glu Arg Lys Cys Cys Val
    210                 215                 220
Glu Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Phe Arg Val Val Ser Val
    290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 17
<211> LENGTH: 454
<212> TYPE: PRT
<213> ORGANISM: Homo Sapiens

<400> SEQUENCE: 17

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Ala
            20                  25                  30
Trp Met Ser Trp Val Arg Gln Ala Pro Gly Lys Gly Leu Glu Trp Val
        35                  40                  45
Gly Arg Ile Lys Ser Lys Thr Asp Gly Gly Thr Thr Asp Tyr Ala Ala
    50                  55                  60
Pro Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
```

Tyr Cys Thr Thr Asp Gly Ala Thr Val Val Thr Pro Gly Tyr Tyr Tyr
            100                 105                 110

Tyr Gly Thr Asp Val Trp Gly Gln Gly Thr Thr Val Thr Val Ser Ser
            115                 120                 125

Ala Ser Thr Lys Gly Pro Ser Val Phe Pro Leu Ala Pro Cys Ser Arg
130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Asn Phe Gly Thr Gln Thr
            195                 200                 205

Tyr Thr Cys Asn Val Asp His Lys Pro Ser Asn Thr Lys Val Asp Lys
        210                 215                 220

Thr Val Glu Arg Lys Cys Cys Val Glu Cys Pro Pro Cys Pro Ala Pro
225                 230                 235                 240

Pro Val Ala Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Phe Arg Val Val Ser Val Leu Thr Val Val His Gln Asp Trp
305                 310                 315                 320

Leu Asn Gly Lys Glu Tyr Lys Cys Lys Val Ser Asn Lys Gly Leu Pro
                325                 330                 335

Ala Pro Ile Glu Lys Thr Ile Ser Lys Thr Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Met Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 18
<211> LENGTH: 453
<212> TYPE: PRT
<213> ORGANISM: Homo Sapiens

<400> SEQUENCE: 18

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Ala Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Glu Gly Pro Tyr Ser Asp Tyr Gly Tyr Tyr Tyr Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Asn Phe Gly Thr Gln Thr Tyr
            195                 200                 205

Thr Cys Asn Val Asp His Lys Pro Ser Asn Thr Lys Val Asp Lys Thr
210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
            325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
```

```
                435                 440                 445
Leu Ser Pro Gly Lys
    450

<210> SEQ ID NO 19
<211> LENGTH: 446
<212> TYPE: PRT
<213> ORGANISM: Homo Sapiens

<400> SEQUENCE: 19

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ser Trp Phe Gly Glu Val Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
```

```
            355                 360                 365
Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 20
<211> LENGTH: 443
<212> TYPE: PRT
<213> ORGANISM: Homo Sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Gly Thr Ala Gly Asp Thr Tyr Tyr Pro Gly Ser Val Lys
    50                  55                  60

Gly Arg Phe Asn Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Ser Trp Tyr Gly Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
```

```
                290                 295                 300
Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 21
<211> LENGTH: 445
<212> TYPE: PRT
<213> ORGANISM: Homo Sapiens

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala His Ser Ser Gly Asn Tyr Tyr Asp Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
```

```
                225                 230                 235                 240
Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 22
<211> LENGTH: 453
<212> TYPE: PRT
<213> ORGANISM: Homo Sapiens

<400> SEQUENCE: 22

Glu Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Thr Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Asn Glu Asp Thr Ala Val Tyr
                85                  90                  95

Tyr Cys Thr Thr Glu Gly Pro Tyr Ser Asn Tyr Gly Tyr Tyr Tyr Tyr
            100                 105                 110

Gly Val Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
```

```
                    165                 170                 175
Val His Thr Phe Pro Ala Val Leu Gln Ser Ser Gly Leu Tyr Ser Leu
                180                 185                 190

Ser Ser Val Val Thr Val Pro Ser Ser Asn Phe Gly Thr Gln Thr Tyr
            195                 200                 205

Thr Cys Asn Val Asp His Lys Pro Ser Asn Thr Lys Val Asp Lys Thr
        210                 215                 220

Val Glu Arg Lys Cys Cys Val Glu Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Phe Arg Val Val Ser Val Leu Thr Val Val His Gln Asp Trp Leu
305                 310                 315                 320

Asn Gly Lys Glu Tyr Lys Cys Lys Val Ser Asn Lys Gly Leu Pro Ala
                325                 330                 335

Pro Ile Glu Lys Thr Ile Ser Lys Thr Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 23
<211> LENGTH: 456
<212> TYPE: PRT
<213> ORGANISM: Homo Sapiens

<400> SEQUENCE: 23

Glu Val Gln Leu Val Glu Ser Gly Gly Gly Leu Val Lys Pro Gly Gly
1               5                   10                  15

Ser Leu Thr Leu Ser Cys Ala Ala Ser Gly Phe Thr Phe Asn Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
```

```
                85                  90                  95
Tyr Cys Thr Thr Glu Tyr Tyr His Ile Leu Thr Gly Ser Phe Tyr Tyr
                   100                 105                 110
Ser Tyr Tyr Gly Met Asp Val Trp Gly Gln Gly Thr Thr Val Thr Val
               115                 120                 125
Ser Ser Ala Ser Thr Lys Gly Pro Ser Val Phe Pro Leu Ala Pro Cys
   130                 135                 140
Ser Arg Ser Thr Ser Glu Ser Thr Ala Ala Leu Gly Cys Leu Val Lys
145                 150                 155                 160
Asp Tyr Phe Pro Glu Pro Val Thr Val Ser Trp Asn Ser Gly Ala Leu
                   165                 170                 175
Thr Ser Gly Val His Thr Phe Pro Ala Val Leu Gln Ser Ser Gly Leu
               180                 185                 190
Tyr Ser Leu Ser Ser Val Val Thr Val Pro Ser Ser Asn Phe Gly Thr
           195                 200                 205
Gln Thr Tyr Thr Cys Asn Val Asp His Lys Pro Ser Asn Thr Lys Val
       210                 215                 220
Asp Lys Thr Val Glu Arg Lys Cys Cys Val Glu Cys Pro Pro Cys Pro
225                 230                 235                 240
Ala Pro Pro Val Ala Gly Pro Ser Val Phe Leu Phe Pro Pro Lys Pro
                   245                 250                 255
Lys Asp Thr Leu Met Ile Ser Arg Thr Pro Glu Val Thr Cys Val Val
               260                 265                 270
Val Asp Val Ser His Glu Asp Pro Glu Val Gln Phe Asn Trp Tyr Val
           275                 280                 285
Asp Gly Val Glu Val His Asn Ala Lys Thr Lys Pro Arg Glu Glu Gln
       290                 295                 300
Phe Asn Ser Thr Phe Arg Val Val Ser Val Leu Thr Val Val His Gln
305                 310                 315                 320
Asp Trp Leu Asn Gly Lys Glu Tyr Lys Cys Lys Val Ser Asn Lys Gly
                   325                 330                 335
Leu Pro Ala Pro Ile Glu Lys Thr Ile Ser Lys Thr Lys Gly Gln Pro
               340                 345                 350
Arg Glu Pro Gln Val Tyr Thr Leu Pro Pro Ser Arg Glu Glu Met Thr
           355                 360                 365
Lys Asn Gln Val Ser Leu Thr Cys Leu Val Lys Gly Phe Tyr Pro Ser
       370                 375                 380
Asp Ile Ala Val Glu Trp Glu Ser Asn Gly Gln Pro Glu Asn Asn Tyr
385                 390                 395                 400
Lys Thr Thr Pro Pro Met Leu Asp Ser Asp Gly Ser Phe Phe Leu Tyr
                   405                 410                 415
Ser Lys Leu Thr Val Asp Lys Ser Arg Trp Gln Gln Gly Asn Val Phe
               420                 425                 430
Ser Cys Ser Val Met His Glu Ala Leu His Asn His Tyr Thr Gln Lys
           435                 440                 445
Ser Leu Ser Leu Ser Pro Gly Lys
   450                 455

<210> SEQ ID NO 24
<211> LENGTH: 445
<212> TYPE: PRT
<213> ORGANISM: Homo Sapiens

<400> SEQUENCE: 24

Gln Val Gln Leu Val Glu Ser Gly Gly Gly Val Val Gln Pro Gly Arg
```

```
              1               5                  10                 15
Ser Leu Arg Leu Ser Cys Ala Ala Ser Gly Phe Thr Phe Ser Ser Tyr
                20                  25                 30

Gly Met His Trp Val Arg Gln Ala Pro Gly Lys Gly Leu Glu Trp Val
                35                  40                 45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                      70                  75                      80

Leu Gln Met Asn Ser Leu Arg Ala Glu Asp Thr Ala Val Tyr Tyr Cys
                85                  90                  95

Ala Ser Ser Ser Asn Phe Tyr Asp Met Asp Val Trp Gly Gln Gly
                100                 105                110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430
```

His Tyr Thr Gln Lys Ser Leu Ser Leu Ser Pro Gly Lys
            435                 440                 445

<210> SEQ ID NO 25
<211> LENGTH: 443
<212> TYPE: PRT
<213> ORGANISM: Homo Sapiens

<400> SEQUENCE: 25

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Asn Tyr
             20                  25                  30

Tyr Trp Ser Trp Ile Arg Gln Ser Ala Gly Lys Gly Leu Glu Trp Ile
         35                  40                  45

Gly Arg Ile Tyr Thr Ser Gly Ser Thr His Tyr Asn Pro Ser Leu Lys
     50                  55                  60

Ser Arg Ile Ile Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Arg Val Phe Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

```
Tyr Pro Ser Asp Ile Ala Val Glu Trp Glu Ser Asn Gly Gln Pro Glu
        370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 26
<211> LENGTH: 447
<212> TYPE: PRT
<213> ORGANISM: Homo Sapiens

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Tyr Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Tyr Ser Asp Tyr Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300
```

```
Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 27
<211> LENGTH: 455
<212> TYPE: PRT
<213> ORGANISM: Homo Sapiens

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Val Tyr
65                  70                  75                  80

Met Glu Leu Ser Ser Leu Arg Ser Glu Asp Thr Ala Val Tyr Tyr Cys
                85                  90                  95

Ala Thr Gly Val Met Ile Thr Phe Gly Gly Val Ile Val Gly His Ser
            100                 105                 110

Tyr Tyr Gly Met Asp Val Trp Gly Gln Gly Thr Thr Val Thr Val Ser
        115                 120                 125

Ser Ala Ser Thr Lys Gly Pro Ser Val Phe Pro Leu Ala Pro Cys Ser
130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Asn Phe Gly Thr Gln
        195                 200                 205

Thr Tyr Thr Cys Asn Val Asp His Lys Pro Ser Asn Thr Lys Val Asp
    210                 215                 220

Lys Thr Val Glu Arg Lys Cys Cys Val Glu Cys Pro Pro Cys Pro Ala
225                 230                 235                 240
```

-continued

Pro Pro Val Ala Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Phe Arg Val Val Ser Val Leu Thr Val His Gln Asp
305                 310                 315                 320

Trp Leu Asn Gly Lys Glu Tyr Lys Cys Lys Val Ser Asn Lys Gly Leu
                325                 330                 335

Pro Ala Pro Ile Glu Lys Thr Ile Ser Lys Thr Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Met Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 28
<211> LENGTH: 455
<212> TYPE: PRT
<213> ORGANISM: Homo Sapiens

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Val Met Ile Thr Phe Gly Gly Val Ile Gly His Ser
            100                 105                 110

Tyr Tyr Gly Met Asp Val Trp Gly Gln Gly Thr Thr Val Thr Val Ser
        115                 120                 125

Ser Ala Ser Thr Lys Gly Pro Ser Val Phe Pro Leu Ala Pro Cys Ser
    130                 135                 140

Arg Ser Thr Ser Glu Ser Thr Ala Ala Leu Gly Cys Leu Val Lys Asp
145                 150                 155                 160

```
Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Asn Phe Gly Thr Gln
        195                 200                 205

Thr Tyr Thr Cys Asn Val Asp His Lys Pro Ser Asn Thr Lys Val Asp
    210                 215                 220

Lys Thr Val Glu Arg Lys Cys Cys Val Glu Cys Pro Pro Cys Pro Ala
225                 230                 235                 240

Pro Pro Val Ala Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Phe Arg Val Val Ser Val Leu Thr Val Val His Gln Asp
305                 310                 315                 320

Trp Leu Asn Gly Lys Glu Tyr Lys Cys Lys Val Ser Asn Lys Gly Leu
                325                 330                 335

Pro Ala Pro Ile Glu Lys Thr Ile Ser Lys Thr Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Met Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 29
<211> LENGTH: 450
<212> TYPE: PRT
<213> ORGANISM: Homo Sapiens

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80
```

```
Met Glu Leu Ser Ser Leu Arg Ser Glu Asp Thr Ala Val Tyr Tyr Cys
            85                  90                  95

Ala Thr Arg Ala Gly Thr Thr Leu Ala Tyr Tyr Tyr Ala Met Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
            195                 200                 205

Val Asp His Lys Pro Ser Asn Thr Lys Val Asp Lys Thr Val Glu Arg
            210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
            325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
   450

<210> SEQ ID NO 30
<211> LENGTH: 442
<212> TYPE: PRT
<213> ORGANISM: Homo Sapiens

<400> SEQUENCE: 30
```

```
Gln Val Gln Leu Gln Glu Ser Gly Pro Gly Leu Val Lys Pro Ser Glu
  1               5                  10                  15
Thr Leu Ser Leu Thr Cys Thr Val Ser Gly Gly Ser Ile Ser Ser Tyr
             20                  25                  30
Tyr Trp Ser Trp Ile Arg Gln Pro Pro Gly Lys Gly Leu Glu Trp Ile
         35                  40                  45
Gly Tyr Ile Tyr Tyr Ser Gly Asn Thr Asn Tyr Asn Pro Ser Leu Lys
     50                  55                  60
Ser Arg Phe Thr Leu Ser Ile Asp Thr Ser Lys Asn Gln Phe Ser Leu
 65                  70                  75                  80
Arg Leu Ser Ser Val Thr Ala Ala Asp Thr Ala Val Tyr Tyr Cys Ala
                 85                  90                  95
Cys Ile Ala Thr Arg Pro Phe Asp Tyr Trp Gly Gln Gly Thr Leu Val
             100                 105                 110
Thr Val Ser Ser Ala Ser Thr Lys Gly Pro Ser Val Phe Pro Leu Ala
         115                 120                 125
Pro Cys Ser Arg Ser Thr Ser Glu Ser Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Asn Phe
            180                 185                 190
Gly Thr Gln Thr Tyr Thr Cys Asn Val Asp His Lys Pro Ser Asn Thr
        195                 200                 205
Lys Val Asp Lys Thr Val Glu Arg Lys Cys Cys Val Glu Cys Pro Pro
210                 215                 220
Cys Pro Ala Pro Pro Val Ala Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Gln Phe Asn Trp
            260                 265                 270
Tyr Val Asp Gly Val Glu Val His Asn Ala Lys Thr Lys Pro Arg Glu
        275                 280                 285
Glu Gln Phe Asn Ser Thr Phe Arg Val Val Ser Val Leu Thr Val Val
290                 295                 300
His Gln Asp Trp Leu Asn Gly Lys Glu Tyr Lys Cys Lys Val Ser Asn
305                 310                 315                 320
Lys Gly Leu Pro Ala Pro Ile Glu Lys Thr Ile Ser Lys Thr Lys Gly
                325                 330                 335
Gln Pro Arg Glu Pro Gln Val Tyr Thr Leu Pro Pro Ser Arg Glu Glu
            340                 345                 350
Met Thr Lys Asn Gln Val Ser Leu Thr Cys Leu Val Lys Gly Phe Tyr
        355                 360                 365
Pro Ser Asp Ile Ala Val Glu Trp Glu Ser Asn Gly Gln Pro Glu Asn
    370                 375                 380
Asn Tyr Lys Thr Thr Pro Pro Met Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
            420                 425                 430
```

```
Gln Lys Ser Leu Ser Leu Ser Pro Gly Lys
        435                 440
```

<210> SEQ ID NO 31
<211> LENGTH: 445
<212> TYPE: PRT
<213> ORGANISM: Homo Sapiens

<400> SEQUENCE: 31

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ile Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asp Ser Ser Gly Asp Tyr Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365
```

```
Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 32
<211> LENGTH: 445
<212> TYPE: PRT
<213> ORGANISM: Homo Sapiens

<400> SEQUENCE: 32

Gln Val Gln Leu Val Gln Ser Gly Ala Glu Val Lys Lys Pro Gly Ala
  1               5                  10                  15

Ser Val Lys Val Ser Cys Lys Val Ser Gly Tyr Thr Leu Thr Glu Leu
                 20                  25                  30

Ser Met His Trp Val Arg Gln Ala Pro Gly Lys Gly Leu Glu Trp Met
             35                  40                  45

Gly Gly Phe Asp Pro Glu Asp Gly Glu Thr Ile Tyr Ala Gln Lys Phe
     50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                 85                  90                  95

Ala Thr Ala Gly Leu Glu Ile Arg Trp Phe Asp Pro Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300
```

```
Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 33
<211> LENGTH: 446
<212> TYPE: PRT
<213> ORGANISM: Homo Sapiens

<400> SEQUENCE: 33

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Ser Tyr Ser Gly Asp Thr Tyr Tyr Asn Pro Ser
    50                  55                  60

Leu Lys Ser Arg Leu Thr Ile Ser Val Asp Thr Ser Lys His Gln Phe
65                  70                  75                  80

Ser Leu Arg Leu Ser Ser Val Thr Ser Ala Asp Thr Ala Val Tyr Tyr
                85                  90                  95

Cys Ala Ser Leu Asp Leu Tyr Gly Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 34
<211> LENGTH: 451
<212> TYPE: PRT
<213> ORGANISM: Homo Sapiens

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Pro Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gln Gly Leu Leu Gly Phe Gly Glu Leu Glu Gly Leu Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

```
Thr Phe Pro Ala Val Leu Gln Ser Ser Gly Leu Tyr Ser Leu Ser Ser
                180                 185                 190

Val Val Thr Val Pro Ser Ser Asn Phe Gly Thr Gln Thr Tyr Thr Cys
            195                 200                 205

Asn Val Asp His Lys Pro Ser Asn Thr Lys Val Asp Lys Thr Val Glu
        210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 35
<211> LENGTH: 456
<212> TYPE: PRT
<213> ORGANISM: Homo Sapiens

<400> SEQUENCE: 35

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Thr Lys Thr Asp Gly Gly Thr Thr Asp Tyr Ala Ala
    50                  55                  60

Pro Val Lys Gly Arg Phe Thr Ile Ser Arg Asp Asp Ser Gln Asn Thr
65                  70                  75                  80

Leu Tyr Leu Gln Met Asn Ser Leu Lys Thr Glu Asp Thr Ala Val Tyr
                85                  90                  95
```

Tyr Cys Thr Thr Glu Tyr Tyr Gly Ile Val Thr Gly Ser Phe Tyr Tyr
            100                 105                 110

Tyr Tyr Tyr Gly Met Asp Val Trp Gly Gln Gly Thr Thr Val Thr Val
        115                 120                 125

Ser Ser Ala Ser Thr Lys Gly Pro Ser Val Phe Pro Leu Ala Pro Cys
130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Asn Phe Gly Thr
        195                 200                 205

Gln Thr Tyr Thr Cys Asn Val Asp His Lys Pro Ser Asn Thr Lys Val
    210                 215                 220

Asp Lys Thr Val Glu Arg Lys Cys Cys Val Glu Cys Pro Pro Cys Pro
225                 230                 235                 240

Ala Pro Pro Val Ala Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Gln Phe Asn Trp Tyr Val
        275                 280                 285

Asp Gly Val Glu Val His Asn Ala Lys Thr Lys Pro Arg Glu Glu Gln
    290                 295                 300

Phe Asn Ser Thr Phe Arg Val Val Ser Val Leu Thr Val Val His Gln
305                 310                 315                 320

Asp Trp Leu Asn Gly Lys Glu Tyr Lys Cys Lys Val Ser Asn Lys Gly
                325                 330                 335

Leu Pro Ala Pro Ile Glu Lys Thr Ile Ser Lys Thr Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Met Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 36
<211> LENGTH: 214
<212> TYPE: PRT
<213> ORGANISM: Homo Sapiens

<400> SEQUENCE: 36

Asp Ile Gln Met Thr Gln Ser Pro Ser Ser Leu Ser Ala Ser Val Gly
1               5                   10                  15

```
Asp Arg Val Thr Ile Thr Cys Gln Ala Ser Gln Asn Ile Ser Asn Phe
            20                  25                  30

Leu Asp Trp Tyr Gln Gln Lys Pro Gly Lys Ala Pro Asn Leu Leu Ile
        35                  40                  45

Tyr Asp Ala Ser Asp Leu Asp Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Val Ser Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
210

<210> SEQ ID NO 37
<211> LENGTH: 214
<212> TYPE: PRT
<213> ORGANISM: Homo Sapiens

<400> SEQUENCE: 37

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Phe
            20                  25                  30

Leu Asp Trp Tyr Gln Gln Lys Pro Gly Lys Ala Pro Lys Leu Leu Ile
        35                  40                  45

Tyr Asp Ala Ser Asp Leu Asp Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Val Ser Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 38
<211> LENGTH: 219
<212> TYPE: PRT
<213> ORGANISM: Homo Sapiens

<400> SEQUENCE: 38

Asp Asn Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 39
<211> LENGTH: 214
<212> TYPE: PRT
<213> ORGANISM: Homo Sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Ile Gly Val Pro Ser Arg Phe Ser Gly
    50                  55                  60
```

```
Ser Gly Ser Gly Thr Asp Phe Ile Phe Thr Ile Ser Ser Leu Gln Pro
 65                  70                  75                  80

Glu Asp Ile Ala Thr Tyr Tyr Cys Gln Gln Tyr Asp Asn Phe Pro Phe
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 40
<211> LENGTH: 213
<212> TYPE: PRT
<213> ORGANISM: Homo Sapiens

<400> SEQUENCE: 40

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Asn Asn Tyr
                 20                  25                  30

Leu Asn Trp Tyr Gln Gln Lys Pro Gly Lys Ala Pro Lys Leu Leu Ile
             35                  40                  45

Tyr Asp Thr Ser Asn Leu Glu Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Leu Thr
                 85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210
```

<210> SEQ ID NO 41
<211> LENGTH: 213
<212> TYPE: PRT
<213> ORGANISM: Homo Sapiens

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln His Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 42
<211> LENGTH: 213
<212> TYPE: PRT
<213> ORGANISM: Homo Sapiens

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Phe Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Ile Thr
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr

```
            115                 120                 125
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 43
<211> LENGTH: 220
<212> TYPE: PRT
<213> ORGANISM: Homo Sapiens

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asp Ser
            20                  25                  30

Ser Asp Asn Lys Asn Tyr Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Ser Leu Thr
65                  70                  75                  80

Ile Ser Ser Leu Gln Ala Glu Asp Val Ala Val Tyr Tyr Cys Gln Gln
                85                  90                  95

Tyr Tyr Ser Asp Pro Phe Thr Phe Gly Pro Gly Thr Lys Val Asp Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 44
<211> LENGTH: 220
<212> TYPE: PRT
<213> ORGANISM: Homo Sapiens

<400> SEQUENCE: 44

Asp Ile Val Met Thr Gln Ser Pro Asp Ser Leu Ala Val Ser Leu Gly
1               5                   10                  15
```

Glu Arg Ala Thr Ile Asn Cys Lys Ser Ser Gln Ser Val Leu Asp Ser
            20                  25                  30

Ser Asp Asn Lys Asn Tyr Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Asp Pro Phe Thr Phe Gly Pro Gly Thr Lys Val Asp Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 45
<211> LENGTH: 213
<212> TYPE: PRT
<213> ORGANISM: Homo Sapiens

<400> SEQUENCE: 45

Asp Ile Gln Met Thr Gln Ser Pro Ser Ser Leu Ser Ala Ser Val Gly
 1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

```
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
            195                 200                 205
Asn Arg Gly Glu Cys
    210

<210> SEQ ID NO 46
<211> LENGTH: 220
<212> TYPE: PRT
<213> ORGANISM: Homo Sapiens

<400> SEQUENCE: 46

Asp Ile Val Met Thr Gln Ser Pro Asp Ser Leu Ala Val Ser Leu Gly
  1               5                  10                  15
Glu Arg Ala Thr Ile Asp Cys Lys Ser Ser Gln Gly Val Leu Asp Ser
             20                  25                  30
Ser Asn Asn Lys Asn Phe Leu Ala Trp Tyr Gln Gln Lys Pro Gly Gln
         35                  40                  45
Pro Pro Lys Leu Leu Ile Tyr Trp Ala Ser Asn Arg Glu Ser Gly Val
 50                  55                  60
Pro Val Arg Phe Ser Gly Ser Gly Ser Gly Thr Asp Phe Thr Leu Thr
65                  70                  75                  80
Ile Ser Ser Leu Gln Ala Glu Asp Val Ala Leu Tyr Tyr Cys Gln Gln
                 85                  90                  95
Tyr Tyr Ser Asp Pro Phe Thr Phe Gly Pro Gly Thr Lys Val Asp Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220

<210> SEQ ID NO 47
<211> LENGTH: 214
<212> TYPE: PRT
<213> ORGANISM: Homo Sapiens

<400> SEQUENCE: 47

Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Ser Ile Ser Asp Tyr
             20                  25                  30
Leu Asn Trp Tyr Gln Gln Lys Pro Gly Lys Ala Pro Asn Leu Leu Ile
         35                  40                  45
Tyr Ala Ala Ser Ser Leu Gln Ser Gly Val Pro Ser Arg Phe Ser Gly
 50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Thr Tyr Ser Asp Pro Phe
                 85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 48
<211> LENGTH: 213
<212> TYPE: PRT
<213> ORGANISM: Homo Sapiens

<400> SEQUENCE: 48

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Leu Thr
                 85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210
```

```
<210> SEQ ID NO 49
<211> LENGTH: 213
<212> TYPE: PRT
<213> ORGANISM: Homo Sapiens

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 50
<211> LENGTH: 220
<212> TYPE: PRT
<213> ORGANISM: Homo Sapiens

<400> SEQUENCE: 50

Asp Ile Val Met Thr Gln Ser Pro Asp Ser Leu Ala Val Ser Leu Gly
1               5                   10                  15

Glu Arg Ala Thr Ile Asp Cys Lys Ser Ser Gln Ser Val Leu Asp Ser
            20                  25                  30

Ser Asn Asn Lys Asn Phe Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Asp Pro Phe Thr Phe Gly Pro Gly Thr Lys Val Asp Ile
            100                 105                 110

Lys Arg Thr Val Ala Ala Pro Ser Val Phe Ile Phe Pro Pro Ser Asp
```

```
                115              120              125
Glu Gln Leu Lys Ser Gly Thr Ala Ser Val Val Cys Leu Leu Asn Asn
130                     135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 51
<211> LENGTH: 218
<212> TYPE: PRT
<213> ORGANISM: Homo Sapiens

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
            20                  25                  30

Tyr Leu Ala Tyr Leu Ala Trp Tyr Gln Gln Lys Pro Gly Gln Ala Pro
        35                  40                  45

Arg Leu Leu Ile Tyr Gly Ala Ser Ser Thr Ala Thr Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Tyr Gly
                85                  90                  95

Ser Ser Pro Ile Thr Phe Gly Gln Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 52
<211> LENGTH: 214
<212> TYPE: PRT
<213> ORGANISM: Homo Sapiens

<400> SEQUENCE: 52

Asp Ile Gln Met Thr Gln Ser Pro Ser Ser Leu Ser Ala Ser Val Gly
1               5                   10                  15
```

Asp Arg Val Thr Ile Thr Cys Gln Ala Ser Gln Asp Ile Ser Asn Phe
            20                  25                  30

Leu Asn Trp Tyr Gln Gln Arg Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 53
<211> LENGTH: 213
<212> TYPE: PRT
<213> ORGANISM: Homo Sapiens

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Tyr Asp Asn Leu Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

```
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 54
<211> LENGTH: 214
<212> TYPE: PRT
<213> ORGANISM: Homo Sapiens

<400> SEQUENCE: 54

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Arg Tyr Asp Leu Pro Ile
                85                  90                  95
Thr Phe Gly Gln Gly Thr Arg Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 55
<211> LENGTH: 213
<212> TYPE: PRT
<213> ORGANISM: Homo Sapiens

<400> SEQUENCE: 55

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Ser Asn Tyr
            20                  25                  30
Leu Asn Trp Tyr Gln Gln Arg Pro Gly Lys Ala Pro Lys Leu Leu Ile
        35                  40                  45
Tyr Asp Ala Ser Asn Leu Glu Thr Gly Val Pro Ser Arg Phe Ser Gly
    50                  55                  60
```

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Leu Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 56
<211> LENGTH: 214
<212> TYPE: PRT
<213> ORGANISM: Homo Sapiens

<400> SEQUENCE: 56

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Phe Ser Asn Tyr
                 20                  25                  30

Leu Ala Trp Tyr Gln Gln Lys Pro Gly Lys Val Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 57
<211> LENGTH: 214
<212> TYPE: PRT
<213> ORGANISM: Homo Sapiens

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Tyr Gln Gln Lys Pro Gly Lys Val Pro Gln Leu Leu Ile
        35                  40                  45

Tyr Val Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Gly Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 214
<212> TYPE: PRT
<213> ORGANISM: Homo Sapiens

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Tyr Gln Gln Lys Pro Gly Lys Val Pro Lys Leu Leu Ile
        35                  40                  45

Tyr Val Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Gly Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly

```
                115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 59
<211> LENGTH: 214
<212> TYPE: PRT
<213> ORGANISM: Homo Sapiens

<400> SEQUENCE: 59

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Asn Leu Leu Ile
        35                  40                  45

His Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Ser Tyr Ile Thr Pro Pro
                85                  90                  95

Ser Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 60
<211> LENGTH: 214
<212> TYPE: PRT
<213> ORGANISM: Homo Sapiens

<400> SEQUENCE: 60

Asp Ile Gln Met Thr Gln Ser Pro Ser Ser Leu Ser Ala Ser Val Gly
  1               5                  10                  15
```

Asp Arg Val Thr Ile Thr Cys Arg Ala Ser Gln Gly Ile Arg Asn Asp
            20                  25                  30

Leu Asp Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Glu Asp Phe Ala Thr Tyr Tyr Cys Leu Gln Tyr Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 61
<211> LENGTH: 214
<212> TYPE: PRT
<213> ORGANISM: Homo Sapiens

<400> SEQUENCE: 61

Asp Ile Gln Met Ile Gln Ser Pro Ser Ser Leu Ser Ala Ser Val Gly
1               5                   10                  15

Asp Arg Val Thr Ile Thr Cys Gln Ala Ser His Asp Ile Ser Asn Tyr
            20                  25                  30

Leu Asn Trp Tyr Gln Gln Lys Pro Gly Lys Ala Pro Lys Phe Leu Ile
        35                  40                  45

Ser Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 62
<211> LENGTH: 219
<212> TYPE: PRT
<213> ORGANISM: Homo Sapiens

<400> SEQUENCE: 62

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Phe Leu Ile Tyr Leu Gly Ser Ile Arg Ala Ser Gly Val Pro
    50                  55                  60

Asp Arg Phe Ser Gly Ser Gly Ser Gly Thr Asp Phe Ala Leu Thr Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 63
<211> LENGTH: 214
<212> TYPE: PRT
<213> ORGANISM: Homo Sapiens

<400> SEQUENCE: 63

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Tyr Ile Gly Ser Ser
            20                  25                  30

Leu His Trp Tyr Gln Gln Thr Pro Asp Gln Ser Pro Lys Leu Leu Ile
        35                  40                  45

Asn Tyr Val Ser Gln Ser Phe Ser Gly Val Pro Ser Arg Phe Ser Gly
    50                  55                  60
```

```
Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 220
<212> TYPE: PRT
<213> ORGANISM: Homo Sapiens

<400> SEQUENCE: 64

Asp Ile Val Met Thr Gln Ser Pro Asp Ser Leu Ala Val Ser Leu Gly
  1               5                  10                  15

Ala Arg Ala Thr Ile Ser Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Thr Leu Gln Ala Glu Asp Val Ala Val Tyr Tyr Cys Gln Gln
                 85                  90                  95

Tyr Tyr Thr Thr Pro Pro Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 65
<211> LENGTH: 213
<212> TYPE: PRT
<213> ORGANISM: Homo Sapiens

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asp Leu Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 66
<211> LENGTH: 214
<212> TYPE: PRT
<213> ORGANISM: Homo Sapiens

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Ile Ile Ser Ser Leu Gln Pro
65                  70                  75                  80

Glu Asp Ile Ala Thr Tyr Tyr Cys Gln Gln Phe Asp Asn Leu Pro Pro
                85                  90                  95

Thr Phe Gly Gly Gly Thr Lys Val Glu Ser Lys Arg Thr Val Ala Ala
            100                 105                 110

Pro Ser Val Phe Ile Phe Pro Pro Ser Asp Glu Gln Leu Lys Ser Gly

-continued

```
                115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 213
<212> TYPE: PRT
<213> ORGANISM: Homo Sapiens

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln His Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 68
<211> LENGTH: 222
<212> TYPE: PRT
<213> ORGANISM: Homo Sapiens

<400> SEQUENCE: 68

Asp Val Val Met Thr Gln Ser Pro Leu Ser Leu Pro Val Thr Leu Gly
1               5                   10                  15
```

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Gly Leu Phe Thr Phe Gly Pro Gly Thr Lys Val
            100                 105                 110

Asp Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 69
<211> LENGTH: 219
<212> TYPE: PRT
<213> ORGANISM: Homo Sapiens

<400> SEQUENCE: 69

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Asn Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Ile Thr Phe Gly Gln Gly Thr Gly Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 70
<211> LENGTH: 125
<212> TYPE: PRT
<213> ORGANISM: Homo Sapiens

<400> SEQUENCE: 70

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ala Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Gly Tyr Ser Gly Tyr Asp Leu Gly Tyr Tyr Gly Met
            100                 105                 110

Asp Val Trp Gly Gln Gly Thr Thr Val Thr Val Ser Ser
            115                 120                 125

<210> SEQ ID NO 71
<211> LENGTH: 121
<212> TYPE: PRT
<213> ORGANISM: Homo Sapiens

<400> SEQUENCE: 71

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Val Ser Ser Gly
             20                  25                  30

Gly Tyr Tyr Trp Ser Trp Ile Arg Gln Pro Pro Gly Lys Gly Leu Glu
         35                  40                  45

Trp Ile Gly Tyr Ile Tyr Tyr Ser Gly Ser Thr Asn Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Ala Gly Ile Ala Ala Thr Gly Thr Leu Phe Asp Cys Trp Gly
            100                 105                 110

Gln Gly Thr Leu Val Thr Val Ser Ser
            115                 120

<210> SEQ ID NO 72
<211> LENGTH: 126
<212> TYPE: PRT
<213> ORGANISM: Homo Sapiens
```

```
<400> SEQUENCE: 72

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Ile His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
 50                      55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Arg Gly Gln Leu Trp Leu Trp Tyr Tyr Tyr Tyr Tyr Gly
                100                 105                 110

Met Asp Val Trp Gly Gln Gly Thr Thr Val Thr Val Ser Ser
            115                 120                 125

<210> SEQ ID NO 73
<211> LENGTH: 119
<212> TYPE: PRT
<213> ORGANISM: Homo Sapiens

<400> SEQUENCE: 73

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Ser Ser Trp Ser Tyr Tyr Gly Met Asp Val Trp Gly Gln Gly
                100                 105                 110

Thr Thr Val Thr Val Ser Ser
            115

<210> SEQ ID NO 74
<211> LENGTH: 129
<212> TYPE: PRT
<213> ORGANISM: Homo Sapiens

<400> SEQUENCE: 74

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Val Ser Asn Ala
                 20                  25                  30

Trp Met Ser Trp Val Arg Gln Ala Pro Gly Lys Gly Leu Glu Trp Val
             35                  40                  45

Gly Arg Ile Lys Ser Lys Thr Asp Gly Gly Thr Thr Asp Asn Ala Ala
 50                      55                  60

Pro Val Lys Gly Arg Phe Thr Ile Ser Arg Asp Asp Ser Lys Asn Thr
 65                  70                  75                  80
```

```
Leu Tyr Leu Gln Met Asn Ser Leu Lys Thr Glu Asp Thr Ala Val Tyr
            85                  90                  95

Tyr Cys Thr Thr Gly Gly Ser Leu Leu Trp Thr Gly Pro Asn Tyr Tyr
            100                 105                 110

Tyr Tyr Gly Met Asp Val Trp Gly Gln Gly Thr Thr Val Thr Val Ser
            115                 120                 125

Ser
```

<210> SEQ ID NO 75
<211> LENGTH: 126
<212> TYPE: PRT
<213> ORGANISM: Homo Sapiens

<400> SEQUENCE: 75

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Thr Thr Glu Tyr Tyr Gly Ser Gly Gly Val Trp Tyr Tyr Gly
            100                 105                 110

Met Asp Val Trp Gly Gln Gly Thr Thr Val Thr Val Ser Ser
            115                 120                 125
```

<210> SEQ ID NO 76
<211> LENGTH: 129
<212> TYPE: PRT
<213> ORGANISM: Homo Sapiens

<400> SEQUENCE: 76

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Trp Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Thr Thr Asp Leu Arg Ile Thr Gly Thr Thr Tyr Tyr Tyr Tyr
            100                 105                 110

Tyr Tyr Gly Met Asp Val Trp Gly Gln Gly Thr Thr Val Thr Val Ser
            115                 120                 125

Ser
```

<210> SEQ ID NO 77

```
<211> LENGTH: 120
<212> TYPE: PRT
<213> ORGANISM: Homo Sapiens

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ser Trp Phe Gly Glu Val Phe Phe Asp Tyr Trp Gly Gln
            100                 105                 110

Gly Thr Leu Val Thr Val Ser Ser
        115                 120

<210> SEQ ID NO 78
<211> LENGTH: 126
<212> TYPE: PRT
<213> ORGANISM: Homo Sapiens

<400> SEQUENCE: 78

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Glu Tyr Tyr Gly Ser Gly Gly Val Trp Tyr Tyr Gly
            100                 105                 110

Met Asp Val Trp Gly Gln Gly Thr Thr Val Thr Val Ser Ser
        115                 120                 125

<210> SEQ ID NO 79
<211> LENGTH: 128
<212> TYPE: PRT
<213> ORGANISM: Homo Sapiens

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
```

```
                50                  55                  60
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Asp Gly Ala Thr Val Val Thr Pro Gly Tyr Tyr Tyr
                100                 105                 110

Tyr Gly Thr Asp Val Trp Gly Gln Gly Thr Thr Val Thr Val Ser Ser
                115                 120                 125

<210> SEQ ID NO 80
<211> LENGTH: 120
<212> TYPE: PRT
<213> ORGANISM: Homo Sapiens

<400> SEQUENCE: 80

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
                 35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Ser Trp Phe Gly Glu Val Phe Phe Asp Tyr Trp Gly Gln
                100                 105                 110

Gly Thr Leu Val Thr Val Ser Ser
                115                 120

<210> SEQ ID NO 81
<211> LENGTH: 120
<212> TYPE: PRT
<213> ORGANISM: Homo Sapiens

<400> SEQUENCE: 81

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
                 35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Phe Tyr Tyr Cys
                 85                  90                  95

Ala Arg Asp Ser Asn Trp Tyr His Asn Trp Phe Asp Pro Trp Gly Gln
                100                 105                 110

Gly Thr Leu Val Thr Val Ser Ser
                115                 120

<210> SEQ ID NO 82
```

```
<211> LENGTH: 120
<212> TYPE: PRT
<213> ORGANISM: Homo Sapiens

<400> SEQUENCE: 82

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Phe Tyr Tyr Cys
                 85                  90                  95

Ala Arg Asp Ser Asn Trp Tyr His Asn Trp Phe Asp Pro Trp Gly Gln
            100                 105                 110

Gly Thr Leu Val Thr Val Ser Ser
            115                 120

<210> SEQ ID NO 83
<211> LENGTH: 128
<212> TYPE: PRT
<213> ORGANISM: Homo Sapiens

<400> SEQUENCE: 83

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
                 20                  25                  30

Trp Met Ser Trp Val Arg Gln Ala Pro Gly Lys Gly Leu Glu Trp Val
             35                  40                  45

Gly Arg Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Asp Gly Ala Thr Val Val Thr Pro Gly Tyr Tyr Tyr
            100                 105                 110

Tyr Gly Thr Asp Val Trp Gly Gln Gly Thr Thr Val Thr Val Ser Ser
            115                 120                 125

<210> SEQ ID NO 84
<211> LENGTH: 127
<212> TYPE: PRT
<213> ORGANISM: Homo Sapiens

<400> SEQUENCE: 84

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
                 20                  25                  30

Trp Met Ser Trp Val Arg Gln Ala Pro Gly Lys Gly Leu Glu Trp Val
             35                  40                  45

Gly Arg Ile Lys Ser Lys Thr Asp Gly Gly Thr Ala Asp Tyr Ala Ala
```

```
                        50                  55                  60
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                     85                  90                  95

Tyr Cys Thr Thr Glu Gly Pro Tyr Ser Asp Tyr Gly Tyr Tyr Tyr Tyr
                    100                 105                 110

Gly Met Asp Val Trp Gly Gln Gly Thr Thr Val Thr Val Ser Ser
                115                 120                 125

<210> SEQ ID NO 85
<211> LENGTH: 120
<212> TYPE: PRT
<213> ORGANISM: Homo Sapiens

<400> SEQUENCE: 85

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
         50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Ser Trp Phe Gly Glu Val Phe Phe Asp Tyr Trp Gly Gln
                100                 105                 110

Gly Thr Leu Val Thr Val Ser Ser
            115                 120

<210> SEQ ID NO 86
<211> LENGTH: 117
<212> TYPE: PRT
<213> ORGANISM: Homo Sapiens

<400> SEQUENCE: 86

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Asp Met His Trp Val Arg Gln Ala Thr Gly Lys Gly Leu Glu Trp Val
             35                  40                  45

Ser Gly Ile Gly Thr Ala Gly Asp Thr Tyr Tyr Pro Gly Ser Val Lys
         50                  55                  60

Gly Arg Phe Asn Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Glu Gly Ser Trp Tyr Gly Phe Asp Tyr Trp Gly Gln Gly Thr Leu
                100                 105                 110

Val Thr Val Ser Ser
            115

<210> SEQ ID NO 87
```

<211> LENGTH: 119
<212> TYPE: PRT
<213> ORGANISM: Homo Sapiens

<400> SEQUENCE: 87

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala His Ser Ser Gly Asn Tyr Tyr Asp Met Asp Val Trp Gly Gln Gly
            100                 105                 110

Thr Thr Val Thr Val Ser Ser
        115

<210> SEQ ID NO 88
<211> LENGTH: 127
<212> TYPE: PRT
<213> ORGANISM: Homo Sapiens

<400> SEQUENCE: 88

Glu Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Thr Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Asn Glu Asp Thr Ala Val Tyr
                85                  90                  95

Tyr Cys Thr Thr Glu Gly Pro Tyr Ser Asn Tyr Gly Tyr Tyr Tyr Tyr
            100                 105                 110

Gly Val Asp Val Trp Gly Gln Gly Thr Thr Val Thr Val Ser Ser
        115                 120                 125

<210> SEQ ID NO 89
<211> LENGTH: 130
<212> TYPE: PRT
<213> ORGANISM: Homo Sapiens

<400> SEQUENCE: 89

Glu Val Gln Leu Val Glu Ser Gly Gly Gly Leu Val Lys Pro Gly Gly
1               5                   10                  15

Ser Leu Thr Leu Ser Cys Ala Ala Ser Gly Phe Thr Phe Asn Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala

```
              50                  55                  60
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Glu Tyr Tyr His Ile Leu Thr Gly Ser Phe Tyr Tyr
                100                 105                 110

Ser Tyr Tyr Gly Met Asp Val Trp Gly Gln Gly Thr Thr Val Thr Val
                115                 120                 125

Ser Ser
    130

<210> SEQ ID NO 90
<211> LENGTH: 119
<212> TYPE: PRT
<213> ORGANISM: Homo Sapiens

<400> SEQUENCE: 90

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
                 35                  40                  45

Ala Val Ile Trp Tyr Asp Gly Ser Asn Lys Tyr Tyr Ala Asp Ser Val
                 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Ser Ser Ser Asn Phe Tyr Asp Met Asp Val Trp Gly Gln Gly
                100                 105                 110

Thr Thr Val Thr Val Ser Ser
                115

<210> SEQ ID NO 91
<211> LENGTH: 117
<212> TYPE: PRT
<213> ORGANISM: Homo Sapiens

<400> SEQUENCE: 91

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Asn Tyr
                 20                  25                  30

Tyr Trp Ser Trp Ile Arg Gln Ser Ala Gly Lys Gly Leu Glu Trp Ile
                 35                  40                  45

Gly Arg Ile Tyr Thr Ser Gly Ser Thr His Tyr Asn Pro Ser Leu Lys
                 50                  55                  60

Ser Arg Ile Ile Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Arg Val Phe Tyr Gly Met Asp Val Trp Gly Gln Gly Thr Thr
                100                 105                 110

Val Thr Val Ser Ser
                115
```

<210> SEQ ID NO 92
<211> LENGTH: 121
<212> TYPE: PRT
<213> ORGANISM: Homo Sapiens

<400> SEQUENCE: 92

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Tyr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Tyr Ser Asp Tyr Tyr Gly Met Asp Val Trp Gly
            100                 105                 110

Gln Gly Thr Thr Val Thr Val Ser Ser
        115                 120

<210> SEQ ID NO 93
<211> LENGTH: 129
<212> TYPE: PRT
<213> ORGANISM: Homo Sapiens

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Val Tyr
65                  70                  75                  80

Met Glu Leu Ser Ser Leu Arg Ser Glu Asp Thr Ala Val Tyr Tyr Cys
                85                  90                  95

Ala Thr Gly Val Met Ile Thr Phe Gly Gly Val Ile Val Gly His Ser
            100                 105                 110

Tyr Tyr Gly Met Asp Val Trp Gly Gln Gly Thr Thr Val Thr Val Ser
        115                 120                 125

Ser

<210> SEQ ID NO 94
<211> LENGTH: 129
<212> TYPE: PRT
<213> ORGANISM: Homo Sapiens

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
 50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Val Met Ile Thr Phe Gly Gly Val Ile Val Gly His Ser
            100                 105                 110

Tyr Tyr Gly Met Asp Val Trp Gly Gln Gly Thr Thr Val Thr Val Ser
            115                 120                 125

Ser

<210> SEQ ID NO 95
<211> LENGTH: 124
<212> TYPE: PRT
<213> ORGANISM: Homo Sapiens

<400> SEQUENCE: 95

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
 50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Arg Ala Gly Thr Thr Leu Ala Tyr Tyr Tyr Ala Met Asp
            100                 105                 110

Val Trp Gly Gln Gly Thr Thr Val Thr Val Ser Ser
            115                 120

<210> SEQ ID NO 96
<211> LENGTH: 116
<212> TYPE: PRT
<213> ORGANISM: Homo Sapiens

<400> SEQUENCE: 96

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Asn Thr Asn Tyr Asn Pro Ser Leu Lys
 50                  55                  60

Ser Arg Phe Thr Leu Ser Ile Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Cys Ile Ala Thr Arg Pro Phe Asp Tyr Trp Gly Gln Gly Thr Leu Val

```
                100                 105                 110

Thr Val Ser Ser
        115

<210> SEQ ID NO 97
<211> LENGTH: 119
<212> TYPE: PRT
<213> ORGANISM: Homo Sapiens

<400> SEQUENCE: 97

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ile Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asp Ser Ser Gly Asp Tyr Tyr Gly Met Asp Val Trp Gly Gln Gly
            100                 105                 110

Thr Thr Val Thr Val Ser Ser
        115

<210> SEQ ID NO 98
<211> LENGTH: 119
<212> TYPE: PRT
<213> ORGANISM: Homo Sapiens

<400> SEQUENCE: 98

Gln Val Gln Leu Val Gln Ser Gly Ala Glu Val Lys Lys Pro Gly Ala
  1               5                  10                  15

Ser Val Lys Val Ser Cys Lys Val Ser Gly Tyr Thr Thr Glu Leu
             20                  25                  30

Ser Met His Trp Val Arg Gln Ala Pro Gly Lys Gly Leu Glu Trp Met
         35                  40                  45

Gly Gly Phe Asp Pro Glu Asp Gly Glu Thr Ile Tyr Ala Gln Lys Phe
     50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Ala Gly Leu Glu Ile Arg Trp Phe Asp Pro Trp Gly Gln Gly
            100                 105                 110

Thr Leu Val Thr Val Ser Ser
        115

<210> SEQ ID NO 99
<211> LENGTH: 120
<212> TYPE: PRT
<213> ORGANISM: Homo Sapiens

<400> SEQUENCE: 99

Gln Val Gln Leu Gln Glu Ser Gly Pro Gly Leu Val Lys Pro Ser Gln
  1               5                  10                  15
```

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
                35                  40                  45

Trp Ile Gly Tyr Ile Ser Tyr Ser Gly Asp Thr Tyr Tyr Asn Pro Ser
 50                  55                  60

Leu Lys Ser Arg Leu Thr Ile Ser Val Asp Thr Ser Lys His Gln Phe
 65                  70                  75                  80

Ser Leu Arg Leu Ser Ser Val Thr Ser Ala Asp Thr Ala Val Tyr Tyr
                 85                  90                  95

Cys Ala Ser Leu Asp Leu Tyr Gly Asp Tyr Phe Asp Tyr Trp Gly Gln
                100                 105                 110

Gly Thr Leu Val Thr Val Ser Ser
            115                 120

<210> SEQ ID NO 100
<211> LENGTH: 125
<212> TYPE: PRT
<213> ORGANISM: Homo Sapiens

<400> SEQUENCE: 100

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Leu Thr Ser Tyr
                20                  25                  30

Gly Ile Ser Trp Val Arg Gln Ala Pro Gly Gln Gly Leu Glu Trp Met
                35                  40                  45

Gly Trp Ile Ser Ala Tyr Asn Gly Asn Pro Asn Tyr Ala Gln Lys Phe
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Gln Gly Leu Leu Gly Phe Gly Glu Leu Glu Gly Leu Phe
                100                 105                 110

Asp Tyr Trp Gly Gln Gly Thr Leu Val Thr Val Ser Ser
            115                 120                 125

<210> SEQ ID NO 101
<211> LENGTH: 130
<212> TYPE: PRT
<213> ORGANISM: Homo Sapiens

<400> SEQUENCE: 101

Glu Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
                35                  40                  45

Gly Arg Ile Lys Thr Lys Thr Asp Gly Gly Thr Thr Asp Tyr Ala Ala
 50                  55                  60

Pro Val Lys Gly Arg Phe Thr Ile Ser Arg Asp Asp Ser Gln Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Glu Tyr Tyr Gly Ile Val Thr Gly Ser Phe Tyr Tyr

```
                100                 105                 110
Tyr Tyr Tyr Gly Met Asp Val Trp Gly Gln Gly Thr Thr Val Thr Val
        115                 120                 125

Ser Ser
    130

<210> SEQ ID NO 102
<211> LENGTH: 107
<212> TYPE: PRT
<213> ORGANISM: Homo Sapiens

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Ser Asn Phe
            20                  25                  30

Leu Asp Trp Tyr Gln Gln Lys Pro Gly Lys Ala Pro Asn Leu Leu Ile
        35                  40                  45

Tyr Asp Ala Ser Asp Leu Asp Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Val Ser Leu Pro Leu
                85                  90                  95

Thr Phe Gly Gly Gly Thr Lys Val Glu Ile Lys
            100                 105

<210> SEQ ID NO 103
<211> LENGTH: 107
<212> TYPE: PRT
<213> ORGANISM: Homo Sapiens

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Phe
            20                  25                  30

Leu Asp Trp Tyr Gln Gln Lys Pro Gly Lys Ala Pro Lys Leu Leu Ile
        35                  40                  45

Tyr Asp Ala Ser Asp Leu Asp Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Val Ser Leu Pro Leu
                85                  90                  95

Thr Phe Gly Gly Gly Thr Lys Val Glu Ile Lys
            100                 105

<210> SEQ ID NO 104
<211> LENGTH: 112
<212> TYPE: PRT
<213> ORGANISM: Homo Sapiens

<400> SEQUENCE: 104

Asp Asn Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30
```

```
Asp Gly Lys Thr Tyr Leu Tyr Trp Tyr Leu Gln Lys Pro Gly Gln Pro
            35                  40                  45

Pro Gln Leu Leu Ile Tyr Glu Ala Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                 85                  90                  95

Ile Gln Leu Pro Leu Thr Phe Gly Gly Gly Thr Lys Val Glu Ile Lys
                100                 105                 110
```

<210> SEQ ID NO 105
<211> LENGTH: 107
<212> TYPE: PRT
<213> ORGANISM: Homo Sapiens

<400> SEQUENCE: 105

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asn Asn Tyr
                 20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Ile Gly Val Pro Ser Arg Phe Ser Gly
 50                  55                  60

Ser Gly Ser Gly Thr Asp Phe Ile Phe Thr Ile Ser Ser Leu Gln Pro
 65                  70                  75                  80

Glu Asp Ile Ala Thr Tyr Tyr Cys Gln Gln Tyr Asp Asn Phe Pro Phe
                 85                  90                  95

Thr Phe Gly Gly Gly Thr Lys Val Glu Ile Lys
                100                 105
```

<210> SEQ ID NO 106
<211> LENGTH: 106
<212> TYPE: PRT
<213> ORGANISM: Homo Sapiens

<400> SEQUENCE: 106

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Asn Asn Tyr
                 20                  25                  30

Leu Asn Trp Tyr Gln Gln Lys Pro Gly Lys Ala Pro Lys Leu Leu Ile
            35                  40                  45

Tyr Asp Thr Ser Asn Leu Glu Pro Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Leu Thr
                 85                  90                  95

Phe Gly Gln Gly Thr Arg Leu Glu Ile Lys
                100                 105
```

<210> SEQ ID NO 107
<211> LENGTH: 106
<212> TYPE: PRT
<213> ORGANISM: Homo Sapiens

<400> SEQUENCE: 107

```
Asp Ile Gln Met Thr Gln Ser Pro Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln His Lys Pro Gly Lys Ala Pro Lys Leu Leu Ile
        35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65              70                  75                  80

Glu Asp Ile Ala Thr Tyr Tyr Cys Gln Gln Tyr Asp Asn Leu Leu Thr
                85                  90                  95

Phe Gly Gly Gly Thr Lys Val Glu Ile Lys
            100                 105
```

<210> SEQ ID NO 108
<211> LENGTH: 106
<212> TYPE: PRT
<213> ORGANISM: Homo Sapiens

<400> SEQUENCE: 108

```
Asp Ile Gln Met Thr Gln Ser Pro Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Phe Leu Ile
        35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65              70                  75                  80

Glu Asp Ile Ala Thr Tyr Tyr Cys Gln Gln Tyr Asp Asn Leu Ile Thr
                85                  90                  95

Phe Gly Gln Gly Thr Arg Leu Glu Ile Lys
            100                 105
```

<210> SEQ ID NO 109
<211> LENGTH: 113
<212> TYPE: PRT
<213> ORGANISM: Homo Sapiens

<400> SEQUENCE: 109

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Asp Ser
            20                  25                  30

Ser Asp Asn Lys Asn Tyr Leu Ala Trp Tyr Gln Lys Pro Gly Gln
        35                  40                  45

Pro Pro Lys Leu Leu Ile Tyr Trp Ala Ser Asn Arg Glu Ser Gly Val
 50                  55                  60

Pro Asp Arg Phe Ser Gly Ser Gly Ser Gly Thr Asp Phe Ser Leu Thr
 65              70                  75                  80

Ile Ser Ser Leu Gln Ala Glu Asp Val Ala Val Tyr Tyr Cys Gln Gln
                85                  90                  95

Tyr Tyr Ser Asp Pro Phe Thr Phe Gly Pro Gly Thr Lys Val Asp Ile
            100                 105                 110
```

Lys

<210> SEQ ID NO 110
<211> LENGTH: 113
<212> TYPE: PRT
<213> ORGANISM: Homo Sapiens

<400> SEQUENCE: 110

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asp Ser
            20                  25                  30

Ser Asp Asn Lys Asn Tyr Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Asp Pro Phe Thr Phe Gly Pro Gly Thr Lys Val Asp Ile
            100                 105                 110

Lys

<210> SEQ ID NO 111
<211> LENGTH: 106
<212> TYPE: PRT
<213> ORGANISM: Homo Sapiens

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Leu Thr
                85                  90                  95

Phe Gly Gly Gly Thr Lys Val Glu Ile Lys
            100                 105

<210> SEQ ID NO 112
<211> LENGTH: 113
<212> TYPE: PRT
<213> ORGANISM: Homo Sapiens

<400> SEQUENCE: 112

Asp Ile Val Met Thr Gln Ser Pro Asp Ser Leu Ala Val Ser Leu Gly
1               5                   10                  15

Glu Arg Ala Thr Ile Asp Cys Lys Ser Ser Gln Gly Val Leu Asp Ser
            20                  25                  30

Ser Asn Asn Lys Asn Phe Leu Ala Trp Tyr Gln Gln Lys Pro Gly Gln
        35                  40                  45

Pro Pro Lys Leu Leu Ile Tyr Trp Ala Ser Asn Arg Glu Ser Gly Val

```
                    50                  55                  60
Pro Val Arg Phe Ser Gly Ser Gly Ser Gly Thr Asp Phe Thr Leu Thr
 65                  70                  75                  80

Ile Ser Ser Leu Gln Ala Glu Asp Val Ala Leu Tyr Tyr Cys Gln Gln
                 85                  90                  95

Tyr Tyr Ser Asp Pro Phe Thr Phe Gly Pro Gly Thr Lys Val Asp Ile
            100                 105                 110

Lys

<210> SEQ ID NO 113
<211> LENGTH: 107
<212> TYPE: PRT
<213> ORGANISM: Homo Sapiens

<400> SEQUENCE: 113

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asp Tyr
                 20                  25                  30

Leu Asn Trp Tyr Gln Gln Lys Pro Gly Lys Ala Pro Asn Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Thr Tyr Ser Asp Pro Phe
                 85                  90                  95

Thr Phe Gly Pro Gly Thr Lys Val Asp Ile Lys
            100                 105

<210> SEQ ID NO 114
<211> LENGTH: 106
<212> TYPE: PRT
<213> ORGANISM: Homo Sapiens

<400> SEQUENCE: 114

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Leu Thr
                 85                  90                  95

Phe Gly Gly Gly Thr Lys Val Glu Ile Lys
            100                 105

<210> SEQ ID NO 115
<211> LENGTH: 106
<212> TYPE: PRT
<213> ORGANISM: Homo Sapiens

<400> SEQUENCE: 115

Asp Ile Gln Met Thr Gln Ser Pro Ser Ser Leu Ser Ala Ser Val Gly
```

```
                1               5                   10                  15
Asp Arg Val Thr Ile Thr Cys Gln Ala Ser Gln Asp Ile Ser Asn Tyr
                    20                  25                  30

Leu Asn Trp Tyr Gln Gln Lys Pro Gly Lys Ala Pro Lys Val Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Leu Thr
                85                  90                  95

Phe Gly Gly Gly Thr Lys Val Glu Ile Lys
                100                 105

<210> SEQ ID NO 116
<211> LENGTH: 113
<212> TYPE: PRT
<213> ORGANISM: Homo Sapiens

<400> SEQUENCE: 116

Asp Ile Val Met Thr Gln Ser Pro Asp Ser Leu Ala Val Ser Leu Gly
1               5                   10                  15

Glu Arg Ala Thr Ile Asp Cys Lys Ser Ser Gln Ser Val Leu Asp Ser
                20                  25                  30

Ser Asn Asn Lys Asn Phe Leu Ala Trp Tyr Gln Gln Lys Pro Gly Gln
            35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Asp Pro Phe Thr Phe Gly Pro Gly Thr Lys Val Asp Ile
                100                 105                 110

Lys

<210> SEQ ID NO 117
<211> LENGTH: 111
<212> TYPE: PRT
<213> ORGANISM: Homo Sapiens

<400> SEQUENCE: 117

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
                20                  25                  30

Tyr Leu Ala Tyr Leu Ala Trp Tyr Gln Gln Lys Pro Gly Gln Ala Pro
            35                  40                  45

Arg Leu Leu Ile Tyr Gly Ala Ser Ser Thr Ala Thr Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Tyr Gly
                85                  90                  95

Ser Ser Pro Ile Thr Phe Gly Gln Gly Thr Arg Leu Glu Ile Lys
                100                 105                 110
```

<210> SEQ ID NO 118
<211> LENGTH: 107
<212> TYPE: PRT
<213> ORGANISM: Homo Sapiens

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Phe
            20                  25                  30

Leu Asn Trp Tyr Gln Gln Arg Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Phe
                85                  90                  95

Thr Phe Gly Pro Gly Thr Lys Val Asp Ile Lys
            100                 105

<210> SEQ ID NO 119
<211> LENGTH: 106
<212> TYPE: PRT
<213> ORGANISM: Homo Sapiens

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Tyr Asp Asn Leu Leu Thr
                85                  90                  95

Phe Gly Gly Gly Thr Lys Val Glu Ile Lys
            100                 105

<210> SEQ ID NO 120
<211> LENGTH: 107
<212> TYPE: PRT
<213> ORGANISM: Homo Sapiens

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

```
Glu Asp Ile Ala Thr Tyr Tyr Cys Gln Arg Tyr Asp Asp Leu Pro Ile
                85                  90                  95

Thr Phe Gly Gln Gly Thr Arg Leu Glu Ile Lys
            100                 105

<210> SEQ ID NO 121
<211> LENGTH: 106
<212> TYPE: PRT
<213> ORGANISM: Homo Sapiens

<400> SEQUENCE: 121

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                20                  25                  30

Leu Asn Trp Tyr Gln Gln Arg Pro Gly Lys Ala Pro Lys Leu Leu Ile
             35                  40                  45

Tyr Asp Ala Ser Asn Leu Glu Thr Gly Val Pro Ser Arg Phe Ser Gly
         50                  55                  60

Ser Gly Ser Gly Thr Asp Phe Thr Phe Thr Ile Ser Ser Leu Gln Pro
 65                 70                  75                  80

Glu Asp Ile Ala Thr Tyr Tyr Cys Gln Gln Tyr Asp Asn Leu Leu Thr
                85                  90                  95

Phe Gly Gly Gly Thr Lys Val Glu Ile Lys
            100                 105

<210> SEQ ID NO 122
<211> LENGTH: 107
<212> TYPE: PRT
<213> ORGANISM: Homo Sapiens

<400> SEQUENCE: 122

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Phe Ser Asn Tyr
                20                  25                  30

Leu Ala Trp Tyr Gln Gln Lys Pro Gly Lys Val Pro Lys Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                 70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
            100                 105

<210> SEQ ID NO 123
<211> LENGTH: 107
<212> TYPE: PRT
<213> ORGANISM: Homo Sapiens

<400> SEQUENCE: 123

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Asn Asn Tyr
                20                  25                  30

Leu Ala Trp Tyr Gln Gln Lys Pro Gly Lys Val Pro Gln Leu Leu Ile
```

```
              35                  40                  45
Tyr Val Ala Ser Thr Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Val Ala Thr Tyr Tyr Cys Gln Lys Tyr Asn Ser Gly Pro Phe
                 85                  90                  95
Thr Phe Gly Pro Gly Thr Lys Val Asp Ile Lys
            100                 105
```

<210> SEQ ID NO 124
<211> LENGTH: 107
<212> TYPE: PRT
<213> ORGANISM: Homo Sapiens

<400> SEQUENCE: 124

```
Asp Ile Gln Met Thr Gln Ser Pro Ser Ser Leu Ser Ala Ser Val Gly
  1                5                  10                  15
Asp Arg Val Thr Ile Thr Cys Arg Ala Ser Gln Gly Ile Asn Asn Tyr
                 20                  25                  30
Leu Ala Trp Tyr Gln Gln Lys Pro Gly Lys Val Pro Lys Leu Leu Ile
              35                  40                  45
Tyr Val Ala Ser Thr Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Val Ala Thr Tyr Tyr Cys Gln Lys Tyr Asn Ser Gly Pro Phe
                 85                  90                  95
Thr Phe Gly Pro Gly Thr Lys Val Asp Ile Lys
            100                 105
```

<210> SEQ ID NO 125
<211> LENGTH: 107
<212> TYPE: PRT
<213> ORGANISM: Homo Sapiens

<400> SEQUENCE: 125

```
Asp Ile Gln Met Thr Gln Ser Pro Ser Ser Leu Ser Ala Ser Val Gly
  1                5                  10                  15
Asp Arg Val Thr Ile Thr Cys Arg Ala Ser Gln Ser Ile Ser Arg Tyr
                 20                  25                  30
Leu Asn Trp Tyr Gln Gln Lys Pro Gly Lys Ala Pro Asn Leu Leu Ile
              35                  40                  45
His Ala Ala Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ile Thr Pro Pro
                 85                  90                  95
Ser Phe Gly Gln Gly Thr Lys Leu Glu Ile Lys
            100                 105
```

<210> SEQ ID NO 126
<211> LENGTH: 107
<212> TYPE: PRT
<213> ORGANISM: Homo Sapiens

<400> SEQUENCE: 126

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Asp Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Asn Ser Leu Gln Pro
 65                  70                  75                  80

Glu Asp Phe Ala Thr Tyr Tyr Cys Leu Gln Tyr Asn Ser Tyr Pro Ile
                 85                  90                  95

Thr Phe Gly Gln Gly Thr Arg Leu Glu Ile Lys
                100                 105

<210> SEQ ID NO 127
<211> LENGTH: 107
<212> TYPE: PRT
<213> ORGANISM: Homo Sapiens

<400> SEQUENCE: 127

Asp Ile Gln Met Ile Gln Ser Pro Ser Ser Leu Ser Ala Ser Val Gly
  1               5                  10                  15

Asp Arg Val Thr Ile Thr Cys Gln Ala Ser His Asp Ile Ser Asn Tyr
             20                  25                  30

Leu Asn Trp Tyr Gln Gln Lys Pro Gly Lys Ala Pro Lys Phe Leu Ile
         35                  40                  45

Ser Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Leu
                 85                  90                  95

Thr Phe Gly Gly Gly Thr Lys Val Glu Ile Lys
                100                 105

<210> SEQ ID NO 128
<211> LENGTH: 112
<212> TYPE: PRT
<213> ORGANISM: Homo Sapiens

<400> SEQUENCE: 128

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Phe Leu Ile Tyr Leu Gly Ser Ile Arg Ala Ser Gly Val Pro
 50                  55                  60

Asp Arg Phe Ser Gly Ser Gly Ser Gly Thr Asp Phe Ala Leu Thr Ile
 65                  70                  75                  80

Ser Arg Val Glu Ala Glu Asp Val Gly Val Tyr Tyr Cys Met Gln Ala
                 85                  90                  95

Leu Gln Thr Pro Arg Thr Phe Gly Gln Gly Thr Lys Val Glu Ile Lys
                100                 105                 110
```

```
<210> SEQ ID NO 129
<211> LENGTH: 107
<212> TYPE: PRT
<213> ORGANISM: Homo Sapiens

<400> SEQUENCE: 129

Glu Ile Val Leu Thr Gln Ser Pro Asp Phe Gln Ser Val Thr Pro Lys
  1               5                  10                  15

Glu Lys Val Thr Ile Thr Cys Arg Ala Ser Gln Tyr Ile Gly Ser Ser
             20                  25                  30

Leu His Trp Tyr Gln Gln Thr Pro Asp Gln Ser Pro Lys Leu Leu Ile
         35                  40                  45

Asn Tyr Val Ser Gln Ser Phe Ser Gly Val Pro Ser Arg Phe Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro Phe
                 85                  90                  95

Thr Phe Gly Pro Gly Thr Lys Val Asp Ile Lys
            100                 105

<210> SEQ ID NO 130
<211> LENGTH: 113
<212> TYPE: PRT
<213> ORGANISM: Homo Sapiens

<400> SEQUENCE: 130

Asp Ile Val Met Thr Gln Ser Pro Asp Ser Leu Ala Val Ser Leu Gly
  1               5                  10                  15

Ala Arg Ala Thr Ile Ser Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Thr Leu Gln Ala Glu Asp Val Ala Val Tyr Tyr Cys Gln Gln
                 85                  90                  95

Tyr Tyr Thr Thr Pro Pro Thr Phe Gly Gln Gly Thr Lys Val Glu Ile
            100                 105                 110

Lys

<210> SEQ ID NO 131
<211> LENGTH: 106
<212> TYPE: PRT
<213> ORGANISM: Homo Sapiens

<400> SEQUENCE: 131

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Asn Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
```

```
                65                  70                  75                  80
Glu Asp Ile Ala Thr Tyr Tyr Cys Gln Gln Tyr Asp Asp Leu Leu Thr
                    85                  90                  95

Phe Gly Gly Gly Thr Lys Val Glu Ile Lys
            100                 105

<210> SEQ ID NO 132
<211> LENGTH: 107
<212> TYPE: PRT
<213> ORGANISM: Homo Sapiens

<400> SEQUENCE: 132

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Ile Ile Ser Ser Leu Gln Pro
 65                  70                  75                  80

Glu Asp Ile Ala Thr Tyr Tyr Cys Gln Gln Phe Asp Asn Leu Pro Pro
                    85                  90                  95

Thr Phe Gly Gly Gly Thr Lys Val Glu Ser Lys
                100                 105

<210> SEQ ID NO 133
<211> LENGTH: 106
<212> TYPE: PRT
<213> ORGANISM: Homo Sapiens

<400> SEQUENCE: 133

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
             20                  25                  30

Leu Asn Trp Tyr Gln His Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Leu Thr
                    85                  90                  95

Phe Gly Gly Gly Thr Lys Val Glu Ile Lys
            100                 105

<210> SEQ ID NO 134
<211> LENGTH: 115
<212> TYPE: PRT
<213> ORGANISM: Homo Sapiens

<400> SEQUENCE: 134

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
             20                  25                  30
```

```
Asp Gly Asn Thr Tyr Leu Asn Trp Phe Gln Gln Arg Pro Gly Gln Ser
            35                  40                  45

Pro Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Arg Gly Leu Phe Thr Phe Gly Pro Gly Thr Lys Val
                100                 105                 110

Asp Ile Lys
        115
```

<210> SEQ ID NO 135
<211> LENGTH: 112
<212> TYPE: PRT
<213> ORGANISM: Homo Sapiens

<400> SEQUENCE: 135

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
                 20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Trp Asp Ser Gly Val Pro
 50                  55                  60

Asp Arg Phe Asn Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Ile Thr Phe Gly Gln Gly Thr Gly Leu Glu Ile Lys
                100                 105                 110
```

<210> SEQ ID NO 136
<211> LENGTH: 7
<212> TYPE: PRT
<213> ORGANISM: Homo Sapiens

<400> SEQUENCE: 136

```
Ser Gly Gly Tyr Tyr Trp Ser
 1               5
```

<210> SEQ ID NO 137
<211> LENGTH: 5
<212> TYPE: PRT
<213> ORGANISM: Homo Sapiens

<400> SEQUENCE: 137

```
Asn Ala Trp Met Ser
 1               5
```

<210> SEQ ID NO 138
<211> LENGTH: 5
<212> TYPE: PRT
<213> ORGANISM: Homo Sapiens

<400> SEQUENCE: 138

```
Thr Ala Trp Met Ser
 1               5
```

```
<210> SEQ ID NO 139
<211> LENGTH: 5
<212> TYPE: PRT
<213> ORGANISM: Homo Sapiens

<400> SEQUENCE: 139

Gly Tyr Tyr Met His
1               5

<210> SEQ ID NO 140
<211> LENGTH: 5
<212> TYPE: PRT
<213> ORGANISM: Homo Sapiens

<400> SEQUENCE: 140

Ala Tyr Tyr Met His
1               5

<210> SEQ ID NO 141
<211> LENGTH: 5
<212> TYPE: PRT
<213> ORGANISM: Homo Sapiens

<400> SEQUENCE: 141

Ser Tyr Asp Met His
1               5

<210> SEQ ID NO 142
<211> LENGTH: 5
<212> TYPE: PRT
<213> ORGANISM: Homo Sapiens

<400> SEQUENCE: 142

Glu Leu Ser Met His
1               5

<210> SEQ ID NO 143
<211> LENGTH: 5
<212> TYPE: PRT
<213> ORGANISM: Homo Sapiens

<400> SEQUENCE: 143

Ser Tyr Gly Met His
1               5

<210> SEQ ID NO 144
<211> LENGTH: 5
<212> TYPE: PRT
<213> ORGANISM: Homo Sapiens

<400> SEQUENCE: 144

Ser Tyr Tyr Trp Ser
1               5

<210> SEQ ID NO 145
<211> LENGTH: 5
<212> TYPE: PRT
<213> ORGANISM: Homo Sapiens

<400> SEQUENCE: 145

Asn Tyr Tyr Trp Ser
1               5

<210> SEQ ID NO 146
<211> LENGTH: 5
```

<212> TYPE: PRT
<213> ORGANISM: Homo Sapiens

<400> SEQUENCE: 146

Gly Tyr Tyr Ile His
1               5

<210> SEQ ID NO 147
<211> LENGTH: 5
<212> TYPE: PRT
<213> ORGANISM: Homo Sapiens

<400> SEQUENCE: 147

Ser Tyr Gly Ile Ser
1               5

<210> SEQ ID NO 148
<211> LENGTH: 16
<212> TYPE: PRT
<213> ORGANISM: Homo Sapiens

<400> SEQUENCE: 148

Tyr Ile Tyr Tyr Ser Gly Ser Thr Asn Tyr Asn Pro Ser Leu Lys Ser
1               5                   10                  15

<210> SEQ ID NO 149
<211> LENGTH: 16
<212> TYPE: PRT
<213> ORGANISM: Homo Sapiens

<400> SEQUENCE: 149

Tyr Ile Ser Tyr Ser Gly Asp Thr Tyr Tyr Asn Pro Ser Leu Lys Ser
1               5                   10                  15

<210> SEQ ID NO 150
<211> LENGTH: 19
<212> TYPE: PRT
<213> ORGANISM: Homo Sapiens

<400> SEQUENCE: 150

Arg Ile Lys Ser Lys Thr Asp Gly Gly Thr Thr Asp Tyr Ala Ala Pro
1               5                   10                  15

Val Lys Gly

<210> SEQ ID NO 151
<211> LENGTH: 19
<212> TYPE: PRT
<213> ORGANISM: Homo Sapiens

<400> SEQUENCE: 151

Arg Ile Lys Ser Lys Thr Asp Gly Gly Thr Thr Asp Asn Ala Ala Pro
1               5                   10                  15

Val Lys Gly

<210> SEQ ID NO 152
<211> LENGTH: 19
<212> TYPE: PRT
<213> ORGANISM: Homo Sapiens

<400> SEQUENCE: 152

Arg Ile Lys Ser Lys Thr Asp Gly Gly Thr Ala Asp Tyr Ala Ala Pro
1               5                   10                  15

Val Lys Gly

-continued

<210> SEQ ID NO 153
<211> LENGTH: 19
<212> TYPE: PRT
<213> ORGANISM: Homo Sapiens

<400> SEQUENCE: 153

Arg Ile Lys Thr Lys Thr Asp Gly Gly Thr Thr Asp Tyr Ala Ala Pro
1               5                   10                  15

Val Lys Gly

<210> SEQ ID NO 154
<211> LENGTH: 19
<212> TYPE: PRT
<213> ORGANISM: Homo Sapiens

<400> SEQUENCE: 154

Arg Ile Lys Ser Lys Thr Asp Gly Trp Thr Thr Asp Tyr Ala Ala Pro
1               5                   10                  15

Val Lys Gly

<210> SEQ ID NO 155
<211> LENGTH: 17
<212> TYPE: PRT
<213> ORGANISM: Homo Sapiens

<400> SEQUENCE: 155

Trp Ile Asn Pro Asn Ser Gly Gly Thr Asn Tyr Ala Gln Lys Phe Gln
1               5                   10                  15

Gly

<210> SEQ ID NO 156
<211> LENGTH: 16
<212> TYPE: PRT
<213> ORGANISM: Homo Sapiens

<400> SEQUENCE: 156

Gly Ile Gly Thr Ala Gly Asp Thr Tyr Tyr Pro Gly Ser Val Lys Gly
1               5                   10                  15

<210> SEQ ID NO 157
<211> LENGTH: 17
<212> TYPE: PRT
<213> ORGANISM: Homo Sapiens

<400> SEQUENCE: 157

Gly Phe Asp Pro Glu Asp Gly Glu Thr Ile Tyr Ala Gln Lys Phe Gln
1               5                   10                  15

Gly

<210> SEQ ID NO 158
<211> LENGTH: 17
<212> TYPE: PRT
<213> ORGANISM: Homo Sapiens

<400> SEQUENCE: 158

Val Ile Trp Tyr Asp Gly Ser Asn Lys Tyr Tyr Ala Asp Ser Val Lys
1               5                   10                  15

Gly

<210> SEQ ID NO 159
<211> LENGTH: 16
<212> TYPE: PRT

<213> ORGANISM: Homo Sapiens

<400> SEQUENCE: 159

Tyr Ile Tyr Tyr Ser Gly Asn Thr Asn Tyr Asn Pro Ser Leu Lys Ser
1               5                   10                  15

<210> SEQ ID NO 160
<211> LENGTH: 17
<212> TYPE: PRT
<213> ORGANISM: Homo Sapiens

<400> SEQUENCE: 160

Val Ile Trp Tyr Asp Gly Ser Asn Glu Tyr Tyr Ala Asp Ser Val Lys
1               5                   10                  15
Gly

<210> SEQ ID NO 161
<211> LENGTH: 16
<212> TYPE: PRT
<213> ORGANISM: Homo Sapiens

<400> SEQUENCE: 161

Arg Ile Tyr Thr Ser Gly Ser Thr His Tyr Asn Pro Ser Leu Lys Ser
1               5                   10                  15

<210> SEQ ID NO 162
<211> LENGTH: 17
<212> TYPE: PRT
<213> ORGANISM: Homo Sapiens

<400> SEQUENCE: 162

Val Ile Trp Tyr Asp Gly Ser Tyr Lys Tyr Tyr Ala Asp Ser Val Lys
1               5                   10                  15
Gly

<210> SEQ ID NO 163
<211> LENGTH: 17
<212> TYPE: PRT
<213> ORGANISM: Homo Sapiens

<400> SEQUENCE: 163

Trp Ile Ser Ala Tyr Asn Gly Asn Thr Asn Tyr Ala Gln Lys Leu Gln
1               5                   10                  15
Gly

<210> SEQ ID NO 164
<211> LENGTH: 17
<212> TYPE: PRT
<213> ORGANISM: Homo Sapiens

<400> SEQUENCE: 164

Trp Ile Ser Ala Tyr Asn Gly Asn Pro Asn Tyr Ala Gln Lys Phe Gln
1               5                   10                  15
Gly

<210> SEQ ID NO 165
<211> LENGTH: 11
<212> TYPE: PRT
<213> ORGANISM: Homo Sapiens

<400> SEQUENCE: 165

Gly Ile Ala Ala Thr Gly Thr Leu Phe Asp Cys
1               5                   10

<210> SEQ ID NO 166
<211> LENGTH: 15
<212> TYPE: PRT
<213> ORGANISM: Homo Sapiens

<400> SEQUENCE: 166

Glu Tyr Tyr Gly Ser Gly Gly Val Trp Tyr Tyr Gly Met Asp Val
1               5                   10                  15

<210> SEQ ID NO 167
<211> LENGTH: 18
<212> TYPE: PRT
<213> ORGANISM: Homo Sapiens

<400> SEQUENCE: 167

Gly Gly Ser Leu Leu Trp Thr Gly Pro Asn Tyr Tyr Tyr Gly Met
1               5                   10                  15

Asp Val

<210> SEQ ID NO 168
<211> LENGTH: 11
<212> TYPE: PRT
<213> ORGANISM: Homo Sapiens

<400> SEQUENCE: 168

Asp Ser Asn Trp Tyr His Asn Trp Phe Asp Pro
1               5                   10

<210> SEQ ID NO 169
<211> LENGTH: 16
<212> TYPE: PRT
<213> ORGANISM: Homo Sapiens

<400> SEQUENCE: 169

Gly Gly Tyr Ser Gly Tyr Asp Leu Gly Tyr Tyr Gly Met Asp Val
1               5                   10                  15

<210> SEQ ID NO 170
<211> LENGTH: 16
<212> TYPE: PRT
<213> ORGANISM: Homo Sapiens

<400> SEQUENCE: 170

Glu Gly Pro Tyr Ser Asp Tyr Gly Tyr Tyr Tyr Gly Met Asp Val
1               5                   10                  15

<210> SEQ ID NO 171
<211> LENGTH: 10
<212> TYPE: PRT
<213> ORGANISM: Homo Sapiens

<400> SEQUENCE: 171

Leu Asp Leu Tyr Gly Asp Tyr Phe Asp Tyr
1               5                   10

<210> SEQ ID NO 172
<211> LENGTH: 9
<212> TYPE: PRT
<213> ORGANISM: Homo Sapiens

<400> SEQUENCE: 172

Glu Gly Ser Trp Tyr Gly Phe Asp Tyr
1               5

```
<210> SEQ ID NO 173
<211> LENGTH: 19
<212> TYPE: PRT
<213> ORGANISM: Homo Sapiens

<400> SEQUENCE: 173

Glu Tyr Tyr His Ile Leu Thr Gly Ser Phe Tyr Tyr Ser Tyr Gly
 1               5                  10                  15
Met Asp Val

<210> SEQ ID NO 174
<211> LENGTH: 19
<212> TYPE: PRT
<213> ORGANISM: Homo Sapiens

<400> SEQUENCE: 174

Glu Tyr Tyr Gly Ile Val Thr Gly Ser Phe Tyr Tyr Tyr Tyr Gly
 1               5                  10                  15
Met Asp Val

<210> SEQ ID NO 175
<211> LENGTH: 15
<212> TYPE: PRT
<213> ORGANISM: Homo Sapiens

<400> SEQUENCE: 175

Arg Ala Gly Thr Thr Leu Ala Tyr Tyr Tyr Tyr Ala Met Asp Val
 1               5                  10                  15

<210> SEQ ID NO 176
<211> LENGTH: 10
<212> TYPE: PRT
<213> ORGANISM: Homo Sapiens

<400> SEQUENCE: 176

Ala Gly Leu Glu Ile Arg Trp Phe Asp Pro
 1               5                  10

<210> SEQ ID NO 177
<211> LENGTH: 10
<212> TYPE: PRT
<213> ORGANISM: Homo Sapiens

<400> SEQUENCE: 177

Ser Ser Gly Asp Tyr Tyr Gly Met Asp Val
 1               5                  10

<210> SEQ ID NO 178
<211> LENGTH: 8
<212> TYPE: PRT
<213> ORGANISM: Homo Sapiens

<400> SEQUENCE: 178

Ile Ala Thr Arg Pro Phe Asp Tyr
 1               5

<210> SEQ ID NO 179
<211> LENGTH: 9
<212> TYPE: PRT
<213> ORGANISM: Homo Sapiens

<400> SEQUENCE: 179

Asp Arg Val Phe Tyr Gly Met Asp Val
 1               5
```

<210> SEQ ID NO 180
<211> LENGTH: 12
<212> TYPE: PRT
<213> ORGANISM: Homo Sapiens

<400> SEQUENCE: 180

Glu Gly Asp Tyr Ser Asp Tyr Tyr Gly Met Asp Val
1               5                   10

<210> SEQ ID NO 181
<211> LENGTH: 17
<212> TYPE: PRT
<213> ORGANISM: Homo Sapiens

<400> SEQUENCE: 181

Asp Arg Gly Gln Leu Trp Leu Trp Tyr Tyr Tyr Tyr Tyr Gly Met Asp
1               5                   10                  15

Val

<210> SEQ ID NO 182
<211> LENGTH: 10
<212> TYPE: PRT
<213> ORGANISM: Homo Sapiens

<400> SEQUENCE: 182

Ser Ser Gly Asn Tyr Tyr Asp Met Asp Val
1               5                   10

<210> SEQ ID NO 183
<211> LENGTH: 10
<212> TYPE: PRT
<213> ORGANISM: Homo Sapiens

<400> SEQUENCE: 183

Ser Ser Ser Asn Phe Tyr Asp Met Asp Val
1               5                   10

<210> SEQ ID NO 184
<211> LENGTH: 18
<212> TYPE: PRT
<213> ORGANISM: Homo Sapiens

<400> SEQUENCE: 184

Asp Leu Arg Ile Thr Gly Thr Thr Tyr Tyr Tyr Tyr Tyr Gly Met
1               5                   10                  15

Asp Val

<210> SEQ ID NO 185
<211> LENGTH: 16
<212> TYPE: PRT
<213> ORGANISM: Homo Sapiens

<400> SEQUENCE: 185

Asp Gln Gly Leu Leu Gly Phe Gly Glu Leu Glu Gly Leu Phe Asp Tyr
1               5                   10                  15

<210> SEQ ID NO 186
<211> LENGTH: 11
<212> TYPE: PRT
<213> ORGANISM: Homo Sapiens

<400> SEQUENCE: 186

Glu Ser Trp Phe Gly Glu Val Phe Phe Asp Tyr

```
<210> SEQ ID NO 187
<211> LENGTH: 20
<212> TYPE: PRT
<213> ORGANISM: Homo Sapiens

<400> SEQUENCE: 187

Gly Val Met Ile Thr Phe Gly Gly Val Ile Val Gly His Ser Tyr Tyr
1               5                   10                  15
Gly Met Asp Val
            20

<210> SEQ ID NO 188
<211> LENGTH: 16
<212> TYPE: PRT
<213> ORGANISM: Homo Sapiens

<400> SEQUENCE: 188

Glu Gly Pro Tyr Ser Asn Tyr Gly Tyr Tyr Tyr Gly Val Asp Val
1               5                   10                  15

<210> SEQ ID NO 189
<211> LENGTH: 17
<212> TYPE: PRT
<213> ORGANISM: Homo Sapiens

<400> SEQUENCE: 189

Asp Gly Ala Thr Val Val Thr Pro Gly Tyr Tyr Tyr Gly Thr Asp
1               5                   10                  15
Val

<210> SEQ ID NO 190
<211> LENGTH: 10
<212> TYPE: PRT
<213> ORGANISM: Homo Sapiens

<400> SEQUENCE: 190

Ser Ser Trp Ser Tyr Tyr Gly Met Asp Val
1               5                   10

<210> SEQ ID NO 191
<211> LENGTH: 16
<212> TYPE: PRT
<213> ORGANISM: Homo Sapiens

<400> SEQUENCE: 191

Arg Ser Ser Gln Ser Leu Val Tyr Ser Asp Gly Asn Thr Tyr Leu Asn
1               5                   10                  15

<210> SEQ ID NO 192
<211> LENGTH: 11
<212> TYPE: PRT
<213> ORGANISM: Homo Sapiens

<400> SEQUENCE: 192

Arg Ala Ser Gln Ser Ile Ser Asp Tyr Leu Asn
1               5                   10

<210> SEQ ID NO 193
<211> LENGTH: 17
<212> TYPE: PRT
<213> ORGANISM: Homo Sapiens

<400> SEQUENCE: 193
```

```
Lys Ser Ser Gln Ser Val Leu Asp Ser Asp Asn Lys Asn Tyr Leu
1               5                   10                  15

Ala

<210> SEQ ID NO 194
<211> LENGTH: 17
<212> TYPE: PRT
<213> ORGANISM: Homo Sapiens

<400> SEQUENCE: 194

Lys Ser Ser Gln Ser Val Leu Asp Ser Ser Asn Asn Lys Asn Phe Leu
1               5                   10                  15

Ala

<210> SEQ ID NO 195
<211> LENGTH: 17
<212> TYPE: PRT
<213> ORGANISM: Homo Sapiens

<400> SEQUENCE: 195

Lys Ser Ser Gln Gly Val Leu Asp Ser Ser Asn Asn Lys Asn Phe Leu
1               5                   10                  15

Ala

<210> SEQ ID NO 196
<211> LENGTH: 11
<212> TYPE: PRT
<213> ORGANISM: Homo Sapiens

<400> SEQUENCE: 196

Arg Ala Ser Gln Ser Ile Ser Arg Tyr Leu Asn
1               5                   10

<210> SEQ ID NO 197
<211> LENGTH: 15
<212> TYPE: PRT
<213> ORGANISM: Homo Sapiens

<400> SEQUENCE: 197

Lys Ser Ser Gln Ser Leu Leu Ser Asp Gly Lys Thr Tyr Leu Tyr
1               5                   10                  15

<210> SEQ ID NO 198
<211> LENGTH: 11
<212> TYPE: PRT
<213> ORGANISM: Homo Sapiens

<400> SEQUENCE: 198

Gln Ala Ser Gln Asp Ile Ser Asn Tyr Leu Asn
1               5                   10

<210> SEQ ID NO 199
<211> LENGTH: 11
<212> TYPE: PRT
<213> ORGANISM: Homo Sapiens

<400> SEQUENCE: 199

Gln Ala Ser Gln Asp Ile Asn Asn Tyr Leu Asn
1               5                   10

<210> SEQ ID NO 200
<211> LENGTH: 11
<212> TYPE: PRT
```

-continued

<213> ORGANISM: Homo Sapiens

<400> SEQUENCE: 200

Gln Ala Ser His Asp Ile Ser Asn Tyr Leu Asn
1               5                   10

<210> SEQ ID NO 201
<211> LENGTH: 11
<212> TYPE: PRT
<213> ORGANISM: Homo Sapiens

<400> SEQUENCE: 201

Gln Ala Ser Gln Asn Ile Ser Asn Phe Leu Asp
1               5                   10

<210> SEQ ID NO 202
<211> LENGTH: 11
<212> TYPE: PRT
<213> ORGANISM: Homo Sapiens

<400> SEQUENCE: 202

Gln Ala Ser Gln Asp Ile Ser Asn Phe Leu Asp
1               5                   10

<210> SEQ ID NO 203
<211> LENGTH: 11
<212> TYPE: PRT
<213> ORGANISM: Homo Sapiens

<400> SEQUENCE: 203

Gln Ala Ser Gln Asp Ile Ser Asn Phe Leu Asn
1               5                   10

<210> SEQ ID NO 204
<211> LENGTH: 17
<212> TYPE: PRT
<213> ORGANISM: Homo Sapiens

<400> SEQUENCE: 204

Lys Ser Ser Gln Ser Val Leu Tyr Ser Ser Asn Asn Lys Asn Tyr Leu
1               5                   10                  15

Ala

<210> SEQ ID NO 205
<211> LENGTH: 11
<212> TYPE: PRT
<213> ORGANISM: Homo Sapiens

<400> SEQUENCE: 205

Arg Ala Ser Gln Gly Phe Ser Asn Tyr Leu Ala
1               5                   10

<210> SEQ ID NO 206
<211> LENGTH: 11
<212> TYPE: PRT
<213> ORGANISM: Homo Sapiens

<400> SEQUENCE: 206

Arg Ala Ser Gln Gly Ile Asn Asn Tyr Leu Ala
1               5                   10

<210> SEQ ID NO 207
<211> LENGTH: 16
<212> TYPE: PRT
<213> ORGANISM: Homo Sapiens

<400> SEQUENCE: 207

Arg Ser Ser Gln Ser Leu Leu His Ser Asn Gly Tyr Asn Tyr Leu Asp
1               5                   10                  15

<210> SEQ ID NO 208
<211> LENGTH: 11
<212> TYPE: PRT
<213> ORGANISM: Homo Sapiens

<400> SEQUENCE: 208

Arg Ala Ser Gln Tyr Ile Gly Ser Ser Leu His
1               5                   10

<210> SEQ ID NO 209
<211> LENGTH: 15
<212> TYPE: PRT
<213> ORGANISM: Homo Sapiens

<400> SEQUENCE: 209

Arg Ala Ser Gln Ser Val Ser Ser Gly Tyr Leu Ala Tyr Leu Ala
1               5                   10                  15

<210> SEQ ID NO 210
<211> LENGTH: 11
<212> TYPE: PRT
<213> ORGANISM: Homo Sapiens

<400> SEQUENCE: 210

Arg Ala Ser Gln Gly Ile Arg Asn Asp Leu Asp
1               5                   10

<210> SEQ ID NO 211
<211> LENGTH: 7
<212> TYPE: PRT
<213> ORGANISM: Homo Sapiens

<400> SEQUENCE: 211

Lys Val Ser Asn Trp Asp Ser
1               5

<210> SEQ ID NO 212
<211> LENGTH: 7
<212> TYPE: PRT
<213> ORGANISM: Homo Sapiens

<400> SEQUENCE: 212

Ala Ala Ser Ser Leu Gln Ser
1               5

<210> SEQ ID NO 213
<211> LENGTH: 7
<212> TYPE: PRT
<213> ORGANISM: Homo Sapiens

<400> SEQUENCE: 213

Trp Ala Ser Thr Arg Glu Ser
1               5

<210> SEQ ID NO 214
<211> LENGTH: 7
<212> TYPE: PRT
<213> ORGANISM: Homo Sapiens

<400> SEQUENCE: 214

```
Trp Ala Ser Asn Arg Glu Ser
1               5

<210> SEQ ID NO 215
<211> LENGTH: 7
<212> TYPE: PRT
<213> ORGANISM: Homo Sapiens

<400> SEQUENCE: 215

Glu Ala Ser Asn Arg Phe Ser
1               5

<210> SEQ ID NO 216
<211> LENGTH: 7
<212> TYPE: PRT
<213> ORGANISM: Homo Sapiens

<400> SEQUENCE: 216

Asp Ala Ser Asn Leu Glu Thr
1               5

<210> SEQ ID NO 217
<211> LENGTH: 7
<212> TYPE: PRT
<213> ORGANISM: Homo Sapiens

<400> SEQUENCE: 217

Asp Thr Ser Asn Leu Glu Pro
1               5

<210> SEQ ID NO 218
<211> LENGTH: 7
<212> TYPE: PRT
<213> ORGANISM: Homo Sapiens

<400> SEQUENCE: 218

Asp Ala Ser Asp Leu Asp Pro
1               5

<210> SEQ ID NO 219
<211> LENGTH: 7
<212> TYPE: PRT
<213> ORGANISM: Homo Sapiens

<400> SEQUENCE: 219

Asp Ala Ser Asn Leu Glu Ile
1               5

<210> SEQ ID NO 220
<211> LENGTH: 7
<212> TYPE: PRT
<213> ORGANISM: Homo Sapiens

<400> SEQUENCE: 220

Ala Ala Ser Thr Leu Gln Ser
1               5

<210> SEQ ID NO 221
<211> LENGTH: 7
<212> TYPE: PRT
<213> ORGANISM: Homo Sapiens

<400> SEQUENCE: 221

Val Ala Ser Thr Leu Gln Ser
1               5
```

<210> SEQ ID NO 222
<211> LENGTH: 7
<212> TYPE: PRT
<213> ORGANISM: Homo Sapiens

<400> SEQUENCE: 222

Tyr Val Ser Gln Ser Phe Ser
1               5

<210> SEQ ID NO 223
<211> LENGTH: 7
<212> TYPE: PRT
<213> ORGANISM: Homo Sapiens

<400> SEQUENCE: 223

Gly Ala Ser Ser Thr Ala Thr
1               5

<210> SEQ ID NO 224
<211> LENGTH: 7
<212> TYPE: PRT
<213> ORGANISM: Homo Sapiens

<400> SEQUENCE: 224

Leu Gly Ser Ile Arg Ala Ser
1               5

<210> SEQ ID NO 225
<211> LENGTH: 9
<212> TYPE: PRT
<213> ORGANISM: Homo Sapiens

<400> SEQUENCE: 225

Met Gln Gly Thr His Trp Pro Ile Thr
1               5

<210> SEQ ID NO 226
<211> LENGTH: 12
<212> TYPE: PRT
<213> ORGANISM: Homo Sapiens

<400> SEQUENCE: 226

Met Gln Gly Thr His Trp Pro Arg Gly Leu Phe Thr
1               5                   10

<210> SEQ ID NO 227
<211> LENGTH: 9
<212> TYPE: PRT
<213> ORGANISM: Homo Sapiens

<400> SEQUENCE: 227

Gln Gln Thr Tyr Ser Asp Pro Phe Thr
1               5

<210> SEQ ID NO 228
<211> LENGTH: 9
<212> TYPE: PRT
<213> ORGANISM: Homo Sapiens

<400> SEQUENCE: 228

Gln Gln Tyr Tyr Ser Asp Pro Phe Thr
1               5

<210> SEQ ID NO 229
<211> LENGTH: 9

```
<212> TYPE: PRT
<213> ORGANISM: Homo Sapiens

<400> SEQUENCE: 229

Gln Gln Ser Tyr Ile Thr Pro Pro Ser
1               5

<210> SEQ ID NO 230
<211> LENGTH: 9
<212> TYPE: PRT
<213> ORGANISM: Homo Sapiens

<400> SEQUENCE: 230

Met Gln Ser Ile Gln Leu Pro Leu Thr
1               5

<210> SEQ ID NO 231
<211> LENGTH: 8
<212> TYPE: PRT
<213> ORGANISM: Homo Sapiens

<400> SEQUENCE: 231

Gln Gln Tyr Asp Asn Leu Ile Thr
1               5

<210> SEQ ID NO 232
<211> LENGTH: 9
<212> TYPE: PRT
<213> ORGANISM: Homo Sapiens

<400> SEQUENCE: 232

Gln Arg Tyr Asp Asp Leu Pro Ile Thr
1               5

<210> SEQ ID NO 233
<211> LENGTH: 8
<212> TYPE: PRT
<213> ORGANISM: Homo Sapiens

<400> SEQUENCE: 233

Gln Gln Tyr Asp Asn Leu Leu Thr
1               5

<210> SEQ ID NO 234
<211> LENGTH: 8
<212> TYPE: PRT
<213> ORGANISM: Homo Sapiens

<400> SEQUENCE: 234

Gln Gln Tyr Asp Asp Leu Leu Thr
1               5

<210> SEQ ID NO 235
<211> LENGTH: 9
<212> TYPE: PRT
<213> ORGANISM: Homo Sapiens

<400> SEQUENCE: 235

Gln Gln Tyr Asp Asn Leu Pro Leu Thr
1               5

<210> SEQ ID NO 236
<211> LENGTH: 9
<212> TYPE: PRT
<213> ORGANISM: Homo Sapiens
```

```
<400> SEQUENCE: 236

Gln Gln Tyr Val Ser Leu Pro Leu Thr
 1               5

<210> SEQ ID NO 237
<211> LENGTH: 9
<212> TYPE: PRT
<213> ORGANISM: Homo Sapiens

<400> SEQUENCE: 237

Gln Gln Tyr Asp Asn Phe Pro Phe Thr
 1               5

<210> SEQ ID NO 238
<211> LENGTH: 9
<212> TYPE: PRT
<213> ORGANISM: Homo Sapiens

<400> SEQUENCE: 238

Gln Gln Phe Asp Asn Leu Pro Pro Thr
 1               5

<210> SEQ ID NO 239
<211> LENGTH: 9
<212> TYPE: PRT
<213> ORGANISM: Homo Sapiens

<400> SEQUENCE: 239

Gln Gln Tyr Tyr Thr Thr Pro Pro Thr
 1               5

<210> SEQ ID NO 240
<211> LENGTH: 9
<212> TYPE: PRT
<213> ORGANISM: Homo Sapiens

<400> SEQUENCE: 240

Gln Gln Tyr Asp Asn Leu Pro Phe Thr
 1               5

<210> SEQ ID NO 241
<211> LENGTH: 9
<212> TYPE: PRT
<213> ORGANISM: Homo Sapiens

<400> SEQUENCE: 241

Gln Lys Tyr Asn Ser Ala Pro Leu Thr
 1               5

<210> SEQ ID NO 242
<211> LENGTH: 9
<212> TYPE: PRT
<213> ORGANISM: Homo Sapiens

<400> SEQUENCE: 242

Gln Lys Tyr Asn Ser Gly Pro Phe Thr
 1               5

<210> SEQ ID NO 243
<211> LENGTH: 9
<212> TYPE: PRT
<213> ORGANISM: Homo Sapiens

<400> SEQUENCE: 243

Met Gln Ala Leu Gln Thr Pro Arg Thr
```

<210> SEQ ID NO 244
<211> LENGTH: 9
<212> TYPE: PRT
<213> ORGANISM: Homo Sapiens

<400> SEQUENCE: 244

His Gln Ser Ser Ser Leu Pro Phe Thr
1               5

<210> SEQ ID NO 245
<211> LENGTH: 9
<212> TYPE: PRT
<213> ORGANISM: Homo Sapiens

<400> SEQUENCE: 245

Gln Gln Tyr Gly Ser Ser Pro Ile Thr
1               5

<210> SEQ ID NO 246
<211> LENGTH: 9
<212> TYPE: PRT
<213> ORGANISM: Homo Sapiens

<400> SEQUENCE: 246

Leu Gln Tyr Asn Ser Tyr Pro Ile Thr
1               5

<210> SEQ ID NO 247
<211> LENGTH: 981
<212> TYPE: DNA
<213> ORGANISM: Homo Sapiens

<400> SEQUENCE: 247

```
gctagcacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag cgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggaccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac tcccatgct ggactccgac     840
ggctccttct tcctctacag caagctcacc gtggacaaga gcaggtggca gcagggggaac     900
gtcttctcat gctccgtgat gcatgaggct ctgcacaacc actacacgca gaagagcctc     960
tccctgtctc cgggtaaatg a                                               981
```

<210> SEQ ID NO 248
<211> LENGTH: 324

```
<212> TYPE: DNA
<213> ORGANISM: Homo Sapiens

<400> SEQUENCE: 248
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                            324

<210> SEQ ID NO 249
<211> LENGTH: 375
<212> TYPE: DNA
<213> ORGANISM: Homo Sapiens

<400> SEQUENCE: 249
caggtgcagc tggtgcagtc tggggctgag gtgaagaagc ctggggcctc agtgaaggtc      60
tcctgcaagg cttctggata caccttcacc gcctactata tgcactgggt gcgacaggcc     120
cctggacaag gcttgagtg gatgggatgg atcaaccccta acagtggtgg cacaaactat      180
gcacagaagt ttcagggcag ggtcaccatg accaggaca cgtccatcag cacagcctac     240
atggagctga gcaggctgag atctgacgac acggccgtgt attactgtgc gagaggtgga     300
tatagtggct acgatttggg ctactactac ggtatggacg tctggggcca agggaccacg     360
gtcaccgtct cctca                                                      375

<210> SEQ ID NO 250
<211> LENGTH: 363
<212> TYPE: DNA
<213> ORGANISM: Homo Sapiens

<400> SEQUENCE: 250
caggtgcagc tgcaggagtc gggcccagga ctggtgaagc cttcggagac cctgtccctc      60
acctgcactg tctctggtgg ctccgtcagc agtggtggtt actactggag ctggatccgg     120
cagcccccag ggaagggact ggagtggatt gggtatatct attacagtgg gagcaccaac     180
tacaacccct ccctcaagag tcgagtcacc atatcagtag acacgtccaa gaaccagttc     240
tccctgaagc tgagctctgt gaccgctgcg gacacggccg tgtattactg tgcggccggt     300
atagcagcca ctggtaccct ctttgactgc tggggccagg gaaccctggt caccgtctcc     360
tca                                                                   363

<210> SEQ ID NO 251
<211> LENGTH: 378
<212> TYPE: DNA
<213> ORGANISM: Homo Sapiens

<400> SEQUENCE: 251
caggtgcagc tggtgcagtc tggggctgag gtgaagaagc ctggggcctc agtgaaggtc      60
tcctgcaagg cttctggata caccttcacc ggctactata tacactgggt gcgacaggcc     120
cctggacaag gcttgagtg gatgggatgg atcaaccccta acagtggtgg cacaaactat     180
gcacagaagt ttcagggcag ggtcaccatg accaggaca cgtccatcag cacagcctac     240
atggagctga gcaggctgag atctgacgac acggccgtgt attactgtgc gagagatcga     300
gggcagctat ggttatggta ctactactac tacggtatgg acgtctgggg ccaagggacc     360
```

```
acggtcaccg tctcctca                                                  378

<210> SEQ ID NO 252
<211> LENGTH: 357
<212> TYPE: DNA
<213> ORGANISM: Homo Sapiens

<400> SEQUENCE: 252
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc cagcagcagc    300
tggtcctact acggtatgga cgtctggggc caagggacca cggtcaccgt ctcctca       357

<210> SEQ ID NO 253
<211> LENGTH: 387
<212> TYPE: DNA
<213> ORGANISM: Homo Sapiens

<400> SEQUENCE: 253
gaggtgcagc tggtggagtc tgggggaggc ttggtaaagc ctggggggtc ccttagactc     60
tcctgtgcag cctctggatt cactgtcagt aacgcctgga tgagctgggt ccgccaggct    120
ccagggaagg ggctggagtg ggttggccgt attaaaagca aaactgatgg tgggacaaca    180
gacaacgctg cacccgtgaa aggcagattc accatctcaa gagatgattc aaaaaacacg    240
ctgtatctgc aaatgaacag cctgaaaacc gaggacacag ccgtgtatta ctgtaccaca    300
ggagggtcat actatggac cgggcccaac tactactact acggtatgga cgtctggggc    360
caagggacca cggtcaccgt ctcctca                                        387

<210> SEQ ID NO 254
<211> LENGTH: 378
<212> TYPE: DNA
<213> ORGANISM: Homo Sapiens

<400> SEQUENCE: 254
gaggtgcagc tggtggagtc tgggggaggc ttggtaaagc ctggggggtc ccttagactc     60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gagtactatg gttcgggggg ggtttggtac tacggtatgg acgtctgggg ccaagggacc    360
acggtcaccg tctcctca                                                  378

<210> SEQ ID NO 255
<211> LENGTH: 387
<212> TYPE: DNA
<213> ORGANISM: Homo Sapiens

<400> SEQUENCE: 255
gaggtgcagc tggtggagtc tgggggaggc ttggtaaagc ctggggggtc ccttagactc     60
tcctgtgcag cctctggatt cactttcagt aacgcctgga tgagctgggt ccgccaggct    120
ccagggaagg ggctggagtg ggttggccgt attaaaagca aaactgatgg ttgggacaaca   180
```

```
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gatctccgta taactggaac tacctattac tactactact acggtatgga cgtctggggc    360
caagggacca cggtcaccgt ctcctca                                        387

<210> SEQ ID NO 256
<211> LENGTH: 360
<212> TYPE: DNA
<213> ORGANISM: Homo Sapiens

<400> SEQUENCE: 256
caggttcagc tggtgcagtc tggagctgag gtgaagaagc ctggggcctc agtgaaggtc    60
tcctgcaagg cttctggtta caccttacc agctatggta tcagctgggt gcgacaggcc    120
cctggacaag gcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagagtcg    300
tggttcgggg aggtattctt tgactactgg ggccagggaa ccctggtcac cgtctcctca    360

<210> SEQ ID NO 257
<211> LENGTH: 378
<212> TYPE: DNA
<213> ORGANISM: Homo Sapiens

<400> SEQUENCE: 257
gaggtgcagc tggtggagtc tgggggaggc ttggtaaagc ctggggggtc ccttagactc    60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gagtactatg gttcgggggg ggtttggtac tacggtatgg acgtctgggg ccaagggacc    360
acggtcaccg tctcctca                                                  378

<210> SEQ ID NO 258
<211> LENGTH: 384
<212> TYPE: DNA
<213> ORGANISM: Homo Sapiens

<400> SEQUENCE: 258
gaggtgcagc tggtggagtc tgggggaggc ttggtaaagc ctggggggtc ccttagactc    60
tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gatggggcta cggtggtaac tccggggtac tactactacg gtacggacgt ctggggccaa    360
gggaccacgg tcaccgtctc ctca                                           384

<210> SEQ ID NO 259
<211> LENGTH: 360
<212> TYPE: DNA
<213> ORGANISM: Homo Sapiens

<400> SEQUENCE: 259
```

```
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagagagtcg     300
tggttcgggg aggtattttt tgactactgg ggccagggaa ccctggtcac cgtctcctca     360
```

<210> SEQ ID NO 260
<211> LENGTH: 360
<212> TYPE: DNA
<213> ORGANISM: Homo Sapiens

<400> SEQUENCE: 260

```
caggtgcagc tggtgcagtc tggggctgag gtgaagaagc ctggggcctc agtgaaggtc      60
tcctgcaagg cttctggata cacctttacc ggctactata tgcactgggt gcgacaggcc     120
cctggacaag ggcttgaatg gatgggatgg atcaaccctaa acagtggtgg cacaaactat    180
gctcagaagt ttcagggcag ggtcaccatg accaggaca cgtccatcag cacagcctac      240
atggagctga gcagactgag atctgacgac acggccttt attactgtgc gagagacagc     300
aactggtacc acaactggtt cgaccccctgg ggccagggaa ccctggtcac cgtctcctca    360
```

<210> SEQ ID NO 261
<211> LENGTH: 360
<212> TYPE: DNA
<213> ORGANISM: Homo Sapiens

<400> SEQUENCE: 261

```
caggtgcagc tggtgcagtc tggggctgag gtgaagaagc ctggggcctc agtgaaggtc      60
tcctgcaagg cttctggata cacctttacc ggctactata tgcactgggt gcgacaggcc     120
cctggacaag ggcttgaatg gatgggatgg atcaaccctaa acagtggtgg cacaaactat    180
gctcagaagt ttcagggcag ggtcaccatg accaggaca cgtccatcag cacagcctac      240
atggagctga gcagactgag atctgacgac acggccttt attactgtgc gagagacagc     300
aactggtacc acaactggtt cgaccccctgg ggccagggaa ccctggtcac cgtctcctca    360
```

<210> SEQ ID NO 262
<211> LENGTH: 384
<212> TYPE: DNA
<213> ORGANISM: Homo Sapiens

<400> SEQUENCE: 262

```
gaggtgcagc tggtggagtc tggggggaggc ttggtaaagc ctgggggggtc ccttagactc     60 tcctgtgcag cctctggatt cactttcagt aacgcctgga tgagctgggt ccgccaggct     120
ccagggaagg ggctggagtg ggttggccgt attaaaagca aaactgatgg tgggacaaca     180
gactacgctg cacccgtgaa aggcagattc accatctcaa gagatgattc aaaaaacacg     240
ctgtatctgc aaatgaacag cctgaaaacc gaggacacag ccgtgtatta ctgtaccaca     300
gatggggcta cggtggtaac tccgggtac tactactacg gtacggacgt ctggggccaa     360
gggaccacgg tcaccgtctc ctca                                             384
```

<210> SEQ ID NO 263
<211> LENGTH: 381
<212> TYPE: DNA
<213> ORGANISM: Homo Sapiens

```
<400> SEQUENCE: 263
gaggtgcaac tggtggagtc tgggggaggc ttggtaaagc ctggggggtc ccttagactc      60
tcctgtgcag cctctggatt cactttcagt aacgcctgga tgagctgggt ccgccaggct    120
ccagggaagg ggctggagtg ggttggccgt attaaaagca aaactgatgg tgggacagca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gaaggtccct acagtgacta cggggtactac tactacggta tggacgtctg gggccaaggg    360
accacggtca ccgtctcctc a                                              381

<210> SEQ ID NO 264
<211> LENGTH: 360
<212> TYPE: DNA
<213> ORGANISM: Homo Sapiens

<400> SEQUENCE: 264
caggttcagc tggtgcagtc tggagctgag gtgaagaagc ctggggcctc agtgaaggtc      60
tcctgcaagg cttctggtta cacctttacc agctatggta tcagctgggt gcgacaggcc    120
cctggacaag ggcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagagtcg    300
tggttcgggg aggtattctt tgactactgg ggccagggaa ccctggtcac cgtctcctca    360

<210> SEQ ID NO 265
<211> LENGTH: 351
<212> TYPE: DNA
<213> ORGANISM: Homo Sapiens

<400> SEQUENCE: 265
gaggtgcagc tggtggagtc tgggggaggc ttggtacagc ctggggggtc cctgagactc      60
tcctgtgcag cctctggatt caccttcagt agctacgaca tgcactgggt ccgccaagct    120
acaggaaaag gtctggagtg ggtctcaggt attggtactg ctggtgacac atactatcca    180
ggctccgtga agggccgatt caacatctcc agagaaaatg ccaagaactc cttgtatctt    240
caaatgaaca gcctgagagc cggggacacg gctgtgtatt actgtgcaag agagggcagc    300
tggtacggct ttgactactg gggccaggga accctggtca ccgtctcctc a             351

<210> SEQ ID NO 266
<211> LENGTH: 357
<212> TYPE: DNA
<213> ORGANISM: Homo Sapiens

<400> SEQUENCE: 266
caggtgcagc tggtggagtc tgggggaggc gtggtccagc ctggggaggtc cctgagactc      60 tcctgtgcag cgtctggatt caccttcagt agctatggca tgcactgggt ccgccaggct    120
ccaggcaagg ggctggagtg ggtggcagtt atatggtatg atggaagtaa tgaatactat    180
gcagactccg tgaagggccg attcaccatc tccagagaca attccaagag cacgctgtat    240
ctgcaaatga acagcctgag agccgaggac acggctgtgt attactgtgc gcactcgtcc    300
gggaactact acgatatgga cgtctggggc caagggacca cggtcaccgt ctcctca       357

<210> SEQ ID NO 267
<211> LENGTH: 381
```

```
<212> TYPE: DNA
<213> ORGANISM: Homo Sapiens

<400> SEQUENCE: 267
gaggtgcagc tggtggagtc tgggggaggc ttggtagagc ctgggggtc ccttagactc     60 tcctgtgcag cctctggatt cactttcagt accgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaaac gaggacacag ccgtgtatta ctgtaccaca    300
gaaggtccct acagtaacta cgggtactac tactacggtg tggacgtctg gggccaaggg    360
accacggtca ccgtctcctc a                                              381

<210> SEQ ID NO 268
<211> LENGTH: 357
<212> TYPE: DNA
<213> ORGANISM: Homo Sapiens

<400> SEQUENCE: 268
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtatg atggaagtaa taatactat     180 gcagactccg tgaagggccg attcaccatc tccagagaca attccaagaa cacgctgtat    240
ctgcaaatga acagcctgag agccgaggac acggctgtgt attactgtgc gagcagctcg    300
tcaaacttct acgatatgga cgtctggggc caagggacca cggtcaccgt ctcctca       357

<210> SEQ ID NO 269
<211> LENGTH: 390
<212> TYPE: DNA
<213> ORGANISM: Homo Sapiens

<400> SEQUENCE: 269
gaggtgcagc tggtggagtc tgggggaggc ttggtaaagc ctgggggtc ccttacactc      60 tcctgtgcag cctctggatt cactttcaat aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
gaatattacc atattttgac tggttcgttc tactactcct actacggtat ggacgtctgg    360
ggccaaggga ccacggtcac cgtctcctca                                     390

<210> SEQ ID NO 270
<211> LENGTH: 351
<212> TYPE: DNA
<213> ORGANISM: Homo Sapiens

<400> SEQUENCE: 270
caggtgcagc tgcaggagtc gggcccagga ctggtgaagc cttcggagac cctgtccctc     60
acctgcactg tctctggtgg ctccatcagt aattactact ggagctggat ccggcagtcc    120
gccgggaagg gactggagtg gattggcgt atctatacca gtgggagcac ccactacaac    180
ccctccctca agagtcgaat catcatgtca gtggacacgt ccaagaacca gttctccctg    240
aagctgagct ctgtgaccgc cgcggacacg gccgtgtatt actgtgcgag agatcgagtc    300
ttctacggta tggacgtctg gggccaaggg accacggtca ccgtctcctc a             351
```

<210> SEQ ID NO 271
<211> LENGTH: 363
<212> TYPE: DNA
<213> ORGANISM: Homo Sapiens

<400> SEQUENCE: 271

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg gtggcagtt atatggtatg atggaagtta taaatactat     180
gcagactccg tgaagggccg attcaccatc tccagagaca attccaagaa cacgctgtat     240
ctgcaaatga acagcctgag agccgaggac acggctgtgt attactgtgc gagagaaggg     300
gattactccg actactacgg tatggacgtc tggggccaag gaccacggt caccgtctcc     360
tca                                                                   363
```

<210> SEQ ID NO 272
<211> LENGTH: 387
<212> TYPE: DNA
<213> ORGANISM: Homo Sapiens

<400> SEQUENCE: 272

```
caggtccagc tggtacagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcctg aagatggtga acaatctac     180
gcacagaagt tccagggcag agtcaccatg accgaggaca catctacaga cacagtttac     240
atggagctga gcagcctgag atctgaggac acggccgtgt attactgtgc aacaggggtt     300
atgattacgt ttgggggagt tatcgttggc cactcctact acggtatgga cgtctggggc     360
caagggacca cggtcaccgt ctcctca                                         387
```

<210> SEQ ID NO 273
<211> LENGTH: 372
<212> TYPE: DNA
<213> ORGANISM: Homo Sapiens

<400> SEQUENCE: 273

```
caggtccagc tggtacagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcctg aagatggtga acaatctac     180
gcacagaagt tccagggcag agtcaccatg accgaggaca catctacaga cacagcctac     240
atggagctga gcagcctgag atctgaggac acggccgtgt attactgtgc aacaagggct     300
ggaacgacgt tggcctacta ctactacgct atggacgtct ggggccaagg gaccacggtc     360
accgtctcct ca                                                         372
```

<210> SEQ ID NO 274
<211> LENGTH: 348
<212> TYPE: DNA
<213> ORGANISM: Homo Sapiens

<400> SEQUENCE: 274

```
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggaacac caactacaac     180
```

```
ccctccctca agagtcgatt caccttatca atagacacgt ccaagaacca gttctccctg    240
aggctgagct ctgtgaccgc tgcggacacg gccgtgtatt actgtgcgtg tatagcaact    300 cggcccttttg actactgggg ccagggaacc ctggtcaccg tctcctca                348
```

<210> SEQ ID NO 275
<211> LENGTH: 357
<212> TYPE: DNA
<213> ORGANISM: Homo Sapiens

<400> SEQUENCE: 275

```
caggtgcagc tggtggagtc tggggggaggc gtggtccagc ctggggaggtc cctgagactc    60 tcctgtgcag cgtcaggatt caccttcatc agctatggca tgcactgggt ccgccaggct   120
ccaggcaagg ggctggagtg ggtggcagtt atatggtatg atggaagtaa taatactat    180 gcagactccg tgaagggccg attcaccatc tccagagaca attccaagaa cacgctgtat    240
ctgcaaatga acagcctgag agccgaggac acggctgtgt attactgtgc ggatagcagt    300
ggcgactact acggtatgga cgtctggggc caagggacca cggtcaccgt ctcctca       357
```

<210> SEQ ID NO 276
<211> LENGTH: 357
<212> TYPE: DNA
<213> ORGANISM: Homo Sapiens

<400> SEQUENCE: 276

```
caggtccagc tggtacagtc tggggctgag gtgaagaagc tggggcctc agtgaaggtc     60 tcctgcaagg tttccggata caccctcact gaattatcca tgcactgggt gcgacaggct   120
cctggaaaag ggcttgagtg gatgggaggt tttgatcctg aagatggtga aacaatctac    180
gcacagaagt tccagggcag agtcaccatg accgaggaca catctacaga cacagcctat    240
atggagctga gcagcctgag atctgaggac acggccgtgt attactgtgc aacagcgggg    300
ctggaaatac ggtggttcga cccctgggc cagggaaccc tggtcaccgt ctcctca        357
```

<210> SEQ ID NO 277
<211> LENGTH: 360
<212> TYPE: DNA
<213> ORGANISM: Homo Sapiens

<400> SEQUENCE: 277

```
caggtgcagc tgcaggagtc gggcccagga ctggtgaagc cttcacagac cctgtccctc     60
acctgcactg tctctggtgg ctccatcagc agtggtggtt actactggag ctggatccgc   120
cagcacccag ggaagggcct ggagtggatt gggtacatct cttacagtgg ggacacctac    180
tacaacccgt ccctcaagag tcgacttacc atatcagtag acacgtctaa gcaccagttc    240
tccctgaggc tgagctctgt gacttccgcg gacacggccg tgtattactg tgcgagtcta    300
gacctctacg gtgactactt tgactactgg ggccagggaa ccctggtcac cgtctcctca    360
```

<210> SEQ ID NO 278
<211> LENGTH: 375
<212> TYPE: DNA
<213> ORGANISM: Homo Sapiens

<400> SEQUENCE: 278

```
caggttcagc tggtgcagtc tggagctgag gtgaagaagc tggggcctc agtgaaggtc      60 tcctgcaagg cttctggtta caccttaacc agctatggta tcagctgggt gcgacaggcc   120
cctggacaag ggcttgagtg gatgggatgg atcagcgctt acaatggtaa cccaaactat    180
```

```
gcacagaagt tccagggcag agtcaccatg accacagaca catccacgag cacagcctac    240
atggagctga ggagcctgag atctgacgac acggccgtgt attactgtgc gagagatcag    300
ggattactag ggttcgggga actcgagggg ctctttgact actggggcca gggaaccctg    360
gtcaccgtct cctca                                                     375

<210> SEQ ID NO 279
<211> LENGTH: 390
<212> TYPE: DNA
<213> ORGANISM: Homo Sapiens

<400> SEQUENCE: 279
gaggtgcagc tggtggagtc tgggggaggc ttggtaaagc ctgggggdtc ccttagactc    60
```

```
gaggtgcagc tggtggagtc tgggggaggc ttggtaaagc ctgggggdtc ccttagactc    60
tcctgtgcag cctctggatt cactttcagt aacgcctgga tgagctgggt ccgccaggct   120
ccagggaagg ggctgagtg ggttggccgt attaaaacca aaactgatgg tgggacaaca    180
gactacgctg cacccgtgaa aggcagattc accatctcaa gagatgattc acaaaacacg    240
ctgtatctgc aaatgaacag cctgaaaacc gaggacacag ccgtgtatta ctgtaccaca    300
gaatattacg gtattgtgac tggttcgttt tattactact actacggtat ggacgtctgg    360
ggccaaggga ccacggtcac cgtctcctca                                     390

<210> SEQ ID NO 280
<211> LENGTH: 321
<212> TYPE: DNA
<213> ORGANISM: Homo Sapiens

<400> SEQUENCE: 280
gacatccaga tgacccagtc tccatcctcc ctgtctgcat ctgtaggaga cagagtcacc    60
atcacttgcc aggcgagtca aaacattagc aactttttag attggtatca gcagaaacca    120
gggaaagccc ctaacctcct gatctacgat gcatccgatt tggatccagg ggtcccatca    180
aggttcagtg gaagtggatc tgggacagat tttactttca ccatcagcag cctacagcct    240
gaagatattg caacatatta ctgtcaacag tatgttagtc tcccgctcac tttcggcgga    300
gggaccaagg tggagatcaa a                                              321

<210> SEQ ID NO 281
<211> LENGTH: 336
<212> TYPE: DNA
<213> ORGANISM: Homo Sapiens

<400> SEQUENCE: 281
gataatgtga tgacccagac tccactctct ctgtccgtca cccctggaca gccggcctcc    60
atctcctgca gtcgagtca gagcctcctg catagtgatg gaagacctta tttgtattgg    120
tacctgcaga agccaggcca gcctccacag ctcctgatct atgaagcttc aaccggttc    180 tctggagtgc cagataggtt cagtggcagc gggtcaggga cagatttcac actgaaaatc    240
agccgggtgg aggctgagga tgttgggggtt tattactgca tgcaaagtat acagcttcct    300
ctcactttcg gcggagggac caaggtggag atcaaa                               336

<210> SEQ ID NO 282
<211> LENGTH: 321
<212> TYPE: DNA
<213> ORGANISM: Homo Sapiens

<400> SEQUENCE: 282
gacatccaga tgacccagtc tccatcctcc ctgtctgcat ctgtaggaga cagagtcacc    60
```

```
atcacttgcc aggcgagtca ggacattaac aactatttaa attggtatca gcagaaacca    120
gggaaagccc ctaagctcct gatctacgat gcatccaatt tggaaatagg ggtcccatca    180
aggttcagtg gaagtggatc tgggacagat ttcattttca ccatcagcag tctgcagcct    240
gaagatattg caacatatta ctgtcaacag tatgataatt tcccgttcac tttcggcgga    300
gggaccaagg tggagatcaa a                                              321
```

<210> SEQ ID NO 283
<211> LENGTH: 318
<212> TYPE: DNA
<213> ORGANISM: Homo Sapiens

<400> SEQUENCE: 283

```
gacatccaga tgacccagtc tccatcctcc ctgtctgcat ctgtaggaga cagagtcacc     60
atcacttgcc aggcgagtca ggacattaac aactatttaa attggtatca gcagaaacca    120
gggaaagccc ctaagctcct gatctacgat acatccaatt tggaaccagg ggtcccatca    180
aggttcagtg gaagtggatc tgggacagat tttactttca ccatcagcag cctgcagcct    240
gaagatattg caacatatta ctgtcaacaa tatgataatc tcctcacctt cggccaaggg    300
acacgactgg aaattaaa                                                  318
```

<210> SEQ ID NO 284
<211> LENGTH: 318
<212> TYPE: DNA
<213> ORGANISM: Homo Sapiens

<400> SEQUENCE: 284

```
gacatccaga tgacccagtc tccatcctcc ctgtctgcat ctgtaggaga cagagtcacc     60
atcacttgcc aggcgagtca ggacattagc aactatttaa attggtatca gcataaacca    120
gggaaagccc ctaaactcct gatctacgat gcatccaatt tggaaacagg ggtcccatca    180
aggttcagtg gaagtggatc tgggacagat tttactttca ccatcagcag cctgcagcct    240
gaagatattg caacatatta ctgtcaacag tatgataatc tgctcacctt cggcggaggg    300
accaaggtgg agatcaaa                                                  318
```

<210> SEQ ID NO 285
<211> LENGTH: 318
<212> TYPE: DNA
<213> ORGANISM: Homo Sapiens

<400> SEQUENCE: 285

```
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagttcct gatctacgat gcatccaatt tggaaacagg ggtcccatca    180
aggtttagtg gaagtggatc tgggacagat tttactttca ccatcagcag cctgcagcct    240
gaagatattg caacatatta ctgtcaacag tatgataatc tgatcacctt cggccaaggg    300
acacgactgg agattaaa                                                  318
```

<210> SEQ ID NO 286
<211> LENGTH: 339
<212> TYPE: DNA
<213> ORGANISM: Homo Sapiens

<400> SEQUENCE: 286

```
gacatcgtga tgacccagtc tccagactcc ctggctgtgt ctctgggcga gagggccacc     60
```

```
atcaactgca agtccagcca gagtgtttta gacagctccg acaataagaa ctacttagct    120
tggtaccagc agaaaccagg acagcctcct aagctgctca tttactgggc atctaaccgg    180
gaatccgggg tccctgaccg attcagtggc agcgggtctg ggacagattt ctctctcacc    240
atcagcagcc tgcaggctga agatgtggca gtttattact gtcagcaata ttatagtgat    300
ccattcactt tcggccctgg gaccaaagtg gatatcaaa                            339

<210> SEQ ID NO 287
<211> LENGTH: 318
<212> TYPE: DNA
<213> ORGANISM: Homo Sapiens

<400> SEQUENCE: 287
gacatccaga tgacccagtc tccatcctcc ctgtctgcat ctgtaggtga cagagtcacc     60
atcacttgcc aggcgagtca ggacattagc aactatttaa attggtatca acagaaacca    120
gggaaagccc ctaaactcct gatctacgat gcatccaatt tggaaacagg ggtcccatca    180
aggttcagtg aagtggatc tgggacagat tttactttca ccatcagcag cctacagcct    240
gaagatattg caacatatta ctgtcaacag tatgataatc tgctcacttt cggcggaggg    300
accaaggtgg agatcaaa                                                   318

<210> SEQ ID NO 288
<211> LENGTH: 339
<212> TYPE: DNA
<213> ORGANISM: Homo Sapiens

<400> SEQUENCE: 288
gacatcgtga tgacccagtc tccagactcc ctggctgtgt ctctgggcga gagggccacc     60
atcgactgca gtccagcca gggtgtttta gacagctcca acaataagaa cttcttagct    120
tggtaccagc agaaaccagg acagcctcct aagctgctca tttactgggc atctaaccgg    180
gaatccgggg tccctgtccg attcagtggc agcgggtctg ggacagattt cactctcacc    240
atcagcagcc tgcaggctga agatgtggca ctttattact gtcagcaata ttatagtgat    300
ccattcactt tcggccctgg gaccaaagtg gatatcaaa                            339

<210> SEQ ID NO 289
<211> LENGTH: 321
<212> TYPE: DNA
<213> ORGANISM: Homo Sapiens

<400> SEQUENCE: 289
gacatccaga tgacccagtc tccatcctcc ctgtctgcat ctgtaggaga cagagtcacc     60
atcacttgcc gggcaagtca gagcattagt gactatttaa attggtatca gcagaaacca    120
gggaaagccc ctaacctcct gatctatgct gcatccagtt tgcagagtgg ggtcccatca    180
aggttcagtg gcagtggatc tgggacagat ttcactctca ccatcagcag tctgcaacct    240
gaagattttg caacttactt ctgtcaacag acttacagtg acccattcac tttcggccct    300
gggaccaaag tggatatcaa a                                               321

<210> SEQ ID NO 290
<211> LENGTH: 318
<212> TYPE: DNA
<213> ORGANISM: Homo Sapiens

<400> SEQUENCE: 290
gacatccaga tgacccagtc tccatcctcc ctgtctgcat ctgtaggaga cagagtcacc     60
```

```
atcacttgcc aggcgagtca ggacattagc aactatttaa attggtatca gcagaaacca      120
gggaaagccc ctaagctcct gatctacgat gcatccaatt tggaaacagg ggtcccatca      180
aggttcagtg gaagtggatc tgggacagat tttactttca ccatcagcag cctacagcct      240
gaagatattg caacatatta ctgtcaacag tatgataatc tgctcacttt cggcggaggg      300
accaaggtgg agatcaaa                                                    318

<210> SEQ ID NO 291
<211> LENGTH: 318
<212> TYPE: DNA
<213> ORGANISM: Homo Sapiens

<400> SEQUENCE: 291
gacatccaga tgacccagtc tccatcctcc ctgtctgcat ctgtaggaga cagagtcacc       60
atcacttgcc aggcgagtca ggacattagc aactatttaa attggtatca gcagaaacca      120
gggaaagccc ctaaggtcct gatctacgat gcatccaatt tggaaacagg ggtcccatca      180
aggttcagtg gaagtggatc tgggacagat tttactttca ccatcagcag cctgcagcct      240
gaagatattg caacatatta ctgtcaacag tatgataatc tcctcacttt cggcggaggg      300
accaaggtgg agatcaaa                                                    318

<210> SEQ ID NO 292
<211> LENGTH: 339
<212> TYPE: DNA
<213> ORGANISM: Homo Sapiens

<400> SEQUENCE: 292
gacatcgtga tgacccagtc tccagactcc ctggctgtgt ctctgggcga gagggccacc       60
atcgactgca agtccagcca gagtgtttta gacagctcca acaataagaa cttcttagct      120
tggtaccagc agaaaccagg acagcctcct aagctgctca tttactgggc atctaaccgg      180
gaatccgggg tccctgaccg attcagtggc agcgggtctg ggacagattt cactctcacc      240
atcagcagcc tgcaggctga agatgtggca gtttattact gtcagcaata ttatagtgat      300
ccattcactt tcggccctgg gaccaaagtg gatatcaaa                             339

<210> SEQ ID NO 293
<211> LENGTH: 333
<212> TYPE: DNA
<213> ORGANISM: Homo Sapiens

<400> SEQUENCE: 293
gaaattgtgt tgacgcagtc tccaggcacc ctgtctttgt ctccagggga aagagccacc       60
ctctcctgca gggccagtca gagtgttagc agcggctact tagcctactt agcctggtac      120
cagcagaaac ctggccaggc tcccaggctc ctcatctatg gtgcatccag cacggccact      180
ggcatcccag acaggttcag tggcagtggg tctgggacag acttcactct caccatcagc      240
agactggagc ctgaagattt tgcagtgtat tactgtcagc agtatggtag ctcaccgatc      300
accttcggcc aagggacacg actggagatt aaa                                   333

<210> SEQ ID NO 294
<211> LENGTH: 321
<212> TYPE: DNA
<213> ORGANISM: Homo Sapiens

<400> SEQUENCE: 294
gacatccaga tgacccagtc tccatcctcc ctgtctgcat ctgtaggaga cagagtcacc       60
```

```
atcacttgcc aggcgagtca ggacattagc aacttttaa attggtatca gcagagacca      120
gggaaagccc ctaagctcct gatctacgat gcatccaatt tggaaacagg ggtcccatca      180
aggttcagtg gaagtggatc tgggacagat tttactttca ccatcagcag cctgcagcct      240
gaagatattg caacatatta ctgtcaacag tatgataatc tcccattcac tttcggccct      300
gggaccaaag tggatatcaa a                                                321

<210> SEQ ID NO 295
<211> LENGTH: 318
<212> TYPE: DNA
<213> ORGANISM: Homo Sapiens

<400> SEQUENCE: 295
gacatccaga tgacccagtc tccatcctcc ctgtctgcat ctgtaggaga cagagtcacc       60
atcacttgcc aggcgagtca ggacattagc aactatttaa attggtatca gcagaaacca      120
gggaaagccc ctaaactcct gatctacgat gcatccaatt tggaaacagg ggtcccatca      180
aggttcagtg gaagtggatc tgggacagat tttactttca ccatcagcag cctgcagcct      240
gaagattttg caacatatta ctgtcaacag tatgataatc tcctcacttt cggcggaggg      300
accaaggtgg agatcaaa                                                    318

<210> SEQ ID NO 296
<211> LENGTH: 321
<212> TYPE: DNA
<213> ORGANISM: Homo Sapiens

<400> SEQUENCE: 296
gacatccaga tgacccagtc tccatcctcc ctgtctgcat ctgtaggaga cagagtcacc       60
atcacttgcc aggcgagtca ggacattagc aactatttaa attggtatca gcagaaacca      120
ggaaaagccc ctaagctcct gatctacgat gcatccaatt tggaaacagg ggtcccatca      180
aggttcagtg gaagtggatc tgggacagat tttactttca ccatcagcag cctgcagcct      240
gaagatattg caacatatta ctgtcaacgg tatgatgatc tcccgatcac cttcggccaa      300
gggacacgac tggagattaa a                                                321

<210> SEQ ID NO 297
<211> LENGTH: 318
<212> TYPE: DNA
<213> ORGANISM: Homo Sapiens

<400> SEQUENCE: 297
gacatccaga tgacccagtc tccatcctcc ctgtctgcat ctgtgggaga cagagtcacc       60
atcacttgcc aggcgagtca ggacattagc aactatttaa attggtatca gcagagacca      120
gggaaagccc ctaagctcct gatctacgat gcatccaatt tggaaacagg ggtcccatca      180
aggttcagtg gaagtggatc tgggacagat tttactttca ccatcagcag cctgcagcct      240
gaagatattg caacatatta ctgtcaacag tatgataatc tgctcacttt cggcggaggg      300
accaaggtgg agatcaaa                                                    318

<210> SEQ ID NO 298
<211> LENGTH: 321
<212> TYPE: DNA
<213> ORGANISM: Homo Sapiens

<400> SEQUENCE: 298
gacatccaga tgacccagtc tccatcctcc ctgtctgcat ctgtaggaga cagagtcacc       60
```

```
atcacttgcc gggcgagtca gggctttagc aattatttag cctggtatca gcagaaacca    120
gggaaagttc ctaagctcct gatctatgct gcatccactt tgcagtcagg ggtcccatct    180
cggttcagtg gcagtggatc tgggacagat ttcactctca ccatcagcag cctgcagcct    240
gaagatgttg caacttatta ctgtcaaaag tataacagtg ccccgctcac tttcggcgga    300
gggaccaagg tggagatcaa a                                              321
```

<210> SEQ ID NO 299
<211> LENGTH: 321
<212> TYPE: DNA
<213> ORGANISM: Homo Sapiens

<400> SEQUENCE: 299

```
gacatccaga tgacccagtc tccatcctcc ctgtctgcat ctgtaggaga cagagtcacc     60
atcacttgcc gggcgagtca ggcattaac aattatttag cctggtatca gcagaaacca    120
gggaaagttc ctcagctcct gatctatgtt gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagtg cccattcac tttcggccct    300 gggaccaaag tggatatcaa a                                              321
```

<210> SEQ ID NO 300
<211> LENGTH: 321
<212> TYPE: DNA
<213> ORGANISM: Homo Sapiens

<400> SEQUENCE: 300

```
gacatccaga tgacccagtc tccatcctcc ctgtctgcat ctgtaggaga cagagtcacc     60
atcacttgcc gggcaagtca gagcattagc aggtatttaa attggtatca gcagaaacca    120
gggaaagccc ctaacctcct gatccatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacatta cccctcccag ttttggccag    300
gggaccaagc tggagatcaa a                                              321
```

<210> SEQ ID NO 301
<211> LENGTH: 321
<212> TYPE: DNA
<213> ORGANISM: Homo Sapiens

<400> SEQUENCE: 301

```
gacatccaga tgacccagtc tccatcctcc ctgtctgcat ctgtaggaga cagagtcacc     60
atcacttgcc gggcaagtca ggcattaga aatgatttag actggtatca gcagaaacca    120
gggaaagccc ctaagcgcct gatctatgct gcatccagtt tgcaaagtgg ggtcccatct    180
aggttcagcg gcagtggatc tgggacagaa ttcactctca caatcaacag cctgcagcct    240
gaagattttg caacttatta ctgtctacag tataatagtt acccgatcac cttcggccaa    300
gggacacgac tggagattaa a                                              321
```

<210> SEQ ID NO 302
<211> LENGTH: 321
<212> TYPE: DNA
<213> ORGANISM: Homo Sapiens

<400> SEQUENCE: 302

```
gacatccaga tgatccagtc tccttcctcc ctgtctgcat ctgtcggaga cagagtcacc     60
```

```
atcacttgcc aggcgagtca cgacattagc aactatttaa attggtatca gcagaaacca    120
gggaaagccc ctaagttcct gatctccgat gcatccaatt tggaaacagg ggtcccatca    180
aggttcagtg gaagtggatc tgggacagat tttactttca ccatcagcag cctgcagcct    240
gaagatattg caacatatta ctgtcaacag tatgataatc tcccgctcac tttcggcgga    300
gggaccaagg tggagatcaa a                                              321

<210> SEQ ID NO 303
<211> LENGTH: 336
<212> TYPE: DNA
<213> ORGANISM: Homo Sapiens

<400> SEQUENCE: 303
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtcaccacag ttcctgatct atttgggttc tattcgggcc    180
tccggggtcc ctgacaggtt cagtggcagt ggatcaggca cagattttgc actgacaatc    240
agcagagtgg aggctgagga tgttggggtt tattactgca tgcaagctct acaaactcct    300
cggacgttcg gccaagggac caaggtggaa atcaaa                              336

<210> SEQ ID NO 304
<211> LENGTH: 321
<212> TYPE: DNA
<213> ORGANISM: Homo Sapiens

<400> SEQUENCE: 304
gaaattgtgc tgactcagtc tccagacttt cagtctgtga ctccaaagga gaaagtcacc     60
atcacctgcc gggccagtca gtacattggt agtagcttac actggtacca gcagacacca    120
gatcagtctc caaagctcct catcaactat gtttcccagt ccttctcagg ggtcccctcg    180
aggttcagtg gcagtggatc tgggacagat ttcaccctca ccatcaatag cctggaagct    240
gaagatgctg caacgtatta ctgtcatcag agtagtagtt taccattcac tttcggccct    300
gggaccaaag tggatatcaa a                                              321

<210> SEQ ID NO 305
<211> LENGTH: 339
<212> TYPE: DNA
<213> ORGANISM: Homo Sapiens

<400> SEQUENCE: 305
gacatcgtga tgacccagtc tccagactcc ctggctgtgt ctctgggcgc gagggccacc     60
atctcctgca agtccagcca gagtgtttta tacagctcca acaataagaa ctacttagct    120
tggtaccagc agaaaccagg ccagcctcct aagctgctca tttactgggc atctacccgg    180
gaatccgggg tccctgaccg attcagtggc agcgggtctg ggacagattt cactctcacc    240
atcagcaccc tgcaggctga agatgtggca gtttattact gtcagcaata ttatactact    300
cctccgacgt tcggccaagg gaccaaggtg gaaatcaaa                           339

<210> SEQ ID NO 306
<211> LENGTH: 318
<212> TYPE: DNA
<213> ORGANISM: Homo Sapiens

<400> SEQUENCE: 306
gacatccaga tgacccagtc tccatcctcc ctgtctgcat ctgtaggaga cagagtcacc     60
```

```
atcacttgcc aggcgagtca ggacattaac aactatttaa attggtatca acagaaacca    120
gggaaagccc ctaaactcct gatctacgat gcatccaatt tggaaacagg ggtcccatca    180
aggttcagtg aagtggatc tgggacagat tttactttca ccatcagcag cctgcagcct     240
gaagatattg caacatatta ctgtcaacag tatgatgatc tgctcacttt cggcggaggg    300
accaaggtgg agatcaaa                                                  318
```

```
<210> SEQ ID NO 307
<211> LENGTH: 10
<212> TYPE: PRT
<213> ORGANISM: Homo Sapiens
<220> FEATURE:
<221> NAME/KEY: VARIANT
<222> LOCATION: 4
<223> OTHER INFORMATION: Xaa = Phe or Leu

<400> SEQUENCE: 307

Gly Tyr Thr Xaa Thr Ser Tyr Gly Ile Ser
 1               5                  10

<210> SEQ ID NO 308
<211> LENGTH: 17
<212> TYPE: PRT
<213> ORGANISM: Homo Sapiens
<220> FEATURE:
<221> NAME/KEY: VARIANT
<222> LOCATION: 9
<223> OTHER INFORMATION: Xaa = Thr or Pro
<220> FEATURE:
<221> NAME/KEY: VARIANT
<222> LOCATION: 15
<223> OTHER INFORMATION: Xaa = Leu or Phe

<400> SEQUENCE: 308

Trp Ile Ser Ala Tyr Asn Gly Asn Xaa Asn Tyr Ala Gln Lys Xaa Gln
 1               5                  10                  15
Gly

<210> SEQ ID NO 309
<211> LENGTH: 16
<212> TYPE: PRT
<213> ORGANISM: Homo Sapiens
<220> FEATURE:
<221> NAME/KEY: VARIANT
<222> LOCATION: 1
<223> OTHER INFORMATION: Xaa = Glu or Asp
<220> FEATURE:
<221> NAME/KEY: VARIANT
<222> LOCATION: 2
<223> OTHER INFORMATION: Xaa = Ser or Gln
<220> FEATURE:
<221> NAME/KEY: VARIANT
<222> LOCATION: 3
<223> OTHER INFORMATION: Xaa = Gly or none
<220> FEATURE:
<221> NAME/KEY: VARIANT
<222> LOCATION: 4, 5
<223> OTHER INFORMATION: Xaa = Leu or none
<220> FEATURE:
<221> NAME/KEY: VARIANT
<222> LOCATION: 6
<223> OTHER INFORMATION: Xaa = Trp or Gly
<220> FEATURE:
<221> NAME/KEY: VARIANT
<222> LOCATION: 10
<223> OTHER INFORMATION: Xaa = Val or Leu
<220> FEATURE:
<221> NAME/KEY: VARIANT
<222> LOCATION: (11)...(11)
<223> OTHER INFORMATION: Xaa = Glu or none
```

```
<220> FEATURE:
<221> NAME/KEY: VARIANT
<222> LOCATION: (12)...(12)
<223> OTHER INFORMATION: Xaa = Gly or none
<220> FEATURE:
<221> NAME/KEY: VARIANT
<222> LOCATION: (13)...(13)
<223> OTHER INFORMATION: Xaa = Phe or Leu

<400> SEQUENCE: 309

Xaa Xaa Xaa Xaa Xaa Xaa Phe Gly Glu Xaa Xaa Xaa Xaa Phe Asp Tyr
 1               5                  10                  15

<210> SEQ ID NO 310
<211> LENGTH: 17
<212> TYPE: PRT
<213> ORGANISM: Homo Sapiens
<220> FEATURE:
<221> NAME/KEY: VARIANT
<222> LOCATION: 4
<223> OTHER INFORMATION: Xaa = Gln or Ser
<220> FEATURE:
<221> NAME/KEY: VARIANT
<222> LOCATION: 8
<223> OTHER INFORMATION: Xaa = Asp or Tyr
<220> FEATURE:
<221> NAME/KEY: VARIANT
<222> LOCATION: 11
<223> OTHER INFORMATION: Xaa = Asn or Asp
<220> FEATURE:
<221> NAME/KEY: VARIANT
<222> LOCATION: 15
<223> OTHER INFORMATION: Xaa = Phe or Tyr

<400> SEQUENCE: 310

Lys Ser Ser Xaa Gly Val Leu Xaa Ser Ser Xaa Asn Lys Asn Xaa Leu
 1               5                  10                  15

Ala

<210> SEQ ID NO 311
<211> LENGTH: 7
<212> TYPE: PRT
<213> ORGANISM: Homo Sapiens
<220> FEATURE:
<221> NAME/KEY: VARIANT
<222> LOCATION: 4
<223> OTHER INFORMATION: Xaa = Asn or Thr

<400> SEQUENCE: 311

Trp Ala Ser Xaa Arg Glu Ser
 1               5

<210> SEQ ID NO 312
<211> LENGTH: 9
<212> TYPE: PRT
<213> ORGANISM: Homo Sapiens
<220> FEATURE:
<221> NAME/KEY: VARIANT
<222> LOCATION: 5
<223> OTHER INFORMATION: Xaa = Ser or Thr
<220> FEATURE:
<221> NAME/KEY: VARIANT
<222> LOCATION: 6
<223> OTHER INFORMATION: Xaa = Asp or Thr
<220> FEATURE:
<221> NAME/KEY: VARIANT
<222> LOCATION: 8
<223> OTHER INFORMATION: Xaa = Phe or Pro

<400> SEQUENCE: 312

Gln Gln Tyr Tyr Xaa Xaa Pro Xaa Thr
 1               5
```

```
<210> SEQ ID NO 313
<211> LENGTH: 10
<212> TYPE: PRT
<213> ORGANISM: Homo Sapiens
<220> FEATURE:
<221> NAME/KEY: VARIANT
<222> LOCATION: 4
<223> OTHER INFORMATION: Xaa = Phe or Val
<220> FEATURE:
<221> NAME/KEY: VARIANT
<222> LOCATION: 5
<223> OTHER INFORMATION: Xaa = Ser or Asn
<220> FEATURE:
<221> NAME/KEY: VARIANT
<222> LOCATION: 6
<223> OTHER INFORMATION: Xaa = Asn or Thr

<400> SEQUENCE: 313

Gly Phe Thr Xaa Xaa Xaa Ala Trp Met Ser
 1               5                  10

<210> SEQ ID NO 314
<211> LENGTH: 19
<212> TYPE: PRT
<213> ORGANISM: Homo Sapiens
<220> FEATURE:
<221> NAME/KEY: VARIANT
<222> LOCATION: 4
<223> OTHER INFORMATION: Xaa = Ser or Thr
<220> FEATURE:
<221> NAME/KEY: VARIANT
<222> LOCATION: 9
<223> OTHER INFORMATION: Xaa = Gly or Trp
<220> FEATURE:
<221> NAME/KEY: VARIANT
<222> LOCATION: 11
<223> OTHER INFORMATION: Xaa = Thr or Ala
<220> FEATURE:
<221> NAME/KEY: VARIANT
<222> LOCATION: 13
<223> OTHER INFORMATION: Xaa = Tyr or Asn

<400> SEQUENCE: 314

Arg Ile Lys Xaa Lys Thr Asp Gly Xaa Thr Xaa Asp Xaa Ala Ala Pro
 1               5                  10                  15
Val Lys Gly

<210> SEQ ID NO 315
<211> LENGTH: 19
<212> TYPE: PRT
<213> ORGANISM: Homo Sapiens
<220> FEATURE:
<221> NAME/KEY: VARIANT
<222> LOCATION: 1
<223> OTHER INFORMATION: Xaa = Glu, Asp or Gly
<220> FEATURE:
<221> NAME/KEY: VARIANT
<222> LOCATION: 2
<223> OTHER INFORMATION: Xaa = Tyr, Leu or none
<220> FEATURE:
<221> NAME/KEY: VARIANT
<222> LOCATION: 3
<223> OTHER INFORMATION: Xaa = Tyr, Arg or Gly
<220> FEATURE:
<221> NAME/KEY: VARIANT
<222> LOCATION: 4
<223> OTHER INFORMATION: Xaa = His, Gly, Ser, or none
<220> FEATURE:
<221> NAME/KEY: VARIANT
<222> LOCATION: 5
<223> OTHER INFORMATION: Xaa = Ile, Ala, Leu, or none
<220> FEATURE:
<221> NAME/KEY: VARIANT
<222> LOCATION: 6
<223> OTHER INFORMATION: Xaa = Leu, Val, Tyr, Pro or none
```

```
<220> FEATURE:
<221> NAME/KEY: VARIANT
<222> LOCATION: (7)...(7)
<223> OTHER INFORMATION: Xaa = Thr, Val, Tyr, Gly, Trp, or none
<220> FEATURE:
<221> NAME/KEY: VARIANT
<222> LOCATION: (8)...(8)
<223> OTHER INFORMATION: Xaa = Gly, Val, Ser, or Thr
<220> FEATURE:
<221> NAME/KEY: VARIANT
<222> LOCATION: (9)...(9)
<223> OTHER INFORMATION: Xaa = Ser, Thr, Asp, Asn, or Gly
<220> FEATURE:
<221> NAME/KEY: VARIANT
<222> LOCATION: (10)...(10)
<223> OTHER INFORMATION: Xaa = Gly, Phe, Pro, or Tyr
<220> FEATURE:
<221> NAME/KEY: VARIANT
<222> LOCATION: (11)...(11)
<223> OTHER INFORMATION: Xaa = Gly, Tyr, or Asn
<220> FEATURE:
<221> NAME/KEY: VARIANT
<222> LOCATION: (12)...(12)
<223> OTHER INFORMATION: Xaa = Val or Tyr
<220> FEATURE:
<221> NAME/KEY: VARIANT
<222> LOCATION: (13)...(13)
<223> OTHER INFORMATION: Xaa = Trp, Ser or Tyr
<220> FEATURE:
<221> NAME/KEY: VARIANT
<222> LOCATION: (17)...(17)
<223> OTHER INFORMATION: Xaa = Met, Thr, or Val

<400> SEQUENCE: 315

Xaa Xaa Xaa Xaa Xaa Xaa Xaa Xaa Xaa Xaa Xaa Xaa Xaa Tyr Tyr Gly
 1               5                   10                  15

Xaa Asp Val

<210> SEQ ID NO 316
<211> LENGTH: 11
<212> TYPE: PRT
<213> ORGANISM: Homo Sapiens
<220> FEATURE:
<221> NAME/KEY: VARIANT
<222> LOCATION: 7
<223> OTHER INFORMATION: Xaa = Ser or Asn

<400> SEQUENCE: 316

Gln Ala Ser Gln Asp Ile Xaa Asn Tyr Leu Asn
 1               5                   10

<210> SEQ ID NO 317
<211> LENGTH: 7
<212> TYPE: PRT
<213> ORGANISM: Homo Sapiens
<220> FEATURE:
<221> NAME/KEY: VARIANT
<222> LOCATION: 2
<223> OTHER INFORMATION: Xaa = Ala or Thr
<220> FEATURE:
<221> NAME/KEY: VARIANT
<222> LOCATION: 7
<223> OTHER INFORMATION: Xaa = Thr or Pro

<400> SEQUENCE: 317

Asp Xaa Ser Asn Leu Glu Xaa
 1               5

<210> SEQ ID NO 318
<211> LENGTH: 8
<212> TYPE: PRT
<213> ORGANISM: Homo Sapiens
```

```
<220> FEATURE:
<221> NAME/KEY: VARIANT
<222> LOCATION: 5
<223> OTHER INFORMATION: Xaa = Asn or Asp
<220> FEATURE:
<221> NAME/KEY: VARIANT
<222> LOCATION: 7
<223> OTHER INFORMATION: Xaa = Leu or Ile

<400> SEQUENCE: 318

Gln Gln Tyr Asp Xaa Leu Xaa Thr
 1               5

<210> SEQ ID NO 319
<211> LENGTH: 10
<212> TYPE: PRT
<213> ORGANISM: Homo Sapiens
<220> FEATURE:
<221> NAME/KEY: VARIANT
<222> LOCATION: 5
<223> OTHER INFORMATION: Xaa = Ser or Ile

<400> SEQUENCE: 319

Gly Phe Thr Phe Xaa Ser Tyr Gly Met His
 1               5                  10

<210> SEQ ID NO 320
<211> LENGTH: 17
<212> TYPE: PRT
<213> ORGANISM: Homo Sapiens
<220> FEATURE:
<221> NAME/KEY: VARIANT
<222> LOCATION: 9
<223> OTHER INFORMATION: Xaa = Glu or Lys

<400> SEQUENCE: 320

Val Ile Trp Tyr Asp Gly Ser Asn Xaa Tyr Tyr Ala Asp Ser Val Lys
 1               5                  10                  15
Gly

<210> SEQ ID NO 321
<211> LENGTH: 10
<212> TYPE: PRT
<213> ORGANISM: Homo Sapiens
<220> FEATURE:
<221> NAME/KEY: VARIANT
<222> LOCATION: 3
<223> OTHER INFORMATION: Xaa = Gly, Ser or Trp
<220> FEATURE:
<221> NAME/KEY: VARIANT
<222> LOCATION: 4
<223> OTHER INFORMATION: Xaa = Asn, Asp or Ser
<220> FEATURE:
<221> NAME/KEY: VARIANT
<222> LOCATION: 5
<223> OTHER INFORMATION: Xaa = Tyr or Phe
<220> FEATURE:
<221> NAME/KEY: VARIANT
<222> LOCATION: 7
<223> OTHER INFORMATION: Xaa = Asp or Gly

<400> SEQUENCE: 321

Ser Ser Xaa Xaa Xaa Tyr Xaa Met Asp Val
 1               5                  10

<210> SEQ ID NO 322
<211> LENGTH: 11
<212> TYPE: PRT
<213> ORGANISM: Homo Sapiens
```

```
<220> FEATURE:
<221> NAME/KEY: VARIANT
<222> LOCATION: 4
<223> OTHER INFORMATION: Xaa = Gln or His
<220> FEATURE:
<221> NAME/KEY: VARIANT
<222> LOCATION: 7
<223> OTHER INFORMATION: Xaa = Ser or Asn
<220> FEATURE:
<221> NAME/KEY: VARIANT
<222> LOCATION: 9
<223> OTHER INFORMATION: Xaa = Phe or Tyr

<400> SEQUENCE: 322

Gln Ala Ser Xaa Asp Ile Xaa Asn Xaa Leu Asn
 1               5                  10

<210> SEQ ID NO 323
<211> LENGTH: 7
<212> TYPE: PRT
<213> ORGANISM: Homo Sapiens
<220> FEATURE:
<221> NAME/KEY: VARIANT
<222> LOCATION: 7
<223> OTHER INFORMATION: Xaa = Thr or Ile

<400> SEQUENCE: 323

Asp Ala Ser Asn Leu Glu Xaa
 1               5

<210> SEQ ID NO 324
<211> LENGTH: 9
<212> TYPE: PRT
<213> ORGANISM: Homo Sapiens
<220> FEATURE:
<221> NAME/KEY: VARIANT
<222> LOCATION: 2
<223> OTHER INFORMATION: Xaa = Gln or Arg
<220> FEATURE:
<221> NAME/KEY: VARIANT
<222> LOCATION: 5
<223> OTHER INFORMATION: Xaa = Asn or Asp
<220> FEATURE:
<221> NAME/KEY: VARIANT
<222> LOCATION: 6
<223> OTHER INFORMATION: Xaa = Leu or Phe
<220> FEATURE:
<221> NAME/KEY: VARIANT
<222> LOCATION: 8
<223> OTHER INFORMATION: Xaa = Phe, Leu or Ile

<400> SEQUENCE: 324

Gln Xaa Tyr Asp Xaa Xaa Pro Xaa Thr
 1               5

<210> SEQ ID NO 325
<211> LENGTH: 12
<212> TYPE: DNA
<213> ORGANISM: Homo Sapiens

<400> SEQUENCE: 325
gggaaaggga aa                                                          12

<210> SEQ ID NO 326
<211> LENGTH: 203
<212> TYPE: PRT
<213> ORGANISM: Homo Sapiens
```

```
<400> SEQUENCE: 326

Ile Pro Val Ile Glu Pro Ser Val Pro Glu Leu Val Val Lys Pro Gly
 1               5                  10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Leu
            180                 185                 190

Val Arg Ile Arg Gly Glu Ala Ala Gln Ile Val
            195                 200
```

HUMAN C-FMS ANTIGEN BINDING PROTEINS

CROSS-REFERENCE TO RELATED APPLICATIONS

This application claims priority to U.S. Provisional Application No. 60/957,148 filed on Aug. 21, 2007, and U.S. Provisional Application No. 61/084,588 filed on Jul. 29, 2008, the disclosures of which are incorporated herein by reference in their entireties for all purposes.

REFERENCE TO SEQUENCE LISTING

The present application is being filed along with a Sequence Listing in electronic format. The Sequence Listing is provided as a file entitled APMOL.007A.TXT, created Aug. 19, 2008, which is 309 KB in size. The information in the electronic format of the Sequence Listing is incorporated herein by reference in its entirety.

BACKGROUND

Many human and mouse tumor cell lines secrete the cytokine CSF-1 (Colony Stimulating Factor-1, also known as Macrophage-Colony Stimulating Factor, M-CSF) that in turn attracts, promotes the survival, and activates monocyte/macrophage cells through the receptor c-fms (Feline McDonough Strain). Tumor associated macrophages (TAMs) (also known as tumor infiltrating macrophages (TIMs)) can be the major component of the tumor stroma comprising as much as 50% of the cell tumor mass. Kelly et al., 1988, *Br. J. Cancer* 57:174-177; Leek et al., 1994, *J. Leukoc. Biol.* 56:423-435. In surveys of primary human tumors, there is widespread evidence for CSF-1 mRNA expression. In addition, many studies have demonstrated that elevated serum CSF-1, the number of TAMs, or the presence of tissue CSF-1 and/or c-fms are associated with a poor prognosis for cancer patients.

TAMs support tumor growth, metastasis and survival by a variety of means, including direct mitogenic activity on tumor cells through secretion of PDGF, TGF-β and EGF and metastasis through production of ECM-degrading enzymes (reviewed in Leek and Harris, 2002, *J. Mammary Gland Biol and Neoplasia* 7:177-189 and Lewis and Pollard, 2006, *Cancer Res* 66:605-612). Another important means of tumor support by TAMs is the contribution to neo-vascularization of tumors via production of various proangiogenic factors such as COX-2, VEGFs, FGFs, EGF, nitric oxide, angiopoietins, and MMPs. Dranoff et al., 2004, *Nat. Rev. Cancer* 4:11-22; MacMicking et al., 1997, *Annu. Rev. Immunol.* 15:323-350; Mantovani et al., 1992, *Immunol. Today* 13:265-270. In addition, CSF-1-derived macrophages can be immunosuppressive via production of various factors such as prostaglandins, indolamine 2,3 dioxigenase, nitric oxide, IL-10, and TGFβ. MacMicking et al., 1997, *Annu. Rev. Immunol.* 15:323-350; Bronte et al., 2001, *J. Immunother.* 24:431-446.

CSF-1 is expressed both as a membrane-bound and as a soluble cytokine (Cerretti et al., 1988, *Mol. Immunol.* 25:761-770; Dobbin et al., 2005, *Bioinformatics* 21:2430-2437; Wong et al., 1987, *Biochem. Pharmacol.* 36:4325-4329) and regulates the survival, proliferation, chemotaxis and activation of macrophages and their precursors (Bourette et al., 2000, *Growth Factors* 17:155-166; Cecchini et al., 1994, *Development* 120:1357-1372; Hamilton, 1997, *J. Leukoc. Biol.* 62:145-155; Hume, 1985, *Sci. Prog.* 69:485-494; Sasmono and Hume, in: *The innate immune response to infection* (eds. Kaufmann, S., Gordon, S. & Medzhitov, R.) 71-94 (ASM Press, New York, 2004); Ross and Auger, in: *The macrophage* (eds. Burke, B. & Lewis, C.) (Oxford University Press, Oxford, 2002)).

The cognate receptor, which is the c-fms proto-oncogene (also known as M-CSFR, CSF-1R or CD115), is a 165-kD glycoprotein with an associated tyrosine kinase activity and belongs to the class III receptor tyrosine kinase family that includes PDGFR-α, PDGFR-β, VEGFR1, VEGFR2, VEGFR3, Flt3 and c-kit. Blume-Jensen and Hunter, 2001, *Nature* 411:355-365; Schlessinger and Ullrich, 1992, *Neuron* 9:383-391; Sherr et al., 1985 *Cell* 41:665-676; van der Geer et al., 1994, *Annu. Rev. Cell. Biol.* 10:251-337. The oncogenic form of c-fms, v-fms, which is carried by the McDonough strain of feline sarcoma virus is mutated to confer constitutively activated protein kinase activity (Sherr et al., 1985, *Cell* 41:665-676; Roussel and Sherr, 2003, *Cell Cycle* 2: 5-6). Expression of c-fms in normal cells is restricted to myelomonocytic cells (including monocytes, tissue macrophages, Kupffer cells, Langerhans cells, microglial cells and osteoclasts), hematopoietic precursors and trophoblasts. Arai et al., 1999, *J. Exp. Med.* 190:1741-1754; Dai et al., 2002, *Blood* 99:111-120; Pixley and Stanley, 2004, *Trends Cell Biol.* 14:628-638. Expression of c-fms has also been demonstrated in some tumor cells (Kirma et al., 2007, *Cancer Res* 67:1918-1926). A variety of in vitro studies and analyses of mutant mice demonstrate that CSF-1 is a ligand for c-fms (see, e.g., Bourette and Rohrschneider, 2000, *Growth Factors* 17:155-166; Wiktor-Jedrzejczak et al., 1990, *Proc. Natl. Acad. Sci. USA.* 87:4828-4832; Yoshida et al., 1990, *Nature* 345:442-444; van Wesenbeeck and van Hul, 2005, *Crit. Rev. Eukaryot. Gene Expr.* 15:133-162). Binding of CSF-1 to c-fms induces autophosphorylation of the receptor at particular sites that result in downstream activation of signaling pathways including PI3-K/AKT and Ras/Raf/MEK/MAPK and macrophage differentiation is mediated primarily through persistent MEK activity (Gosse et al., 2005, *Cellular Signaling* 17:1352-1362). Very recent evidence indicates that interleukin-34 (IL-34) is also a ligand for c-fms (Lin, et al. 2008, *Science* 320:807-811).

SUMMARY

Antigen-binding proteins that bind c-fms, including human c-fms, are described herein. The human c-fms antigen-binding proteins were found to inhibit, interfere with, or modulate at least one of the biological responses related to c-fms, and, as such, are useful for ameliorating the effects of c-fms-related diseases or disorders. Binding of certain antigen-binding proteins to c-fms can, therefore, have one or more of the following activities: inhibiting, interfering with, or modulating c-fms-CSF-1 binding or signaling, inhibiting c-fms-IL-34 binding or signaling, reducing monocyte migration into tumors, and/or reducing the accumulation of tumor-associated macrophages (TAMs).

One embodiment includes expression systems, including cell lines, for the production of c-fms receptor antigen binding proteins and methods for diagnosing and treating diseases related to human c-fms.

Some of the isolated antigen-binding proteins that are described comprise (A) one or more heavy chain complementary determining regions (CDRHs) selected from the group consisting of: (i) a CDRH1 selected from the group consisting of SEQ ID NOs:136-147; (ii) a CDRH2 selected from the group consisting of SEQ ID NOs:148-164; (iii) a CDRH3 selected from the group consisting of SEQ ID NOs:165-190; and (iv) a CDRH of (i), (ii) and (iii) that contains one or more amino acid substitutions, deletions or insertions that collectively total no more than four amino acids; (B) one or more light chain complementary determining regions (CDRLs) selected from the group consisting of: (i) a CDRL1 selected from the group consisting of SEQ ID NOs:191-210; (ii) a CDRL2 selected from the group consisting of SEQ ID NOs: 211-224; (iii) a CDRL3 selected from the group consisting of SEQ ID NOs:225-246; and (iv) a CDRL of (i), (ii) and (iii) that contains one or more amino acid substitutions, deletions or insertions that collectively total no more than four amino acids; or (C) one or more heavy chain CDRHs of (A) and one or more light chain CDRLs of (B).

In one embodiment, the isolated antigen-binding protein may comprise at least one or two CDRH of the above-mentioned (A) and at least one or two CDRL of the above-mentioned (B). In yet another aspect, the isolated antigen-binding protein includes a CDRH1, a CDRH2, a CDRH3, a CDRL1, a CDRL2 and a CDRL3.

In certain antigen binding proteins, the CDRH of the above-mentioned (A) is further selected from the group consisting of: (i) a CDRH1 selected from the group consisting of SEQ ID NOs:136-147; (ii) a CDRH2 selected from the group consisting of SEQ ID NOs:148-164; (iii) a CDRH3 selected from the group consisting of SEQ ID NOs:165-190; and (iv) a CDRH of (i), (ii) and (iii) that contains one or more amino acid substitutions, deletions or insertions of no more than two amino acids; the CDRL of the above-mentioned (B) is selected from the group consisting of: (i) a CDRL1 selected from the group consisting of SEQ ID NOs:191-210; (ii) a CDRL2 selected from the group consisting of SEQ ID NOs: 211-224; (iii) a CDRL3 amino acid sequence selected from the group consisting of SEQ ID NOs:225-246; and (iv) a CDRL of (i), (ii) and (iii) that contains one or more amino acid substitutions, deletions or insertions of no more than two amino acids; or (C) one or more heavy chain CDRHs of (A) and one or more light chain CDRLs of (B).

In yet another embodiment, the isolated antigen-binding protein may comprise (A) a CDRH selected from the group consisting of (i) a CDRH1 selected from the group consisting of SEQ ID NOs:136-147; (ii) a CDRH2 selected from the group consisting of SEQ ID NOs:148-164; and (iii) a CDRH3 selected from the group consisting of SEQ ID NOs:165-190; (B) a CDRL selected from the group consisting of (i) a CDRL1 selected from the group consisting of SEQ ID NOs: 191-210; (ii) a CDRL2 selected from the group consisting of SEQ ID NOs:211-224; and (iii) a CDRL3 selected from the group consisting of SEQ ID NOs:225-246; or (C) one or more heavy chain CDRHs of (A) and one or more light chain CDRLs of (B). In one embodiment, the isolated antigen-binding protein may include (A) a CDRH1 of SEQ ID NOs: 136-147, a CDRH2 of SEQ ID NOs:148-164, and a CDRH3 of SEQ ID NOs:165-190, and (B) a CDRL1 of SEQ ID NOs:191-210, a CDRL2 of SEQ ID NOs:211-224, and a CDRL3 of SEQ ID NOs:225-246. In another embodiment, the variable heavy chain ($V_H$) has at least 90% sequence identity with an amino acid sequence selected from the group consisting of SEQ ID NOs:70-101, and/or the variable light chain ($V_L$) has at least 90% sequence identity with an amino acid sequence selected from the group consisting of SEQ ID NOs:102-135. In a further embodiment, the $V_H$ is selected from the group consisting of SEQ ID NOs:70-101, and/or the $V_L$ is selected from the group consisting of SEQ ID NOs:102-135.

In another aspect, an isolated antigen binding protein is provided that specifically binds to an epitope containing the c-fms subdomains Ig-like 1-1 and Ig-like 1-2 of human c-fms.

In yet another aspect, an isolated antigen binding protein is provided that binds c-fms that comprises: (A) one or more heavy chain CDRs (CDRHs) selected from the group consisting of (i) a CDRH1 with at least 80% sequence identity to SEQ ID NOs:136-147; (ii) a CDRH2 with at least 80% sequence identity to SEQ ID NOs:148-164; and (iii) a CDRH3 with at least 80% sequence identity to SEQ ID NOs: 165-190; (B) one or more light chain CDRs (CDRLs) selected from the group consisting of: (i) a CDRL1 with at least 80% sequence identity to SEQ ID NOs:191-210; (ii) a CDRL2 with at least 80% sequence identity to SEQ ID NOs: 211-224; and (iii) a CDRL3 with at least 80% sequence identity to SEQ ID NOs:225-246; or (C) one or more heavy chain CDRHs of (A) and one or more light chain CDRLs of (B). In one embodiment, the isolated antigen-binding protein includes (A) one or more CDRHs selected from the group consisting of: (i) a CDRH1 with at least 90% sequence identity to SEQ ID NOs:136-147; (ii) a CDRH2 with at least 90% sequence identity to SEQ ID NOs:148-164; and (iii) a CDRH3 with at least 90% sequence identity to SEQ ID NOs: 165-190; (B) one or more CDRLs selected from the group consisting of: (i) a CDRL1 with at least 90% sequence identity to SEQ ID NOs:191-210; (ii) a CDRL2 with at least 90% sequence identity to SEQ ID NOs:211-224; and (iii) a CDRL3 with at least 90% sequence identity to SEQ ID NOs: 225-246; or (C) one or more heavy chain CDRHs of (A) and one or more light chain CDRLs of (B).

Another embodiment is an isolated antigen-binding protein that binds c-fms, the antigen-binding protein including one or a combination of CDRs having the consensus sequences described below. Groups A, B, and C refer to sequences derived from phylogenetically related clones. In one aspect, the CDRs from the various groups may be mixed and matched. In another aspect, the antigen binding protein comprises two or more CDRHs from one and the same group A, B, or C. In again another aspect, the antigen binding protein comprises two or more CDRLs from the same group A, B, or C. In again another aspect, the antigen binding protein comprises at least two or three CDRHs, and/or at least two or three CDRLs from the same group A, B, or C. The consensus sequences for the different groups are as follows:

Group A: (a) a CDRH1 of the generic formula GYTX$_1$TSYGIS (SEQ ID NO:307), wherein X$_1$ is selected from the group consisting of F and L; (b) a CDRH2 of the generic formula WISAYNGNX$_1$NYAQKX$_2$QG (SEQ ID NO:308), wherein X$_1$ is selected from the group consisting of T and P, and X$_2$ is selected from the group consisting of L and F; (c) a CDRH3 of the generic formula X$_1$X$_2$X$_3$X$_4$X$_5$FGEX$_6$X$_7$X$_8$X$_9$FDY (SEQ ID NO:309), wherein X$_1$ is selected from the group consisting of E and D, X$_2$ is selected from the group consisting of S and Q, X$_3$ is selected from the group consisting of G and no amino acid, X$_4$ is selected from the group consisting of L and no amino acid, X$_5$ is selected from the group consisting of W and G, X$_6$ is selected from the group consisting of V and L, X$_7$ is selected from the group consisting of E and no amino acid, X$_8$ is selected from the group consisting of G and no amino acid, and X$_9$ is selected from the group consisting of F and L; (d) a CDRL 1 of the generic formula KSSX$_1$GVLX$_2$SSX$_3$NKNX$_4$LA (SEQ ID NO:310), wherein X$_1$ is selected from the group consisting of Q and S, X$_2$ is selected from the group consisting of D and Y, X$_3$ is selected from the group consisting of N and D, and X$_4$ is selected from the group consisting of F and Y; (e) a CDRL2 of the generic formula WASX$_1$RES (SEQ ID NO:311), wherein X$_1$ is selected from the group consisting of N and T; and f. a CDRL3 of the generic formula QQYYX$_1$X$_2$PX$_3$T (SEQ ID NO:312), wherein X$_1$ is selected from the group consisting of S and T, $X_2$ is selected from the group consisting of D and T, and $X_3$ is selected from the group consisting of F and P.

Group B: (a) a CDRH1 having the generic formula GFTX$_1$X$_2$X$_3$AWMS (SEQ ID NO:313), wherein $X_1$ is selected from the group consisting of F and V, $X_2$ is selected from the group consisting of S and N, and $X_3$ is selected from the group consisting of N and T; (b) a CDRH2 having the generic formula RIKX$_1$KTDGX$_2$TX$_3$DX$_4$AAPVKG (SEQ ID NO:314), wherein $X_1$ is selected from the group consisting of S and T, $X_2$ is selected from the group consisting of G and W, $X_3$ is selected from the group consisting of T and A, and $X_4$ is selected from the group consisting of Y and N; (c) a CDRH3 having the generic formula X$_1$X$_2$X$_3$X$_4$X$_5$X$_6$X$_7$X$_8$X$_9$X$_{10}$X$_{11}$X$_{12}$X$_{13}$YYGX$_{14}$DV (SEQ ID NO:315), wherein $X_1$ is selected from the group consisting of E, D and G, $X_2$ is selected from the group consisting of Y, L and no amino acid, $X_3$ is selected from the group consisting of Y, R, G and no amino acid, $X_4$ is selected from the group consisting of H, G, S and no amino acid, $X_5$ is selected from the group consisting of I, A, L and no amino acid, $X_6$ is selected from the group consisting of L, V, T, P and no amino acid, $X_7$ is selected from the group consisting of T, V, Y, G, W and no amino acid, $X_8$ is selected from the group consisting of G, V, S and T, $X_9$ is selected from the group consisting of S, T, D, N and G, $X_{10}$ is selected from the group consisting of G, F, P, and Y, $X_{11}$ is selected from the group consisting of G, Y and N, $X_{12}$ is selected from the group consisting of V and Y, $X_{13}$ is selected from the group consisting of W, S and Y, and $X_{14}$ is selected from the group consisting of M, T and V; (d) a CDRL1 having the generic formula QASQDIX$_1$NYLN (SEQ ID NO:316), wherein $X_1$ is selected from the group consisting of S and N; (e) a CDRL2 having the generic formula DX$_1$SNLEX$_2$ (SEQ ID NO:317), wherein $X_1$ is selected from the group consisting of A and T, and $X_2$ is selected from the group consisting of T and P; and (f) a CDRL3 having the generic formula QQYDX$_1$LX$_2$T (SEQ ID NO:318), wherein $X_1$ is selected from the group consisting of N and D, and $X_2$ is selected from the group consisting of L and I.

Group C: (a) a CDRH1 having the generic formula GFTFX$_1$SYGMH (SEQ ID NO:319), wherein $X_1$ is selected from the group consisting of S and I; (b) a CDRH2 having the generic formula VIWYDGSNX$_1$YYADSVKG (SEQ ID NO:320), wherein $X_1$ is selected from the group consisting of E and K; (c) a CDRH3 having the generic formula SSX$_1$X$_2$X$_3$YX$_4$MDV (SEQ ID NO:321), wherein $X_1$ is selected from the group consisting of G, S and W, $X_2$ is selected from the group consisting of N, D and S, $X_3$ is selected from the group consisting of Y and F, and $X_4$ is selected from the group consisting of D and G; (d) a CDRL1 having the generic formula QASX$_1$DIX$_2$NX$_3$LN (SEQ ID NO:322), wherein $X_1$ is selected from the group consisting of Q and H, $X_2$ is selected from the group consisting of S and N, and $X_3$ is selected from the group consisting of F and Y; (e) a CDRL2 having the generic formula DASNLEX$_1$ (SEQ ID NO:323), wherein $X_1$ is selected from the group consisting of T and I; and (f) a CDRL3 having the generic formula QX$_1$YDX$_2$X$_3$PX$_4$T (SEQ ID NO:324), wherein $X_1$ is selected from the group consisting of Q and R, $X_2$ is selected from the group consisting of N and D, $X_3$ is selected from the group consisting of L and F, and $X_4$ is selected from the group consisting of F, L and I.

In yet another embodiment, the isolated antigen binding protein described hereinabove comprises a first amino acid sequence comprising at least one CDRH and a second amino acid sequence comprising at least one CDRL. In one embodiment, the first and the second amino acid sequences are covalently bonded to each other. In a further embodiment, the first amino acid sequence of the isolated antigen-binding protein includes the CDRH3 of SEQ ID NOs:165-190, CDRH2 of SEQ ID NOs:148-164, and CDRH1 of SEQ ID NOs:136-147, and the second amino acid sequence of the isolated antigen binding protein comprises the CDRL3 of SEQ ID NOs:225-246, CDRL2 of SEQ ID NOs:211-224, and CDRL1 of SEQ ID NOs:191-210.

In one aspect, the isolated antigen-binding proteins provided herein can be a monoclonal antibody, a polyclonal antibody, a recombinant antibody, a human antibody, a humanized antibody, a chimeric antibody, a multispecific antibody, or an antibody fragment thereof. In another embodiment, the antibody fragment of the isolated antigen-binding proteins can be an Fab fragment, an Fab' fragment, an F(ab')$_2$ fragment, an Fv fragment, a diabody, or a single chain antibody molecule. In a further embodiment, the isolated antigen binding protein is a human antibody and can be of the IgG1-, IgG2-, IgG3-, or IgG4-type.

In yet another aspect, the isolated antigen-binding protein can compete for binding to the extracellular portion of human c-fms with an antigen binding protein of one of the isolated antigen-binding proteins provided. In one embodiment, the isolated antigen binding protein can reduce monocyte chemotaxis, inhibit monocyte migration into tumors, inhibit accumulation of tumor associated macrophage in a tumor or inhibit accumulation of macrophages in a disease tissue when administered to a patient.

In a further aspect, also provided are isolated nucleic acid molecules that encode the antigen-binding proteins that bind to c-fms. In some instances, the isolated nucleic acid molecules are operably-linked to a control sequence.

In another aspect, also provided are expression vectors and host cells transformed or transfected with the expression vectors that comprise the aforementioned isolated nucleic acid molecules that encode antigen-binding proteins that can bind to c-fms.

In another aspect, also provided are methods of preparing the antigen-binding proteins that includes the step of preparing the antigen binding protein from a host cell that secretes the antigen-binding protein.

In yet another aspect, a pharmaceutical composition is provided comprising at least one of the aforementioned antigen-binding proteins provided and a pharmaceutically acceptable excipient. In one embodiment, the pharmaceutical composition may comprise an additional active agent that is selected from the group consisting of a radioisotope, radionuclide, a toxin, or a therapeutic and a chemotherapeutic group.

Embodiments of the invention further provide a method for treating or preventing a condition associated with c-fms in a patient, comprising administering to a patient an effective amount of at least one isolated antigen-binding protein. In one embodiment, the condition is cancer that is selected from the group consisting of breast cancer, prostate cancer, colorectal cancer, endometrial adenocarcinoma, leukemia, lymphoma, melanoma, esophageal squamous cell cancer, gastric cancer, astrocytic cancer, endometrial cancer, cervical cancer, bladder cancer, renal cancer, bladder cancer, lung cancer, and ovarian cancer.

In another aspect, the invention provides a method of inhibiting binding of CSF-1 to the extracellular portion of c-fms in a patient comprising administering an effective amount of at least one antigen-binding protein provided herein.

In yet another aspect, also provided is a method of inhibiting autophosphorylation of human c-fms in a patient comprising administering an effective amount of at least one antigen binding protein provided herein.

Further provided, as yet another aspect, is a method of reducing monocyte chemotaxis in a patient comprising administering an effective amount of at least one antigen binding protein.

In one aspect, also provided is a method of inhibiting monocyte migration into tumors in a patient comprising administering an effective amount of at least one antigen binding protein.

In another aspect, also provided is a method of inhibiting accumulation of tumor associated macrophage in a tumor in a patient comprising administering an effective amount of at least one antigen binding protein.

These and other aspects will be described in greater detail herein. Each of the aspects provided can encompass various embodiments provided herein. It is therefore anticipated that each of the embodiments involving one element or combinations of elements can be included in each aspect described. Other features, objects, and advantages of the disclosed are apparent in the detailed description that follows.

BRIEF DESCRIPTION OF THE DRAWINGS

FIG. 1A shows a sequence comparison of the heavy chain variable regions provided herein. FIG. 1B shows a sequence comparison of the light chain variable regions provided herein. The CDR and framework regions are indicated.

FIG. 3 demonstrates the inhibition of AML-5 proliferation by the various hybridoma anti-c-fms supernatants.

FIG. 8 shows the amino sequence (SEQ ID NO:1) of the extracellular domain region of human c-fms.

DETAILED DESCRIPTION

Figure 2:
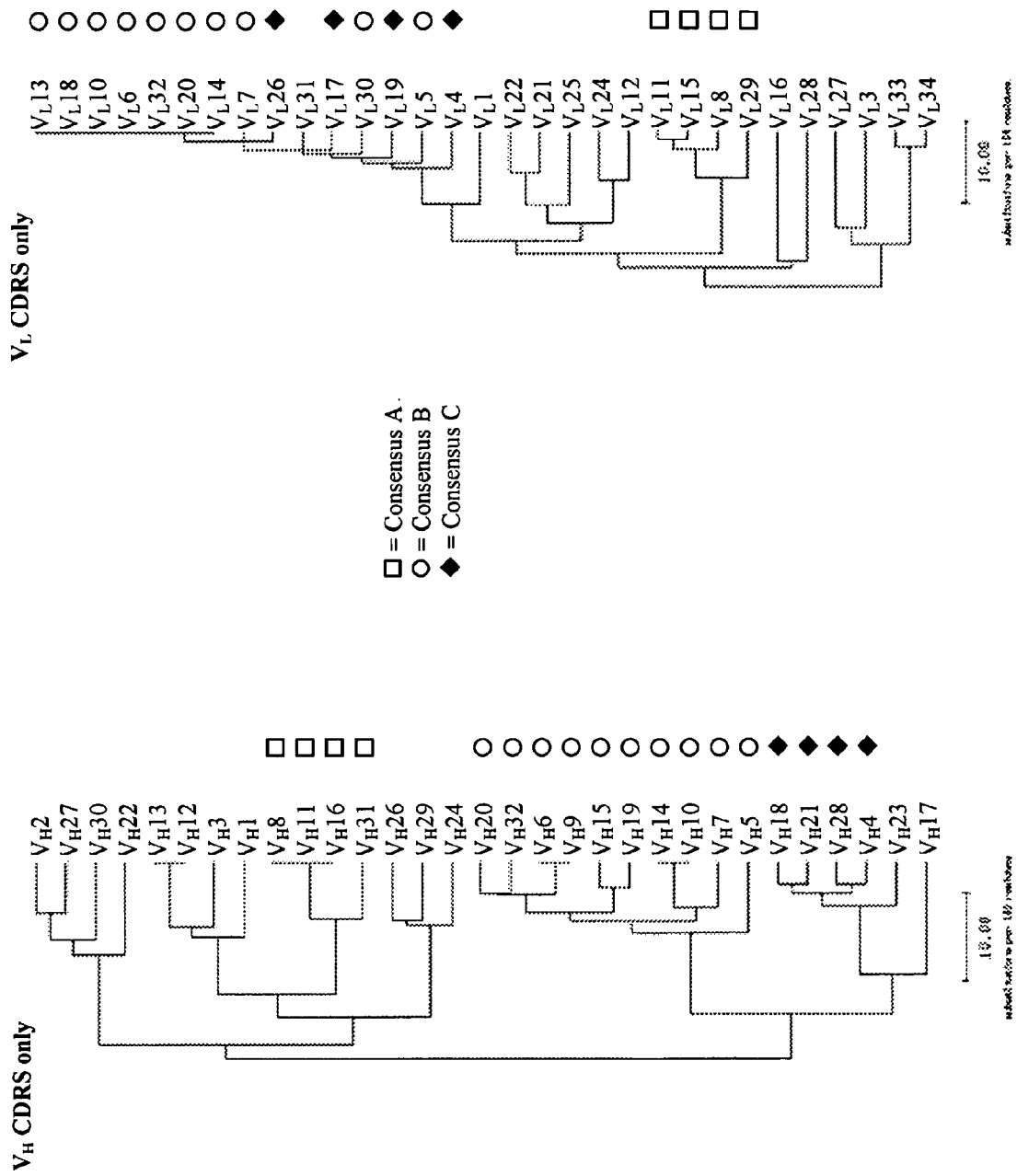
FIG. 2 shows the lineage analysis for 29 anti-c-fms hybridomas. Amino acid sequences corresponding to either the variable heavy ($V_H$) or variable light ($V_L$) domain of all cloned hybridomas were aligned and compared to one another to resolve antibody diversity. Dendrograms representing these comparative alignments are shown wherein horizontal branch length corresponds to the relative number of substitutions (differences) between any two sequences or sequence clades (groups of closely related sequences). Sequences grouped together for determination of consensus sequences are indicated.

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only, and is not intended to limit the scope of the disclosed, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

Definitions

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transduction" means the transfer of genes from one bacterium to another, usually by bacteriophage. "Transduction" also refers to the acquisition and transfer of eukaryotic cellular sequences by replication defective retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, Molecular Cloning: A Laboratory Manual, supra; Davis et al., 1986, *Basic Methods in Molecular Biology*, Elsevier; Chu et al., 1981, *Gene* 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The terms "polypeptide" or "protein" are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass c-fms antigen-binding proteins, antibodies, or sequences that have deletions from, additions to, and/or substitutions of one or more amino acids of an antigen-binding protein. The term "polypeptide fragment" refers to a polypeptide that has an amino-terminal deletion, a carboxyl-terminal deletion, and/or an internal deletion as compared with the full-length protein. Such fragments may also contain modified amino acids as compared with the full-length protein. In certain embodiments, fragments are about five to 500 amino acids long. For example, fragments may be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a c-fms-binding antibody, useful fragments include but are not limited to a CDR region, a variable domain of a heavy or light chain, a portion of an antibody chain or just its variable region including two CDRs, and the like.

The term "isolated protein" referred means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins.

A "derivative" of a polypeptide is a polypeptide (e.g., an antigen binding protein, or an antibody) that has been chemically modified in some manner distinct from insertion, deletion, or substitution variants, e.g., via conjugation to another chemical moiety.

The term "naturally occurring" as used throughout the specification in connection with biological materials such as polypeptides, nucleic acids, host cells, and the like, refers to materials which are found in nature.

An "antigen binding protein" as used herein means a protein that specifically binds a specified target antigen, such as c-fms or human c-fms.

An antigen binding protein is said to "specifically bind" its target antigen when the dissociation constant ($K_D$) is $\leq 10^{-8}$ M. The antibody specifically binds antigen with "high affinity" when the $K_D$ is $\leq 5 \times 10^{-9}$ M, and with "very high affinity" when the $K_D$ is $\leq 5 \times 10^{-10}$ M. In one embodiment, the antibody has a $K_D$ of $\leq 10^{-9}$ M and an off-rate of about $1 \times 10^{-4}$/sec. In one embodiment, the off-rate is about $1 \times 10^{5}$/sec. In other embodiments, the antibodies will bind to c-fms, or human c-fms with a $K_D$ of between about $10^{-8}$ M and $10^{-10}$ M, and in yet another embodiment it will bind with a $K_D \leq 2 \times 10^{-10}$.

"Antigen binding region" means a protein, or a portion of a protein, that specifically binds a specified antigen. For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs"). Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen.

In certain aspects, recombinant antigen binding proteins that bind c-fms protein, or human c-fms, are provided. In this context, a "recombinant protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" as such is a species of an antigen binding protein. An intact antibody generally will comprise at least two full-length heavy chains and two full-length light chains, but in some instances may include fewer chains such as antibodies naturally occurring in camelids which may comprise only heavy chains. Antibodies may be derived solely from a single source, or may be "chimeric," that is, different portions of the antibody may be derived from two different antibodies as described further below. The antigen binding proteins, antibodies, or binding fragments may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and mutations thereof, examples of which are described below.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains may be of any isotype, including IgG (including IgG1, IgG2, IgG3 and IgG4 subtypes), IgA (including IgA1 and IgA2 subtypes), IgM and IgE.

The term "immunologically functional fragment" (or simply "fragment") of an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope. In one aspect, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of antigen binding proteins, including intact antibodies. Immunologically functional immunoglobulin fragments include, but are not limited to, Fab, Fab', F(ab')$_2$, Fv, domain antibodies and single-chain antibodies, and may be derived from any mammalian source, including but not limited to human, mouse, rat, camelid or rabbit. It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

An "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

An "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an F(ab')$_2$ molecule.

An "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. No. 4,946,778 and No. 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antigen binding protein" or "bivalent antibody" comprises two antigen binding sites. In some instances, the two binding sites have the same antigen specificities. Bivalent antigen binding proteins and bivalent antibodies may be bispecific, see, infra.

A multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein or multispecific antibody and may be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553. The two binding sites of a bispecific antigen binding protein or antibody will bind to two different epitopes, which may reside on the same or different protein targets.

The term "neutralizing antigen binding protein" or "neutralizing antibody" refers to an antigen binding protein or antibody, respectively, that binds to a ligand, prevents binding of the ligand to its binding partner and interrupts the biological response that otherwise would result from the ligand binding to its binding partner. In assessing the binding and specificity of an antigen binding protein, e.g., an antibody or immunologically functional fragment thereof, an antibody or fragment will substantially inhibit binding of a ligand to its binding partner when an excess of antibody reduces the quantity of binding partner bound to the ligand by at least about 20%, 30%, 40%, 50%, 60%, 70%, 80%, 85%, 90%, 95%, 97%, 99% or more (as measured in an in vitro competitive binding assay). In the case of a c-fms antigen binding proteins, such a neutralizing molecule will diminish the ability of c-fms to bind CSF-1. In some embodiments, the neutilizing antigen binding protein inhibits the ability of c-fms to bind IL-34. In other embodiments, the neutilizing antigen binding protein inhibits the ability of c-fms to bind CSF-1 and IL-34.

The term "compete" when used in the context of antigen binding proteins (e.g., neutralizing antigen binding proteins or neutralizing antibodies) that compete for the same epitope means competition between antigen binding proteins is determined by an assay in which the antigen binding protein (e.g., antibody or immunologically functional fragment thereof) under test prevents or inhibits specific binding of a reference antigen binding protein (e.g., a ligand, or a reference antibody) to a common antigen (e.g., c-fms or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619) solid phase direct labeled assay, solid phase direct labeled sandwich assay (see, e.g., Harlow and Lane, 1988, *Antibodies, A Laboratory Manual*, Cold Spring Harbor Press); solid phase direct label RIA using 1-125 label (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. J. Immunol.* 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 95%, or 97% or more.

The term "antigen" refers to a molecule or a portion of a molecule capable of being bound by a selective binding agent, such as an antigen binding protein (including, e.g., an antibody or immunological functional fragment thereof), and additionally capable of being used in an animal to produce antibodies capable of binding to that antigen. An antigen may possess one or more epitopes that are capable of interacting with different antigen binding proteins, e.g., antibodies.

The term "epitope" is the portion of a molecule that is bound by an antigen binding protein (for example, an antibody). The term includes any determinant capable of specifically binding to an antigen binding protein, such as an antibody or to a T-cell receptor. An epitope can be contiguous or non-contiguous (e.g., in a polypeptide, amino acid residues that are not contiguous to one another in the polypeptide sequence but that within in context of the molecule are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are aligned in a way that gives the largest match between the sequences. The computer program used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. USA.* 89:10915-10919 for the BLOSUM 62 comparison matrix) is also used by the algorithm.

Recommended parameters for determining percent identity for polypeptides or nucleotide sequences using the GAP program are the following:

Algorithm: Needleman et al., 1970, *J. Mol. Biol.* 48:443-453;

Comparison matrix: BLOSUM 62 from Henikoff et al., 1992, supra;
Gap Penalty: 12 (but with no penalty for end gaps)
Gap Length Penalty: 4
Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods presented herein successfully treat cancer by decreasing the incidence of cancer, causing remission of cancer and/or ameliorating a symptom associated with cancer or an inflammatory disease.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with cancer. In some embodiments, the effective amount is a therapeutically effective amount or a prophylactically effective amount. A "therapeutically effective amount" is an amount sufficient to remedy a disease state (e.g. cancer) or symptoms, particularly a state or symptoms associated with the disease state, or otherwise prevent, hinder, retard or reverse the progression of the disease state or any other undesirable symptom associated with the disease in any way whatsoever. A "prophylactically effective amount" is an amount of a pharmaceutical composition that, when administered to a subject, will have the intended prophylactic effect, e.g., preventing or delaying the onset (or reoccurrence) of cancer, or reducing the likelihood of the onset (or reoccurrence) of cancer or cancer symptoms. The full therapeutic or prophylactic effect does not necessarily occur by administration of one dose, and may occur only after administration of a series of doses. Thus, a therapeutically or prophylactically effective amount may be administered in one or more administrations.

"Amino acid" includes its normal meaning in the art. The twenty naturally-occurring amino acids and their abbreviations follow conventional usage. See, Immunology—A Synthesis, 2nd Edition, (E. S. Golub and D. R. Green, eds.), Sinauer Associates: Sunderland, Mass. (1991), incorporated herein by reference for any purpose. Stereoisomers (e.g., D-amino acids) of the twenty conventional amino acids, unnatural amino acids such as [alpha]-, [alpha]-disubstituted amino acids, N-alkyl amino acids, and other unconventional amino acids may also be suitable components for polypeptides and are included in the phrase "amino acid." Examples of unconventional amino acids include: 4-hydroxyproline, [gamma]-carboxyglutamate, [epsilon]-N,N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

General Overview

Antigen-binding proteins that bind c-fms protein, including human c-fms (hc-fms) protein are provided herein. The antigen binding proteins provided are polypeptides into which one or more complementary determining regions (CDRs), as described herein, are embedded and/or joined. In some antigen binding proteins, the CDRs are embedded into a "framework" region, which orients the CDR(s) such that the proper antigen binding properties of the CDR(s) is achieved. In general, antigen binding proteins that are provided can interfere with, block, reduce or modulate the interaction between CSF-1 and c-fms.

Certain antigen binding proteins described herein are antibodies or are derived from antibodies. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof. The various structures are further described herein below.

The antigen binding proteins provided herein have been demonstrated to bind to the extracellular domain of c-fms, in particular human c-fms. As described further in the examples below, certain antigen binding proteins were tested and found to bind to epitopes different from those bound by a number of other anti-c-fms antibodies. The antigen binding proteins that are provided compete with CSF-1 and thereby prevent CSF-1 from binding to its receptor. In certain embodiments, antigen binding proteins inhibit binding between IL-34 and c-fms. In other embodiments, the antigen binding proteins inhibit the ability of c-fms to bind both CSF-1 and IL-34. As a consequence, the antigen binding proteins provided herein are capable of inhibiting c-fms activity. In particular, antigen binding proteins binding to these epitopes can have one or more of the following activities: inhibiting, inter alia, c-fms autophosphorylation, induction of c-fms signal transduction pathways, c-fms induced cell growth, monocyte chemotaxis accumulation of tumor associated macrophages in a tumor or in the stroma of a tumor, production of tumor-promoting factors and other physiological effects induced by c-fms upon CSF-1 binding. The antigen binding proteins that are disclosed herein have a variety of utilities. Some of the antigen binding proteins, for instance, are useful in specific binding assays, affinity purification of c-fms, in particular hc-fms or its ligands and in screening assays to identify other antagonists of c-fms activity. Some of the antigen-binding proteins are useful for inhibiting binding of CSF-1 to c-fms, or inhibiting autophosphorylation of c-fms.

The antigen-binding proteins can be used in a variety of treatment applications, as explained herein. For example, certain c-fms antigen-binding proteins are useful for treating conditions associated with c-fms, such as reducing monocyte chemotaxis in a patient, inhibiting monocyte migration into tumors, inhibiting accumulation of tumor associated macrophage in a tumor or inhibiting angiogenesis, as is further described herein. In certain embodiments, the antigen binding proteins inhibit the ability of TAMs to promote tumor growth, progression and/or metastasis. In addition, in cases where the tumor cells themselves express and use c-fms, antibody binding to c-fms could inhibit their growth/survival. Other uses for the antigen binding proteins include, for example, diagnosis of c-fms-associated diseases or conditions and screening assays to determine the presence or absence of c-fms. Some of the antigen binding proteins described herein are useful in treating consequences, symptoms, and/or the pathology associated with c-fms activity. These include, but are not limited to, various types of cancer and inflammatory disease and well as cancer cachexia. In some embodiments, the antigen binding proteins can be used to treat various bone disorders.

C-fms

Colony-stimulating factor 1 (CSF-1) promotes the survival, proliferation, and differentiation of mononuclear phagocyte lineages. CSF-1 exerts its activities by binding to the cell-surface c-fms receptor, resulting in autophosphorylation by receptor c-fms kinase and a subsequent cascade of intracellular signals.

The terms "c-fms," "c-fms receptor," "human c-fms", and "human c-fms receptor" refer to a cell surface receptor that binds to a ligand, including, but not limited to, CSF-1 and as a result initiates a signal transduction pathway within the cell. In some embodiments, the receptor can bind IL-34 or both CSF-1 and IL-34. The antigen binding proteins disclosed herein bind to c-fms, in particular human c-fms. An exemplary extracellular domain of human c-fms amino acid sequence is depicted in SEQ ID NO:1. As described below, c-fms proteins may also include fragments. As used herein, the terms are used interchangeably to mean a receptor, in particular a human receptor that binds specifically to CSF-1.

The term human c-fms (h-cfms) receptor as used herein also includes naturally occurring alleles, including the mutations A245S, V279M and H362R. The term c-fms also includes post-translational modifications of the c-fms amino acid sequence. For example, the extracellular domain (ECD) of human c-fms (residues 20-512 of the receptor) has eleven possible N-linked glycosylation sites in the sequence. Thus, the antigen binding proteins may bind to or be generated from proteins glycosylated at one or more of the positions.

The c-fms signal transduction pathway is up-regulated in a number of human pathologies that involve chronic activation of tissue macrophage populations. Increases in CSF-1 production are also associated with the accumulation of tissue macrophages seen in various inflammatory diseases such as inflammatory bowel disease. In addition, the growth of several tumor types is associated with overexpression of CSF-1 and c-fms receptor in cancer cells and/or tumor stroma.

C-fms Receptor Antigen Binding Proteins

A variety of selective binding agents useful for regulating the activity of c-fms are provided. These agents include, for instance, antigen binding proteins that contain an antigen binding domain (e.g., single chain antibodies, domain antibodies, immunoadhesions, and polypeptides with an antigen binding region) and specifically bind to a c-fms polypeptide, in particular human c-fms. Some of the agents, for example, are useful in inhibiting the binding of CSF-1 to c-fms, and can thus be used to inhibit, interfere with or modulate one or more activities associated with c-fms signaling. In certain embodiments, the antigen binding proteins can be used to inhibit binding between IL-34 and c-fms. In some embodiments, the antigen binding proteins interfere with the ability of c-fms to bind both CSF-1 and IL-34.

In general, the antigen binding proteins that are provided typically comprise one or more CDRs as described herein (e.g., 1, 2, 3, 4, 5 or 6). In some instances, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or may be completely synthetic in nature. Examples of various polypeptide structures are further described below.

In certain embodiments, the polypeptide structure of the antigen binding proteins is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen binding protein is an immunological fragment of an antibody (e.g., a Fab, a Fab', a F(ab')$_2$, or a scFv). The various structures are further described and defined herein.

Certain of the antigen binding proteins as provided herein specifically bind to human c-fms. In a specific embodiment, the antigen binding protein specifically binds to human c-fms protein having the amino acid sequence of SEQ ID NO:1.

In embodiments where the antigen binding protein is used for therapeutic applications, an antigen binding protein can inhibit, interfere with or modulate one or more biological activities of c-fms. In this case, an antigen binding protein binds specifically and/or substantially inhibits binding of human c-fms to CSF-1 when an excess of antibody reduces the quantity of human c-fms bound to CSF-1, or vice versa, by at least about 20%, 30%, 40%, 50%, 60%, 70%, 80%, 85%, 90%, 95%, 97%, 99% or more (for example by measuring binding in an in vitro competitive binding assay). C-fms has many distinct biological effects, which can be measured in many different assays in different cell types; examples of such assays are provided herein.

Naturally Occurring Antibody Structure

Some of the antigen binding proteins that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contain three C region domains known as $C_H1$, $C_H2$ and $C_H3$. The antibodies that are provided can have any of these isotypes and subtypes. In certain embodiments, the c-fms antibody is of the IgG1, IgG2, or IgG4 subtype.

In full-length light and heavy chains, the variable and constant regions are joined by a "J" region of about twelve or more amino acids, with the heavy chain also including a "D" region of about ten more amino acids. See, e.g. Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site.

One example of an IgG2 heavy constant domain of an exemplary c-fms monoclonal antibody has the amino acid sequence:

(SEQ. ID NO: 2; asterisk corresponds to stop codon)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

-continued
FYPSDIAVEWESNGQPENNYKTTPPMLDSDGSFFLYSKLTVDKSRWQQGN

VFSCSVMHEALHNHYTQKSLSLSPGK*.

One example of a kappa light Constant domain of an exemplary c-fms monoclonal antibody has the amino acid sequence:

(SEQ ID NO: 3; asterisk corresponds to stop codon)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC*.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., c-fms). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, *J. Mol. Biol.* 196:901-917; Chothia et al., 1989, *Nature* 342:878-883.

The various heavy chain and light chain variable regions provided herein are depicted in TABLE 2. Each of these variable regions may be attached to the above heavy and light chain constant regions to form a complete antibody heavy and light chain, respectively. Further, each of the so generated heavy and light chain sequences may be combined to form a complete antibody structure. It should be understood that the heavy chain and light chain variable regions provided herein can also be attached to other constant domains having different sequences than the exemplary sequences listed above.

Specific examples of some of the full length light and heavy chains of the antibodies that are provided and their corresponding amino acid sequences are summarized in TABLE 1.

TABLE 1

Exemplary Heavy and Light Chains

| Reference | Designation | SEQ ID NO. | Amino Acid Sequence |
|---|---|---|---|
| H1 109 1N1G1 | H1 | 4 | QVQLVQSGAEVKKPGASVKVSCKASGYTFTAYYMHWVRQAPGQ GLEWMGWINPNSGGTNYAQKFQGRVTMTRDTSISTAYMELSRL RSDDTAVYYCARGGYSGYDLGYYYGMDVWGQGTTVTVSSASTK GPSVFPLAPCSRSTSESTAALGCLVKDYFPEPVTVSWNSGALT SGVHTFPAVLQSSGLYSLSSVVTVPSSNFGTQTYTCNVDHKPS NTKVDKTVERKCCVECPPCPAPPVAGPSVFLFPPKPKDTLMIS RTPEVTCVVVDVSHEDPEVQFNWYVDGVEVHNAKTKPREEQFN STFRVVSVLTVVHQDWLNGKEYKCKVSNKGLPAPIEKTISKTK GQPREPQVYTLPPSREEMTKNQVSLTCLVKGFYPSDIAVEWES NGQPENNYKTTPPMLDSDGSFFLYSKLTVDKSRWQQGNVFSCS VMHEALHNHYTQKSLSLSPGK |
| H1 13 1N1G1 | H2 | 5 | QVQLQESGPGLVKPSETLSLTCTVSGGSVSSGGYYWSWIRQPP GKGLEWIGYIYYSGSTNYNPSLKSRVTISVDTSKNQFSLKLSS VTAADTAVYYCAAGIAATGTLFDCWGQGTLVTVSSASTKGPSV FPLAPCSRSTSESTAALGCLVKDYFPEPVTVSWNSGALTSGVH TFPAVLQSSGLYSLSSVVTVPSSNFGTQTYTCNVDHKPSNTKV DKTVERKCCVECPPCPAPPVAGPSVFLFPPKPKDTLMISRTPE VTCVVVDVSHEDPEVQFNWYVDGVEVHNAKTKPREEQFNSTFR VSVLTVVHQDWLNGKEYKCKVSNKGLPAPIEKTISKTKGQPRE PQVYTLPPSREEMTKNQVSLTCLVKGFYPSDAVEWESNGQPEN NYKTTPPMLDSDGSFFLYSKLTVDKSRWQQGNVFSCSVMHEAL HNHYTQKSLSLSPGK |

TABLE 1-continued

Exemplary Heavy and Light Chains

| Reference | Designation | SEQ ID NO. | Amino Acid Sequence |
|---|---|---|---|
| H1 131 1N1G1 | H3 | 6 | QVQLVQSGAEVKKPGASVKVSCKASGYTFTGYYIHWVRQAPGQ GLEWMGWINPNSGGTNYAQKFQGRVTMTRDTSISTAYMELSRL RSDDTAVYYCARDRGQLWLWYYYYYGMDVWGQGTTVTVSSAST KGPSVFPLAPCSRSTSESTAALGCLVKDYFPEPVTVSWNSGAL TSGVHTFPAVLQSSGLYSLSSVVTVPSSNFGTQTYTCNVDHKP SNTKVDKTVERKCCVECPPCPAPPVAGPSVFLFPPKPKDTLMI SRTPEVTCVVVDVSHEDPEVQFNWYVDGVEVHNAKTKPREEQF NSTFRVVSVLTWHQDWLNGKEYKCKVSNKGLPAPIEKTISKTK GQPREPQVYTLPPSREEMTKNQVSLTCLVKGFYPSDIAVEWES NGQPENNYKTTPPMLDSDGSFFLYSKLTVDKSRWQQGNVFSCS VMHEALHNHYTQKSLSLSPGK |
| H1 134 1N1G1 | H4 | 7 | QVQLVESGGGVVQPGRSLRLSCAASGFTFSSYGMHWVRQAPGK GLEWVAVIWYDGSNKYYADSVKGRFTISRDNSKNTLYLQMNSL RAEDTAVYYCASSSWSYYGMDVWGQGTTVTVSSASTKGPSVFP LAPCSRSTSESTAALGCLVKDYFPEPVTVSWNSGALTSGVHTF PAVLQSSGLYSLSSVVTVPSSNFGTQTYTCNVDHKPSNTKVDK TVERKCCVECPPCPAPPVAGPSVFLFPPKPKDTLMISRTPEVT CVVVDVSHEDPEVQFNWYVDGVEVHNAKTKPREEQFNSTFRVV SVLTVVHQDWLNGKEYKCKVSNKGLPAPIEKTISKTKGQPREP QVYTLPPSREEMTKNQVSLTCLVKGFYPSDAVEWESNGQPENN YKTTPPMLDSDGSFFLYSKLTVDKSRWQQGNVFSCSVMHEALH NHYTQKSLSLSPGK |
| H1 143 1N1G1 | H5 | 8 | EVQLVESGGGLVKPGGSLRLSCAASGFTVSNAWMSWVRQAPGK GLEWVGRIKSKTDGGTTDNAAPVKGRFTISRDDSKNTLYLQMN SLKTEDTAVYYCTTGGSLLWTGPNYYYYGMDVWGQGTTVTVSS ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKPRE EQFNSTFRVVSVLTVVHQDWLNGKEYKCKVSNKGLPAPIEKTI SKTKGQPREPQVYTLPPSREEMTKNQVSLTCLVKGFYPSDIAV EWESNGQPENNYKTTPPMLDSDGSFFLYSKLTVDKSRWQQGNV FSCSVMHEALHNHYTQKSLSLSPGK |
| H1 144 1N1G1 | H6 | 9 | EVQLVESGGGLVKPGGSLRLSCAASGFTFSNAWMSWVRQAPGK GLEWVGRIKSKTDGGTTDYAAPVKGRFTISRDDSKNTLYLQMN SLKTEDTAVYYCTTEYYGSGGVWYYGMDVWGQGTTVTVSSAST KGPSVFPLAPCSRSTSESTAALGCLVKDYFPEPVTVSWNSGAL TSGVHTFPAVLQSSGLYSLSSVVTVPSSNFGTQTYTCNVDHKP SNTKVDKTVERKCCVECPPCPAPPVAGPSVFLFPPKPKDTLMI SRTPEVTCVVVDVSHEDPEVQFNWYVDGVEVHNAKTKPREEQF NSTFRVVSVLTVVHQDWLNGKEYKCKVSNKGLPAPIEKTISKT KGQPREPQVYTLPPSREEMTKNQVSLTCLVKGFYPSDIAVEWE SNGQPENNYKTTPPMLDSDGSFFLYSKLTVDKSRWQQGNVFSC SVMHEALHNHYTQKSLSLSPGK |
| H1 16 1N1G1 | H7 | 10 | EVQLVESGGGLVKPGGSLRLSCAASGFTFSNAWMSWVRQAPGK GLEWVGRIKSKTDGWTTDYAAPVKGRFTISRDDSKNTLYLQMN SLKTEDTAVYYCTTDLRITGTTYYYYYYGMDVWGQGTTVTVSS ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKPRE EQFNSTFRVVSVLTWHQDWLNGKEYKCKVSNKGLPAPIEKTIS KTKGQPREPQVYTLPPSREEMTKNQVSLTCLVKGFYPSDIAVE WESNGQPENNYKTTPPMLDSDGSFFLYSKLTVDKSRWQQGNVF SCSVMHEALHNHYTQKSLSLSPGK |
| H1 2 1N1G1 | H8 | 11 | QVQLVQSGAEVKKPGASVKVSCKASGYTFTSYGISWVRQAPGQ GLEWMGWISAYNGNTNYAQKLQGRVTMTTDTSTSTAYMELRSL RSDDTAVYYCARESWFGEVFFDYWGQGTLVTVSSASTKGPSVF PLAPCSRSTSESTAALGCLVKDYFPEPVTVSWNSGALTSGVHT FPAVLQSSGLYSLSSWTVPSSNFGTQTYTCNVDHKPSNTKVDK TVERKCCVECPPCPAPPVAGPSVFLFPPKPKDTLMISRTPEVT CVVVDVSHEDPEVQFNWYVDGVEVHNAKTKPREEQFNSTFRVV SVLTVVHQDWLNGKEYKCKVSNKGLPAPIEKTISKTKGQPREP QVYTLPPSREEMTKNQVSLTCLVKGFYPSDIAVEWESNGQPEN NYKTTPPMLDSDGSFFLYSKLTVDKSRWQQGNVFSCSVMHEAL HNHYTQKSLSLSPGK |

TABLE 1-continued

Exemplary Heavy and Light Chains

| Reference | Designation | SEQ ID NO. | Amino Acid Sequence |
|---|---|---|---|
| H1 26 1N1G1 | H9 | 12 | EVQLVESGGGLVKPGGSLRLSCAASGFTFSNAWMSWVRQAPGK GLEWVGRIKSKTDGGTTDYAAPVKGRFTISRDDSKNTLYLQMN SLKTEDTAVYYCTTEYYGSGGVWYYGMDVWGQGTTVTVSSAST KGPSVFPLAPCSRSTSESTAALGCLVKDYFPEPVTVSWNSGAL TSGVHTFPAVLQSSGLYSLSSWTVPSSNFGTQTYTCNVDHKPS NTKVDKTVERKCCVECPPCPAPPVAGPSVFLFPPKPKDTLMIS RTPEVTCVVVDVSHEDPEVQFNWYVDGVEVHNAKTKPREEQFN STFRVVSVLTWHQDWLNGKEYKCKVSNKGLPAPIEKTISKTKG QPREPQVYTLPPSREEMTKNQVSLTCLVKGFYPSDIAVEWESN GQPENNYKTTPPMLDSDGSFFLYSKLTVDKSRWQQGNVFSCSV MHEALHNHYTQKSLSLSPGK |
| H1 27 1N1G1 | H10 | 13 | EVQLVESGGGLVKPGGSLRLSCAASGFTFSNAWMSWVRQAPGK GLEWVGRIKSKTDGGTTDYAAPVKGRFTISRDDSKNTLYLQMN SLKTEDTAVYYCTTDGATVVTPGYYYYGTDVWGQGTTVTVSSA STKGPSVFPLAPCSRSTSESTAALGCLVKDYFPEPVTVSWNSG ALTSGVHTFPAVLQSSGLYSLSSWTVPSSNFGTQTYTCNVDHK PSNTKVDKTVERKCCVECPPCPAPPVAGPSVFLFPPKPKDTLM ISRTPEVTCVVVDVSHEDPEVQFNWYVDGVEVHNAKTKPREEQ FNSTFRVVSVLTVVHQDWLNGKEYKCKVSNKGLPAPIEKTISK TKGQPREPQVYTLPPSREEMTKNQVSLTCLVKGFYPSDIAVEW ESNGQPENNYKTTPPMLDSDGSFFLYSKLTVDKSRWQQGNVFS CSVMHEALHNHYTQKSLSLSPGK |
| H1 30 1N1G1 | H11 | 14 | QVQLVQSGAEVKKPGASVKVSCKASGYTFTSYGISWVRQAPGQ GLEWMGWISAYNGNTNYAQKLQGRVTMTTDTSTSTAYMELRSL RSDDTAVYYCARESWFGEVFFDYWGQGTLVTVSSASTKGPSVF PLAPCSRSTSESTAALGCLVKDYFPEPVTVSWNSGALTSGVHT FPAVLQSSGLYSLSSWTVPSSNFGTQTYTCNVDHKPSNTKVDK TVERKCCVECPPCPAPPVAGPSVFLFPPKPKDTLMISRTPEVT CVVVDVSHEDPEVQFNWYVDGVEVHNAKTKPREEQFNSTFRVV SVLTVVHQDWLNGKEYKCKVSNKGLPAPIEKTISKTKGQPREP QVYTLPPSREEMTKNQVSLTCLVKGFYPSDIAVEWESNGQPEN NYKTTPPMLDSDGSFFLYSKLTVDKSRWQQGNVFSCSVMHEAL HNHYTQKSLSLSPGK |
| H1 33-1 1N1G1 | H12 | 15 | QVQLVQSGAEVKKPGASVKVSCKASGYTFTGYYMHWVRQAPGQ GLEWMGWINPNSGGTNYAQKFQGRVTMTRDTSISTAYMELSRL RSDDTAFYYCARDSNWYHNWFDPWGQGTLVTVSSASTKGPSVF PLAPCSRSTSESTAALGCLVKDYFPEPVTVSWNSGALTSGVHT FPAVLQSSGLYSLSSVVTVPSSNFGTQTYTCNVDHKPSNTKVD KTVERKCCVECPPCPAPPVAGPSVFLFPPKPKDTLMISRTPEV TCVVVDVSHEDPEVQFNWYVDGVEVHNAKTKPREEQFNSTFRV VSVLTVVHQDWLNGKEYKCKVSNKGLPAPIEKTISKTKGQPRE PQVYTLPPSREEMTKNQVSLTCLVKGFYPSDAVEWESNGQPEN NYKTTPPMLDSDGSFFLYSKLTVDKSRWQQGNVFSCSVMHEAL HNHYTQKSLSLSPGK |
| H1 33 1N1G1 | H13 | 16 | QVQLVQSGAEVKKPGASVKVSCKASGYTFTGYYMHWVRQAPGQ GLEWMGWINPNSGGTNYAQKFQGRVTMTRDTSISTAYMELSRL RSDDTAFYYCARDSNWYHNWFDPWGQGTLVTVSSASTKGPSVF PLAPCSRSTSESTAALGCLVKDYFPEPVTVSWNSGALTSGVHT FPAVLQSSGLYSLSSWTVPSSNFGTQTYTCNVDHKPSNTKVDK TVERKCCVECPPCPAPPVAGPSVFLFPPKPKDTLMISRTPEVT CVVVDVSHEDPEVQFNWYVDGVEVHNAKTKPREEQFNSTFRWS VLTVVHQDWLNGKEYKCKVSNKGLPAPIEKTISKTKGQPREPQ VYTLPPSREEMTKNQVSLTCLVKGFYPSDAVEWESNGQPENNY KTTPPMLDSDGSFFLYSKLTVDKSRWQQGNVFSCSVMHEALHN HYTQKSLSLSPGK |
| H1 34 1N1G1 | H14 | 17 | EVQLVESGGGLVKPGGSLRLSCAASGFTFSNAWMSWVRQAPGK GLEWVGRIKSKTDGGTTDYAAPVKGRFTISRDDSKNTLYLQMN SLKTEDTAVYYCTTDGATVVTPGYYYYGTDVWGQGTTVTVSSA STKGPSVFPLAPCSRSTSESTAALGCLVKDYFPEPVTVSWNSG ALTSGVHTFPAVLQSSGLYSLSSVVTVPSSNFGTQTYTCNVDH KPSNTKVDKTVERKCCVECPPCPAPPVAGPSVFLFPPKPKDTL MISRTPEVTCVVVDVSHEDPEVQFNWYVDGVEVHNAKTKPREE QFNSTFRVVSVLTVVHQDWLNGKEYKCKVSNKGLPAPIEKTIS KTKGQPREPQVYTLPPSREEMTKNQVSLTCLVKGFYPSDIAVE WESNGQPENNYKTTPPMLDSDGSFFLYSKLTVDKSRWQQGNVF SCSVMHEALHNHYTQKSLSLSPGK |

TABLE 1-continued

Exemplary Heavy and Light Chains

| Reference | Designation | SEQ ID NO. | Amino Acid Sequence |
|---|---|---|---|
| H1 39 1N1G1 | H15 | 18 | EVQLVESGGGLVKPGGSLRLSCAASGFTFSNAWMSWVRQAPGK GLEWVGRIKSKTDGGTADYAAPVKGRFTISRDDSKNTLYLQMN SLKTEDTAVYYCTTEGPYSDYGYYYYGMDVWGQGTTVTSSAS TKGPSVFPLAPCSRSTSESTAALGCLVKDYFPEPVTVSWNSGA LTSGVHTFPAVLQSSGLYSLSSVVTVPSSNFGTQTYTCNVDHK PSNTKVDKTVERKCCVECPPCPAPPVAGPSVFLFPPKPKDTLM ISRTPEVTCVVVDVSHEDPEVQFNWYVDGVEVHNAKTKPREEQ FNSTFRVVSVLTWHQDWLNGKEYKCKVSNKGLPAPIEKTISKT KGQPREPQVYTLPPSREEMTKNQVSLTCLVKGFYPSDIAVEWE SNGQPENNYKTTPPMLDSDGSFFLYSKLTVDKSRWQQGNVFSC SVMHEALHNHYTQKSLSLSPGK |
| H1 42 1N1G1 | H16 | 19 | QVQLVQSGAEVKKPGASVKVSCKASGYTFTSYGISWVRQAPGQ GLEWMGWISAYNGNTNYAQKLQGRVTMTTDTSTSTAYMELRSL RSDDTAVYYCARESWFGEVFFDYWGQGTLVTVSSASTKGPSVF PLAPCSRSTSESTAALGCLVKDYFPEPVTVSWNSGALTSGVHT FPAVLQSSGLYSLSSWTVPSSNFGTQTYTCNVDHKPSNTKVDK TVERKCCVECPPCPAPPVAGPSVFLFPPKPKDTLMISRTPEVT CVVVDVSHEDPEVQFNWYVDGVEVHNAKTKPREEQFNSTFRVV SVLTVVHQDWLNGKEYKCKVSNKGLPAPIEKTISKTKGQPREP QVYTLPPSREEMTKNQVSLTCLVKGFYPSDIAVEWESNGQPEN NYKTTPPMLDSDGSFFLYSKLTVDKSRWQQGNVFSCSVMHEAL HNHYTQKSLSLSPGK |
| H1 64 1N1G1 | H17 | 20 | EVQLVESGGGLVQPGGSLRLSCAASGFTFSSYDMHWVRQATGK GLEWVSGIGTAGDTYYPGSVKGRFNISRENAKNSLYLQMNSLR AGDTAVYYCAREGSWYGFDYWGQGTLVTVSSASTKGPSVFPLA PCSRSTSESTAALGCLVKDYFPEPVTVSWNSGALTSGVHTFPA VLQSSGLYSLSSWTVPSSNFGTQTYTCNVDHKPSNTKVDKTVE RKCCVECPPCPAPPVAGPSVFLFPPKPKDTLMISRTPEVTCVV VDVSHEDPEVQFNWYVDGVEVHNAKTKPREEQFNSTFRVVSVL TVVHQDWLNGKEYKCKVSNKGLPAPIEKTISKTKGQPREPQVY TLPPSREEMTKNQVSLTCLVKGFYPSDIAVEWESNGQPENNYK TTPPMLDSDGSFFLYSKLTVDKSRWQQGNVFSCSVMHEALHNH YTQKSLSLSPGK |
| H1 66 1N1G1 | H18 | 21 | QVQLVESGGGVVQPGRSLRLSCAASGFTFSSYGMHWVRQAPGK GLEWVAVIWYDGSNEYYADSVKGRFTISRDNSKSTLYLQMNSL RAEDTAVYYCAHSSGNYYDMDVWGQGTTVTVSSASTKGPSVFP LAPCSRSTSESTAALGCLVKDYFPEPVTVSWNSGALTSGVHTF PAVLQSSGLYSLSSVVTVPSSNFGTQTYTCNVDHKPSNTKVDK TVERKCCVECPPCPAPPVAGPSVFLFPPKPKDTLMISRTPEVT CVVVDVSHEDPEVQFNWYVDGVEVHNAKTKPREEQFNSTFRVV SVLTVVHQDWLNGKEYKCKVSNKGLPAPIEKTISKTKGQPREP QVYTLPPSREEMTKNQVSLTCLVKGFYPSDIAVEWESNGQPEN NYKTTPPMLDSDGSFFLYSKLTVDKSRWQQGNVFSCSVMHEAL HNHYTQKSLSLSPGK |
| H1 72 1N1G1 | H19 | 22 | EVQLVESGGGLVEPGGSLRLSCAASGFTFSTAWMSWVRQAPGK GLEWVGRIKSKTDGGTTDYAAPVKGRFTISRDDSKNTLYLQMN SLKNEDTAVYYCTTEGPYSNYGYYYYGVDVWGQGTTVTSSAS TKGPSVFPLAPCSRSTSESTAALGCLVKDYFPEPVTVSWNSGA LTSGVHTFPAVLQSSGLYSLSSVVTVPSSNFGTQTYTCNVDHK PSNTKVDKTVERKCCVECPPCPAPPVAGPSVFLFPPKPKDTLM ISRTPEVTCVVVDVSHEDPEVQFNWYVDGVEVHNAKTKPREEQ FNSTFRVVSVLTVVHQDWLNGKEYKCKVSNKGLPAPIEKTISK TKGQPREPQVYTLPPSREEMTKNQVSLTCLVKGFYPSDIAVEW ESNGQPENNYKTTPPMLDSDGSFFLYSKLTVDKSRWQQGNVFS CSVMHEALHNHYTQKSLSLSPGK |
| H2 103 1N1G2 | H20 | 23 | EVQLVESGGGLVKPGGSLTLSCAASGFTFNNAWMSWVRQAPGK GLEWVGRIKSKTDGGTTDYAAPVKGRFTISRDDSKNTLYLQMN SLKTEDTAVYYCTTEYYHILTGSFYYSYYGMDVWGQGTTVTVS SASTKGPSVFPLAPCSRSTSESTAALGCLVKDYFPEPVTVSWN SGALTSGVHTFPAVLQSSGLYSLSSVVTVPSSNFGTQTYTCNV DHKPSNTKVDKTVERKCCVECPPCPAPPVAGPSVFLFPPKPKD TLMISRTPEVTCVVVDVSHEDPEVQFNWYVDGVEVHNAKTKPR EEQFNSTFRVVSVLTVVHQDWLNGKEYKCKVSNKGLPAPIEKT ISKTKGQPREPQVYTLPPSREEMTKNQVSLTCLVKGFYPSDIA VEWESNGQPENNYKTTPPMLDSDGSFFLYSKLTVDKSRWQQGN VFSCSVMHEALHNHYTQKSLSLSPGK |

TABLE 1-continued

Exemplary Heavy and Light Chains

| Reference | Designation | SEQ ID NO. | Amino Acid Sequence |
|---|---|---|---|
| H1 90 1N1G1 | H21 | 24 | QVQLVESGGGVVQPGRSLRLSCAASGFTFSSYGMHWVRQAPGK GLEWVAVIWYDGSNKYYADSVKGRFTISRDNSKNTLYLQMNSL RAEDTAVYYCASSSSNFYDMDVWGQGTTVTVSSASTKGPSVFP LAPCSRSTSESTAALGCLVKDYFPEPVTVSWNSGALTSGVHTF PAVLQSSGLYSLSSVVTVPSSNFGTQTYTCNVDHKPSNTKVDK TVERKCCVECPPCPAPPVAGPSVFLFPPKPKDTLMISRTPEVT CVVVDVSHEDPEVQFNWYVDGVEVHNAKTKPREEQFNSTFRVV SVLTVVHQDWLNGKEYKCKVSNKGLPAPIEKTISKTKGQPREP QVYTLPPSREEMTKNQVSLTCLVKGFYPSDAVEWESNGQPENN YKTTPPMLDSDGSFFLYSKLTVDKSRWQQGNVFSCSVMHEALH NHYTQKSLSLSPGK |
| H2 131 1N1G2 | H22 | 25 | QVQLQESGPGLVKPSETLSLTCTVSGGSISNYYWSWIRQSAGK GLEWIGRIYTSGSTHYNPSLKSRIIMSVDTSKNQFSLKLSSVT AADTAVYYCARDRVFYGMDVWGQGTTVTVSSASTKGPSVFPLA PCSRSTSESTAALGCLVKDYFPEPVTVSWNSGALTSGVHTFPA VLQSSGLYSLSSVVTVPSSNFGTQTYTCNVDHKPSNTKVDKTV ERKCCVECPPCPAPPVAGPSVFLFPPKPKDTLMISRTPEVTCV VVDVSHEDPEVQFNWYVDGVEVHNAKTKPREEQFNSTFRWSVL TVVHQDWLNGKEYKCKVSNKGLPAPIEKTISKTKGQPREPQVY TLPPSREEMTKNQVSLTCLVKGFYPSDIAVEWESNGQPENNYK TTPPMLDSDGSFFLYSKLTVDKSRWQQGNVFSCSVMHEALHNH YTQKSLSLSPGK |
| H2 291 1N1G2 | H23 | 26 | QVQLVESGGGVVQPGRSLRLSCAASGFTFSSYGMHWVRQAPGK GLEWVAVIWYDGSYKYYADSVKGRFTISRDNSKNTLYLQMNSL RAEDTAVYYCAREGDYSDYYGMDVWGQGTTVTVSSASTKGPSV FPLAPCSRSTSESTAALGCLVKDYFPEPVTVSWNSGALTSGVH TFPAVLQSSGLYSLSSVVTVPSSNFGTQTYTCNVDHKPSNTKV DKTVERKCCVECPPCPAPPVAGPSVFLFPPKPKDTLMISRTPE VTCVVVDVSHEDPEVQFNWYVDGVEVHNAKTKPREEQFNSTFR VVSVLTVVHQDWLNGKEYKCKVSNKGLPAPIEKTISKTKGQPR EPQVYTLPPSREEMTKNQVSLTCLVKGFYPSDIAVEWESNGQP ENNYKTTPPMLDSDGSFFLYSKLTVDKSRWQQGNVFSCSVMHE ALHNHYTQKSLSLSPGK |
| H2 360 1N1G2 | H24 | 27 | QVQLVQSGAEVKKPGASVKVSCKVSGYTLTELSMHWVRQAPGK GLEWMGGFDPEDGETIYAQKFQGRVTMTEDTSTDTVYMELSSL RSEDTAVYYCATGVMITFGGVIVGHSYYGMDVWGQGTTVTVSS ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKPRE EQFNSTFRVVSVLTVVHQDWLNGKEYKCKVSNKGLPAPIEKTI SKTKGQPREPQVYTLPPSREEMTKNQVSLTCLVKGFYPSDIAV EWESNGQPENNYKTTPPMLDSDGSFFLYSKLTVDKSRWQQGNV FSCSVMHEALHNHYTQKSLSLSPGK |
| H2 360 1N1G2 SM | H25 | 28 | QVQLVQSGAEVKKPGASVKVSCKVSGYTLTELSMHWVRQAPGK GLEWMGGFDPEDGETIYAQKFQGRVTMTEDTSTDTAYMELSSL RSEDTAVYYCATGVMITFGGVIVGHSYYGMDVWGQGTTVTVSS ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKPRE EQFNSTFRVVSVLTVVHQDWLNGKEYKCKVSNKGLPAPIEKTI SKTKGQPREPQVYTLPPSREEMTKNQVSLTCLVKGFYPSDIAV EWESNGQPENNYKTTPPMLDSDGSFFLYSKLTVDKSRWQQGNV FSCSVMHEALHNHYTQKSLSLSPGK |
| H2 369 1N1G2 | H26 | 29 | QVQLVQSGAEVKKPGASVKVSCKVSGYTLTELSMHWVRQAPGK GLEWMGGFDPEDGETIYAQKFQGRVTMTEDTSTDTAYMELSSL RSEDTAVYYCATRAGTTLAYYYYAMDVWGQGTTVTVSSASTKG PSVFPLAPCSRSTSESTAALGCLVKDYFPEPVTVSWNSGALTS GVHTFPAVLQSSGLYSLSSVVTVPSSNFGTQTYTCNVDHKPSN TKVDKTVERKCCVECPPCPAPPVAGPSVFLFPPKPKDTLMISR TPEVTCVVVDVSHEDPEVQFNWYVDGVEVHNAKTKPREEQFNS TFRVVSVLTVVHQDWLNGKEYKCKVSNKGLPAPIEKTISKTKG QPREPQVYTLPPSREEMTKNQVSLTCLVKGFYPSDIAVEWESN GQPENNYKTTPPMLDSDGSFFLYSKLTVDKSRWQQGNVFSCSV MHEALHNHYTQKSLSLSPGK |

TABLE 1-continued

Exemplary Heavy and Light Chains

| Reference | Designation | SEQ ID NO. | Amino Acid Sequence |
|---|---|---|---|
| H2 380 1N1G2 | H27 | 30 | QVQLQESGPGLVKPSETLSLTCTVSGGSISSYYWSWIRQPPGK GLEWIGYIYYSGNTNYNPSLKSRFTLSIDTSKNQFSLRLSSVT AADTAVYYCACIATRPFDWGQGTLVTVSSASTKGPSVFPLAP CSRSTSESTAALGCLVKDYFPEPVTVSWNSGALTSGVHTFPAV LQSSGLYSLSSVVTVPSSNFGTQTYTCNVDHKPSNTKVDKTVE RKCCVECPPCPAPPVAGPSVFLFPPKPKDTLMISRTPEVTCVV VDVSHEDPEVQFNWYVDGVEVHNAKTKPREEQFNSTFRVVSVL TVVHQDWLNGKEYKCKVSNKGLPAPIEKTISKTKGQPREPQVY TLPPSREEMTKNQVSLTCLVKGFYPSDIAVEWESNGQPENNYK TTPPMLDSDGSFFLYSKLTVDKSRWQQGNVFSCSVMHEALHNH YTQKSLSLSPGK |
| H2 475 1N1G2 | H28 | 31 | QVQLVESGGGVVQPGRSLRLSCAASGFTFISYGMHWVRQAPGK GLEWVAVIWYDGSNKYYADSVKGRFTISRDNSKNTLYLQMNSL RAEDTAVYYCADSSGDYYGMDVWGQGTTVTVSSASTKGPSVFP LAPCSRSTSESTAALGCLVKDYFPEPVTVSWNSGALTSGVHTF PAVLQSSGLYSLSSVVTVPSSNFGTQTYTCNVDHKPSNTKVDK TVERKCCVECPPCPAPPVAGPSVFLFPPKPKDTLMISRTPEVT CVVVDVSHEDPEVQFNWYVDGVEVHNAKTKPREEQFNSTFRVV SVLTVVHQDWLNGKEYKCKVSNKGLPAPIEKTISKTKGQPREP QVYTLPPSREEMTKNQVSLTCLVKGFYPSDIAVEWESNGQPEN NYKTTPPMLDSDGSFFLYSKLTVDKSRWQQGNVFSCSVMHEAL HNHYTQKSLSLSPGK |
| H2 508 1N1G2 | H29 | 32 | QVQLVQSGAEVKKPGASVKVSCKVSGYTLTELSMHWVRQAPGK GLEWMGGFDPEDGETIYAQKFQGRVTMTEDTSTDTAYMELSSL RSEDTAVYYCATAGLEIRWFDPWGQGTLVTVSSASTKGPSVFP LAPCSRSTSESTAALGCLVKDYFPEPVTVSWNSGALTSGVHTF PAVLQSSGLYSLSSVVTVPSSNFGTQTYTCNVDHKPSNTKVDK TVERKCCVECPPCPAPPVAGPSVFLFPPKPKDTLMISRTPEVT CVVVDVSHEDPEVQFNWYVDGVEVHNAKTKPREEQFNSTFRVV SVLTVVHQDWLNGKEYKCKVSNKGLPAPIEKTISKTKGQPREP QVYTLPPSREEMTKNQVSLTCLVKGFYPSDIAVEWESNGQPEN NYKTTPPMLDSDGSFFLYSKLTVDKSRWQQGNVFSCSVMHEAL HNHYTQKSLSLSPGK |
| H2 534 1N1G2 | H30 | 33 | QVQLQESGPGLVKPSQTLSLTCTVSGGSISSGGYYWSWIRQHP GKGLEWIGYISYSGDTYYNPSLKSRLTISVDTSKHQFSLRLSS VTSADTAVYYCASLDLYGDYFDYWGQGTLVTVSSASTKGPSVF PLAPCSRSTSESTAALGCLVKDYFPEPVTVSWNSGALTSGVHT FPAVLQSSGLYSLSSVVTVPSSNFGTQTYTCNVDHKPSNTKVD KTVERKCCVECPPCPAPPVAGPSVFLFPPKPKDTLMISRTPEV TCVVVDVSHEDPEVQFNWYVDGVEVHNAKTKPREEQFNSTFRV VSVLTVVHQDWLNGKEYKCKVSNKGLPAPIEKTISKTKGQPRE PQVYTLPPSREEMTKNQVSLTCLVKGFYPSDIAVEWESNGQPE NNYKTTPPMLDSDGSFFLYSKLTVDKSRWQQGNVFSCSVMHEA LHNHYTQKSLSLSPGK |
| H2 550 1N1G2 | H31 | 34 | QVQLVQSGAEVKKPGASVKVSCKASGYTLTSYGISWVRQAPGQ GLEWMGWISAYNGNPNYAQKFQGRVTMTTDTSTSTAYMELRSL RSDDTAVYYCARDQGLLGFGELEGLFDYWGQGTLVTVSSASTK GPSVFPLAPCSRSTSESTAALGCLVKDYFPEPVTVSWNSGALT AGVHTFPAVLQSSGLYSLSSVVTVPSSNFGTQTYTCNVDHKPS NTKVDKTVERKCCVECPPCPAPPVAGPSVFLFPPKPKDTLMIS RTPEVTCVVVDVSHEDPEVQFNWYVDGVEVHNAKTKPREEQFN STFRVVSVLTVVHQDWLNGKEYKCKVSNKGLPAPIEKTISKTK GQPREPQVYTLPPSREEMTKNQVSLTCLVKGFYPSDIAVEWES NGQPENNYKTTPPMLDSDGSFFLYSKLTVDKSRWQQGNVFSCS VMHEALHNHYTQKSLSLSPGK |
| H2 65 1N1G2 | H32 | 35 | EVQLVESGGGLVKPGGSLRLSCAASGFTFSNAWMSWVRQAPGK GLEWVGRIKTKTDGGTTDYAAPVKGRFTISRDDSQNTLYLQMN SLKTEDTAVYYCTTEYYGIVTGSFYYYYGMDVWGQGTTVTVS SASTKGPSVFPLAPCSRSTSESTAALGCLVKDYFPEPVTVSWN SGALTSGVHTFPAVLQSSGLYSLSSVVTVPSSNFGTQTYTCNV DHKPSNTKVDKTVERKCCVECPPCPAPPVAGPSVFLFPPKPKD TLMISRTPEVTCVVVDVSHEDPEVQFNWYVDGVEVHNAKTKPR EEQFNSTFRVVSVLTWHQDWLNGKEYKCKVSNKGLPAPIEKTI SKTKGQPREPQVYTLPPSREEMTKNQVSLTCLVKGFYPSDIAV EWESNGQPENNYKTTPPMLDSDGSFFLYSKLTVDKSRWQQGNV FSCSVMHEALHNHYTQKSLSLSPGK |

TABLE 1-continued

Exemplary Heavy and Light Chains

| Reference | Designation | SEQ ID NO. | Amino Acid Sequence |
|---|---|---|---|
| H1 109 1N1K | L1 | 36 | DIQMTQSPSSLSASVGDRVTITCQASQNISNFLDWYQQKPGKA PNLLIYDASDLDPGVPSRFSGSGSGTDFTFTISSLQPEDIATY YCQQYVSLPLTFGGGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H1 109 1N1K SM | L2 | 37 | DIQMTQSPSSLSASVGDRVTITCQASQDISNFLDWYQQKPGKA PKLLIYDASDLDPGVPSRFSGSGSGTDFTFTISSLQPEDIATY YCQQYVSLPLTFGGGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H11 31 1N1K | L3 | 38 | DNVMTQTPLSLSVTPGQPASISCKSSQSLLHSDGKTYLYWYLQ KPGQPPQLLIYEASNRFSGVPDRFSGSGSGTDFTLKISRVEAE DVGVYYCMQSIQLPLTFGGGTKVEIKRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| H11 34 1N1K | L4 | 39 | DIQMTQSPSSLSASVGDRVTITCQASQDINNYLNWYQQKPGKA PKLLIYDASNLEIGVPSRFSGSGSGTDFIFTISSLQPEDIATY YCQQYDNFPFTFGGGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H1 143 1N1K | L5 | 40 | DIQMTQSPSSLSASVGDRVTITCQASQDINNYLNWYQQKPGKA PKLLIYDTSNLEPGVPSRFSGSGSGTDFTFTISSLQPEDIATY YCQQYDNLLTFGQGTRLEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| H1 144 1N1K | L6 | 41 | DIQMTQSPSSLSASVGDRVTITCQASQDISNYLNWYQHKPGKA PKLLIYDASNLETGVPSRFSGSGSGTDFTFTISSLQPEDIATY YCQQYDNLLTFGGGTKVEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| H1 16 1N1K | L7 | 42 | DIQMTQSPSSLSASVGDRVTITCQASQDISNYLNWYQQKPGKA PKFLIYDASNLETGVPSRFSGSGSGTDFTFTISSLQPEDIATY YCQQYDNLITFGQGTRLEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| H1 2 1N1K | L8 | 43 | DIVMTQSPDSLAVSLGERATINCKSSQSVLDSSDNKYLAWYQ QKPGQPPKLLIYWASNRESGVPDRFSGSGSGTDFSLTISSLQA EDVAVYYCQQYYSDPFTFGPGTKVDIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| H1 2 1N1K SM | L9 | 44 | DIVMTQSPDSLAVSLGERATINCKSSQSVLDSSDNKYLAWYQ QKPGQPPKLLIYWASNRESGVPDRFSGSGSGTDFTLTISSLQA EDVAVYYCQQYYSDPFTFGPGTKVDIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| H1 27 1N1K | L10 | 45 | DIQMTQSPSSLSASVGDRVTITCQASQDISNYLNWYQQKPGKA PKLLIYDASNLETGVPSRFSGSGSGTDFTFTISSLQPEDIATY YCQQYDNLLTFGGGTKVEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| H1 30 1N1K | L11 | 46 | DIVMTQSPDSLAVSLGERATIDCKSSQGVLDSSNNKNFLAWYQ QKPGQPPKLLIYWASNRESGVPVRFSGSGSGTDFTLTISSLQA EDVALYYCQQYYSDPFTFGPGTKVDIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| H1 33-1 1N1K | L12 | 47 | DIQMTQSPSSLSASVGDRVTITCRASQSISDYLNWYQQKPGKA PNLLIYAASSLQSGVPSRFSGSGSGTDFTLTISSLQPEDFATY FCQQTYSDPFTFGPGTKVDIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |

TABLE 1-continued

Exemplary Heavy and Light Chains

| Reference | Designation | SEQ ID NO. | Amino Acid Sequence |
|---|---|---|---|
| H1 34 1N1K | L13 | 48 | DIQMTQSPSSLSASVGDRVTITCQASQDISNYLNWYQQKPGKA PKLLIYDASNLETGVPSRFSGSGSGTDFTFTISSLQPEDIATY YCQQYDNLLTFGGGTKVEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| H1 39 1N1K | L14 | 49 | DIQMTQSPSSLSASVGDRVTITCQASQDISNYLNWYQQKPGKA PKVLIYDASNLETGVPSRFSGSGSGTDFTFTISSLQPEDIATY YCQQYDNLLTFGGGTKVEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| H1 42 1N1K | L15 | 50 | DIVMTQSPDSLAVSLGERATIDCKSSQSVLDSSNNKNFLAWYQ QKPGQPPKLLIYWASNRESGVPDRFSGSGSGTDFTLTISSLQA EDVAVYYCQQYYSDPFTFGPGTKVDIKRTVAAPSVFIFPPSDE QLKSGTASWCLLNNFYPREAKVQWKVDNALQSGNSQESVTEQD SKDSTYSLSSTLTLSKADYEKHKVYACEVTHQGLSSPVTKSFN RGEC |
| H1 64 1N1K | L16 | 51 | EIVLTQSPGTLSLSPGERATLSCRASQSVSSGYLAYLAWYQQK PGQAPRLLIYGASSTATGIPDRFSGSGSGTDFTLTISRLEPED FAVYYCQQYGSSPITFGQGTRLEIKRTVAAPSVFIFPPSDEQL KSGTASVVCLLNNFYPREAKVQWKVDNALQSGNSQESVTEQDS KDSTYSLSSTLTLSKADYEKHKVYACEVTHQGLSSPVTKSFNR GEC |
| H1 66 1N1K | L17 | 52 | DIQMTQSPSSLSASVGDRVTITCQASQDISNFLNWYQQRPGKA PKLLIYDASNLETGVPSRFSGSGSGTDFTFTISSLQPEDIATY YCQQYDNLPFTFGPGTKVDIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H1 72 1N1K | L18 | 53 | DIQMTQSPSSLSASVGDRVTITCQASQDISNYLNWYQQKPGKA PKLLIYDASNLETGVPSRFSGSGSGTDFTFTISSLQPEDFATY YCQQYDNLLTFGGGTKVEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| H1 90 1N1K | L19 | 54 | DIQMTQSPSSLSASVGDRVTITCQASQDISNYLNWYQQKPGKA PKLLIYDASNLETGVPSRFSGSGSGTDFTFTISSLQPEDIATY YCQRYDDLPITFGQGTRLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H2 103 1N1K | L20 | 55 | DIQMTQSPSSLSASVGDRVTITCQASQDISNYLNWYQQRPGKA PKLLIYDASNLETGVPSRFSGSGSGTDFTFTISSLQPEDIATY YCQQYDNLLTFGGGTKVEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| H2 131 1N1K | L21 | 56 | DIQMTQSPSSLSASVGDRVTITCRASQGFSNYLAWYQQKPGKV PKLLIYAASTLQSGVPSRFSGSGSGTDFTLTISSLQPEDVATY YCQKYNSAPLTFGGGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H2 360 1N1K | L22 | 57 | DIQMTQSPSSLSASVGDRVTITCRASQGINNYLAWYQQKPGKV PQLLIYVASTLQSGVPSRFSGSGSGTDFTLTISSLQPEDVATY YCQKYNSGPFTFGPGTKVDIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H2 360 1N1K SM | L23 | 58 | DIQMTQSPSSLSASVGDRVTITCRASQGINNYLAWYQQKPGKV PKLLIYVASTLQSGVPSRFSGSGSGTDFTLTISSLQPEDVATY YCQKYNSGPFTFGPGTKVDIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H2 369 1N1K | L24 | 59 | DIQMTQSPSSLSASVGDRVTITCRASQSISRYLNWYQQKPGKA PNLLIHAASSLQSGVPSRFSGSGSGTDFTLTISSLQPEDFATY YCQQSYITPPSFGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |

TABLE 1-continued

Exemplary Heavy and Light Chains

| Reference | Designation | SEQ ID NO. | Amino Acid Sequence |
|---|---|---|---|
| H2 380 1N1K | L25 | 60 | DIQMTQSPSSLSASVGDRVTITCRASQGIRNDLDWYQQKPGKA PKRLIYAASSLQSGVPSRFSGSGSGTEFTLTINSLQPEDFATY YCLQYNSYPITFGQGTRLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H2 475 1N1K | L26 | 61 | DIQMIQSPSSLSASVGDRVTITCQASHDISNYLNWYQQKPGKA PKFLISDASNLETGVPSRFSGSGSGTDFTFTISSLQPEDIATY YCQQYDNLPLTFGGGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H2 508 1N1K | L27 | 62 | DIVMTQSPLSLPVTPGEPASISCRSSQSLLHSNGYNYLDWYLQ KPGQSPQFLIYLGSIRASGVPDRFSGSGSGTDFALTISRVEAE DVGVYYCMQALQTPRTFGQGTKVEIKRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| H2 534 1N1K | L28 | 63 | EIVLTQSPDFQSVTPKEKVTITCRASQYIGSSLHWYQQTPDQS PKLLINYVSQSFSGVPSRFSGSGSGTDFTLTINSLEAEDAATY YCHQSSSLPFTFGPGTKVDIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H2 550 1N1K | L29 | 64 | DIVMTQSPDSLAVSLGARATISCKSSQSVLYSSNNKNYLAWYQ QKPGQPPKLLIYWASTRESGVPDRFSGSGSGTDFTLTISTLQA EDVAVYYCQQYYTTPPTFGQGTKVEIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSF NRGEC |
| H2 65 1N1K | L30 | 65 | DIQMTQSPSSLSASVGDRVTITCQASQDINNYLNWYQQKPGKA PKLLIYDASNLETGVPSRFSGSGSGTDFTFTISSLQPEDIATY YCQQYDDLLTFGGGTKVEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| H1 13 1N1K | L31 | 66 | DIQMTQSPSSLSASVGDRVTITCQASQDISNYLNWYQQKPGKA PKLLIYDASNLETGVPSRFSGSGSGTDFTFIISSLQPEDIATY YCQQFDNLPPTFGGGTKVESKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| H1 26 1N1K | L32 | 67 | DIQMTQSPSSLSASVGDRVTITCQASQDISNYLNWYQHKPGKA PKLLIYDASNLETGVPSRFSGSGSGTDFTFTISSLQPEDIATY YCQQYDNLLTFGGGTKVEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC |
| H1 13H1 13 1NVK2KK | L33 | 68 | DVVMTQSPLSLPVTLGQPASISCRSSQSLVYSDGNTYLNWFQQ RPGQSPRRLIYKVSNWDSGVPDRFSGSGSGTDFTLKISRVEAE DVGVYYCMQGTHWPRGLFTFGPGTKVDIKRTVAAPSVFIFPPS DEQLKSGTASVVCLLNNFYPREAKVQWKVDNALQSGNSQESVT EQDSKDSTYSLSSTLTLSKADYEKHKVYACEVTHQGLSSPVTK SFNRGEC |
| H1 26H1 26 1NVK2KK | L34 | 69 | DVVMTQSPLSLPVTLGQPASISCRSSQSLVYSDGNTYLNWFQQ RPGQSPRRLIYKVSNWDSGVPDRFNGSGSGTDFTLKISRVEAE DVGVYYCMQGTHWPITFGQGTGLEIKRTVAAPSVFIFPPSDEQ LKSGTASVVCLLNNFYPREAKVQWKVDNALQSGNSQESVTEQDS KDSTYSLSSTLTLSKADYEKHKVYACEVTHQGLSSPVTKSFNR GEC |

Again, each of the exemplary heavy chains (H1, H2, H3 etc.) listed in TABLE 1 can be combined with any of the exemplary light chains shown in TABLE 1 to form an antibody. Examples of such combinations include H1 combined with any of L1 through L34; H2 combined with any of L1 through L34; H3 combined with any of L1 through L34, and so on. In some instances, the antibodies include at least one heavy chain and one light chain from those listed in TABLE 1. In some instances, the antibodies comprise two different heavy chains and two different light chains listed in TABLE 1. In other instances, the antibodies contain two identical light chains and two identical heavy chains. As an example, an antibody or immunologically functional fragment may include two H1 heavy chains and two L1 light chains, or two H2 heavy chains and two L2 light chains, or two H3 heavy chains and two L3 light chains and other similar combinations of pairs of light chains and pairs of heavy chains as listed in TABLE 1.

Other antigen binding proteins that are provided are variants of antibodies formed by combination of the heavy and light chains shown in TABLE 1 and comprise light and/or heavy chains that each have at least 70%, 75%, 80%, 85%, 90%, 95%, 97% or 99% identity to the amino acid sequences of these chains. In some instances, such antibodies include at least one heavy chain and one light chain, whereas in other instances the variant forms contain two identical light chains and two identical heavy chains.

Variable Domains of Antibodies

Also provided are antigen binding proteins that contain an antibody heavy chain variable region selected from the group consisting of $V_H1$, $V_H2$, $V_H3$, $V_H4$, $V_H5$, $V_H6$, $V_H7$, $V_H8$, $V_H9$, $V_H10$, $V_H11$, $V_H12$, $V_H13$, $V_H14$, $V_H15$, $V_H16$, $V_H17$, $V_H18$, $V_H19$, $V_H20$, $V_H21$, $V_H22$, $V_H23$, $V_H24$, $V_H25$, $V_H26$, $V_H27$, $V_H28$, $V_H29$, $V_H30$, $V_H31$, and $V_H32$, and/or an antibody light chain variable region selected from the group consisting of $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, $V_L21$, $V_L22$, $V_L23$, $V_L24$, $V_L25$, $V_L26$, $V_L27$, $V_L28$, $V_L29$, $V_L30$, $V_L31$, $V_L32$, $V_L33$, and $V_L34$, as shown in TABLE 2 below, and immunologically functional fragments, derivatives, muteins and variants of these light chain and heavy chain variable regions.

Sequence alignments of the various heavy and light chain variable regions, respectively, are provided in FIGS. 1A and 1B.

Antigen binding proteins of this type can generally be designated by the formula "$V_Hx/V_Ly$," where "x" corresponds to the number of heavy chain variable regions and "y" corresponds to the number of the light chain variable regions (in general, x and y are each 1 or 2) as listed in TABLE 2:

TABLE 2

Exemplary $V_H$ and $V_L$ Chains

| Reference | Designation | SEQ ID NO. | Amino Acid Sequence |
|---|---|---|---|
| H1 109 1N1G1 | $V_H1$ | 70 | QVQLVQSGAEVKKPGASVKVSCKASGYTFTAYYMHWVRQAPGQ GLEWMGWINPNSGGTNYAQKFQGRVTMTRDTSISTAYMELSRLR SDDTAVYYCARGGYSGYDLGYYYGMDVWGQGTTVTVSS |
| H1 13 1N1G1 | $V_H2$ | 71 | QVQLQESGPGLVKPSETLSLTCTVSGGSVSSGGYYWSWIRQPPG KGLEWIGYIYYSGSTNYNPSLKSRVTISVDTSKNQFSLKLSSVTAAD TAVYYCAAGIAATGTLFDCWGQGTLVTVSS |
| H1 131 1N1G1 | $V_H3$ | 72 | QVQLVQSGAEVKKPGASVKVSCKASGYTFTGYYIHWVRQAPGQG LEWMGWINPNSGGTNYAQKFQGRVTMTRDTSISTAYMELSRLRS DDTAVYYCARDRGQLWLWYYYYYGMDVWGQGTTVTVSS |
| H1 134 1N1G1 | $V_H4$ | 73 | QVQLVESGGGVVQPGRSLRLSCAASGFTFSSYGMHWVRQAPGK GLEWVAVIWYDGSNKYYADSVKGRFTISRDNSKNTLYLQMNSLRA EDTAVYYCASSSWSYYGMDVWGQGTTVTVSS |
| H1 143 1N1G1 | $V_H5$ | 74 | EVQLVESGGGLVKPGGSLRLSCAASGFTVSNAWMSWVRQAPGK GLEWVGRIKSKTDGGTTDNAAPVKGRFTISRDDSKNTLYLQMNSL KTEDTAVYYCTTGGSLLWTGPNYYYYGMDVWGQGTTVTVSS |
| H1 144 1N1G1 | $V_H6$ | 75 | EVQLVESGGGLVKPGGSLRLSCAASGFTFSNAWMSWVRQAPGK GLEWVGRIKSKTDGGTTDYAAPVKGRFTISRDDSKNTLYLQMNSL KTEDTAVYYCTTEYYGSGGVWYYGMDVWGQGTTVTVSS |
| H1 16 1N1G1 | $V_H7$ | 76 | EVQLVESGGGLVKPGGSLRLSCAASGFTFSNAWMSWVRQAPGK GLEWVGRIKSKTDGWTTDYAAPVKGRFTISRDDSKNTLYLQMNSL KTEDTAVYYCTTDLRITGTTYYYYYGMDVWGQGTTVTVSS |
| H1 2 1N1G1 | $V_H8$ | 77 | QVQLVQSGAEVKKPGASVKVSCKASGYTFTSYGISWVRQAPGQG LEWMGWISAYNGNTNYAQKLQGRVTMTTDTSTSTAYMELRSLRS DDTAVYYCARESWFGEVFFDYWGQGTLVTVSS |
| H1 26 1N1G1 | $V_H9$ | 78 | EVQLVESGGGLVKPGGSLRLSCAASGFTFSNAWMSWVRQAPGK GLEWVGRIKSKTDGGTTDYAAPVKGRFTISRDDSKNTLYLQMNSL KTEDTAVYYCTTEYYGSGGVWYYGMDVWGQGTTVTVSS |
| H1 27 1N1G1 | $V_H10$ | 79 | EVQLVESGGGLVKPGGSLRLSCAASGFTFSNAWMSWVRQAPGK GLEWVGRIKSKTDGGTTDYAAPVKGRFTISRDDSKNTLYLQMNSL KTEDTAVYYCTTDGATVVTPGYYYYGTDVWGQGTTVTVSS |
| H1 30 1N1G1 | $V_H11$ | 80 | QVQLVQSGAEVKKPGASVKVSCKASGYTFTSYGISWVRQAPGQG LEWMGWISAYNGNTNYAQKLQGRVTMTTDTSTSTAYMELRSLRS DDTAVYYCARESWFGEVFFDYWGQGTLVTVSS |
| H1 33-1 1N1G1 | $V_H12$ | 81 | QVQLVQSGAEVKKPGASVKVSCKASGYTFTGYYMHWVRQAPGQ GLEWMGWINPNSGGTNYAQKFQGRVTMTRDTSISTAYMELSRLR SDDTAFYYCARDSNWYHNWFDPWGQGTLVTVSS |
| H1 33 1N1G1 | $V_H13$ | 82 | QVQLVQSGAEVKKPGASVKVSCKASGYTFTGYYMHWVRQAPGQ GLEWMGWINPNSGGTNYAQKFQGRVTMTRDTSISTAYMELSRLR SDDTAFYYCARDSNWYHNWFDPWGQGTLVTVSS |
| H1 34 1N1G1 | $V_H14$ | 83 | EVQLVESGGGLVKPGGSLRLSCAASGFTFSNAWMSWVRQAPGK GLEWVGRIKSKTDGGTTDYAAPVKGRFTISRDDSKNTLYLQMNSL KTEDTAVYYCTTDGATVVTPGYYYYGTDVWGQGTTVTVSS |

TABLE 2-continued

Exemplary V_H and V_L Chains

| Reference | Designation | SEQ ID NO. | Amino Acid Sequence |
|---|---|---|---|
| H1 39 1N1G1 | $V_H15$ | 84 | EVQLVESGGGLVKPGGSLRLSCAASGFTFSNAWMSWVRQAPGK GLEWVGRIKSKTDGGTADYAAPVKGRFTISRDDSKNTLYLQMNSL KTEDTAVYYCTTEGPYSDYGYYYYGMDVWGQGTTVTVSS |
| H1 42 1N1G1 | $V_H16$ | 85 | QVQLVQSGAEVKKPGASVKVSCKASGYTFTSYGISWVRQAPGQG LEWMGWISAYNGNTNYAQKLQGRVTMTTDTSTSTAYMELRSLRS DDTAVYYCARESWFGEVFFDYWGQGTLVTVSS |
| H1 64 1N1G1 | $V_H17$ | 86 | EVQLVESGGGLVQPGGSLRLSCAASGFTFSSYDMHWVRQATGKG LEWVSGIGTAGDTYYPGSVKGRFNISRENAKNSLYLQMNSLRAGD TAVYYCAREGSWYGFDYWGQGTLVTVSS |
| H1 66 1N1G1 | $V_H18$ | 87 | QVQLVESGGGVVQPGRSLRLSCAASGFTFSSYGMHWVRQAPGK GLEWVAVIWYDGSNEYYADSVKGRFTISRDNSKSTLYLQMNSLRA EDTAVYYCAHSSGNYYDMDVWGQGTTVTVSS |
| H1 72 1N1G1 | $V_H19$ | 88 | EVQLVESGGGLVEPGGSLRLSCAASGFTFSTAWMSWVRQAPGK GLEWVGRIKSKTDGGTTDYAAPVKGRFTISRDDSKNTLYLQMNSL KNEDTAVYYCTTEGPYSNYGYYYYGVDVWGQGTTVTVSS |
| H2 103 1N1G2 | $V_H20$ | 89 | EVQLVESGGGLVKPGGSLTLSCAASGFTFNNAWMSWVRQAPGK GLEWVGRIKSKTDGGTTDYAAPVKGRFTISRDDSKNTLYLQMNSL KTEDTAVYYCTTEYYHILTGSFYYSYYGMDVWGQGTTVTVSS |
| H1 90 1N1G1 | $V_H21$ | 90 | QVQLVESGGGVVQPGRSLRLSCAASGFTFSSYGMHWVRQAPGK GLEWVAVIWYDGSNKYYADSVKGRFTISRDNSKNTLYLQMNSLRA EDTAVYYCASSSSNFYDMDVWGQGTTVTVSS |
| H2 131 1N1G2 | $V_H22$ | 91 | QVQLQESGPGLVKPSETLSLTCTVSGGSISNYYWSWIRQSAGKGL EWIGRIYTSGSTHYNPSLKSRIIMSVDTSKNQFSLKLSSVTAADTAV YYCARDRVFYGMDVWGQGTTVTVSS |
| H2 291 1N1G2 | $V_H23$ | 92 | QVQLVESGGGVVQPGRSLRLSCAASGFTFSSYGMHWVRQAPGK GLEWVAVIWYDGSYKYYADSVKGRFTISRDNSKNTLYLQMNSLRA EDTAVYYCAREGDYSDYYGMDVWGQGTTVTVSS |
| H2 360 1N1G2 | $V_H24$ | 93 | QVQLVQSGAEVKKPGASVKVSCKVSGYTLTELSMHWVRQAPGKG LEWMGGFDPEDGETIYAQKFQGRVTMTEDTSTDTVYMELSSLRSE DTAVYYCATGVMITFGGIVGHSYYGMDVWGQGTTVTVSS |
| H2 360 1N1G2 SM | $V_H25$ | 94 | QVQLVQSGAEVKKPGASVKVSCKVSGYTLTELSMHWVRQAPGKG LEWMGGFDPEDGETIYAQKFQGRVTMTEDTSTDTAYMELSSLRSE DTAVYYCATGVMITFGGIVGHSYYGMDVWGQGTTVTVSS |
| H2 369 1N1G2 | $V_H26$ | 95 | QVQLVQSGAEVKKPGASVKVSCKVSGYTLTELSMHWVRQAPGKG LEWMGGFDPEDGETIYAQKFQGRVTMTEDTSTDTAYMELSSLRSE DTAVYYCATRAGTTLAYYYYAMDVWGQGTTVTVSS |
| H2 380 1N1G2 | $V_H27$ | 96 | QVQLQESGPGLVKPSETLSLTCTVSGGSISSYYWSWIRQPPGKGL EWIGYIYYSGNTNYNPSLKSRFTLSIDTSKNQFSLRLSSVTAADTAV YYCACIATRPFDYWGQGTLVTVSS |
| H2 475 1N1G2 | $V_H28$ | 97 | QVQLVESGGGVVQPGRSLRLSCAASGFTFISYGMHWVRQAPGKG LEWVAVIWYDGSNKYYADSVKGRFTISRDNSKNTLYLQMNSLRAE DTAVYYCADSSGDYYGMDVWGQGTTVTVSS |
| H2 508 1N1G2 | $V_H29$ | 98 | QVQLVQSGAEVKKPGASVKVSCKVSGYTLTELSMHWVRQAPGKG LEWMGGFDPEDGETIYAQKFQGRVTMTEDTSTDTAYMELSSLRSE DTAVYYCATAGLEIRWFDPWGQGTLVTVSS |
| H2 534 1N1G2 | $V_H30$ | 99 | QVQLQESGPGLVKPSQTLSLTCTVSGGSISSGGYYWSWIRQHPG KGLEWIGYISYSGDTYYNPSLKSRLTISVDTSKHQFSLRLSSVTSAD TAVYYCASLDLYGDYFDYWGQGTLVTVSS |
| H2 550 1N1G2 | $V_H31$ | 100 | QVQLVQSGAEVKKPGASVKVSCKASGYTLTSYGISWVRQAPGQG LEWMGWISAYNGNPNYAQKFQGRVTMTTDTSTSTAYMELRSLRS DDTAVYYCARDQGLLGFGELEGLFDYWGQGTLVTVSS |
| H2 65 1N1G2 | $V_H32$ | 101 | EVQLVESGGGLVKPGGSLRLSCAASGFTFSNAWMSWVRQAPGK GLEWVGRIKTKTDGGTTDYAAPVKGRFTISRDDSQNTLYLQMNSL KTEDTAVYYCTTEYYGIVTGSFYYYYGMDVWGQGTTVTVSS |
| H1 109 1N1K | $V_L1$ | 102 | DIQMTQSPSSLSASVGDRVTITCQASQNISNFLDWYQQKPGKAPN LLIYDASDLDPGVPSRFSGSGSGTDFTFTISSLQPEDIATYYCQQYV SLPLTFGGGTKVEIK |

TABLE 2-continued

Exemplary V_H and V_L Chains

| Reference | Designation | SEQ ID NO. | Amino Acid Sequence |
|---|---|---|---|
| H1 109 1N1K SM | V_L2 | 103 | DIQMTQSPSSLSASVGDRVTITCQASQDISNFLDWYQQKPGKAPK LLIYDASDLDPGVPSRFSGSGSGTDFTFTISSLQPEDIATYYCQQYV SLPLTFGGGTKVEIK |
| H1 131 1N1K | V_L3 | 104 | DNVMTQTPLSLSVTPGQPASISCKSSQSLLHSDGKTYLYWLQKP GQPPQLLIYEASNRFSGVPDRFSGSGSGTDFTLKISRVEAEDVGVY YCMQSIQLPLTFGGGTKVEIK |
| H1 134 1N1K | V_L4 | 105 | DIQMTQSPSSLSASVGDRVTITCQASQDINNYLNWYQQKPGKAPK LLIYDASNLEIGVPSRFSGSGSGTDFIFTISSLQPEDIATYYCQQYDN FPFTFGGGTKVEIK |
| H1 143 1N1K | V_L5 | 106 | DIQMTQSPSSLSASVGDRVTITCQASQDINNYLNWYQQKPGKAPK LLIYDTSNLEPGVPSRFSGSGSGTDFTFTISSLQPEDIATYYCQQYD NLLTFGQGTRLEIK |
| H1 144 1N1K | V_L6 | 107 | DIQMTQSPSSLSASVGDRVTITCQASQDISNYLNWYQHKPGKAPK LLIYDASNLETGVPSRFSGSGSGTDFTFTISSLQPEDIATYYCQQYD NLLTFGGGTKVEIK |
| H1 16 1N1K | V_L7 | 108 | DIQMTQSPSSLSASVGDRVTITCQASQDISNYLNWYQQKPGKAPK FLIYDASNLETGVPSRFSGSGSGTDFTFTISSLQPEDIATYYCQQYD NLITFGQGTRLEIK |
| H1 2 1N1K | V_L8 | 109 | DIVMTQSPDSLAVSLGERATINCKSSQSVLDSSDNKNYLAWYQQK PGQPPKLLIYWASNRESGVPDRFSGSGSGTDFSLTISSLQAEDVAV YYCQQYYSDPFTFGPGTKVDIK |
| H1 2 1N1K SM | V_L9 | 110 | DIVMTQSPDSLAVSLGERATINCKSSQSVLDSSDNKNYLAWYQQK PGQPPKLLIYWASNRESGVPDRFSGSGSGTDFTLTISSLQAEDVAV YYCQQYYSDPFTFGPGTKVDIK |
| H1 27 1N1K | V_L10 | 111 | DIQMTQSPSSLSASVGDRVTITCQASQDISNYLNWYQQKPGKAPK LLIYDASNLETGVPSRFSGSGSGTDFTFTISSLQPEDIATYYCQQYD NLLTFGGGTKVEIK |
| H1 30 1N1K | V_L11 | 112 | DIVMTQSPDSLAVSLGERATIDCKSSQGVLDSSNNKNFLAWYQQK PGQPPKLLIYWASNRESGVPVRFSGSGSGTDFTLTISSLQAEDVAL YYCQQYYSDPFTFGPGTKVDIK |
| H1 33-1 1N1K | V_L12 | 113 | DIQMTQSPSSLSASVGDRVTITCRASQSISDYLNWYQQKPGKAPN LLIYAASSLQSGVPSRFSGSGSGTDFTLTISSLQPEDFATYFCQQTY SDPFTFGPGTKVDIK |
| H1 34 1N1K | V_L13 | 114 | DIQMTQSPSSLSASVGDRVTITCQASQDISNYLNWYQQKPGKAPK LLIYDASNLETGVPSRFSGSGSGTDFTFTISSLQPEDIATYYCQQYD NLLTFGGGTKVEIK |
| H1 39 1N1K | V_L14 | 115 | DIQMTQSPSSLSASVGDRVTITCQASQDISNYLNWYQQKPGKAPK V_LIYDASNLETGVPSRFSGSGSGTDFTFTISSLQPEDIATYYCQQYD NLLTFGGGTKVEIK |
| H1 42 1N1K | V_L15 | 116 | DIVMTQSPDSLAVSLGERATIDCKSSQSVLDSSNNKNFLAWYQQK PGQPPKLLIYWASNRESGVPDRFSGSGSGTDFTLTISSLQAEDVAV YYCQQYYSDPFTFGPGTKVDIK |
| H1 64 1N1K | V_L16 | 117 | EIV_LTQSPGTLSLSPGERATLSCRASQSVSSGYLAYLAWYQQKPG QAPRLLIYGASSTATGIPDRFSGSGSGTDFTLTISRLEPEDFAVYYC QQYGSSPITFGQGTRLEIK |
| H1 66 1N1K | V_L17 | 118 | DIQMTQSPSSLSASVGDRVTITCQASQDISNFLNWYQQRPGKAPK LLIYDASNLETGVPSRFSGSGSGTDFTFTISSLQPEDIATYYCQQYD NLPFTFGPGTKVDIK |
| H1 72 1N1K | V_L18 | 119 | DIQMTQSPSSLSASVGDRVTITCQASQDISNYLNWYQQKPGKAPK LLIYDASNLETGVPSRFSGSGSGTDFTFTISSLQPEDFATYYCQQY DNLLTFGGGTKVEIK |
| H1 90 1N1K | V_L19 | 120 | DIQMTQSPSSLSASVGDRVTITCQASQDISNYLNWYQQKPGKAPK LLIYDASNLETGVPSRFSGSGSGTDFTFTISSLQPEDIATYYCQRYD DLPITFGQGTRLEIK |
| H2 103 1N1K | V_L20 | 121 | DIQMTQSPSSLSASVGDRVTITCQASQDISNYLNWYQQRPGKAPK LLIYDASNLETGVPSRFSGSGSGTDFTFTISSLQPEDIATYYCQQYD NLLTFGGGTKVEIK |

TABLE 2-continued

Exemplary $V_H$ and $V_L$ Chains

| Reference | Designation | SEQ ID NO. | Amino Acid Sequence |
|---|---|---|---|
| H2 131 1N1K | $V_L$21 | 122 | DIQMTQSPSSLSASVGDRVTITCRASQGFSNYLAWYQQKPGKVPK LLIYAASTLQSGVPSRFSGSGSGTDFTLTISSLQPEDVATYYCQKY NSAPLTFGGGTKVEIK |
| H2 360 1N1K | $V_L$22 | 123 | DIQMTQSPSSLSASVGDRVTITCRASQGINNYLAWYQQKPGKVPQ LLIYVASTLQSGVPSRFSGSGSGTDFTLTISSLQPEDVATYYCQKY NSGPFTFGPGTKVDIK |
| H2 360 1N1K SM | $V_L$23 | 124 | DIQMTQSPSSLSASVGDRVTITCRASQGINNYLAWYQQKPGKVPK LLIYVASTLQSGVPSRFSGSGSGTDFTLTISSLQPEDVATYYCQKY NSGPFTFGPGTKVDIK |
| H2 369 1N1K | $V_L$24 | 125 | DIQMTQSPSSLSASVGDRVTITCRASQSISRYLNWYQQKPGKAPN LLIHAASSLQSGVPSRFSGSGSGTDFTLTISSLQPEDFATYYCQQS YITPPSFGQGTKLEIK |
| H2 380 1N1K | $V_L$25 | 126 | DIQMTQSPSSLSASVGDRVTITCRASQGIRNDLDWYQQKPGKAPK RLIYAASSLQSGVPSRFSGSGSGTEFTLTINSLQPEDFATYYCLQY NSYPITFGQGTRLEIK |
| H2 475 1N1K | $V_L$26 | 127 | DIQMIQSPSSLSASVGDRVTITCQASHDISNYLNWYQQKPGKAPKF LISDASNLETGVPSRFSGSGSGTDFTFTISSLQPEDIATYYCQQYDN LPLTFGGGTKVEIK |
| H2 508 1N1K | $V_L$27 | 128 | DIVMTQSPLSLPVTPGEPASISCRSSQSLLHSNGYNYLDWYLQKPG QSPQFLIYLGSIRASGVPDRFSGSGSGTDFALTISRVEAEDVGVYY CMQALQTPRTFGQGTKVEIK |
| H2 534 1N1K | $V_L$28 | 129 | EIV$_L$TQSPDFQSVTPKEKVTITCRASQYIGSSLHWYQQTPDQSPKL LINYVSQSFSGVPSRFSGSGSGTDFTLTINSLEAEDAATYYCHQSS SLPFTFGPGTKVDIK |
| H2 550 1N1K | $V_L$29 | 130 | DIVMTQSPDSLAVSLGARATISCKSSQSV$_L$YSSNNKNYLAWYQQK PGQPPKLLIYWASTRESGVPDRFSGSGSGTDFTLTISTLQAEDVAV YYCQQYYTTPPTFGQGTKVEIK |
| H2 65 1N1K | $V_L$30 | 131 | DIQMTQSPSSLSASVGDRVTITCQASQDINNYLNWYQQKPGKAPK LLIYDASNLETGVPSRFSGSGSGTDFTFTISSLQPEDIATYYCQQYD DLLTFGGGTKVEIK |
| H1 13 1N1K | $V_L$31 | 132 | DIQMTQSPSSLSASVGDRVTITCQASQDISNYLNWYQQKPGKAPK LLIYDASNLETGVPSRFSGSGSGTDFTFIISSLQPEDIATYYCQQFD NLPPTFGGGTKVESK |
| H1 26 1N1K | $V_L$32 | 133 | DIQMTQSPSSLSASVGDRVTITCQASQDISNYLNWYQHKPGKAPK LLIYDASNLETGVPSRFSGSGSGTDFTFTISSLQPEDIATYYCQQYD NLLTFGGGTKVEIK |
| H1 13H1 13 1NVK2KK | $V_L$33 | 134 | DVVMTQSPLSLPVTLGQPASISCRSSQSLVYSDGNTYLNWFQQRP GQSPRRLIYKVSNWDSGVPDRFSGSGSGTDFTLKISRVEAEDVGV YYCMQGTHWPRGLFTFGPGTKVDIK |
| H1 26H1 26 1NVK2KK | $V_L$34 | 135 | DVVMTQSPLSLPVTLGQPASISCRSSQSLVYSDGNTYLNWFQQRP GQSPRRLIYKVSNWDSGVPDRFNGSGSGTDFTLKISRVEAEDVGV YYCMQGTHWPITFGQGTGLEIK |

Each of the heavy chain variable regions listed in TABLE 2 may be combined with any of the light chain variable regions shown in TABLE 2 to form an antigen binding protein. Examples of such combinations include $V_H$1 combined with any of $V_L$1, $V_L$2, $V_L$3, $V_L$4, $V_L$5, $V_L$6, $V_L$7, $V_L$8, $V_L$9, $V_L$10, $V_L$11, $V_L$12, $V_L$13, $V_L$14, $V_L$15, $V_L$16, $V_L$17, $V_L$18, $V_L$19, $V_L$20, $V_L$21, $V_L$22, $V_L$23, $V_L$24, $V_L$25, $V_L$26, $V_L$27, $V_L$28, $V_L$29, $V_L$30, $V_L$31, $V_L$32, $V_L$33, or $V_L$34; $V_H$2 combined with any of $V_L$1, $V_L$2, $V_L$3, $V_L$4, $V_L$5, $V_L$6, $V_L$7, $V_L$8, $V_L$9, $V_L$10, $V_L$11, $V_L$12, $V_L$13, $V_L$14, $V_L$15, $V_L$16, $V_L$17, $V_L$18, $V_L$19, $V_L$20, $V_L$21, $V_L$22, $V_L$23, $V_L$24, $V_L$25, $V_L$26, $V_L$27, $V_L$28, $V_L$29, or $V_L$30, or $V_H$3 combined with any of $V_L$1, $V_L$2, $V_L$3, $V_L$4, $V_L$5, $V_L$6, $V_L$7, $V_L$8, $V_L$9, $V_L$10, $V_L$11, $V_L$12, $V_L$13, $V_L$14, $V_L$15, $V_L$16, $V_L$17, $V_L$18, $V_L$19, $V_L$20, $V_L$21, $V_L$22, $V_L$23, $V_L$24, $V_L$25, $V_L$26, $V_L$27, $V_L$28, $V_L$29, $V_L$30, $V_L$31, $V_L$32, $V_L$33, or $V_L$34, and so on.

In some instances, the antigen binding protein includes at least one heavy chain variable region and/or one light chain variable region from those listed in TABLE 2. In some instances, the antigen binding protein includes at least two different heavy chain variable regions and/or light chain variable regions from those listed in TABLE 2. An example of such an antigen binding protein comprises (a) one $V_H$1, and (b) one of $V_H$2, $V_H$3, $V_H$4, $V_H$5, $V_H$6, $V_H$7, $V_H$8, $V_H$9, $V_H$10, $V_H$11, $V_H$12, $V_H$13, $V_H$14, $V_H$15, $V_H$16, $V_H$17, $V_H$18, $V_H$19, $V_H$20, $V_H$21, $V_H$22, $V_H$23, $V_H$24, $V_H$25, $V_H$26, $V_H$27, $V_H$28, $V_H$29, $V_H$30, $V_H$31, or $V_H$32. Another example comprises (a) one $V_H$2, and (b) one of $V_H$1, $V_H$3, $V_H$4, $V_H$5, $V_H$6, $V_H$7, $V_H$8, $V_H$9, $V_H$10, $V_H$11, $V_H$12, $V_H$13, $V_H$14, $V_H$15, $V_H$16, $V_H$17, $V_H$18, $V_H$19, $V_H$20, $V_H$21, $V_H$22, $V_H$23, $V_H$24, $V_H$25, $V_H$26, $V_H$27, $V_H$28, $V_H$29, $V_H$30, $V_H$31, or $V_H$32. Again another example comprises (a) one $V_H3$, and (b) one of $V_H1$, $V_H2$, $V_H4$, $V_H5$, $V_H6$, $V_H7$, $V_H8$, $V_H9$, $V_H10$, $V_H11$, $V_H12$, $V_H13$, $V_H14$, $V_H15$, $V_H16$, $V_H17$, $V_H18$, $V_H19$, $V_H20$, $V_H21$, $V_H22$, $V_H23$, $V_H24$, $V_H25$, $V_H26$, $V_H27$, $V_H28$, $V_H29$, $V_H30$, $V_H31$, or $V_H32$ etc.

Again another example of such an antigen binding protein comprises (a) one $V_L1$, and (b) one of $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, $V_L21$, $V_L22$, $V_L23$, $V_L24$, $V_L25$, $V_L26$, $V_L27$, $V_L28$, $V_L29$, $V_L30$, $V_L31$, $V_L32$, $V_L33$, or $V_L34$. Again another example of such an antigen binding protein comprises (a) one $V_L2$, and (b) one of $V_L1$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, $V_L21$, $V_L22$, $V_L23$, $V_L24$, $V_L25$, $V_L26$, $V_L27$, $V_L28$, $V_L29$, $V_L30$, $V_L31$, $V_L32$, $V_L33$, and $V_L34$. Again another example of such an antigen binding protein comprises (a) one $V_L3$, and (b) one of $V_L1$, $V_L2$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, $V_L21$, $V_L22$, $V_L23$, $V_L24$, $V_L25$, $V_L26$, $V_L27$, $V_L28$, $V_L29$, $V_L30$, $V_L31$, $V_L32$, $V_L33$, or $V_L34$, etc.

The various combinations of heavy chain variable regions may be combined with any of the various combinations of light chain variable regions.

In other instances, the antigen binding protein contains two identical light chain variable regions and/or two identical heavy chain variable regions. As an example, the antigen binding protein may be an antibody or immunologically functional fragment that includes two light chain variable regions and two heavy chain variable regions in combinations of pairs of light chain variable regions and pairs of heavy chain variable regions as listed in TABLE 2.

Some antigen binding proteins that are provided comprise a heavy chain variable domain comprising a sequence of amino acids that differs from the sequence of a heavy chain variable domain selected from $V_H1$, $V_H2$, $V_H3$, $V_H4$, $V_H5$, $V_H6$, $V_H7$, $V_H8$, $V_H9$, $V_H10$, $V_H11$, $V_H12$, $V_H13$, $V_H14$, $V_H15$, $V_H16$, $V_H17$, $V_H18$, $V_H19$, $V_H20$, $V_H21$, $V_H22$, $V_H23$, $V_H24$, $V_H25$, $V_H26$, $V_H27$, $V_H28$, $V_H29$, $V_H30$, $V_H31$, and $V_H32$ at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The heavy chain variable region in some antigen binding proteins comprises a sequence of amino acids that has at least 70%, 75%, 80%, 85%, 90%, 95%, 97% or 99% sequence identity to the amino acid sequences of the heavy chain variable region of $V_H1$, $V_H2$, $V_H3$, $V_H4$, $V_H5$, $V_H6$, $V_H7$, $V_H8$, $V_H9$, $V_H10$, $V_H11$, $V_H12$, $V_H13$, $V_H14$, $V_H15$, $V_H16$, $V_H17$, $V_H18$, $V_H19$, $V_H20$, $V_H21$, $V_H22$, $V_H23$, $V_H24$, $V_H25$, $V_H26$, $V_H27$, $V_H28$, $V_H29$, $V_H30$, $V_H31$, and $V_H32$.

Certain antigen binding proteins comprise a light chain variable domain comprising a sequence of amino acids that differs from the sequence of a light chain variable domain selected from $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, $V_L21$, $V_L22$, $V_L23$, $V_L24$, $V_L25$, $V_L26$, $V_L27$, $V_L28$, $V_L29$, $V_L30$, $V_L31$, $V_L32$, $V_L33$, or $V_L34$ at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The light chain variable region in some antigen binding proteins comprises a sequence of amino acids that has at least 70%, 75%, 80%, 85%, 90%, 95%, 97% or 99% sequence identity to the amino acid sequences of the light chain variable region of $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, $V_L21$, $V_L22$, $V_L23$, $V_L24$, $V_L25$, $V_L26$, $V_L27$, $V_L28$, $V_L29$, $V_L30$, $V_L31$, $V_L32$, $V_L33$, or $V_L34$.

Still other antigen binding proteins, e.g., antibodies or immunologically functional fragments, include variant forms of a variant heavy chain and a variant light chain as just described.

CDRs

The antigen binding proteins disclosed herein are polypeptides into which one or more CDRs are grafted, inserted and/or joined. An antigen binding protein can have 1, 2, 3, 4, 5 or 6 CDRs. An antigen binding protein thus can have, for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3"). Some antigen binding proteins include both a CDRH3 and a CDRL3. Specific heavy and light chain CDRs are identified in TABLES 3A and 3B, respectively.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. Certain antibodies that are disclosed herein comprise one or more amino acid sequences that are identical or have substantial sequence identity to the amino acid sequences of one or more of the CDRs presented in TABLE 3A (CDRHs) and TABLE 3B (CDRLs).

TABLE 3A

Exemplary CDRH Sequences

| Contained in Reference | Designation | Amino Acid Sequence/ SEQ ID NO. |
|---|---|---|
| H1 13 1N1G1; H2 534 1NG2 | CDRH 1-1 | SGGYYWS [SEQ ID NO: 136] |
| H1 26 1N1G1; H1 143 1N1G1; H1 144 1N1G1; H1 39 1N1G1; H2 103 1N1G2; H2 65 1N1G2; H1 16 1N1G1; H1 34 1N1G1; H1 27 1N1G1 | CDRH 1-2 | NAWMS [SEQ ID NO: 137] |
| H1 72 1N1G1 | CDRH 1-3 | TAWMS [SEQ ID NO: 138] |
| H1 33 1N1G1; H1 33 1 1N1G1 | CDRH 1-4 | GYYMH [SEQ ID NO: 139] |
| H1 109 1N1G1 | CDRH 1-5 | AYYMH [SEQ ID NO: 140] |
| H1 4 1N1G1 | CDRH 1-6 | SYDMH [SEQ ID NO: 141] |
| H2 369 1N1G2; H2 508 1N1G2; H2 360 1N1G2 | CDRH 1-7 | ELSMH [SEQ ID NO: 142] |

TABLE 3A-continued

Exemplary CDRH Sequences

| Contained in Reference | Designation | Amino Acid Sequence/ SEQ ID NO. |
|---|---|---|
| H2 475 1N1G2 H1 66 1N1G1; H1 90 1N1G1; H1 134 1N1G1 H2 291 1N1G2 | CDRH 1-8 | SYGMH [SEQ ID NO: 143] |
| H2 380 1n1g2 | CDRH 1-9 | SYYWS [SEQ ID NO: 144] |
| H2 131 1N1G2 | CDRH 1-10 | NYYWS [SEQ ID NO: 145] |
| H1 131 1N1G1 | CDRH 1-11 | GYYIH [SEQ ID NO: 146] |
| H2 550 1N1G2; H1 2 1N1G1; H1 30 1N1G1; H1 42 1N1G1 | CDRH 1-12 | SYGIS [SEQ ID NO: 147] |
| H1 13 1N1G1 | CDRH 2-1 | YIYYSGSTNYNPSLKS [SEQ ID NO: 148] |
| H2 534 1N1G2 | CDRH 2-2 | YISYSGDTYYNPSLKS [SEQ ID NO: 149] |
| H1 26 1N1G1; H1 144 1N1G1; H2 103 1N1G2; H1 72 1N1G1; H1 34 1N1G1; H1 27 1N1G1 | CDRH 2-3 | RIKSKTDGGTTDYAAPVKG [SEQ ID NO: 150] |
| H1 143 1N1G1 | CDRH 2-4 | RIKSKTDGGTTDNAAPVKG [SEQ ID NO: 151] |
| H1 39 1N1G1 | CDRH 2-5 | RIKSKTDGGTADYAAPVKG [SEQ ID NO: 152] |
| H2 65 1N1G2 | CDRH 2-6 | RIKTKTDGGTTDYAAPVKG [SEQ ID NO: 153] |
| H1 16 1N1G1 | CDRH 2-7 | RIKSKTDGWTTDYAAPVKG [SEQ ID NO: 154] |
| H1 33 1N1G1; H1 33 1 1N1G1; H1 109 1N1G1; H1 131 1N1G1 | CDRH 2-8 | WINPNSGGTNYAQKFQG [SEQ ID NO: 155] |
| H1 4 1N1G1 | CDRH 2-9 | GIGTAGDTYYPGSVKG [SEQ ID NO: 156] |
| H2 369 1N1G2; H2 508 1N1G2; H2 360 1N1G2 | CDRH 2-10 | GFDPEDGETIYAQKFQG [SEQ ID NO: 157] |
| H2 475 1N1G2; H1 90 1N1G1; H1 134 1N1G1 | CDRH 2-11 | VIWYDGSNKYYADSVKG [SEQ ID NO: 158] |
| H2 380 1N1G2 | CDRH 2-12 | YIYYSGNTNYNPSLKS [SEQ ID NO: 159] |
| H1 66 1N1G1 | CDRH 2-13 | VIWYDGSNEYYADSVKG [SEQ ID NO: 160] |
| H2 131 1N1G2 | CDRH 2-14 | RIYTSGSTHYNPSLKS [SEQ ID NO: 161] |
| H2 291 1N1G2 | CDRH 2-15 | VIWYDGSYKYYADSVKG [SEQ ID NO: 162] |
| H1 2 1N1G1; H1 30 1N1G1; H1 42 1N1G1 | CDRH 2-16 | WISAYNGNTNYAQKLQG [SEQ ID NO: 163] |
| H2 550 1N1G2 | CDRH 2-17 | WISAYNGNPNYAQKFQG [SEQ ID NO: 164] |
| H1 13 1N1G1 | CDRH 3-1 | GIAATGTLFDC [SEQ ID NO: 165] |
| H1 26 1N1G1; H1 144 1N1G1 | CDRH 3-2 | EYYGSGGVWYYGMDV [SEQ ID NO: 166] |
| H1 143 1N1G1 | CDRH 3-3 | GGSLLWTGPNYYYYGMDV [SEQ ID NO: 167] |
| H1 33 1N1G1; H1 33 1 1N1G1 | CDRH 3-4 | DSNWYHNWFDP [SEQ ID NO: 168] |
| H1 109 1N1G1 | CDRH 3-5 | GGYSGYDLGYYYGMDV [SEQ ID NO: 169] |
| H1 39 1N1G1 | CDRH 3-6 | EGPYSDYGYYYYGMDV [SEQ ID NO: 170] |
| H1 534 1N1G1 | CDRH 3-7 | LDLYGDYFDY [SEQ ID NO: 171] |
| H1 4 1N1G1 | CDRH 3-8 | EGSWYGFDY [SEQ ID NO: 172] |
| H1 103 1N1G1 | CDRH 3-9 | EYYHILTGSFYYSYYGMDV [SEQ ID NO: 173] |
| H2 65 1N1G2 | CDRH 3-10 | EYYGIVTGSFYYYYGMDV [SEQ ID NO: 174] |
| H2 369 1N1G2 | CDRH 3-11 | RAGTTLAYYYYAMDV [SEQ ID NO: 175] |
| H2 508 1N1G2 | CDRH 3-12 | AGLEIRWFDP [SEQ ID NO: 176] |
| H2 475 1N1G2 | CDRH 3-13 | SSGDYYGMDV [SEQ ID NO: 177] |
| H2 380 1N1G2 | CDRH 3-14 | IATRPFDY [SEQ ID NO: 178] |
| H2 131 1N1G2 | CDRH 3-15 | DRVFYGMDV [SEQ ID NO: 179] |
| H2 291 1N1G2 | CDRH 3-16 | EGDYSDYYGMDV [SEQ ID NO: 180] |
| H1 131 1N1G1 | CDRH 3-17 | DRGQLWLWYYYYYGMDV [SEQ ID NO: 181] |
| H1 66 1N1G1 | CDRH 3-18 | SSGNYYDMDV [SEQ ID NO: 182] |
| H1 90 1N1G1 | CDRH 3-19 | SSSNFYDMDV [SEQ ID NO: 183] |
| H1 16 1N1G1 | CDRH 3-20 | DLRITGTTYYYYYGMDV [SEQ ID NO: 184] |
| H2 550 1N1G2 | CDRH 3-21 | DQGLLGFGELEGLFDY [SEQ ID NO: 185] |
| H1 2 1N1G1; H1 30 1N1G1; H1 42 1N1G1 | CDRH 3-22 | ESWFGEVFFDY [SEQ ID NO: 186] |

TABLE 3A-continued

Exemplary CDRH Sequences

| Contained in Reference | Designation | Amino Acid Sequence/ SEQ ID NO. |
|---|---|---|
| H2 360 1N1G2 | CDRH 3-23 | GVMITFGGVIVGHSYYGMDV [SEQ ID NO: 187] |
| H1 72 1N1G1 | CDRH 3-24 | EGPYSNYGYYYYGVDV [SEQ ID NO: 188] |
| H1 34 1N1G1; H1 27 1N1G1 | CDRH 3-25 | DGATVVTPGYYYYGTDV [SEQ ID NO: 189] |
| H1 134 1N1G1 | CDRH 3-26 | SSWSYYGMDV [SEQ ID NO: 190] |

TABLE 3B

Exemplary CDRL Sequences

| Contained in Reference | Designation | Amino Acid Sequence/ SEQ ID NO. |
|---|---|---|
| H1 26H1 26 1VK2KK; H1 13H1 13 1NVK2KK | CDRL 1-1 | RSSQSLVYSDGNTYLN [SEQ ID NO: 191] |
| H1 33 1 1N1K | CDRL 1-2 | RASQSISDYLN [SEQ ID NO: 192] |
| H1 2 1N1K | CDRL 1-3 | KSSQSVLDSSDNKNYLA [SEQ ID NO: 193] |
| H1 42 1N1K | CDRL 1-4 | KSSQSVLDSSNNKNFLA [SEQ ID NO: 194] |
| H1 30 1N1K | CDRL 1-5 | KSSQGVLDSSNNKNFLA [SEQ ID NO: 195] |
| H2 369 1N1K | CDRL 1-6 | RASQSISRYLN [SEQ ID NO: 196] |
| Hi 131 1N1K | CDRL 1-7 | KSSQSLLSDGKTYLY [SEQ ID NO: 197] |
| H1 16 1N1K; H1 90 1N1K; H1 34 1N1K; H1 72 1N1K; H2 103 1N1K; H1 27 1N1K; H1 144 1N1K; H1 39 1N1K; H1 13 1N1K; H1 26 1N1K | CDRL 1-8 | QASQDISNYLN [SEQ ID NO: 198] |
| H1 143 1N1K; H2 65 1N1K; H1 134 1N1K | CDRL 1-9 | QASQDINNYLN [SEQ ID NO: 199] |
| H2 475 1N1K | CDRL 1-10 | QASHDISNYLN [SEQ ID NO: 200] |
| H1 109 1N1K | CDRL 1-11 | QASQNISNFLD [SEQ ID NO: 201] |
| H1 109 1N1K SM | CDRL 1-12 | QASQDISNFLD [SEQ ID NO: 202] |
| H1 66 1N1K | CDRL 1-13 | QASQDISNFLN [SEQ ID NO: 203] |
| H2 550 1N1K | CDRL 1-14 | KSSQSVLYSSNNKNYLA [SEQ ID NO: 204] |

TABLE 3B-continued

Exemplary CDRL Sequences

| Contained in Reference | Designation | Amino Acid Sequence/ SEQ ID NO. |
|---|---|---|
| H2 131 1N1K | CDRL 1-15 | RASQGFSNYLA [SEQ ID NO: 205] |
| H2 360 1N1K | CDRL 1-16 | RASQGINNYLA [SEQ ID NO: 206] |
| H2 508 1N1K | CDRL 1-17 | RSSQSLLHSNGYNYLD [SEQ ID NO: 207] |
| H2 534 1N1K | CDRL 1-18 | RASQYIGSSLH [SEQ ID NO: 208] |
| H1 64 1N1K | CDRL 1-19 | RASQSVSSGYLAYLA [SEQ ID NO: 209] |
| H2 380 1N1K | CDRL 1-20 | RASQGIRNDLD [SEQ ID NO: 210] |
| H1 26H1 26 1NVK2KK; H1 13H1 13 1NVK2KK | CDRL 2-1 | KVSNWDS [SEQ ID NO: 211] |
| H1 33 1 1N1K; H2 369 1N1K; H2 380 1N1K | CDRL 2-2 | AASSLQS [SEQ ID NO: 212] |
| H2 550 1N1K | CDRL 2-3 | WASTRES [SEQ ID NO: 213] |
| H1 2 1N1K; H1 42 1N1K; H1 30 1N1K | CDRL 2-4 | WASNRES [SEQ ID NO: 214] |
| H1 131 1N1K | CDRL 2-5 | EASNRFS [SEQ ID NO: 215] |
| H1 16 1N1K; H1 90 1N1K; H1 34 1N1K; H2 65 1N1K; H1 72 1N1K; H2 475 1N1K; H2 103 1N1K; H1 27 1N1K; H1 144 1N1K; H1 39 1N1K; H1 13 1N1K; H1 26 1N1K; H1 66 1N1K | CDRL 2-6 | DASNLET [SEQ ID NO: 216] |
| H1 143 1N1K | CDRL 2-7 | DTSNLEP [SEQ ID NO: 217] |
| H1 109 1N1K | CDRL 2-8 | DASDLDP [SEQ ID NO: 218] |
| H1 134 1N1K | CDRL 2-9 | DASNLEI [SEQ ID NO: 219] |
| H2 131 1N1K | CDRL 2-10 | AASTLQS [SEQ ID NO: 220] |
| H2 360 1N1K | CDRL 2-11 | VASTLQS [SEQ ID NO: 221] |
| H2 534 1N1K | CDRL 2-12 | YVSQSFS [SEQ ID NO: 222] |
| H1 64 1N1K | CDRL 2-13 | GASSTAT [SEQ ID NO: 223] |
| h2 508 1N1K | CDRL 2-14 | LGSIRAS [SEQ ID NO: 224] |

TABLE 3B-continued

Exemplary CDRL Sequences

| Contained in Reference | Designation | Amino Acid Sequence/ SEQ ID NO. |
|---|---|---|
| H1 26H1 26 1NVK2KK | CDRL 3-1 | MQGTHWPIT [SEQ ID NO: 225] |
| H1 13H1 13 1NVK2KK | CDRL 3-2 | MQGTHWPRGLFT [SEQ ID NO: 226] |
| H1 33 1 1N1K | CDRL 3-3 | QQTYSDPFT [SEQ ID NO: 227] |
| H1 2 1N1K; H1 42 1N1K; H1 30 1N1K | CDRL 3-4 | QQYYSDPFT [SEQ ID NO: 228] |
| H2 369 1N1K | CDRL 3-5 | QQSYITPPS [SEQ ID NO: 229] |
| H1 131 1N1K | CDRL 3-6 | MQSIQLPLT [SEQ ID NO: 230] |
| H1 16 1N1K | CDRL 3-7 | QQYDNLIT [SEQ ID NO: 231] |
| H1 90 1N1K | CDRL 3-8 | QRYDDLPIT [SEQ ID NO: 232] |
| H1 143 1N1K; H1 34 1N1K; H1 72 1N1K; H2 103 1N1K; H1 27 1N1K; H1 144 1N1K; H1 39 1N1K; H1 26 1N1K | CDRL 3-9 | QQYDNLLT [SEQ ID NO: 233] |
| H2 65 1N1K | CDRL 3-10 | QQYDDLLT [SEQ ID NO: 234] |
| H2 475 1N1K | CDRL 3-11 | QQYDNLPLT [SEQ ID NO: 235] |
| H2 109 1N1K | CDRL 3-12 | QQYVSLPLT [SEQ ID NO: 236] |
| H1 134 1N1K | CDRL 3-13 | QQYDNFPFT [SEQ ID NO: 237] |
| H1 13 1N1K | CDRL 3-14 | QQFDNLPPT [SEQ ID NO: 238] |
| H2 550 1N1K | CDRL 3-15 | QQYYTTPPT [SEQ ID NO: 239] |
| H1 66 1N1K | CDRL 3-16 | QQYDNLPFT [SEQ ID NO: 240] |
| H2 131 1N1K | CDRL 3-17 | QKYNSAPLT [SEQ ID NO: 241] |
| H2 360 1N1K | CDRL 3-18 | QKYNSGPFT [SEQ ID NO: 242] |
| H2 508 1N1K | CDRL 3-19 | MQALQTPRT [SEQ ID NO: 243] |
| H2 534 1N1K | CDRL 3-20 | HQSSSLPFT [SEQ ID NO: 244] |
| H1 64 1N1K | CDRL 3-21 | QQYGSSPIT [SEQ ID NO: 245] |
| H2 380 1N1K | CDRL 3-22 | LQYNSYPIT [SEQ ID NO: 246] |

The structure and properties of CDRs within a naturally occurring antibody has been described, supra. Briefly, in a traditional antibody, the CDRs are embedded within a framework in the heavy and light chain variable region where they constitute the regions responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). The CDRs provided herein, however, may not only be used to define the antigen binding domain of a traditional antibody structure, but may be embedded in a variety of other polypeptide structures, as described herein.

In one aspect, the CDRs provided are (a) a CDRH selected from the group consisting of (i) a CDRH1 selected from the group consisting of SEQ ID NO:136-147; (ii) a CDRH2 selected from the group consisting of SEQ ID NO:148-164; (iii) a CDRH3 selected from the group consisting of SEQ ID NO:165-190; and (iv) a CDRH of (i), (ii) and (iii) that contains one or more amino acid substitutions, deletions or insertions of no more than five, four, three, two, or one amino acids; (B) a CDRL selected from the group consisting of (i) a CDRL1 selected from the group consisting of SEQ ID NO:191-210; (ii) a CDRL2 selected from the group consisting of SEQ ID NO:211-224; (iii) a CDRL3 selected from the group consisting of SEQ ID NO:225-246; and (iv) a CDRL of (i), (ii) and (iii) that contains one or more amino acid substitutions, deletions or insertions of no more than five, four, three, two, or one amino acids amino acids.

In another aspect, an antigen binding protein includes 1, 2, 3, 4, 5, or 6 variant forms of the CDRs listed in TABLES 3A and 3B, each having at least 80%, 85%, 90% or 95% sequence identity to a CDR sequence listed in TABLES 3A and 3B. Some antigen binding proteins include 1, 2, 3, 4, 5, or 6 of the CDRs listed in TABLES 3A and 3B, each differing by no more than 1, 2, 3, 4 or 5 amino acids from the CDRs listed in these tables.

In yet another aspect, the CDRs disclosed herein include consensus sequences derived from groups of related monoclonal antibodies. As described herein, a "consensus sequence" refers to amino acid sequences having conserved amino acids common among a number of sequences and variable amino acids that vary within a given amino acid sequences. The CDR consensus sequences provided include CDRs corresponding to each of CDRH1, CDRH2, CDRH3, CDRL1, CDRL2 and CDRL3.

Consensus sequences were determined using standard phylogenic analyses of the CDRs corresponding to the $V_H$ and $V_L$ of anti-c-fms antibodies. The consensus sequences were determined by keeping the CDRs contiguous within the same sequence corresponding to a $V_H$ or $V_L$. Briefly, amino acid sequences corresponding to the entire variable domains of either $V_H$ or $V_L$ were converted to FASTA formatting for ease in processing comparative alignments and inferring phylogenies. Next, framework regions of these sequences were replaced with an artificial linker sequence ("GGGAAAGG-GAAA" (SEQ ID NO:325)) so that examination of the CDRs alone could be performed without introducing any amino acid position weighting bias due to coincident events (e.g., such as unrelated antibodies that serendipitously share a common germline framework heritage) while still keeping CDRs contiguous within the same sequence corresponding to a $V_H$ or $V_L$. $V_H$ or $V_L$ sequences of this format were then subjected to sequence similarity alignment interrogation using a program that employs a standard ClutalW-like algorithm (see, Thompson et al., 1994, Nucleic Acids Res. 22:4673-4680). A gap creation penalty of 8.0 was employed along with a gap extension penalty of 2.0. This program likewise generated phylograms (phylogenic tree illustrations) based on sequence similarity alignments using either UPGMA (unweighted pair group method using arithmetic averages) or Neighbor-Joining methods (see, Saitou and Nei, 1987, *Molecular Biology and Evolution* 4:406-425) to construct and illustrate similarity and distinction of sequence groups via branch length comparison and grouping. Both methods produced similar results but UPGMA-derived trees were ultimately used as the method employs a simpler and more conservative set of assumptions. UPGMA-derived trees are shown in FIG. 2 where similar groups of sequences were defined as having fewer than 15 substitutions per 100 residues (see, legend in tree illustrations for scale) amongst individual sequences within the group and were used to define consensus sequence collections.

As illustrated in FIG. 2, lineage analysis of a variety of the antigen binding proteins provided herein resulted in three groups of closely related phylogenically clones, designated as Groups A, B, and C.

The consensus sequences of the various CDR regions of Group A are:

a. a CDRH1 of the generic formula GYTX$_1$TSYGIS (SEQ ID NO:307), wherein X$_1$ is selected from the group consisting of F and L;

b. a CDRH2 of the generic formula WISAYNGNX$_1$NYAQKX$_2$QG (SEQ ID NO:308), wherein X$_1$ is selected from the group consisting of T and P, and X$_2$ is selected from the group consisting of L and F;

c. a CDRH3 of the generic formula X$_1$X$_2$X$_3$X$_4$X$_5$FGEX$_6$X$_7$X$_8$X$_9$FDY (SEQ ID NO:309), wherein X$_1$ is selected from the group consisting of E and D, X$_2$ is selected from the group consisting of S and Q, X$_3$ is selected from the group consisting of G and no amino acid, X$_4$ is selected from the group consisting of L and no amino acid, X$_5$ is selected from the group consisting of W and G, X$_6$ is selected from the group consisting of V and L, X$_7$ is selected from the group consisting of E and no amino acid, X$_8$ is selected from the group consisting of G and no amino acid, and X$_9$ is selected from the group consisting of F and L;

d. a CDRL1 of the generic formula KSSX$_1$GVLX$_2$SSX$_3$NKNX$_4$LA (SEQ ID NO:310), wherein X$_1$ is selected from the group consisting of Q and S, X$_2$ is selected from the group consisting of D and Y, X$_3$ is selected from the group consisting of N and D, and X$_4$ is selected from the group consisting of F and Y;

e. a CDRL2 of the generic formula WASX$_1$RES (SEQ ID NO:311), wherein X$_1$ is selected from the group consisting of N and T; and f. a CDRL3 of the generic formula QQYYX$_1$X$_2$PX$_3$T (SEQ ID NO:312), wherein X$_1$ is selected from the group consisting of S and T, X$_2$ is selected from the group consisting of D and T, and X$_3$ is selected from the group consisting of F and P.

The consensus sequences of the various CDR regions of Group B are:

a. a CDRH1 having the generic formula GFTX$_1$X$_2$X$_3$AWMS (SEQ ID NO:313), wherein X$_1$ is selected from the group consisting of F and V, X$_2$ is selected from the group consisting of S and N, and X$_3$ is selected from the group consisting of N and T;

b. a CDRH2 having the generic formula RIKX$_1$KTDGX$_2$TX$_3$DX$_4$AAPVKG (SEQ ID NO:314), wherein X$_1$ is selected from the group consisting of S and T, X$_2$ is selected from the group consisting of G and W, X$_3$ is selected from the group consisting of T and A, and X$_4$ is selected from the group consisting of Y and N;

c. a CDRH3 having the generic formula X$_1$X$_2$X$_3$X$_4$X$_5$X$_6$X$_7$X$_8$X$_9$X$_{10}$X$_{11}$X$_{12}$X$_{13}$YYGX$_{14}$DV (SEQ ID NO:315), wherein X$_1$ is selected from the group consisting of E, D and G, X$_2$ is selected from the group consisting of Y, L and no amino acid, X$_3$ is selected from the group consisting of Y, R, G and no amino acid, X$_4$ is selected from the group consisting of H, G, S and no amino acid, X$_5$ is selected from the group consisting of I, A, L and no amino acid, X$_6$ is selected from the group consisting of L, V, T, P and no amino acid, X$_7$ is selected from the group consisting of T, V, Y, G, W and no amino acid, X$_8$ is selected from the group consisting of G, V, S and T, X$_9$ is selected from the group consisting of S, T, D, N and G, X$_{10}$ is selected from the group consisting of G, F, P, and Y, X$_{11}$ is selected from the group consisting of G, Y and N, X$_{12}$ is selected from the group consisting of V and Y, X$_{13}$ is selected from the group consisting of W, S and Y, and X$_{14}$ is selected from the group consisting of M, T and V;

d. a CDRL1 having the generic formula QASQDIX$_1$NYLN (SEQ ID NO:316), wherein X$_1$ is selected from the group consisting of S and N;

e. a CDRL2 having the generic formula DX$_1$SNLEX$_2$ (SEQ ID NO:317), wherein X$_1$ is selected from the group consisting of A and T, and X$_2$ is selected from the group consisting of T and P; and f. a CDRL3 having the generic formula QQYDX$_1$LX$_2$T (SEQ ID NO:318), wherein X$_1$ is selected from the group consisting of N and D, and X$_2$ is selected from the group consisting of L and I.

The consensus sequences of the various CDR regions of Group C are:

a. a CDRH1 having the generic formula GFTFX$_1$SYGMH (SEQ ID NO:319), wherein X$_1$ is selected from the group consisting of S and I;

b. a CDRH2 having the generic formula VIWYDGSNX$_1$YYADSVKG (SEQ ID NO:320), wherein X$_1$ is selected from the group consisting of E and K;

c. a CDRH3 having the generic formula SSX$_1$X$_2$X$_3$YX$_4$MDV (SEQ ID NO:321), wherein X$_1$ is selected from the group consisting of G, S and W, X$_2$ is selected from the group consisting of N, D and S, X$_3$ is selected from the group consisting of Y and F, and X$_4$ is selected from the group consisting of D and G;

d. a CDRL1 having the generic formula QASX$_1$DIX$_2$NX$_3$LN (SEQ ID NO:322), wherein X$_1$ is selected from the group consisting of Q and H, X$_2$ is selected from the group consisting of S and N, and X$_3$ is selected from the group consisting of F and Y;

e. a CDRL2 having the generic formula DASNLEX$_1$ (SEQ ID NO:323), wherein X$_1$ is selected from the group consisting of T and I; and f. a CDRL3 having the generic formula QX$_1$YDX$_2$X$_3$PX$_4$T (SEQ ID NO:324), wherein X$_1$ is selected from the group consisting of Q and R, X$_2$ is selected from the group consisting of N and D, X$_3$ is selected from the group consisting of L and F, and X$_4$ is selected from the group consisting of F, L and I.

In some cases the antigen binding protein comprises at least one CDRH1, CDRH2, or CDRH3 having one of the above consensus sequences. In some cases, the antigen binding protein comprises at least one CDRL1, CDRL2, or CDRL3 having one of the above consensus sequences. In other cases, the antigen binding protein comprises at least two CDRHs according to the above consensus sequences, and/or at least two CDRLs according to the above consensus sequences. In one aspect, the CDRHs and/or CDRLs are derived from different groups A, B, and C. In other cases, the antigen binding protein comprises at least two CDRHs from the same group A, B, or C, and/or at least two CDRLs from the same group A, B, or C. In other aspects, the antigen binding protein comprises a CDRH1, CDRH2, and CDRH3 sequence from the same of the above groups A, B, or C, and/or a CDRL1, CDRL2, and CDRL3 sequence from the same of the above groups A, B, or C.

Hence, some antigen binding proteins that are provided include 1, 2, 3, 4, 5 or all 6 of the CDRs from the Group A consensus sequences. Thus certain antigen binding proteins, for instance, include a CDRH1, a CDRH2, a CDRH3, a CDRL1, a CDRL2 and a CDRL3 from the Group A consensus sequences set forth above. Other antigen binding proteins that are provided include 1, 2, 3, 4, 5 or all 6 of the CDRs from the Group B consensus sequences. Thus certain antigen binding proteins include, for instance, a CDRH1, a CDRH2, a CDRH3, a CDRL1, a CDRL2 and a CDRL3 from the Group B consensus sequences set forth above. Still other antigen binding proteins that are provided include 1, 2, 3, 4, 5 or all 6 of the CDRs from the Group C consensus sequences. Thus certain antigen binding proteins include, for instance, a CDRH1, a CDRH2, a CDRH3, a CDRL1, a CDRL2 and a CDRL3 from the Group A consensus sequences set forth above.

Exemplary Antigen Binding Proteins

According to one aspect, provided is an isolated antigen-binding protein that binds c-fms comprising (A) one or more heavy chain complementary determining regions (CDRHs) selected from the group consisting of: (i) a CDRH1 selected from the group consisting of SEQ ID NO:136-147; (ii) a CDRH2 selected from the group consisting of SEQ ID NO:148-164; (iii) a CDRH3 selected from the group consisting of SEQ ID NO:165-190; and (iv) a CDRH of (i), (ii) and (iii) that contains one or more amino acid substitutions, deletions or insertions of no more than five, four, three, four, two or one amino acids; (B) one or more light chain complementary determining regions (CDRLs) selected from the group consisting of: (i) a CDRL1 selected from the group consisting of SEQ ID NO:191-210; (ii) a CDRL2 selected from the group consisting of SEQ ID NO:211-224; (iii) a CDRL3 selected from the group consisting of SEQ ID NO:225-246; and (iv) a CDRL of (i), (ii) and (iii) that contains one or more amino acid substitutions, deletions or insertions of no more than five, four, three, four, two or one amino acids; or (C) one or more heavy chain CDRHs of (A) and one or more light chain CDRLs of (B).

In yet another embodiment, the isolated antigen-binding protein may comprise (A) a CDRH selected from the group consisting of (i) a CDRH1 selected from the group consisting of SEQ ID NO:136-147; (ii) a CDRH2 selected from the group consisting of SEQ ID NO:148-164; and (iii) a CDRH3 selected from the group consisting of SEQ ID NO:165-190; (B) a CDRL selected from the group consisting of (i) a CDRL1 selected from the group consisting of SEQ ID NO:191-210; (ii) a CDRL2 selected from the group consisting of SEQ ID NO:211-224; and (iii) a CDRL3 selected from the group consisting of SEQ ID NO:225-246; or (C) one or more heavy chain CDRHs of (A) and one or more light chain CDRLs of (B). In one embodiment, the isolated antigen-binding protein may include (A) a CDRH1 of SEQ ID NO:136-147, a CDRH2 of SEQ ID NO:148-164, and a CDRH3 of SEQ ID NO:165-190, and (B) a CDRL1 of SEQ ID NO:191-210, a CDRL2 of SEQ ID NO:211-224, and a CDRL3 of SEQ ID NO:225-246.

In another embodiment, the variable heavy chain (VH) has at least 70%, 75%, 80%, 85%, 90%, 95%, 97% or 99% sequence identity with an amino acid sequence selected from the group consisting of SEQ ID NO:70-101, and/or the variable light chain (VL) has at least 70%, 75%, 80%, 85%, 90%, 95%, 97% or 99% sequence identity with an amino acid sequence selected from the group consisting of SEQ ID NO:102-135. In a further embodiment, the VH is selected from the group consisting of SEQ ID NO: 70-101, and/or the VL is selected from the group consisting of SEQ ID NO: 102-135.

In another aspect, also provided is an isolated antigen binding protein that specifically binds to an epitope containing the c-fms subdomains Ig-like 1-1 and Ig-like 1-2 of c-fms.

In a further aspect, there is a provision of an isolated antigen-binding protein that binds c-fms, the antigen-binding protein including a CDRH3 selected from the group consisting of (1) a CDRH3 selected from the group consisting of SEQ ID NOs:165-190, (2) a CDRH3 that differs in amino acid sequence from the CDRH3 of (i) by an amino acid addition, deletion or substitution of not more than two amino acids; and (3) a CDRH3 amino acid sequence selected from the group consisting of (a) $X_1X_2X_3X_4X_5FGEX_6X_7X_8X_9FDY$ (SEQ ID NO:309), wherein $X_1$ is selected from the group consisting of E and D, $X_2$ is selected from the group consisting of S and Q, $X_3$ is selected from the group consisting of G and no amino acid, $X_4$ is selected from the group consisting of L and no amino acid, $X_5$ is selected from the group consisting of W and G, $X_6$ is selected from the group consisting of V and L, $X_7$ is selected from the group consisting of E and no amino acid, $X_8$ is selected from the group consisting of G and no amino acid, and $X_9$ is selected from the group consisting of F and L (CDRH3 consensus sequence derived from above described phylogenetic Group A); (b) $X_1X_2X_3X_4X_5X_6X_7X_8X_9X_{10}X_{11}X_{12}X_{13}YYGX_{14}DV$ (SEQ ID NO:315), wherein $X_1$ is selected from the group consisting of E, D and G, $X_2$ is selected from the group consisting of Y, L and no amino acid, $X_3$ is selected from the group consisting of Y, R, G and no amino acid, $X_4$ is selected from the group consisting of H, G, S and no amino acid, $X_5$ is selected from the group consisting of I, A, L and no amino acid, $X_6$ is selected from the group consisting of L, V, T, P and no amino acid, $X_7$ is selected from the group consisting of T, V, Y, G, W and no amino acid, $X_8$ is selected from the group consisting of G, V, S and T, $X_9$ is selected from the group consisting of S, T, D, N and G, $X_{10}$ is selected from the group consisting of G, F, P, and Y, $X_{11}$ is selected from the group consisting of G, Y and N, $X_{12}$ is selected from the group consisting of V and Y, $X_{13}$ is selected from the group consisting of W, S and Y, and $X_{14}$ is selected from the group consisting of M, T and V (CDRH3 consensus sequence derived from above described phylogenetic Group B); and (c) $SSX_1X_2X_3YX_4MDV$ (SEQ ID NO:321), wherein $X_1$ is selected from the group consisting of G, S and W, $X_2$ is selected from the group consisting of N, D and S, $X_3$ is selected from the group consisting of Y and F, and $X_4$ is selected from the group consisting of D and G (CDRH3 consensus sequence derived from above described phylogenetic Group C); or (B) a light chain complementary determining region (CDRL) selected from the group consisting of (1) a CDRL3 selected from the group consisting of SEQ ID NOs:225-246, (2) a CDRL3 that differs in amino acid sequence from the CDRL3 of (i) by an amino acid addition, deletion or substitution of not more than two amino acids; and (3) a CDRL3 amino acid sequence selected from the group consisting of (a) $QQYYX_1X_2PX_3T$ (SEQ ID NO:312), wherein $X_1$ is selected from the group consisting of S and T, $X_2$ is selected from the group consisting of D and T, and $X_3$ is selected from the group consisting of F and P (CDRL3 consensus sequence derived from above described phylogenetic Group A); (b) QQYDX$_1$LX$_2$T (SEQ ID NO:318), wherein X$_1$ is selected from the group consisting of N and D, and X$_2$ is selected from the group consisting of L and I (CDRL3 consensus sequence derived from above described phylogenetic Group B); and (c) QX$_1$YDX$_2$X$_3$PX$_4$T (SEQ ID NO:324), wherein X$_1$ is selected from the group consisting of Q and R, X$_2$ is selected from the group consisting of N and D, X$_3$ is selected from the group consisting of L and F, and X$_4$ is selected from the group consisting of F, L and I (CDRL3 consensus sequence derived from above described phylogenetic Group C).

In one embodiment, the antigen binding protein that binds c-fms comprises a CDRH3 according to a consensus sequence of groups A, B, or C, and/or a CDRL3 according to a consensus sequence of groups A, B, or C, and a CDRH1 and/or CDRH2 of any the above groups, and/or a CDRL1 and/or a CDRL2 of any of the above groups.

In one embodiment, the isolated antigen binding protein that binds c-fms comprises a CDRH3 and/or a CDRL3 of Group A, see, supra, and a CDR selected from the group consisting of:

(1) a CDRH1 selected from the group consisting of (a) a CDRH1 of SEQ ID NOs:136-147; (b) a CDRH1 that differs in amino acid sequence from the CDRH1 of (a) by an amino acid addition, deletion or substitution of not more than two amino acids; and (c) a CDRH1 amino acid sequence selected from the group consisting of GYTX$_1$TSYGIS (SEQ ID NO:307), wherein X$_1$ is selected from the group consisting of F and L;

(2) CDRH2 selected from the group consisting of (a) a CDRH2 of SEQ ID NOs:148-164; (b) a CDRH2 that differs in amino acid sequence from the CDRH2 of (a) by an amino acid addition, deletion or substitution of not more than two amino acids; and (c) a CDRH2 amino acid sequence selected from the group consisting of WISAYNGNX$_1$NYAQKX$_2$QG (SEQ ID NO:308), wherein X$_1$ is selected from the group consisting of T and P, and X$_2$ is selected from the group consisting of L and F;

(3) a CDRL1 selected from the group consisting of (a) a CDRL1 of SEQ ID NOs:191-210; (b) a CDRL1 that differs in amino acid sequence from the CDRL1 of (a) by an amino acid addition, deletion or substitution of not more than two amino acids; and (c) a CDRL1 amino acid sequence selected from the group consisting of KSSX$_1$GVLX$_2$SSX$_3$NKNX$_4$LA (SEQ ID NO:310), wherein X$_1$ is selected from the group consisting of Q and S, X$_2$ is selected from the group consisting of D and Y, X$_3$ is selected from the group consisting of N and D, and X$_4$ is selected from the group consisting of F and Y; and (4) a CDRL2 selected from the group consisting of: (a) a CDRL2 of SEQ ID NOs:211-224; (b) a CDRL2 that differs in amino acid sequence from the CDRL2 of (a) by an amino acid addition, deletion or substitution of not more than two amino acids; and (c) a CDRL2 amino acid sequence selected from the group consisting of WASX$_1$RES (SEQ ID NO:311), wherein X$_1$ is selected from the group consisting of N and T.

In one embodiment, the isolated antigen binding protein that binds c-fms comprises a CDRH3 and/or a CDRL3 of Group B, see, supra, and a CDR selected from the group consisting of:

(1) a CDRH1 selected from the group consisting of (a) a CDRH1 of SEQ ID NOs:136-147; (b) a CDRH1 that differs in amino acid sequence from the CDRH1 of (a) by an amino acid addition, deletion or substitution of not more than two amino acids; and (c) a CDRH1 amino acid sequence selected from the group consisting of GFTX$_1$X$_2$X$_3$AWMS (SEQ ID NO:313), wherein X$_1$ is selected from the group consisting of F and V, X$_2$ is selected from the group consisting of S and N, and X$_3$ is selected from the group consisting of N and T;

(2) a CDRH2 selected from the group consisting of (a) a CDRH2 of SEQ ID NOs:148-164; (b) a CDRH2 that differs in amino acid sequence from the CDRH2 of (a) by an amino acid addition, deletion or substitution of not more than two amino acids; and (c) a CDRH2 amino acid sequence selected from the group consisting of RIKX$_1$KTDGX$_2$TX$_3$DX$_4$AAPVKG (SEQ ID NO:314), wherein X$_1$ is selected from the group consisting of S and T, X$_2$ is selected from the group consisting of G and W, X$_3$ is selected from the group consisting of T and A, and X$_4$ is selected from the group consisting of Y and N;

(3) a CDRL1 selected from the group consisting of (a) a CDRL1 of SEQ ID NOs:191-210; (b) a CDRL1 that differs in amino acid sequence from the CDRL1 of (a) by an amino acid addition, deletion or substitution of not more than two amino acids; and (c) a CDRL1 amino acid sequence selected from the group consisting of QASQDIX$_1$NYLN (SEQ ID NO:316), wherein X$_1$ is selected from the group consisting of S and N; and (4) a CDRL2 selected from the group consisting of (a) a CDRL2 of SEQ ID NOs:211-224; (b) a CDRL2 that differs in amino acid sequence from the CDRL2 of (a) by an amino acid addition, deletion or substitution of not more than two amino acids; and (c) a CDRL2 amino acid sequence selected from the group consisting of DX$_1$SNLEX$_2$ (SEQ ID NO:317), wherein X$_1$ is selected from the group consisting of A and T, and X$_2$ is selected from the group consisting of T and P.

In one embodiment, the isolated antigen binding protein that binds c-fms comprises a CDRH3 and a CDRL3 of Group C, see, supra, and a CDR selected from the group consisting of (1) a CDRH1 selected from the group consisting of (a) a CDRH1 of SEQ ID NOs:136-147; (b) a CDRH1 that differs in amino acid sequence from the CDRH1 of (a) by an amino acid addition, deletion or substitution of not more than two amino acids; and (c) a CDRH1 amino acid sequence selected from the group consisting of GFTFX$_1$SYGMH (SEQ ID NO:319), wherein X$_1$ is selected from the group consisting of S and I;

(2) a CDRH2 selected from the group consisting of (a) a CDRH2 of SEQ ID NOs:148-164; (b) a CDRH2 that differs in amino acid sequence from the CDRH2 of (a) by an amino acid addition, deletion or substitution of not more than two amino acids; and (c) a CDRH2 amino acid sequence selected from the group consisting of VIWYDGSNX$_1$YYADSVKG (SEQ ID NO:320), wherein X$_1$ is selected from the group consisting of E and K;

(3) a CDRL1 selected from the group consisting of (a) a CDRL1 of SEQ ID NOs:191-210; (b) a CDRL1 that differs in amino acid sequence from the CDRL1 of (a) by an amino acid addition, deletion or substitution of not more than two amino acids; and (c) a CDRL1 amino acid sequence selected from the group consisting of QASX$_1$DIX$_2$NX$_3$LN (SEQ ID NO:322), wherein X$_1$ is selected from the group consisting of Q and H, X$_2$ is selected from the group consisting of S and N, and X$_3$ is selected from the group consisting of F and Y;

(4) a CDRL2 selected from the group consisting of (a) a CDRL2 of SEQ ID NOs:211-224; (b) a CDRL2 that differs in amino acid sequence from the CDRL2 of (a) by an amino acid addition, deletion or substitution of not more than two amino acids; and (c) a CDRL2 amino acid sequence selected from the group consisting of DASNLEX$_1$ (SEQ ID NO:323), wherein X$_1$ is selected from the group consisting of T and I.

In yet another embodiment, the isolated antigen binding protein described hereinabove comprises a first amino acid sequence comprising at least one of the above CDRH consensus sequences, and a second amino acid sequence comprising at least one of the above CDRL consensus sequences. In one aspect, the first amino acid sequence comprises at least two of the above CDRH consensus sequences, and/or the second amino acid sequence comprises at least two of the above consensus sequences. In again another aspect, the first amino acid sequence comprises at least two CDRHs of the same of the above groups A, B, or C, and/or the second amino acid sequence comprises at least two CDRLs of the same of the above groups A, B, or C. In yet other aspects, the first and second amino acid sequence comprise at least one CDRH and one CDRL, respectively, of the same of the above groups A, B, or C. In yet a further aspect, the first amino acid sequence comprises a CDRH1, a CDRH2, and a CDRH3 of the same of the above groups A, B, or C, and/or the second amino acid sequence comprises a CDRL1, a CDRL2, and a CDRL3 of the same of the above groups A, B, or C.

In certain embodiments, the first and the second amino acid sequence are covalently bonded to each other.

In a further embodiment, the first amino acid sequence of the isolated antigen-binding protein includes the CDRH3 of SEQ ID NO:165-190, CDRH2 of SEQ ID NO:148-164, and CDRH1 of SEQ ID NO:136-147, and/or the second amino acid sequence of the isolated antigen binding protein comprises the CDRL3 of SEQ ID NO:225-246, CDRL2 of SEQ ID NO:211-224, and CDRL1 of SEQ ID NO:191-210.

In a further embodiment, the antigen binding protein comprises at least two CDRH sequences of heavy chain sequences H1, H2, H3, H4, H5, H6, H7, H8, H9, H10, H11, H12, H13, H14, H15, H16, H17, H18, H19, H20, H21, H22, H23, H24, H25, H26, H27, H28, H29, H30, H31, or H32, as shown in TABLE 4A. In again a further embodiment, the antigen binding protein comprises at least two CDRL sequences of light chain sequences L1, L2, L3, L4, L5, L6, L7, L8, L9, L10, L11, L12, L13, L14, L15, L16, L17, L18, L19, L20, L21, L22, L23, L24, L25, L26, L27, L28, L29, L30, L31, L32, L33, or L34, as shown in TABLE 4B. In again a further embodiment, the antigen binding protein comprises at least two CDRH sequences of heavy chain sequences H1, H2, H3, H4, H5, H6, H7, H8, H9, H10, H11, H12, H13, H14, H15, H16, H17, H18, H19, H20, H21, H22, H23, H24, H25, H26, H27, H28, H29, H30, H31, or H32, as shown in TABLE 4A, and at least two CDRLs of light chain sequences L1, L2, L3, L4, L5, L6, L7, L8, L9, L10, L11, L12, L13, L14, L15, L16, L17, L18, L19, L20, L21, L22, L23, L24, L25, L26, L27, L28, L29, L30, L31, L32, L33, or L34, as shown in TABLE 4B.

In again another embodiment, the antigen binding protein comprises the CDRH1, CDRH2, and CDRH3 sequences of heavy chain sequences H1, H2, H3, H4, H5, H6, H7, H8, H9, H10, H11, H12, H13, H14, H15, H16, H17, H18, H19, H20, H21, H22, H23, H24, H25, H26, H27, H28, H29, H30, H31, or H32, as shown in TABLE 4A. In yet another embodiment, the antigen binding protein comprises the CDRL1, CDRL2, and CDRL3 sequences of light chain sequences L1, L2, L3, L4, L5, L6, L7, L8, L9, L10, L11, L12, L13, L14, L15, L16, L17, L18, L19, L20, L21, L22, L23, L24, L25, L26, L27, L28, L29, L30, L31, L32, L33, or L34, as shown in TABLE 4B.

In yet another embodiment, the antigen binding protein comprises all six CDRs of H1 and L1, or H1 and L2, or H2 and L31, or H2 and L33, or H3 and L3, or H4 and L4, or H5 and L5, or H6 and L6, or H7 and L7, or H8 and L8, or H8 and L9, or H9 and L32, or H9 and L34, or H10 and L10, or H11 and L11, or H12 and L12, or H13 and L12, or H14 and L13, or H15 and L14, or H16 and L15, or H17 and L16, or H18 and L17, or H19 and L18, or H20 and L20, or H21 and L19, or H22 and L21, or H24 and L22, or H25 and L23, or H26 and L24, or H27 and L25, or H28 and L26, or H29 and L27, or H30 and L28, or H31 and L29, or H32 and L30, as shown in TABLES 4A and 4B.

The sequence information for specific antibodies prepared and identified as described in the Examples below are summarized in Table 4C. For ease of reference, in some instances an abbreviated form of the reference number is used herein in which the last number of the reference is dropped. Thus, for instance, 1.109.1 is sometime simply referred to as 1.109; 1.109.1 SM is referred to as 1.109 SM; 1.2.1 is referred to as 1.2; 1.2.1 SM is referred to as 1.2 SM; 2.360.1 is referred to as 2.360, 2.360.1 SM is referred to as 2.360 SM; etc.

TABLE 4A

| Reference | Full Heavy (H#) | Full Heavy SEQ ID NO | Variable Heavy (VH#) | Variable Heavy SEQ ID NO | CDRH1 (CDRH1-#) | CDRH1 SEQ ID NO | CDRH2 (CDRH2-#) | CDRH2 SEQ ID NO | CDRH3 (CDRH3-#) | CDRH3 SEQ ID NO |
|---|---|---|---|---|---|---|---|---|---|---|
| H1 109 1N1G1 | H1 | 4 | $V_H1$ | 70 | CDRH 1-5 | 140 | CDRH 2-8 | 155 | CDRH 3-5 | 169 |
| H1 13 1N1G1 | H2 | 5 | $V_H2$ | 71 | CDRH 1-1 | 136 | CDRH 2-1 | 148 | CDRH 3-1 | 165 |
| H1 131 1N1G1 | H3 | 6 | $V_H3$ | 72 | CDRH 1-11 | 146 | CDRH 2-8 | 155 | CDRH 3-17 | 181 |
| H1 134 1N1G1 | H4 | 7 | $V_H4$ | 73 | CDRH 1-8 | 143 | CDRH 2-11 | 158 | CDRH 3-26 | 190 |
| H1 143 1N1G1 | H5 | 8 | $V_H5$ | 74 | CDRH 1-2 | 137 | CDRH 2-4 | 151 | CDRH 3-3 | 167 |
| H1 144 1N1G1 | H6 | 9 | $V_H6$ | 75 | CDRH 1-2 | 137 | CDRH 2-3 | 150 | CDRH 3-2 | 166 |
| H1 16 1N1G1 | H7 | 10 | $V_H7$ | 76 | CDRH 1-2 | 137 | CDRH 2-7 | 154 | CDRH 3-20 | 184 |
| H1 2 1N1G1 | H8 | 11 | $V_H8$ | 77 | CDRH 1-12 | 147 | CDRH 2-16 | 163 | CDRH 3-22 | 186 |
| H1 26 1N1G1 | H9 | 12 | $V_H9$ | 78 | CDRH 1-2 | 137 | CDRH 2-3 | 150 | CDRH 3-2 | 166 |
| H1 27 1N1G1 | H10 | 13 | $V_H10$ | 79 | CDRH 1-2 | 137 | CDRH 2-3 | 150 | CDRH 3-25 | 189 |
| H1 30 1N1G1 | H11 | 14 | $V_H11$ | 80 | CDRH 1-12 | 147 | CDRH 2-16 | 163 | CDRH 3-22 | 186 |
| H1 33-1 1N1G1 | H12 | 15 | $V_H12$ | 81 | CDRH 1-4 | 139 | CDRH 2-8 | 155 | CDRH 3-4 | 168 |
| H1 33 1N1G1 | H13 | 16 | $V_H13$ | 82 | CDRH 1-4 | 139 | CDRH 2-8 | 155 | CDRH 3-4 | 168 |
| H1 34 1N1G1 | H14 | 17 | $V_H14$ | 83 | CDRH 1-2 | 137 | CDRH 2-3 | 150 | CDRH 3-25 | 189 |
| H1 39 1N1G1 | H15 | 18 | $V_H15$ | 84 | CDRH 1-2 | 137 | CDRH 2-5 | 152 | CDRH 3-6 | 170 |
| H1 42 1N1G1 | H16 | 19 | $V_H16$ | 85 | CDRH 1-12 | 147 | CDRH 2-16 | 163 | CDRH 3-22 | 186 |
| H1 64 1N1G1 | H17 | 20 | $V_H17$ | 86 | CDRH 1-6 | 141 | CDRH 2-9 | 156 | CDRH 3-8 | 172 |
| H1 66 1N1G1 | H18 | 21 | $V_H18$ | 87 | CDRH 1-8 | 143 | CDRH 2-13 | 160 | CDRH 3-18 | 182 |
| H1 72 1N1G1 | H19 | 22 | $V_H19$ | 88 | CDRH 1-3 | 138 | CDRH 2-3 | 150 | CDRH 3-24 | 188 |
| H2 103 1N1G2 | H20 | 23 | $V_H20$ | 89 | CDRH 1-2 | 137 | CDRH 2-3 | 150 | CDRH 3-9 | 173 |
| H1 90 1N1G1 | H21 | 24 | $V_H21$ | 90 | CDRH 1-8 | 143 | CDRH 2-11 | 158 | CDRH 3-19 | 183 |
| H2 131 1N1G2 | H22 | 25 | $V_H22$ | 91 | CDRH 1-10 | 145 | CDRH 2-14 | 161 | CDRH 3-15 | 179 |
| H2 291 1N1G2 | H23 | 26 | $V_H23$ | 92 | CDRH 1-8 | 143 | CDRH 2-15 | 162 | CDRH 3-16 | 180 |

TABLE 4A-continued

| Reference | Full Heavy (H#) | Full Heavy SEQ ID NO | Variable Heavy (VH#) | Variable Heavy SEQ ID NO | CDRH1 (CDRH1-#) | CDRH1 SEQ ID NO | CDRH2 (CDRH2-#) | CDRH2 SEQ ID NO | CDRH3 (CDRH3-#) | CDRH3 SEQ ID NO |
|---|---|---|---|---|---|---|---|---|---|---|
| H2 360 1N1G2 | H24 | 27 | $V_H24$ | 93 | CDRH 1-7 | 142 | CDRH 2-10 | 157 | CDRH 3-23 | 187 |
| H2 360 1N1G2SM | H25 | 28 | $V_H25$ | 94 | CDRH 1-7 | 142 | CDRH 2-10 | 157 | CDRH 3-23 | 187 |
| H2 369 1N1G2 | H26 | 29 | $V_H26$ | 95 | CDRH 1-7 | 142 | CDRH 2-10 | 157 | CDRH 3-11 | 175 |
| H2 380 1N1G2 | H27 | 30 | $V_H27$ | 96 | CDRH 1-9 | 144 | CDRH 2-12 | 159 | CDRH 3-14 | 178 |
| H2 475 1N1G2 | H28 | 31 | $V_H28$ | 97 | CDRH 1-8 | 143 | CDRH 2-11 | 158 | CDRH 3-13 | 177 |
| H2 508 1N1G2 | H29 | 32 | $V_H29$ | 98 | CDRH 1-7 | 142 | CDRH 2-10 | 157 | CDRH 3-12 | 176 |
| H2 534 1N1G2 | H30 | 33 | $V_H30$ | 99 | CDRH 1-1 | 136 | CDRH 2-2 | 149 | CDRH 3-7 | 171 |
| H2 550 1N1G2 | H31 | 34 | $V_H31$ | 100 | CDRH 1-12 | 147 | CDRH 2-17 | 164 | CDRH 3-21 | 185 |
| H2 65 1N1G2 | H32 | 35 | $V_H32$ | 101 | CDRH 1-2 | 137 | CDRH 2-6 | 153 | CDRH 3-10 | 174 |

TABLE 4B

| Reference | Full Light (L#) | Full Light SEQ ID NO | Variable Light (VL#) | Variable Light SEQ ID NO | CDRL1 (CDRL1-#) | CDRL1 SEQ ID NO | CDRL2 (CDRL2-#) | CDRL2 SEQ ID NO | CDRL3 (CDRL3-#) | CDRL3 SEQ ID NO |
|---|---|---|---|---|---|---|---|---|---|---|
| H1 109 1N1K | L1 | 36 | $V_L1$ | 102 | CDRL 1-12 | 202 | CDRL 2-8 | 218 | CDRL3-12 | 236 |
| H1 109 1N1K SM | L2 | 37 | $V_L2$ | 103 | CDRL 1-11 | 201 | CDRL 2-8 | 218 | CDRL3-12 | 236 |
| H1 131 1N1K | L3 | 38 | $V_L3$ | 104 | CDRL 1-7 | 197 | CDRL 2-5 | 215 | CDRL3-6 | 230 |
| H1 134 1N1K | L4 | 39 | $V_L4$ | 105 | CDRL 1-9 | 199 | CDRL 2-9 | 219 | CDRL3-13 | 237 |
| H1 143 1N1K | L5 | 40 | $V_L5$ | 106 | CDRL 1-9 | 199 | CDRL 2-7 | 217 | CDRL3-9 | 233 |
| H1 144 1N1K | L6 | 41 | $V_L6$ | 107 | CDRL 1-8 | 198 | CDRL 2-6 | 216 | CDRL3-9 | 233 |
| H1 16 1N1K | L7 | 42 | $V_L7$ | 108 | CDRL 1-8 | 198 | CDRL 2-6 | 216 | CDRL3-7 | 231 |
| H1 2 1N1K | L8 | 43 | $V_L8$ | 109 | CDRL 1-3 | 193 | CDRL 2-4 | 214 | CDRL3-4 | 228 |
| H1 2 1N1K SM | L9 | 44 | $V_L9$ | 110 | CDRL 1-3 | 193 | CDRL 2-4 | 214 | CDRL3-4 | 228 |
| H1 27 1N1K | L10 | 45 | $V_L10$ | 111 | CDRL 1-8 | 198 | CDRL 2-6 | 216 | CDRL3-9 | 233 |
| H1 30 1N1K | L11 | 46 | $V_L11$ | 112 | CDRL 1-5 | 195 | CDRL 2-4 | 214 | CDRL3-4 | 228 |
| H1 33-1 1N1K | L12 | 47 | $V_L12$ | 113 | CDRL 1-2 | 192 | CDRL 2-2 | 212 | CDRL3-3 | 227 |
| H1 34 1N1K | L13 | 48 | $V_L13$ | 114 | CDRL 1-8 | 198 | CDRL 2-6 | 216 | CDRL3-9 | 233 |
| H1 39 1N1K | L14 | 49 | $V_L14$ | 115 | CDRL 1-8 | 198 | CDRL 2-6 | 216 | CDRL3-9 | 233 |
| H1 42 1N1K | L15 | 50 | $V_L15$ | 116 | CDRL 1-4 | 194 | CDRL 2-4 | 214 | CDRL3-4 | 228 |
| H1 64 1N1K | L16 | 51 | $V_L16$ | 117 | CDRL 1-19 | 209 | CDRL 2-13 | 223 | CDRL3-21 | 245 |
| H1 66 1N1K | L17 | 52 | $V_L17$ | 118 | CDRL 1-13 | 203 | CDRL 2-6 | 216 | CDRL3-16 | 240 |
| H1 72 1N1K | L18 | 53 | $V_L18$ | 119 | CDRL 1-8 | 198 | CDRL 2-6 | 216 | CDRL3-9 | 233 |
| H1 90 1N1K | L19 | 54 | $V_L19$ | 120 | CDRL 1-8 | 198 | CDRL 2-6 | 216 | CDRL3-8 | 232 |
| H2 103 1N1K | L20 | 55 | $V_L20$ | 121 | CDRL 1-8 | 198 | CDRL 2-6 | 216 | CDRL3-9 | 233 |
| H2 131 1N1K | L21 | 56 | $V_L21$ | 122 | CDRL 1-15 | 205 | CDRL 2-10 | 220 | CDRL3-17 | 241 |
| H2 360 1N1K | L22 | 57 | $V_L22$ | 123 | CDRL 1-16 | 206 | CDRL 2-11 | 221 | CDRL3-18 | 242 |
| H2 360 1N1K SM | L23 | 58 | $V_L23$ | 124 | CDRL 1-16 | 206 | CDRL 2-11 | 221 | CDRL3-18 | 242 |
| H2 369 1N1K | L24 | 59 | $V_L24$ | 125 | CDRL 1-6 | 196 | CDRL 2-2 | 212 | CDRL3-5 | 229 |
| H2 380 1N1K | L25 | 60 | $V_L25$ | 126 | CDRL 1-20 | 210 | CDRL 2-2 | 212 | CDRL3-22 | 246 |
| H2 475 1N1K | L26 | 61 | $V_L26$ | 127 | CDRL 1-10 | 200 | CDRL 2-6 | 216 | CDRL3-11 | 235 |
| H2 508 1N1K | L27 | 62 | $V_L27$ | 128 | CDRL 1-17 | 207 | CDRL 2-14 | 224 | CDRL3-19 | 243 |
| H2 534 1N1K | L28 | 63 | $V_L28$ | 129 | CDRL 1-18 | 208 | CDRL 2-12 | 222 | CDRL3-20 | 244 |
| H2 550 1N1K | L29 | 64 | $V_L29$ | 130 | CDRL 1-14 | 204 | CDRL 2-3 | 213 | CDRL3-15 | 239 |
| H2 65 1N1K | L30 | 65 | $V_L30$ | 131 | CDRL 1-9 | 199 | CDRL 2-6 | 216 | CDRL3-10 | 234 |
| H1 13 1N1K | L31 | 66 | $V_L31$ | 132 | CDRL 1-8 | 198 | CDRL 2-6 | 216 | CDRL3-14 | 238 |
| H1 26 1N1K | L32 | 67 | $V_L32$ | 133 | CDRL 1-8 | 198 | CDRL 2-6 | 216 | CDRL3-9 | 233 |
| H1 13H1 13 1NVK2KK | L33 | 68 | $V_L33$ | 134 | CDRL 1-1 | 191 | CDRL 2-1 | 211 | CDRL3-2 | 226 |
| H1 26H1 26 1NVK2KK | L34 | 69 | $V_L34$ | 135 | CDRL 1-1 | 191 | CDRL 2-1 | 211 | CDRL3-1 | 225 |

TABLE 4C

| Ref. No. | Full Heavy SEQ ID NO | Full Light SEQ ID NO: | Variable Heavy SEQ ID NO | Variable Light SEQ ID NO | CDRH1 SEQ ID NO | CDRH2 SEQ ID NO | CDRH3 SEQ ID NO | CDRL1 SEQ ID NO | CDRL2 SEQ ID NO | CDRL3 SEQ ID NO |
|---|---|---|---|---|---|---|---|---|---|---|
| 1.109.1 | 4 | 36 | 70 | 102 | 140 | 155 | 169 | 202 | 218 | 236 |
| 1.109.1 SM | 4 | 37 | 70 | 103 | 140 | 155 | 169 | 201 | 218 | 236 |
| 1.13.1 | 5 | 66 | 71 | 132 | 136 | 148 | 165 | 198 | 216 | 238 |
| 1.13.13.1 | 5 | 68 | 71 | 134 | 136 | 148 | 165 | 191 | 211 | 226 |
| 1.131.1 | 6 | 38 | 72 | 104 | 146 | 155 | 181 | 197 | 215 | 230 |
| 1.134.1 | 7 | 39 | 73 | 105 | 143 | 158 | 190 | 199 | 219 | 237 |
| 1.143.1 | 8 | 40 | 74 | 106 | 137 | 151 | 167 | 199 | 217 | 233 |
| 1.144.1 | 9 | 41 | 75 | 107 | 137 | 150 | 166 | 198 | 216 | 233 |
| 1.16.1 | 10 | 42 | 76 | 108 | 137 | 154 | 184 | 198 | 216 | 231 |
| 1.2.1 | 11 | 43 | 77 | 109 | 147 | 163 | 186 | 193 | 214 | 228 |
| 1.2.1 SM | 11 | 44 | 77 | 110 | 147 | 163 | 186 | 193 | 214 | 228 |

TABLE 4C-continued

| Ref. No. | Full Heavy SEQ ID NO | Full Light SEQ ID NO: | Variable Heavy SEQ ID NO | Variable Light SEQ ID NO | CDRH1 SEQ ID NO | CDRH2 SEQ ID NO | CDRH3 SEQ ID NO | CDRL1 SEQ ID NO | CDRL2 SEQ ID NO | CDRL3 SEQ ID NO |
|---|---|---|---|---|---|---|---|---|---|---|
| 1.26.1 | 12 | 67 | 78 | 133 | 137 | 150 | 166 | 198 | 216 | 233 |
| 1.26.26.1 | 12 | 69 | 78 | 135 | 137 | 150 | 166 | 191 | 211 | 225 |
| 1.27.1 | 13 | 45 | 79 | 111 | 137 | 150 | 189 | 198 | 216 | 233 |
| 1.30.1 | 14 | 46 | 80 | 112 | 147 | 163 | 186 | 195 | 214 | 228 |
| 1.33-1.1 | 15 | 47 | 81 | 113 | 139 | 155 | 168 | 192 | 212 | 227 |
| 1.33.1 | 16 | 47 | 82 | 113 | 139 | 155 | 168 | 192 | 212 | 227 |
| 1.34.1 | 17 | 48 | 83 | 114 | 137 | 150 | 189 | 198 | 216 | 233 |
| 1.39.1 | 18 | 49 | 84 | 115 | 137 | 152 | 170 | 198 | 216 | 233 |
| 1.42.1 | 19 | 50 | 85 | 116 | 147 | 163 | 186 | 194 | 214 | 228 |
| 1.64.1 | 20 | 51 | 86 | 117 | 141 | 156 | 172 | 209 | 223 | 245 |
| 1.66.1 | 21 | 52 | 87 | 118 | 143 | 160 | 182 | 203 | 216 | 240 |
| 1.72.1 | 22 | 53 | 88 | 119 | 138 | 150 | 188 | 198 | 216 | 233 |
| 2.103.1 | 23 | 55 | 89 | 121 | 137 | 150 | 173 | 198 | 216 | 233 |
| 1.90.1 | 24 | 54 | 90 | 120 | 143 | 158 | 183 | 198 | 216 | 232 |
| 2.131.1 | 25 | 56 | 91 | 122 | 145 | 161 | 179 | 205 | 220 | 241 |
| 2.291.1 | 26 | | 92 | | 143 | 162 | 180 | | | |
| 2.360.1 | 27 | 57 | 93 | 123 | 142 | 157 | 187 | 206 | 221 | 242 |
| 2.360.1 SM | 28 | 58 | 94 | 124 | 142 | 157 | 187 | 206 | 221 | 242 |
| 2.369.1 | 29 | 59 | 95 | 125 | 142 | 157 | 175 | 196 | 212 | 229 |
| 2.380.1 | 30 | 60 | 96 | 126 | 144 | 159 | 178 | 210 | 212 | 246 |
| 2.475.1 | 31 | 61 | 97 | 127 | 143 | 158 | 177 | 200 | 216 | 235 |
| 2.508.1 | 32 | 62 | 98 | 128 | 142 | 157 | 176 | 207 | 224 | 243 |
| 2.534.1 | 33 | 63 | 99 | 129 | 136 | 149 | 171 | 208 | 222 | 244 |
| 2.550.1 | 34 | 64 | 100 | 130 | 147 | 164 | 185 | 204 | 213 | 239 |
| 2.65.1 | 35 | 65 | 101 | 131 | 137 | 153 | 174 | 199 | 216 | 234 |

In one aspect, the isolated antigen-binding proteins provided herein can be a monoclonal antibody, a polyclonal antibody, a recombinant antibody, a human antibody, a humanized antibody, a chimeric antibody, a multispecific antibody, or an antibody fragment thereof.

In another embodiment, the antibody fragment of the isolated antigen-binding proteins provided herein can be a Fab fragment, a Fab' fragment, an F(ab')$_2$ fragment, an Fv fragment, a diabody, or a single chain antibody molecule.

In a further embodiment, the isolated antigen binding protein provided herein is a human antibody and can be of the IgG1-, IgG2- IgG3- or IgG4-type.

In another embodiment, the antigen binding protein consists of a just a light or a heavy chain polypeptide as set forth in Tables 4A-4C. In some embodiments, the antigen binding protein consists just of a variable light or variable heavy domain such as those listed in Tables 4A-4C. Such antigen binding proteins can be pegylated with one or more PEG molecules.

In yet another aspect, the isolated antigen-binding protein provided herein can be coupled to a labeling group and can compete for binding to the extracellular portion of human c-fms with an antigen binding protein of one of the isolated antigen-binding proteins provided herein. In one embodiment, the isolated antigen binding protein provided herein can reduce monocyte chemotaxis, inhibit monocyte migration into tumors or inhibit accumulation and function of tumor associated macrophage in a tumor when administered to a patient.

As will be appreciated by those in the art, for any antigen binding protein with more than one CDR from the depicted sequences, any combination of CDRs independently selected from the depicted sequences is useful. Thus, antigen binding proteins with one, two, three, four, five or six of independently selected CDRs can be generated. However, as will be appreciated by those in the art, specific embodiments generally utilize combinations of CDRs that are non-repetitive, e.g., antigen binding proteins are generally not made with two CDRH2 regions, etc.

Some of the antigen binding proteins provided are discussed in more detail below.

Antigen Binding Proteins and Binding Epitopes and Binding Domains

When an antigen binding protein is said to bind an epitope within specified residues, such as c-fms, or the extracellular domain of c-fms, for example, what is meant is that the antigen binding protein specifically binds to a specified portion of c-fms. In some embodiments, the antigen binding protein specifically binds to a polypeptide consisting of the specified residues (e.g., a specified segment of c-fms). Such an antigen binding protein typically does not contact every residue within c-fms, or the extracellular domain of c-fms. Nor does every single amino acid substitution or deletion within c-fms, or the extracellular domain of c-fms, necessarily significantly affect binding affinity.

Epitope specificity and the binding domain(s) of an antigen binding protein can be determined by a variety of methods. Some methods, for example, can use truncated portions of an antigen. Other methods utilize antigen mutated at one or more specific residues.

With respect to methods using truncated portions of an antigen, in one exemplary approach, a collection of overlapping peptides can be used. The overlapping peptides consist of about 15 amino acids spanning the sequence of the antigen and differing in increments of a small number of amino acids (e.g., three amino acids). The peptides are immobilized within the wells of a microtiter dish or at different locations on a membrane. Immobilization can be effected by biotinylating one terminus of the peptides. Optionally, different samples of the same peptide can be biotinylated at the amino- and the carboxy-terminus and immobilized in separate wells for purposes of comparison. This is useful for identifying end-specific antigen binding proteins. Optionally, additional peptides can be included terminating at a particular amino acid of interest. This approach is useful for identifying end-specific antigen binding proteins to internal fragments of c-fms (or the extracellular domain of c-fms). An antigen binding protein or immunologically functional fragment is screened for specific binding to each of the various peptides. The epitope is defined as occurring with a segment of amino acids that is common to all peptides to which the antigen binding protein shows specific binding. Details regarding a specific approach for defining an epitope are set forth in Example 12.

As demonstrated in Example 12, in one embodiment the antigen binding proteins provided herein are capable of binding a polypeptide that includes the Ig-like domain 1 and the Ig-like domain 2 in combination; however, they do not bind a polypeptide containing primarily the Ig-like domain 1 or primarily the Ig-like domain 2 alone. The binding epitopes of such antigen binding proteins are thus composed three-dimensionally of the Ig-like 1 and Ig-like 2 domains in combination. As highlighted in FIG. 8, these two domains comprise amino acids 20 through 223 of c-fms extracellular domain, which has the following amino acid sequence:

```
                                            (SEQ ID NO: 326)
IPVIEPSVPELVVKPGATVTLRCVGNGSVEWDGPPSPHWTLYSDGSSSIL

STNNATFQNTGTYRCTEPGDPLGGSAAIHLYVKDPARPWNVLAQEVVVFE

DQDALLPCLLTDPVLEAGVSLVRVRGRPLMRHTNYSFSPWHGFTIHRAKF

IQSQDYQCSALMGGRKVMSISIRLKVQKVIPGPPALTLVPALVRIRGEAA

QIV.
```

The amino acid sequence used in Example 12 to represent the Ig-like 1 domain corresponds to amino acids 20-126 of the sequence depicted in FIG. 8 (i.e., amino acids 20-126 of SEQ ID NO: 1, namely IPVIEPSVPELVVKPGATVTL-RCVGNGSVEWDGPPSPHWTLYS-DGSSSILSTNNATFQNTGTYRCT EPGDPLGGSAAIH-LYVKDPARPWNVLAQEVVVFEDQDALLP). The amino acid sequence used to represent the Ig-like 2 domain alone corresponded to amino acids 85-223 of the sequence depicted in FIG. 8 (i.e., amino acids 85-223 of SEQ ID NO: 1, namely

```
TEPGDPLGGSAAIHLYVKDPARPWNVLAQEVVVFEDQDALLPCLLTDPVL

EAGVSLVRVRGRPLMRHTNYSFSPWHGFTIHRAKFIQSQDYQCSALMGGR

KVMSISIRLKVQKVIPGPPALTLVPALVRIRGEAAQIV).
```

Thus, an antigen binding protein in one embodiment can bind or specifically bind to a region within a cfms protein (e.g., the mature full length protein), where the region has the amino acid sequence specified in SEQ ID NO:326. In some embodiments, the antigen binding protein binds or specifically binds to a polypeptide consisting essentially of or consisting of the amino acids residues as set forth in SEQ ID NO:326.

In another embodiment, the antigen binding protein can bind or specifically bind to a polypeptide consisting of SEQ ID NO:326 but not to a polypeptide consisting of amino acids 20-126 of the sequence depicted in FIG. 8 (i.e., amino acids 20-126 of SEQ ID NO:1). In another aspect, the antigen binding protein can bind or specifically bind to a polypeptide consisting of SEQ ID NO:326 but not to a polypeptide consisting of amino acids 85-223 of the sequence depicted in FIG. 8 (i.e., amino acids 85-223 of SEQ ID NO:1). In yet another embodiment, the antigen binding protein can bind or specifically bind to a polypeptide consisting of SEQ ID NO:326 but not to a polypeptide consisting of amino acids 20-126 of the sequence depicted in FIG. 8 (i.e., amino acids 20-126 of SEQ ID NO:1) or to a polypeptide consisting of amino acids 85-223 of the sequence depicted in FIG. 8 (i.e., amino acids 85-223 of SEQ ID NO:1).

In another approach, the domain(s)/region(s) containing residues that are in contact with or are buried by an antibody can be identified by mutating specific residues in an antigen (e.g., a wild-type antigen) and determining whether the antigen binding protein can bind the mutated protein. By making a number of individual mutations, residues that play a direct role in binding or that are in sufficiently close proximity to the antibody such that a mutation can affect binding between the antigen binding protein and antigen can be identified. From a knowledge of these amino acids, the domain(s) or region(s) of the antigen that contain residues in contact with the antigen binding protein or covered by the antibody can be elucidated. Such a domain typically includes the binding epitope of an antigen binding protein. One specific example of this general approach utilizes an arginine/glutamic acid scanning protocol (see, e.g., Nanevicz, T., et al., 1995, *J. Biol. Chem.*, 270:37, 21619-21625 and Zupnick, A., et al., 2006, *J. Biol. Chem.*, 281:29, 20464-20473). In general, arginine and glutamic acids are substituted (typically individually) for an amino acid in the wild-type polypeptide because these amino acids are charged and bulky and thus have the potential to disrupt binding between an antigen binding protein and an antigen in the region of the antigen where the mutation is introduced. Arginines and lysines that exist in the wild-type antigen are replaced with glutamic acid. A variety of such individual mutants are obtained and the collected binding results analyzed to determine what residues affect binding.

Example 14 describes arginine/glutamic acid scanning of human c-fms for c-fms binding proteins provided herein. A series of 95 mutant human c-fms antigens were created, with each mutant antigen having a single mutation. Binding of each mutant c-fms antigen with selected c-fms antigen binding proteins provided herein was measured and compared to the ability of these selected binding proteins to bind wild-type c-fms antigen (SEQ ID NO:1). A reduction in binding between an antigen binding protein and a mutant c-fms antigen as used herein means that there is a reduction in binding affinity (e.g., as measured by known methods such as Biacore testing as described in the examples) and/or a reduction in the total binding capacity of the antigen binding protein (e.g., as evidenced by a decrease in Bmax in a plot of antigen binding protein concentration versus antigen concentration). A significant reduction in binding indicates that the mutated residue is directly involved in binding to the antigen binding protein or is in close proximity to the binding protein when the binding protein is bound to antigen.

In some embodiments, a significant reduction in binding means that the binding affinity and/or capacity between an antigen binding protein and a mutant c-fms antigen is reduced by greater than 40%, greater than 50%, greater than 55%, greater than 60%, greater than 65%, greater than 70%, greater than 75%, greater than 80%, greater than 85%, greater than 90% or greater than 95% relative to binding between the binding protein and a wild type c-fms antigen (e.g., the extracellular domain shown in SEQ ID NO:1). In certain embodiments, binding is reduced below detectable limits. In some embodiments, a significant reduction in binding is evidenced when binding of an antigen binding protein to a mutant c-fms antigen is less than 50% (e.g., less than 45%, 40%, 35%, 30%, 25%, 20%, 15% or 10%) of the binding observed between the antigen binding protein and a wild-type c-fms antigen (e.g., the extracellular domain shown in SEQ ID NO:1). Such binding measurements can be made using a variety of binding assays known in the art. A specific example of one such assay is described in Example 14.

In some embodiments, antigen binding proteins are provided that exhibit significantly lower binding for a mutant c-fms antigen in which a residue in a wild-type c-fms antigen (e.g., SEQ ID NO:1) is substituted with arginine or glutamic acid. In one such embodiment, binding of an antigen binding protein is significantly reduced for a mutant c-fms antigen having any one or more (e.g., 1, 2, 3 or 4) of the following mutations: E29R, Q121R, T152R, and K185E as compared to a wild-type c-fms (e.g., SEQ ID NO:1). In the shorthand notation used here, the format is: Wild type residue: Position in polypeptide: Mutant residue, with the numbering of the residues as indicated in SEQ ID NO:1. In some embodiments, binding of an antigen binding protein is significantly reduced for a mutant c-fms antigen having any one or more (e.g., 1, 2, 3, 4 or 5) of the following mutations: E29R, Q121R, S172R, G274R, and Y276R as compared to a wild-type c-fms (e.g., SEQ ID NO:1). In another embodiment, an antigen binding protein exhibits significantly lower binding for a mutant c-fms antigen containing any one or more (e.g., 1, 2, 3, 4, 5 etc. up to 23) of the following mutations: R106E, H151R, T152R, Y154R, S155R, W159R, Q171R, S172R, Q173R, G183R, R184E, K185E, E218R, A220R, S228R, H239R, N240R, K259E, G274R, N275R, Y276R, S277R, and N282R as compared to a wild-type c-fms (e.g., SEQ ID NO:1). In even more embodiments, binding of an antigen binding protein is significantly reduced for a mutant c-fms antigen containing any one or more (e.g., 1, 2, 3, 4 or 5) of the following mutations: K102E, R144E, R146E, D174R, and A226R as compared to binding to a wild-type c-fms (e.g., SEQ ID NO:1). In still other embodiments, an antigen binding protein exhibits significantly reduced binding for a mutant c-fms antigen containing any one or more (e.g., 1, 2, 3, 4, 5, 6, 7 or 8) of the following mutations: W50R, A74R, Y100R, D122R, T130R, G161R, Y175R, and A179R as compared to a wild-type c-fms (e.g., SEQ ID NO:1).

Although the mutant forms just listed are referenced with respect to the wild-type extracellular domain sequence shown in SEQ ID NO:1, it will be appreciated that in an allelic variant of c-fms the amino acid at the indicated position could differ. Antigen binding proteins showing significantly lower binding for such allelic forms of c-fms are also contemplated. Accordingly, in one embodiment, an antigen binding protein has significantly reduced binding for an allelic c-fms antigen as compared to a wild-type c-fms (e.g., SEQ ID NO:1) where one or more of the following residues (e.g., 1, 2, 3 or 4) of the allelic antigen are replaced with arginine or glutamic acid as indicated: 29R, 121R, 152R, and 185E (Position in polypeptide: Mutant residue, with the numbering of the residues as indicated in SEQ ID NO:1). In some embodiments, an antigen binding protein exhibits significantly reduced binding for an allelic c-fms antigen in which one or more (e.g., 1, 2, 3, 4 or 5) of the following residues are replaced with arginine or glutamic acid as indicated: 29R, 121R, 172R, 274R, and 276R as compared to its ability to bind a wild-type c-fms (e.g., SEQ ID NO:1). In another embodiment, an antigen binding protein shows significantly reduced binding for an allelic c-fms antigen in which one or more (e.g., 1, 2, 3, 4, 5 etc. up to 23) of the following residues are replaced with arginine or glutamic acid as indicated: 106E, 151R, 152R, 154R, 155R, 159R, 171R, 172R, 173R, 183R, 184E, 185E, 218R, 220R, 228R, 239R, 240R, 259E, 274R, 275R, 276R, 277R, and 282R as compared to its ability to bind a wild-type c-fms (e.g., SEQ ID NO:1). In even more embodiments, an antigen binding protein has significantly reduced binding for an allelic c-fms antigen in which any one or more (e.g., 1, 2, 3, 4 or 5) of the following residues are replaced with arginine or glutamic acid as indicated: 102E, 144E, 146E, 174R, and 226R as compared to its ability to bind a wild-type c-fms (e.g., SEQ ID NO:1). In still other embodiments, an antigen binding protein exhibits significantly reduced binding for an allelic c-fms antigen in which any one or more (e.g., 1, 2, 3, 4, 5, 6, 7 or 8) of the following residues are replaced with arginine or glutamic acid as indicated: 50R, 74R, 100R, 122R, 130R, 161R, 175R, and 179R as compared to its ability to bind a wild-type c-fms (e.g., SEQ ID NO:1).

In some embodiments, binding of an antigen binding protein is significantly reduced for a mutant c-fms antigen in which the residue at a selected position in the wild-type c-fms antigen is mutated to any other residue. For instance, in one embodiment, an antigen binding protein exhibits significantly reduced binding for a mutant c-fms antigen containing a single amino acid substitution at one or more (e.g., 1, 2, 3 or 4) of positions 29, 121, 152, and 185 (where the positions are as indicated in SEQ ID NO:1) as compared to its ability to bind a wild-type c-fms (e.g., SEQ ID NO:1). In some embodiments, an antigen binding protein has significantly reduced binding for a mutant c-fms antigen containing a single amino acid substitution at one or more (e.g., 1, 2, 3, 4 or 5) of positions 29, 121, 172, 274 and 276 of SEQ ID NO:1 as compared to its ability to bind a wild-type c-fms (e.g., SEQ ID NO:1). In another embodiment, binding of an antigen binding protein is significantly reduced for a mutant c-fms antigen containing a single amino acid substitution at one or more (e.g., 1, 2, 3, 4, 5 etc. up to 23) of positions 106, 151, 152, 154, 155, 159, 171, 172, 173, 183, 184, 185, 218, 220, 228, 239, 240, 259, 274, 275, 276, 277, and 282 of SEQ ID NO:1 as compared to binding to a wild-type c-fms of SEQ ID NO:1. In even more embodiments, an antigen binding protein has significantly lower binding for a mutant c-fms antigen containing a single amino acid substitution at one or more (e.g., 1, 2, 3, 4 or 5) of positions 102, 144, 146, 174, and 226 of SEQ ID NO:1 as compared to its ability to bind a wild-type c-fms (e.g., SEQ ID NO:1). In still other embodiments, an antigen binding protein has significantly lower binding for a mutant c-fms antigen containing a single amino acid substitution at one or more (e.g., 1, 2, 3, 4, 5, 6, 7 or 8) of positions 50, 74, 100, 122, 130, 161, 175, and 179 as compared to its ability to bind a wild-type c-fms (e.g., SEQ ID NO:1).

As noted above, residues directly involved in binding or covered by an antigen binding protein can be identified from scanning results. These residues can thus provide an indication of the domains or regions of SEQ ID NO:1 that contain the binding region(s) to which antigen binding proteins binds. As can be seen from the results summarized in Example 14, in one embodiment an antigen binding protein binds to a domain containing amino acids 29-185 of SEQ ID NO:1. In another embodiment, the antigen binding protein binds to a region containing amino acids 29-276 of SEQ ID NO:1. In other embodiments, the antigen binding protein binds to a region containing amino acids 106-282 of SEQ ID NO:1. In still other embodiments, the antigen binding protein binds to region containing amino acids 102-226 of SEQ ID NO:1. In yet another embodiment, the antigen binding protein binds to a region containing amino acids 50-179 of SEQ ID NO:1. In some embodiments, the antigen binding proteins binds to the foregoing regions within a fragment of the full length sequence of SEQ ID NO:1. In other embodiments, antigen binding proteins bind to polypeptides consisting of these regions. In certain embodiments, an antigen binding protein binds to a region containing amino acids 90-282 of SEQ ID NO:1. In another embodiment, an antigen binding protein binds to one or both of the following regions: amino acids 90-185 and amino acids 217-282 of SEQ ID NO:1. In yet another embodiment, an antigen binding protein binds to one or both of the following regions: amino acids 121-185 and amino acids 217-277 of SEQ ID NO:1.

Competing Antigen Binding Proteins

In another aspect, antigen binding proteins are provided that compete with one of the exemplified antibodies or functional fragments binding to the epitope described above for specific binding to c-fms. Such antigen binding proteins may also bind to the same epitope as one of the herein exemplified antigen binding proteins, or an overlapping epitope. Antigen binding proteins and fragments that compete with or bind to the same epitope as the exemplified antigen binding proteins are expected to show similar functional properties. The exemplified antigen binding proteins and fragments include those described above, including those with the heavy and light chains, variable region domains and CDRs included in TABLES 1, 2, 3, and 4A-C. Thus, as a specific example, the antigen binding proteins that are provided include those that compete with an antibody having:

(a) all 6 of the CDRs listed for an antibody listed in Table 4C;

(b) a $V_H$ and a $V_L$ listed for an antibody listed in Table 4C; or (c) two light chains and two heavy chains as specified for an antibody listed in Table 4C.

Monoclonal Antibodies

The antigen binding proteins that are provided include monoclonal antibodies that bind to c-fms. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag41, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a c-fms immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a c-fms polypeptide. Such hybridoma cell lines, and anti-c-fms monoclonal antibodies produced by them, are aspects of the present application.

Monoclonal antibodies secreted by a hybridoma cell line can be purified using any technique known in the art. Hybridomas or mAbs may be further screened to identify mAbs with particular properties, such as the ability to block a Wnt induced activity. Examples of such screens are provided in the examples below.

Chimeric and Humanized Antibodies

Chimeric and humanized antibodies based upon the foregoing sequences are also provided. Monoclonal antibodies for use as therapeutic agents may be modified in various ways prior to use. One example is a chimeric antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, Proc. Natl. Acad. Sci. USA 81:6851-6855, which are hereby incorporated by reference. CDR grafting is described, for example, in U.S. Pat. No. 6,180,370, No. 5,693,762, No. 5,693,761, No. 5,585,089, and No. 5,530,101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally-occurring variable regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. No. 5,585,089, and No. 5,693,762; Jones et al., 1986, Nature 321:522-525; Riechmann et al., 1988, Nature 332:323-27; Verhoeyen et al., 1988, Science 239:1534-1536).

In one aspect, the CDRs of the light and heavy chain variable regions of the antibodies provided herein (see, TABLE 3) are grafted to framework regions (FRs) from antibodies from the same, or a different, phylogenetic species. For example, the CDRs of the heavy and light chain variable regions $V_H1$, $V_H2$, $V_H3$, $V_H4$, $V_H5$, $V_H6$, $V_H7$, $V_H8$, $V_H9$, $V_H10$, $V_H11$, $V_H12$, $V_H13$, $V_H14$, $V_H15$, $V_H16$, $V_H17$, $V_H18$, $V_H19$, $V_H20$, $V_H21$, $V_H22$, $V_H23$, $V_H24$, $V_H25$, $V_H26$, $V_H27$, $V_H28$, $V_H29$, $V_H30$, $V_H31$, and $V_H32$, and/or $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, $V_L21$, $V_L22$, $V_L23$, $V_L24$, $V_L25$, $V_L26$, $V_L27$, $V_L28$, $V_L29$, $V_L30$, $V_L31$, $V_L32$, $V_L33$ and $V_L34$ can be grafted to consensus human FRs. To create consensus human FRs, FRs from several human heavy chain or light chain amino acid sequences may be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of anti-c-fms antibody are not replaced, while the rest of the FR amino acids are replaced. A "rare amino acid" is a specific amino acid that is in a position in which this particular amino acid is not usually found in an FR. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In certain embodiments, constant regions from species other than human can be used along with the human variable region(s) to produce hybrid antibodies.

Fully Human Antibodies

Fully human antibodies are also provided. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. No. 5,545,807; No. 6,713,610; No. 6,673,986; No. 6,162,963; No. 5,545,807; No. 6,300,129; No. 6,255,458; No. 5,877, 397; No. 5,874,299 and No. 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., 1994, *Nature* 368:856-859). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies (Lonberg et al., supra.; Lonberg and Huszar, 1995, *Intern. Rev. Immunol.* 13: 65-93; Harding and Lonberg, 1995, *Ann. NY Acad. Sci.* 764:536-546). The preparation of HuMab mice is described in detail in Taylor et al., 1992, *Nucleic Acids Research* 20:6287-6295; Chen et al., 1993, *International Immunology* 5:647-656; Tuaillon et al., 1994, *J. Immunol.* 152:2912-2920; Lonberg et al., 1994, *Nature* 368:856-859; Lonberg, 1994, *Handbook of Exp. Pharmacology* 113:49-101; Taylor et al., 1994, *International Immunology* 6:579-591; Lonberg and Huszar, 1995, *Intern. Rev. Immunol.* 13:65-93; Harding and Lonberg, 1995, *Ann. N.Y Acad. Sci.* 764:536-546; Fishwild et al., 1996, *Nature Biotechnology* 14:845-851; the foregoing references are hereby incorporated by reference in their entirety for all purposes. See, further U.S. Pat. No. 5,545,806; No. 5,569,825; No. 5,625,126; No. 5,633,425; No. 5,789,650; No. 5,877,397; No. 5,661,016; No. 5,814, 318; No. 5,874,299; and No. 5,770,429; as well as U.S. Pat. No. 5,545,807; International Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., 1997, *Nature Genetics* 15:146-156, which are hereby incorporated by reference. For example, the HCo7 and HCo12 transgenic mice strains can be used to generate anti-c-fms antibodies. Further details regarding the production of human antibodies using transgenic mice are provided in the examples below.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., 1991, *J. Mol. Biol.* 227:381; and Marks et al., 1991, *J. Mol. Biol.* 222:581). Phage display techniques mimic immune selection through the display of antibody repertoires on the surface of filamentous bacteriophage, and subsequent selection of phage by their binding to an antigen of choice. One such technique is described in PCT Publication No. WO 99/10494 (hereby incorporated by reference), which describes the isolation of high affinity and functional agonistic antibodies for MPL- and msk-receptors using such an approach.

Bispecific or Bifunctional Antigen Binding Proteins

The antigen binding proteins that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553.

Various Other Forms

Some of the antigen binding proteins that are provided are variant forms of the antigen binding proteins disclosed above (e.g., those having the sequences listed in TABLES 1-4). For instance, some of the antigen binding proteins have one or more conservative amino acid substitutions in one or more of the heavy or light chains, variable regions or CDRs listed in TABLES 1-4.

Naturally-occurring amino acids may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, e.g., Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In some aspects, those which are within ±1 are included, and in other aspects, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in other embodiments, those which are within ±1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in TABLE 5.

TABLE 5

Conservative Amino Acid Substitutions

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the 3-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for c-fms neutralizing activity, (see examples below) thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See, Moult, 1996, *Curr. Op. in Biotech.* 7:422-427; Chou et al., 1974, *Biochem.* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% can have similar structural topologies. The recent growth of the protein structural database (PDB) has provided enhanced predictability of secondary structure, including the potential number of folds within a polypeptide's or protein's structure. See, Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See, Holm, 1999, supra; and Brenner, 1997, supra).

In some embodiments, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antigen binding protein). Examples of art-recognized polypeptide secondary and tertiary structures are described in Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, *Nature* 354:105, which are each incorporated herein by reference.

Additional preferred antibody variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteines.

The heavy and light chains, variable regions domains and CDRs that are disclosed can be used to prepare polypeptides that contain an antigen binding region that can specifically bind to a c-fms polypeptide. For example, one or more of the CDRs listed in TABLES 3 and 4 can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., a c-fms polypeptide or epitope thereof).

Mimetics (e.g., "peptide mimetics" or "peptidomimetics") based upon the variable region domains and CDRs that are described herein are also provided. These analogs can be peptides, non-peptides or combinations of peptide and non-peptide regions. Fauchere, 1986, *Adv. Drug Res.* 15:29; Veber and Freidinger, 1985, *TINS* p. 392; and Evans et al., 1987, *J. Med. Chem.* 30:1229, which are incorporated herein by reference for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics are proteins that are structurally similar to an antibody displaying a desired biological activity, such as here the ability to specifically bind c-fms, but have one or more peptide linkages optionally replaced by a linkage selected from: —$CH_2NH$—, —$CH_2S$—, —$CH_2$—$CH_2$—, —CH—CH-(cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments to generate more stable proteins. In addition, constrained peptides comprising a consensus sequence or a substantially identical consensus sequence variation may be generated by methods known in the art (Rizo and Gierasch, 1992, *Ann. Rev. Biochem.* 61:387), incorporated herein by reference), for example, by adding internal cysteine residues capable of forming intramolecular disulfide bridges which cyclize the peptide.

Derivatives of the antigen binding proteins that are described herein are also provided. The derivatized antigen binding proteins can comprise any molecule or substance that imparts a desired property to the antibody or fragment, such as increased half-life in a particular use. The derivatized antigen binding protein can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antigen binding protein for a particular use (e.g., administration to a subject, such as a human subject, or other in vivo or in vitro uses). Examples of molecules that can be used to derivatize an antigen binding protein include albumin (e.g., human serum albumin) and polyethylene glycol (PEG). Albumin-linked and PEGylated derivatives of antigen binding proteins can be prepared using techniques well known in the art. Certain antigen binding proteins include a pegylated single chain polypeptide as described herein. In one embodiment, the antigen binding protein is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of c-fms antigen binding proteins with other proteins or polypeptides, such as by expression of recombinant fusion proteins comprising heterologous polypeptides fused to the N-terminus or C-terminus of a c-fms antigen binding protein. For example, the conjugated peptide may be a heterologous signal (or leader) polypeptide, e.g., the yeast alpha-factor leader, or a peptide such as an epitope tag. C-fms antigen binding protein-containing fusion proteins can comprise peptides added to facilitate purification or identification of the c-fms antigen binding protein (e.g., poly-His). A c-fms antigen binding protein also can be linked to the FLAG peptide as described in Hopp et al., 1988, *Bio/Technology* 6:1204; and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more c-fms antigen binding proteins may be employed as c-fms antagonists. Oligomers may be in the form of covalently-linked or non-covalently-linked dimers, trimers, or higher oligomers. Oligomers comprising two or more c-fms antigen binding proteins are contemplated for use, with one example being a homodimer. Other oligomers include heterodimers, homotrimers, heterotrimers, homotetramers, heterotetramers, etc.

One embodiment is directed to oligomers comprising multiple c-fms-binding polypeptides joined via covalent or non-covalent interactions between peptide moieties fused to the c-fms antigen binding proteins. Such peptides may be peptide linkers (spacers), or peptides that have the property of promoting oligomerization. Leucine zippers and certain polypeptides derived from antibodies are among the peptides that can promote oligomerization of c-fms antigen binding proteins attached thereto, as described in more detail below.

In particular embodiments, the oligomers comprise from two to four c-fms antigen binding proteins. The c-fms antigen binding protein moieties of the oligomer may be in any of the forms described above, e.g., variants or fragments. Preferably, the oligomers comprise c-fms antigen binding proteins that have c-fms binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11.

One embodiment is directed to a dimer comprising two fusion proteins created by fusing a c-fms antigen binding protein to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 and U.S. Pat. No. 5,426,048 and No. 5,262,522, is a single chain polypeptide extending from the N-terminal hinge region to the native C-terminus of the Fc region of a human IgG1 antibody. Another useful Fc polypeptide is the Fc mutein described in U.S. Pat. No. 5,457,035, and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of a c-fms antigen binding protein such as disclosed herein may be substituted for the variable portion of an antibody heavy and/or light chain.

Alternatively, the oligomer is a fusion protein comprising multiple c-fms antigen binding proteins, with or without peptide linkers (spacer peptides). Among the suitable peptide linkers are those described in U.S. Pat. No. 4,751,180 and No. 4,935,233.

Another method for preparing oligomeric c-fms antigen binding protein derivatives involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-278. In one approach, recombinant fusion proteins comprising a c-fms antigen binding protein fragment or derivative fused to a leucine zipper peptide are expressed in suitable host cells, and the soluble oligomeric c-fms antigen binding protein fragments or derivatives that form are recovered from the culture supernatant.

Some antigen binding proteins that are provided have an on-rate ($k_a$) for c-fms of at least $10^4$/M×seconds, at least $10^5$/M×seconds, at least $10^6$/M×seconds measured, for instance, as described in the examples below. Certain antigen binding proteins that are provided have a slow dissociation rate or off-rate. Some antigen binding proteins, for instance, have a $k_d$ (off-rate) of $1×10^{-2}$ s$^{-1}$, or $1×10^{-3}$ s$^{-1}$, or $1×10^{-4}$ s$^{-1}$, or $1×10^{-5}$ s$^{-1}$. In certain embodiments, the antigen binding protein has a $K_D$ (equilibrium binding affinity) of less than 25 pM, 50 pM, 100 pM, 500 pM, 1 nM, 5 nM, 10 nM, 25 nM or 50 nM.

Another aspect provides an antigen-binding protein having a half-life of at least one day in vitro or in vivo (e.g., when administered to a human subject). In one embodiment, the antigen binding protein has a half-life of at least three days. In another embodiment, the antibody or portion thereof has a half-life of four days or longer. In another embodiment, the antibody or portion thereof has a half-life of eight days or longer. In another embodiment, the antibody or antigen-binding portion thereof is derivatized or modified such that it has a longer half-life as compared to the underivatized or unmodified antibody. In another embodiment, the antigen binding protein contains point mutations to increase serum half life, such as described in WO 00/09560, published Feb. 24, 2000, incorporated by reference.

Glycosylation

The antigen-binding protein may have a glycosylation pattern that is different or altered from that found in the native species. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence may be altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev, Biochem.*, pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118: 131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Hence, aspects include glycosylation variants of the antigen binding proteins wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked sites are created. Antibodies typically have a N-linked glycosylation site in the Fc region.

Labels and Effector Groups

In some embodiments, the antigen-binding comprises one or more labels. The term "labeling group" or "label" means any detectable label. Examples of suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used as is seen fit.

The term "effector group" means any group coupled to an antigen binding protein that acts as a cytotoxic agent. Examples for suitable effector groups are radioisotopes or radionuclides (e.g., $^3$H, $^{14}$C, $^{15}$N, $^{35}$S, $^{90}$Y, $^{99}$Tc, $^{111}$In, $^{125}$I, $^{131}$I). Other suitable groups include toxins, therapeutic groups, or chemotherapeutic groups. Examples of suitable groups include calicheamicin, auristatins, geldanamycin and maytansine. In some embodiments, the effector group is coupled to the antigen binding protein via spacer arms of various lengths to reduce potential steric hindrance.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in MOLECULAR PROBES HANDBOOK by Richard P. Haugland, hereby expressly incorporated by reference.

Suitable proteinaceous fluorescent labels also include, but are not limited to, green fluorescent protein, including a *Renilla, Ptilosarcus,* or *Aequorea* species of GFP (Chalfie et al., 1994, *Science* 263:802-805), EGFP (Clontech Labs., Inc., Genbank Accession Number U55762), blue fluorescent protein (BFP, Quantum Biotechnologies, Inc., Quebec, Canada; Stauber, 1998, *Biotechniques* 24:462-471; Heim et al., 1996, *Curr. Biol.* 6:178-182), enhanced yellow fluorescent protein (EYFP, Clontech Labs., Inc.), luciferase (Ichiki et al., 1993, *J. Immunol.* 150:5408-5417), β galactosidase (Nolan et al., 1988, *Proc. Natl. Acad. Sci. USA.* 85:2603-2607) and *Renilla* (WO92/15673, WO95/07463, WO98/14605, WO98/26277, WO99/49019, U.S. Pat. No. 5,292,658, No. 5,418,155, No. 5,683,888, No. 5,741,668, No. 5,777,079, No. 5,804,387, No. 5,874,304, No. 5,876,995, No. 5,925,558).

Nucleic Acids Encoding C-fms Antigen Binding Proteins

Nucleic acids that encode for the antigen binding proteins described herein, or portions thereof, are also provided, including nucleic acids encoding one or both chains of an antibody, or a fragment, derivative, mutein, or variant thereof, polynucleotides encoding heavy chain variable regions or only CDRs, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids). TABLE 6 shows exemplary nucleic acid sequences encoding an IgG2 heavy chain constant region and IgG2 kappa light chain constant region. Any variable region provided herein may be attached to these constant regions to form complete heavy and light chain sequences. However, it should be understood that these constant regions sequences are provided as specific examples only. In some embodiments, the variable region sequences are joined to other constant region sequences that are known in the art. Exemplary nucleic acid sequences encoding heavy and light chain variable regions are provided in TABLE 7.

TABLE 6

Exemplary Nucleic Acid Sequences Encoding Heavy And Light Chain Constant Regions

| Type | Nucleic Acid Sequence/SEQ ID NO. |
|---|---|
| IgG2 heavy chain | gctagcaccaagggcccatcggtcttcccctggcgccc tgctccaggagcacctccgagagcacagcggccctgggc tgcctggtcaaggactacttccccgaaccggtgacggtg tcgtggaactcaggcgctctgaccagcggcgtgcacacc ttcccagctgtcctacagtcctcaggactctactccctc agcagcgtggtgaccgtgccctccagcaacttcggcacc cagacctacacctgcaacgtagatcacaagcccagcaac accaaggtggacaagacagttgagcgcaaatgttgtgtc gagtgcccaccgtgcccagcaccacctgtggcaggaccg tcagtcttcctcttccccccaaaacccaaggacaccctc atgatctcccggacccctgaggtcacgtgcgtggtggtg gacgtgagccacgaagaccccgaggtccagttcaactgg tacgtggacggcgtggaggtgcataatgccaagacaaag ccacgggaggagcagttcaacagcacgttccgtgtggtc agcgtcctcaccgttgtgcaccaggactggctgaacggc aaggagtacaagtgcaaggtctccaacaaaggcctccca gcccccatcgagaaaaccatctccaaaaccaaagggcag ccccgagaaccacaggtgtacaccctgcccccatcccgg gaggagatgaccaagaaccaggtcagcctgacctgcctg gtcaaaggcttctaccccagcgacatcgccgtggagtgg gagagcaatgggcagccggagaacaactacaagaccaca cctcccatgctggactccgacggctccttcttcctctac agcaagctcaccgtggacaagagcaggtggcagcagggg aacgtcttctcatgctccgtgatgcatgaggctctgcac aaccactacacgcagaagagcctctccctgtctccgggt aaatga [SEQ ID NO: 247] |
| IgG2 kappa light chain | cgtacggtggctgcaccatctgtcttcatcttcccgcca tctgatgagcagttgaaatctggaactgcctctgttgtg tgcctgctgaataacttctatcccagagaggccaaagta cagtggaaggtggataacgccctccaatcgggtaactcc caggagagtgtcacagagcaggacagcaaggacagcacc tacagcctcagcagcaccctgacgctgagcaaagcagac tacgagaaacacaaagtctacgcctgcgaagtcacccat cagggcctgagctcgcccgtcacaaagagcttcaacagg ggagagtgttag [SEQ ID NO: 248] |

TABLE 7 shows exemplary nucleic acid sequences encoding heavy chain and light chain variable regions, in which the various CDRH1, CDRH2, CDRH3, CDRL1, CDRL2, and CDRL3 sequences are embedded.

TABLE 7

Exemplary Nucleic Acid Sequences Encoding Heavy And Light Chain Variable Regions

| Reference | Designation | Nucleic Acid Sequence/SEQ ID NO. |
|---|---|---|
| H1 109 1N1G1 | $V_H1$ | caggtgcagctggtgcagtctggggctgaggtgaagaagcctggggcctcagtgaaggtctcctgcaagg cttctggatacaccttcaccgcctactatatgcactgggtgcgacaggcccctggacaagggcttgagtgga tgggatggatcaaccctaacagtggtggcacaaactatgcacagaagtttcagggcagggtcaccatgac cagggacacgtccatcagcacagcctacatggagctgagcaggctgagatctgacgacacggccgtgta ttactgtgcgagaggtggatatagtggctacgatttgggctactactacggtatggacgtctggggccaagg gaccacggtcaccgtctcctca [SEQ ID NO: 249] |

TABLE 7-continued

Exemplary Nucleic Acid Sequences Encoding Heavy And Light Chain Variable Regions

| Reference | Designation | Nucleic Acid Sequence/SEQ ID NO. |
|---|---|---|
| H1 13 1N1G1 | $V_H2$ | caggtgcagctgcaggagtcgggcccaggactggtgaagccttcggagaccctgtccctcacctgcactgt<br>ctctggtggctccgtcagcagtggtggttactactggagctggatccggcagcccccagggaagggactgg<br>agtggattgggtatatctattacagtgggagcaccaactacaaccccctcctcaagagtcgagtcaccatat<br>cagtagacacgtccaagaaccagttctccctgaagctgagctctgtgaccgctgcggacacggccgtgtat<br>tactgtgcggccggtatagcagccactggtaccctctttgactgctggggccaggaaccctggtcaccgtct<br>cctca<br>[SEQ. ID NO: 250] |
| H1 131 1N1 G1 | $V_H3$ | caggtgcagctggtgcagtctggggctgaggtgaagaagcctggggcctcagtgaaggtctcctgcaagg<br>cttctggatacaccttcaccggctactatatacactgggcgacaggcccctggacaagggcttgagtgga<br>tgggatggatcaaccctaacagtggtggcacaaactatgcacagaagtttcagggcagggtcaccatgac<br>cagggacacgtccatcagcacagcctacatggagctgagcaggctgagatctgacgacacggccgtgta<br>ttactgtgcgagagatcgagggcagctatggttatggtactactactactacggtatggacgtctggggccaa<br>gggaccacggtcaccgtctcctca<br>[SEQ ID NO: 251] |
| H1 134 1N1G1 | $V_H4$ | caggtgcagctggtggagtctgggggaggcgtggtccagcctggagggtccctgagactctcctgtgcagc<br>gtctggattcaccttcagtagctatggcatgcactgggtccgccaggctccaggcaaggggctggagtgggt<br>ggcagttatatggtatgatggaagtaataaatactatgcagactccgtgaagggccgattcaccatctccag<br>agacaattccaagaacacgctgtatctgcaaatgaacagcctgagagccgaggacacggctgtgtattac<br>tgtgccagcagcagctggtcctactacggtatggacgtctggggccaagggaccacggtcaccgtctcctc<br>a<br>[SEQ ID NO: 252] |
| H1 143 1N1G1 | $V_H5$ | gaggtgcagctggtggagtctgggggaggcttggtaaagcctggggggtcccttagactctcctgtgcagc<br>ctctggattcactgtcagtaacgcctggatgagctgggtccgccaggctccagggaaggggctggagtgg<br>gttggccgtattaaaagcaaaactgatggtgggacaacagacaacgctgcacccgtgaaaggcagattc<br>accatctcaagagatgattcaaaaaacacgctgtatctgcaaatgaacagcctgaaaaccgaggacaca<br>gccgtgtattactgtaccacaggagggtcattactatggaccgggcccaactactactactacggtatggac<br>gtctggggccaagggaccacggtcaccgtctcctca<br>[SEQ ID NO: 253] |
| H1 144 1N1G1 | $V_H6$ | gaggtgcagctggtggagtctgggggaggcttggtaaagcctggggggtcccttagactctcctgtgcagc<br>ctctggattcactttcagtaacgcctggatgagctgggtccgccaggctccagggaaggggctggagtggg<br>ttggccgtattaaaagcaaaactgatggtgggacaacagactacgctgcacccgtgaaaggcagattcac<br>catctcaagagatgattcaaaaaacacgctgtatctgcaaatgaacagcctgaaaaccgaggacacagc<br>cgtgtattactgtaccacagagtactatggttcggggggggtttggtactacggtatggacgtctggggccaa<br>gggaccacggtcaccgtctcctca<br>[SEQ ID NO: 254] |
| H1 16 1N1G1 | $V_H7$ | gaggtgcagctggtggagtctgggggaggcttggtaaagcctggggggtcccttagactctcctgtgcagc<br>ctctggattcacttttcagtaacgcctggatgagctgggtccgccaggctccagggaaggggctggagtggg<br>ttggccgtattaaaagcaaaactgatggttggacaacagactacgctgcacccgtgaaaggcagattcac<br>catctcaagagatgattcaaaaaacacgctgtatctgcaaatgaacagcctgaaaaccgaggacacagc<br>cgtgtattactgtaccacagatactccgtataactggaactacctattactactactacggtatggacgtctg<br>gggccaagggaccacggtcaccgtctcctca<br>[SEQ ID NO: 255] |
| H1 2 1N1G1 | $V_H8$ | caggttcagctggtgcagtctggagctgaggtgaagaagcctgggcctcagtgaaggtctcctgcaagg<br>cttctggttacacctttaccagctatggtatcagctgggtgcgacaggcccctggacaagggcttgagtggat<br>gggatggatcagcgcttacaatggtaacacaaactatgcacagaagttccagggcagagtcaccatgac<br>cacagacacatccacgagcacagcctacatggagctgaggagcctgagatctgacgacacggccgtgt<br>attactgtgcgagagagtcgtggttcggggaggtattctttgactactggggccagggaaccctggtcaccgt<br>ctcctca<br>[SEQ ID NO: 256] |
| H1 26 1N1G1 | $V_H9$ | gaggtgcagctggtggagtctgggggaggcttggtaaagcctggggggtcccttagactctcctgtgcagc<br>ctctggattcactttcagtaacgcctggatgagctgggtccgccaggctccagggaaggggctggagtggg<br>ttggccgtattaaaagcaaaactgatggtgggacaacagactacgctgcacccgtgaaaggcagattcac<br>catctcaagagatgattcaaaaaacacgctgtatctgcaaatgaacagcctgaaaaccgaggacacagc<br>cgtgtattactgtaccacagagtactatggttcggggggggtttggtactacggtatggacgtctggggccaa<br>gggaccacggtcaccgtctcctca<br>[SEQ ID NO: 257] |
| H1 27 1N1G1 | $V_H10$ | gaggtgcagctggtggagtctgggggaggcttggtaaagcctggggggtcccttagactctcctgtgcagc<br>ctctggattcactttcagtaacgcctggatgagctgggtccgccaggctccagggaaggggctggagtggg<br>ttggccgtattaaaagcaaaactgatggtgggacaacagactacgctgcacccgtgaaaggcagattcac<br>catctcaagagatgattcaaaaaacacgctgtatctgcaaatgaacagcctgaaaaccgaggacacagc<br>cgtgtattactgtaccacagatggggctacggtggtaactccggggtactactacggtacggacgtctg<br>gggccaagggaccacggtcaccgtctcctca<br>[SEQ ID NO: 258] |

TABLE 7-continued

Exemplary Nucleic Acid Sequences Encoding Heavy And Light Chain Variable Regions

| Reference | Designation | Nucleic Acid Sequence/SEQ ID NO. |
|---|---|---|
| H1 30 1N1G1 | $V_H 11$ | caggttcagctggtgcagtctggagctgaggtgaagaagcctggggcctcagtgaaggtctcctgcaagg cttctggttacacctttaccagctatggtatcagctgggtgcgacaggcccctggacaagggcttgagtggat gggatggatcagcgcttacaatggtaacacaaactatgcacagaagctccagggcagagtcaccatgac cacagacacatccacgagcacagcctacatggagctgaggagcctgagatctgacgacacggccgtgt attactgtgcgagagagtcgtggttcggggaggtattttttgactactggggccagggaaccctggtcaccgt ctcctca [SEQ ID NO: 259] |
| H1 33 1-1N1G1 | $V_H 12$ | caggtgcagctggtgcagtctggggctgaggtgaagaagcctggggcctcagtgaaggtctcctgcaagg cttctggatacacctttaccggctactatatgcactgggtgcgacaggcccctggacaagggcttgaatgga tgggatggatcaaccctaacagtggtggcacaaactatgctcagaagtttcagggcagggtcaccatgac cagggacacgtccatcagcacagcctacatggagctgagcagactgagatctgacgacacggccttttatt actgtgcgagagacagcaactggtaccacaactggttcgaccctggggccagggaaccctggtcaccg tctcctca [SEQ ID NO: 260] |
| H1 33 1N1G1 | $V_H 13$ | caggtgcagctggtgcagtctggggctgaggtgaagaagcctggggcctcagtgaaggtctcctgcaagg cttctggatacacctttaccggctactatatgcactgggtgcgacaggcccctggacaagggcttgaatgga tgggatggatcaaccctaacagtggtggcacaaactatgctcagaagtttcagggcagggtcaccatgac cagggacacgtccatcagcacagcctacatggagctgagcagactgagatctgacgacacggccttttatt actgtgcgagagacagcaactggtaccacaactggttcgaccctggggccagggaaccctggtcaccg tctcctca [SEQ ID NO: 261] |
| H1 34 1N1G1 | $V_H 14$ | gaggtgcagctggtggagtctgggggaggcttggtaaagcctggggggtcccttagactctcctgtgcagc ctctggattcactttcagtaacgcctggatgagctgggtccgccaggctccagggaaggggctggagtggg ttggccgtattaaaagcaaaactgatggtgggaacagacgactacgctgcacccgtgaaaggcagattcac catctcaagagatgattcaaaaaacacgctgtatctgcaaatgaacagcctgaaaaccgaggacacagc cgtgtattactgtaccacagatggggctacggtggtaactccggggtactactactacggtacggacgtctg gggccaagggaccacggtcaccgtctcctca [SEQ ID NO: 262] |
| H1 39 1N1G1 | $V_H 15$ | gaggtgcaactggtggagtctgggggaggcttggtaaagcctggggggtcccttagactctcctgtgcagc ctctggattcactttcagtaacgcctggatgagctgggtccgccaggctccagggaaggggctggagtggg ttggccgtattaaaagcaaaactgatggtgggacagcagactacgctgcacccgtgaaaggcagattcac catctcaagagatgattcaaaaaacacgctgtatctgcaaatgaacagcctgaaaaccgaggacacagc cgtgtattactgtaccacagaaggtccctacagtgactacgggtactactactacggtatggacgtctggggc caagggaccacggtcaccgtctcctca [SEQ ID NO: 263] |
| H1 42 1N1G1 | $V_H 16$ | caggttcagctggtgcagtctggagctgaggtgaagaagcctggggcctcagtgaaggtctcctgcaagg cttctggttacacctttaccagctatggtatcagctgggtgcgacaggcccctggacaagggcttgagtggat gggatggatcagcgcttacaatggtaacacaaactatgcacagaagctccagggcagagtcaccatgac cacagacacatccacgagcacagcctacatggagctgaggagcctgagatctgacgacacggccgtgt attactgtgcgagagagtcgtggttcggggaggtattctttgactactggggccagggaaccctggtcaccgt ctcctca [SEQ ID NO: 264] |
| H1 64 1N1G1 | $V_H 17$ | gaggtgcagctggtggagtctgggggaggcttggtacagcctggggggtccctgagactctcctgtgcagc ctctggattcacctttcagtagctacgacatgcactgggtccgccaagctacaggaaaaggtctggagtgggt ctcaggtattggtactgctggtgacacatactatccaggctccgtgaagggccgattcaacatctccagaga aaatgccaagaactccttgtatcttcaaatgaacagcctgagagccggggacacggctgtgtattactgtgc aagagagggcagctggtacggctttgactactggggccagggaaccctggtcaccgtctcctca [SEQ ID NO: 265] |
| H1 66 1N1G1 | $V_H 18$ | caggtgcagctggtggagtctgggggaggcgtggtccagcctggggaggtccctgagactctcctgtgcagc gtctggattcaccttcagtagctatggcatgcactgggtccgccaggctccaggcaaggggctggagtggt ggcagttatatggtatgatggaagtaataatactatgcagactccgtgaagggccgattcaccatctccag agacaattccaagagcacgctgtatctgcaaatgaacagcctgagagccgaggacacggctgtgtattac tgtgcgcactcgtccgggaactactacgatatggacgtctgggggcaagggaccacggtcaccgtctcctc a [SEQ ID NO: 266] |
| $V_H 19$ | $V_H 19$ | gaggtgcagctggtggagtctgggggaggcttggtagagcctggggggtcccttagactctcctgtgcagc ctctggattcactttcagtaccgcctggatgagctgggtccgccaggctccagggaaggggctggagtggg ttggccgtattaaaagcaaaactgatggtgggacaacagactacgctgcacccgtgaaaggcagattcac catctcaagagatgattcaaaaaacacgctgtatctgcaaatgaacagcctgaaaaccgaggacacagc cgtgtattactgtaccacagaaggtccctacagtaactacgggtactactactacggtgtggacgtctggggc caagggaccacggtcaccgtctcctca [SEQ ID NO: 267] |

TABLE 7-continued

Exemplary Nucleic Acid Sequences Encoding Heavy And Light Chain Variable Regions

| Reference | Designation | Nucleic Acid Sequence/SEQ ID NO. |
|---|---|---|
| H1 90 1N1G1 | $V_H$20 | Caggtgcagctggtggagtctgggggaggcgtggtccagcctggggaggtccctgagactctcctgtgcag cgtctggattcaccttcagtagctatggcatgcactgggtccgccaggctccaggcaaggggctggagtgg gtggcagttatatggtatgatggaagtaataaatactatgcagactccgtgaagggccgattcaccatctcca gagacaattccaagaacacgctgtatctgcaaatgaacagcctgagagccgaggacacggctgtgtatta ctgtgcgagcagctcgtcaaacttctacgatatggacgtctgggggccaagggaccacggtcaccgtctcctc a [SEQ ID NO: 268] |
| H2 103 1N1G2 | $V_H$21 | gaggtgcagctggtggagtctgggggaggcttggtaaagcctggggggtcccttacactctcctgtgcagc ctctggattcactttcaataacgcctggatgagctgggtccgccaggctccagggaaggggctggagtggg ttggccgtattaaaagcaaaactgatggtgggacaacagactacgctgcacccgtgaaaggcagattcac catctcaagagatgattcaaaaaacacgctgtatctgcaaatgaacagcctgaaaaccgaggacacagc cgtgtattactgtaccacagaatattaccatatttgactggttcgttctactactcctactacggtatggacgtc tggggggccaagggaccacggtcaccgtctcctca [SEQ ID NO: 269] |
| H2 131 1N1G2 | $V_H$22 | caggtgcagctgcaggagtcgggcccaggactggtgaagccttcggagaccctgtccctcacctgcactgt ctctggtggctccatcagtaattactactggagctggatccggcagtccgccgggaagggactggagtgga ttgggcgtatctataccagtgggagcacccactacaacccctccctcaagagtcgaatcatcatgtcagtgg acacgtccaagaaccagttctccctgaagctgagctctgtgaccgccgcggacacggccgtgtattactgtg cgagagatcgagtcttctacgatatggacgtctgggggccaagggaccacggtcaccgtctcctca [SEQ ID NO: 270] |
| H2 291 1N1G2 | $V_H$23 | caggtgcagctggtggagtctgggggaggcgtggtccagcctggggaggtccctgagactctcctgtgcagc gtctggattcaccttcagtagctatggcatgcactgggtccgccaggctccaggcaaggggctggagtgggt ggcagttatatggtatgatggaagttataaatactatgcagactccgtgaagggccgattcaccatctccaga gacaattccaagaacacgctgtatctgcaaatgaacagcctgagagccgaggacacggctgtgtattact gtgcgagaaggggattactccgactactacggtatggacgtctgggggccaagggaccacggtcaccg tctcctca [SEQ ID NO: 271] |
| H2 360 1NG2 | $V_H$24 | caggtccagctggtacagtctggggctgaggtgaagaagcctggggcctcagtgaaggtctcctgcaagg tttccggatacaccctcactgaattatccatgcactgggtgcgacaggctcctggaaaagggcttgagtggat gggaggttttgatcctgaagatggtgaaacaatctacgcacagaagttccagggcagagtcaccatgacc gaggacacatctacagacacagtttacatggagctgagcagcctgagatctgaggacacggccgtgtatt actgtgcaacaggggttatgattacgtttgggggagttatcgttggccactcctactacggtatggacgtctgg ggccaagggaccacggtcaccgtctcctca [SEQ ID NO: 272] |
| H2 369 1N1G2 | $V_H$26 | caggtccagctggtacagtctggggctgaggtgaagaagcctggggcctcagtgaaggtctcctgcaagg tttccggatacaccctcactgaattatccatgcactgggtgcgacaggctcctggaaaagggcttgagtggat gggaggttttgatcctgaagatggtgaaacaatctacgcacagaagttccagggcagagtcaccatgacc gaggacacatctacagacacagctacatggagctgagcagcctgagatctgaggacacggccgtgtatt actgtgcaacaagggctggaacgacgttggcctactactactacgctatggacgtctgggggccaagggac cacggtcaccgtctcctca [SEQ ID NO: 273] |
| H2 380 1N1G2 | $V_H$27 | caggtgcagctgcaggagtcgggcccaggactggtgaagccttcggagaccctgtccctcacctgcactgt ctctggtggctccatcagtagttactactggagctggatccggcagcccccagggaaggggactggagtgga ttgggtatatctattacagtgggaacaccaactacaacccctccctcaagagtcgattcaccttatcaataga cacgtccaagaaccagttctccctgaggctgagctctgtgaccgctgcggacacggccgtgtattactgtgc gtgtatagcaactcggcccttgactactggggccagggaaccctggtcaccgtctcctca [SEQ ID NO: 274] |
| H2 475 1N1G2 | $V_H$28 | caggtgcagctggtggagtctgggggaggcgtggtccagcctggggaggtccctgagactctcctgtgcagc gtcaggattcaccttcatcagctatggcatgcactgggtccgccaggctccaggcaaggggctggagtggg tggcagtttatatggtatgatggaagtaataaatactatgcagactccgtgaagggccgattcaccatctccag agacaattccaagaacacgctgtatctgcaaatgaacagcctgagagccgaggacacggctgtgtattac tgtgcggatagcagtggcgactactacggtatggacgtctgggggccaagggaccacggtcaccgtctcctc a [SEQ ID NO: 275] |
| H2 508 1N1G2 | $V_H$29 | caggtccagctggtacagtctggggctgaggtgaagaagcctggggcctcagtgaaggtctcctgcaagg tttccggatacaccctcactgaattatccatgcactgggtgcgacaggctcctggaaaagggcttgagtggat gggaggttttgatcctgaagatggtgaaacaatctacgcacagaagttccagggcagagtcaccatgacc gaggacacatctacagacacagcctatatggagctgagcagcctgagatctgaggacacggccgtgtatt actgtgcaacagcggggctggaaatacggtggttcgacccctgggggcagggaaccctggtcaccgtctc ctca [SEQ ID NO: 276] |

TABLE 7-continued

Exemplary Nucleic Acid Sequences Encoding Heavy And Light Chain Variable Regions

| Reference | Designation | Nucleic Acid Sequence/SEQ ID NO. |
|---|---|---|
| H2 534 1N1G2 | $V_H 30$ | caggtgcagctgcaggagtcgggcccaggactggtgaagccttcacagaccctgtccctcacctgcactgt<br>ctctggtggctccatcagcagtggtggttactactggagctggatccgccagcacccagggaagggcctgg<br>agtggattgggtacatctcttacagtggggacacctactacaacccgtccctcaagagtcgacttaccatatc<br>agtagacacgtctaagcaccagttctccctgaggctgagctctgtgacttccgcggacacggccgtgtatta<br>ctgtgcgagtctagacctctacggtgactactttgactactggggccagggaaccctggtcaccgtctcctca<br>[SEQ ID NO: 277] |
| H2 550 1N1G2 | $V_H 31$ | caggttcagctggtgcagtctggagctgaggtgaagaagcctggggcctcagtgaaggtctcctgcaagg<br>cttctggttacacccttaaccagctatggtatcagctgggtgcgacaggcccctggacaagggcttgagtggat<br>gggatggatcagcgcttacaatggtaacccaaaactatgcacagaagttccagggcagagtcaccatgacc<br>acagacacatccacgagcacagcctacatggagctgaggagcctgagatctgacgacacggccgtgtat<br>tactgtgcgagagatcagggattactagggttcggggaactcgaggggctctttgactactggggccaggg<br>aaccctggtcaccgtctcctca<br>[SEQ ID NO: 278] |
| H2 65 1N1G2 | $V_H 32$ | gaggtgcagctggtggagtctgggggaggcttggtaaagcctggggggtcccttagactctcctgtgcagc<br>ctctggattcactttcagtaacgcctggatgagctgggtccgccaggctccaggaaggggctggagtggg<br>ttggccgtattaaaaccaaaactgatggtgggacaacagactacgctgcacccgtgaaaggcagattcac<br>catctcaagagatgattcacaaaaacacgctgtatctgcaaatgaacagcctgaaaaccgaggacacagc<br>cgtgtattactgtaccacagaatattacgtattgtgactggttcgttttattactactactacggtatggacgtc<br>tggggccaagggaccacggtcaccgtctcctca<br>[SEQ ID NO: 279] |
| H1 109 1N1K | $V_L 1$ | gacatccagatgacccagtctccatcctcccctgtctgcatctgtaggagacagagtcaccatcacttgccag<br>gcgagtcaaaacattagcaactttttagattggtatcagcagaaaccagggaaagcccctaacctcctgatc<br>tacgatgcatccgatttggatccaggggtcccatcaaggttcagtggaagtggatctgggacagattttacttt<br>caccatcagcagcctacagcctgaagatattgcaacatattactgtcaacagtatgttagtctcccgctcactt<br>tcggcggagggaccaaggtggagatcaaa<br>[SEQ ID NO: 280] |
| H1 131 1N1K | $V_L 3$ | gataatgtgatgacccagactccactctctctgtccgtcaccccctggacagccggcctccatctcctgcaagt<br>cgagtcagagcctcctgcatagtgatgggaagacctatttgtattggtacctgcagaagccaggccagcctc<br>cacagctcctgatctatgaagcttccaaccggttctctggagtgccagataggttcagtggcagcgggtcag<br>ggacagatttcacactgaaaatcagccgggtggaggctgaggatgttggggtttattactgcatgcaaagta<br>tacagcttcctctcacttttcggcggagggaccaaggtggagatcaaa<br>[SEQ ID NO: 281] |
| H1 134 1N1K | $V_L 4$ | gacatccagatgacccagtctccatcctcccctgtctgcatctgtaggagacagagtcaccatcacttgccag<br>gcgagtcaggacattaacaactatttaaattggtatcagcagaaaccagggaaagcccctaagctcctgat<br>ctacgatgcatccaattttggaaatagggtcccatcaaggttcagtggaagtggatctgggacagatttcattt<br>tcaccatcagcagtctgcagcctgaagatattgcaacatattactgtcaacagtatgataatttcccgttcactt<br>tcggcggagggaccaaggtggagatcaaa<br>[SEQ ID NO: 282] |
| H1 143 1N1K | $V_L 5$ | gacatccagatgacccagtctccatcctcccctgtctgcatctgtaggagacagagtcaccatcacttgccag<br>gcgagtcaggacattaacaactatttaaattggtatcagcagaaaccagggaaagcccctaagctcctgat<br>ctacgatacatccaatttggaaccaggggtcccatcaaggttcagtggaagtggatctgggacagattttact<br>ttcaccatcagcagcctgcagcctgaagatattgcaacatattactgtcaacaatatgataatctcctcaccctt<br>cggccaagggacacgactggaaattaaa<br>[SEQ ID NO: 283] |
| H1 144 1N1K | $V_L 6$ | gacatccagatgacccagtctccatcctcccctgtctgcatctgtaggagacagagtcaccatcacttgccag<br>gcgagtcaggacattagcaactatttaaattggtatcagcataaaccagggaaagcccctaaactcctgat<br>ctacgatgcatccaatttggaaacaggggtcccatcaaggttcagtggaagtggatctgggacagatttact<br>ttcaccatcagcagcctgcagcctgaagatattgcaacatattactgtcaacagtatgataatctgctcaccctt<br>cggcggagggaccaaggtggagatcaaa<br>[SEQ ID NO: 284] |
| H1 16 1N1K | $V_L 7$ | gacatccagatgacccagtctccatcctcccctgtctgcatctgtaggagacagagtcaccatcacttgccag<br>gcgagtcaggacattagcaactatttaaattggtatcagcagaaaccagggaaagcccctaagttcctgat<br>ctacgatgcatccaatttggaaacaggggtcccatcaaggttagtggaagtggatctgggacagattttactt<br>tcaccatcagcagcctgcagcctgaagatattgcaacatattactgtcaacagtatgataatctgatcaccttc<br>ggccaagggacacgactggagattaaa<br>[SEQ ID NO: 285] |
| H1 2 1N1K | $V_L 8$ | gacatcgtgatgacccagtctccagactcctggctgtgtctctgggcgagagggccaccatcaactgcaa<br>gtccagccagagtgttttagacagctccgacaataagaactacttagcttggtaccagcagaaaccaggac<br>agcctcctaagctgctcatttactgggcatctaaccgggaatccggggtccctgaccgattcagtggcagcg<br>ggtctgggacagatttctctctcaccatcagcagcctgcaggctgaagatgtggcagtttattactgtcagcaa<br>tattatagtgatccattcactttcggccctgggaccaaagtggatatcaaa<br>[SEQ ID NO: 286] |

TABLE 7-continued

Exemplary Nucleic Acid Sequences Encoding Heavy And Light
Chain Variable Regions

| Reference | Designation | Nucleic Acid Sequence/SEQ ID NO. |
|---|---|---|
| H1 27 1N1K | $V_L$10 | gacatccagatgacccagtctccatcctccctgtctgcatctgtaggtgacagagtcaccatcacttgccagg<br>cgagtcaggacattagcaactatttaaattggtatcaacagaaaccagggaaagcccctaaactcctgatc<br>tacgatgcatccaatttggaaacaggggtcccatcaaggttcagtggaagtggatctgggacagattttacttt<br>caccatcagcagcctacagcctgaagatattgcaacatattactgtcaacagtatgataatctgctcactttcg<br>gcggagggaccaaggtggagatcaaa<br>[SEQ ID NO: 287] |
| H1 30 1N1K | $V_L$11 | gacatcgtgatgacccagtctccagactccctggctgtgtctctgggcgagagggccaccatcgactgcaa<br>gtccagccagggtgttttagacagctccaacaataagaacttcttagcttggtaccagcagaaaccaggac<br>agcctcctaagctgctcatttactgggcatctaacccgggaatccggggtccctgtccgattcagtggcagcg<br>ggtctgggacagatttcactctcaccatcagcagcctgcaggctgaagatgtggcactttattactgtcagca<br>atattatagtgatccattcactttcggccctgggaccaaagtggatatcaaa<br>[SEQ ID NO: 288] |
| H1 33-1 1N1K | $V_L$12 | gacatccagatgacccagtctccatcctccctgtctgcatctgtaggagacagagtcaccatcacttgccgg<br>gcaagtcagagcattagtgactatttaaattggtatcagcagaaaccagggaaagcccctaacctcctgat<br>ctatgctgcatccagtttgcagagtggggtcccatcaaggttcagtggcagtggatctgggacagattttcact<br>ctcaccatcagcagtctgcaacctgaagattttgcaacttacttctgtcaacagacttacagtgacccattcact<br>ttcggccctgggaccaaagtggatatcaaa<br>[SEQ ID NO: 289] |
| H1 34 1N1K | $V_L$13 | gacatccagatgacccagtctccatcctccctgtctgcatctgtaggagacagagtcaccatcacttgccag<br>gcgagtcaggacattagcaactatttaaattggtatcagcagaaaccagggaaagcccctaagctcctgat<br>ctacgatgcatccaatttggaaacaggggtcccatcaaggttcagtggaagtggatctgggacagattttact<br>ttcaccatcagcagcctacagcctgaagatattgcaacatattactgtcaacagtatgataatctgctcactttc<br>ggcggagggaccaaggtggagatcaaa<br>[SEQ ID NO: 290] |
| H1 39 1N1K | $V_L$14 | gacatccagatgacccagtctccatcctccctgtctgcatctgtaggagacagagtcaccatcacttgccag<br>gcgagtcaggacattagcaactatttaaattggtatcagcagaaaccagggaaagcccctaaggtcctgat<br>ctacgatgcatccaatttggaaacaggggtcccatcaaggttcagtggaagtggatctgggacagattttact<br>ttcaccatcagcagcctgcagcctgaagatattgcaacatattactgtcaacagtatgataatctcctcactttc<br>ggcggagggaccaaggtggagatcaaa<br>[SEQ ID NO: 291] |
| H1 42 1N1K | $V_L$15 | gacatcgtgatgacccagtctccagactccctggctgtgtctctgggcgagagggccaccatcgactgcaa<br>gtccagccagagtgttttagacagctccaacaataagaacttcttagcttggtaccagcagaaaccaggac<br>agcctcctaagctgctcatttactgggcatctaacccgggaatccggggtccctgaccgattcagtggcagcg<br>ggtctgggacagatttcactctcaccatcagcagcctgcaggctgaagatgtggcagtttattactgtcagca<br>atattatagtgatccattcactttcggccctgggaccaaagtggatatcaaa<br>[SEQ ID NO: 292] |
| H1 64 1N1K | $V_L$16 | gaaattgtgttgacgcagtctccaggcaccctgtctttgtctccaggggaaagagccaccctctcctgcagg<br>gccagtcagagtgttagcagcggctacttagcctacttagcctggtaccagcagaaacctggccaggctcc<br>caggctcctcatctatggtgcatccagcacggccactggcatcccagacaggttcagtggcagtgggtctg<br>ggacagacttcactctcaccatcagcagactggagcctgaagattttgcagtgtattactgtcagcagtatgg<br>tagctcaccgatcaccttcggccaagggacacgactggagattaaa<br>[SEQ ID NO: 293] |
| H1 66 1N1K | $V_L$17 | gacatccagatgacccagtctccatcctccctgtctgcatctgtaggagacagagtcaccatcacttgccag<br>gcgagtcaggacattagcaactttttaaattggtatcagcagagaccagggaaagcccctaagctcctgat<br>ctacgatgcatccaatttggaaacaggggtcccatcaaggttcagtggaagtggatctgggacagattttact<br>ttcaccatcagcagcctgcagcctgaagatattgcaacatattactgtcaacagtatgataatctcccattcac<br>tttcggccctgggaccaaagtggatatcaaa<br>[SEQ ID NO: 294] |
| H1 72 1N1K | $V_L$18 | gacatccagatgacccagtctccatcctccctgtctgcatctgtaggagacagagtcaccatcacttgccag<br>gcgagtcaggacattagcaactatttaaattggtatcagcagaaaccagggaaagcccctaaactcctgat<br>ctacgatgcatccaatttggaaacaggggtcccatcaaggttcagtggaagtggatctgggacagattttact<br>ttcaccatcagcagcctgcagcctgaagattttgcaacatattactgtcaacagtatgataatctcctcactttc<br>ggcggagggaccaaggtggagatcaaa<br>[SEQ ID NO: 295] |
| H1 90 1N1K | $V_L$19 | gacatccagatgacccagtctccatcctccctgtctgcatctgtaggagacagagtcaccatcacttgccag<br>gcgagtcaggacattagcaactatttaaattggtatcagcagaaaccagggaaagcccctaagctcctgat<br>ctacgatgcatccaatttggaaacaggggtcccatcaaggttcagtggaagtggatctgggacagattttact<br>ttcaccatcagcagcctgcagcctgaagatattgcaacatattactgtcaacggtatgatgatctcccgatca<br>ccttcggccaagggacacgactggagattaaa<br>[SEQ ID NO: 296] |

TABLE 7-continued

Exemplary Nucleic Acid Sequences Encoding Heavy And Light Chain Variable Regions

| Reference | Designation | Nucleic Acid Sequence/SEQ ID NO. |
|---|---|---|
| H2 103 1N1K | $V_L$20 | gacatccagatgacccagtctccatcctccctgtctgcatctgtgggagacagagtcaccatcacttgccag gcgagtcaggacattagcaactatttaaattggtatcagcagagaccagggaaagcccctaagctcctgat ctacgatgcatccaatttggaaacaggggtcccatcaaggttcagtggaagtggatctgggacagatttact ttcaccatcagcagcctgcagcctgaagatattgcaacatattactgtcaacagtatgataatctgctcactttc ggcggagggaccaaggtggagatcaaa [SEQ ID NO: 297] |
| H2 131 1N1K | $V_L$21 | gacatccagatgacccagtctccatcctccctgtctgcatctgtaggagacagagtcaccatcacttgccgg gcgagtcagggctttagcaattatttagcctggtatcagcagaaaccagggaaagttcctaagctcctgatct atgctgcatccactttgcagtcaggggtcccatctcggttcagtggcagtggatctgggacagatttcactctc accatcagcagcctgcagcctgaagatgttgcaacttattactgtcaaaagtataacagtgccccgctcactt tcggcggagggaccaaggtggagatcaaa [SEQ ID NO: 298] |
| H2 360 1N1K | $V_L$22 | gacatccagatgacccagtctccatcctccctgtctgcatctgtaggagacagagtcaccatcacttgccgg gcgagtcagggcattaacaattatttagcctggtatcagcagaaaccagggaaagttcctcagctcctgatc tatgttgcatccactttgcaatcaggggtcccatctcggttcagtggcagtggatctgggacagatttcactctc accatcagcagcctgcagcctgaagatgttgcaacttattactgtcaaaagtataacagtggcccattcacttt cggccctgggaccaaagtggatatcaaa [SEQ ID NO: 299] |
| H2 369 1N1K | $V_L$24 | gacatccagatgacccagtctccatcctccctgtctgcatctgtaggagacagagtcaccatcacttgccgg gcaagtcagagcattagcaggtatttaaattggtatcagcagaaaccagggaaagcccctaacctcctgat ccatgctgcatccagtttgcaaagtggggtcccatcaaggttcagtggcagtggatctgggacagatttcact ctcaccatcagcagtctgcaacctgaagattttgcaacttactactgtcaacagagttacattacccctcccag ttttggccaggggaccaagctggagatcaaa [SEQ ID NO: 300] |
| H2 380 1N1K | $V_L$25 | gacatccagatgacccagtctccatcctccctgtctgcatctgtaggagacagagtcaccatcacttgccgg gcaagtcagggcattagaaatgatttagactggtatcagcagaaaccagggaaagcccctaagcgcctg atctatgctgcatccagtttgcaaagtggggtcccatctaggttcagcggcagtggatctgggacagaattca ctctcacaatcaacagcctgcagcctgaagattttgcaacttattactgtctacagtataatagttacccgatca ccttcggccaagggacacgactggagattaaa [SEQ ID NO: 301] |
| H2 475 1N1K | $V_L$26 | gacatccagatgatccagtctccttcctccctgtctgcatctgtcggagacagagtcaccatcacttgccagg cgagtcacgacattagcaactatttaaattggtatcagcagaaaccagggaaagcccctaagttcctgatct ccgatgcatccaatttggaaacaggggtcccatcaaggttcagtggaagtggatctgggacagattttactttt caccatcagcagcctgcagcctgaagatattgcaacatattactgtcaacagtatg ataatctcccgctcact ttcggcggagggaccaaggtggagatcaaa [SEQ ID NO: 302] |
| H2 508 1N1K $V_L$27 | H2 508 1N1K $V_L$27 | gatattgtgatgactcagtctccactctccctgcccgtcaccccctggagagccggcctccatctcctgcaggtc tagtcagagcctcctgcatagtaatggatacaactatttggattggtacctgcagaagccagggcagtcacc acagttcctgatctatttgggttctatcgggcctccggggtccctgacaggttcagtggcagtggatcaggca cagattttgcactgacaatcagcagagtggaggctgaggatgttgggggtttattactgcatgcaagctctaca aactcctcggacgttcggccaagggaccaaggtggaaatcaaa [SEQ ID NO: 303] |
| H2 534 1N1K $V_L$28 | H2 534 1N1K $V_L$28 | gaaattgtgctgactcagtctccagactttcagtctgtgactccaaaggagaaagtcaccatcacctgccgg gccagtcagtacattggtagtagcttacactggtaccagcagacaccagatcagtctccaaagctcctcatc aactatgtttcccagtcctctcaggggtcccctcgaggttcagtggcagtggatctgggacagatttcaccct caccatcaatagcctggaagctgaagatgctgcaacgtattactgtcatcagagtagtagtttaccattcactt tcggccctgggaccaaagtggatatcaaa [SEQ ID NO: 304] |
| H2 550 1N1K $V_L$29 | H2 550 1N1K $V_L$29 | gacatcgtgatgacccagtctccagactcctggctgtgtctctgggcgcgagggccaccatctcctgcaag tccagccagagtgttttatacagctccaacaataagaactacttagcttggtaccagcagaaaccaggcca gcctcctaagctgctcatttactgggcatctacccgggaatccggggtccctgaccgattcagtggcagcgg gtctgggacagatttcactctcaccatcagcaccctgcaggctgaagatgtggcagtttattactgtcagcaat attatactactcctccgacgttcggccaagggaccaaggtggaaatcaaa [SEQ ID NO: 305] |
| H2 65 1N1K $V_L$30 | H2 65 1N2K $V_L$30 | gacatccagatgacccagtctccatcctccctgtctgcatctgtaggagacagagtcaccatcacttgccag gcgagtcaggacattaacaactatttaaattggtatcaacagaaaccagggaaagcccctaaactcctgat ctacgatgcatccaatttggaaacaggggtcccatcaaggttcagtggaagtggatctgggacagattttact ttcaccatcagcagcctgcagcctgaagatattgcaacatattactgtcaacagtatgatgatctgctcactttc ggcggagggaccaaggtggagatcaaa [SEQ ID NO: 306] |

Nucleic acids encoding certain antigen binding proteins, or portions thereof (e.g., full length antibody, heavy or light chain, variable domain, or CDRH1, CDRH2, CDRH3, CDRL1, CDRL2, or CDRL3) may be isolated from B-cells of mice that have been immunized with c-fms or an immunogenic fragment thereof. The nucleic acid may be isolated by conventional procedures such as polymerase chain reaction (PCR). Phage display is another example of a known technique whereby derivatives of antibodies and other antigen binding proteins may be prepared. In one approach, polypeptides that are components of an antigen binding protein of interest are expressed in any suitable recombinant expression system, and the expressed polypeptides are allowed to assemble to form antigen binding protein molecules.

The nucleic acids provided in TABLES 6 and 7 are exemplary only. Due to the degeneracy of the genetic code, each of the polypeptide sequences listed in TABLES 1-4 or otherwise depicted herein are also encoded by a large number of other nucleic acid sequences besides those provided. One of ordinary skill in the art will appreciate that the present application thus provides adequate written description and enablement for each degenerate nucleotide sequence encoding each antigen binding protein.

An aspect further provides nucleic acids that hybridize to other nucleic acids (e.g., nucleic acids comprising a nucleotide sequence listed in TABLE 6 and TABLE 7) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1× SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65%, 70%, 75%, 80%, 85%, 90%, 95%, 98% or 99% identical to each other typically remain hybridized to each other.

The basic parameters affecting the choice of hybridization conditions and guidance for devising suitable conditions are set forth by, for example, Sambrook, Fritsch, and Maniatis (2001, Molecular Cloning: A Laboratory Manual, Cold Spring Harbor Laboratory Press, Cold Spring Harbor, N.Y., supra; and Current Protocols in Molecular Biology, 1995, Ausubel et al., eds., John Wiley & Sons, Inc., sections 2.10 and 6.3-6.4), and can be readily determined by those having ordinary skill in the art based on, e.g., the length and/or base composition of the nucleic acid.

Changes can be introduced by mutation into a nucleic acid, thereby leading to changes in the amino acid sequence of a polypeptide (e.g., an antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively changes the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody. In one embodiment, a nucleic acid encoding any antigen binding protein described herein can be mutated to alter the amino acid sequence using molecular biology techniques that are well-established in the art. Example 4, for instance, describes how nucleic acid sequences (see Table 6) were mutated to introduce one or more amino acid substitutions into certain antigen binding proteins to produce antigen binding proteins 1.2 SM 1.109 SM and 2.360 SM. Additional antigen binding proteins containing other mutations can be produced in a similar way.

Another aspect provides nucleic acid molecules that are suitable for use as primers or hybridization probes for the detection of nucleic acid sequences. A nucleic acid molecule can comprise only a portion of a nucleic acid sequence encoding a full-length polypeptide, for example, a fragment that can be used as a probe or primer or a fragment encoding an active portion (e.g., a c-fms binding portion) of a polypeptide.

Probes based on the sequence of a nucleic acid can be used to detect the nucleic acid or similar nucleic acids, for example, transcripts encoding a polypeptide. The probe can comprise a label group, e.g., a radioisotope, a fluorescent compound, an enzyme, or an enzyme co-factor. Such probes can be used to identify a cell that expresses the polypeptide.

Another aspect provides vectors comprising a nucleic acid encoding a polypeptide or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors can comprise a nucleic acid in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see, Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see, id.). It will be appreciated by those skilled in the art that the design of the expression vector can depend on such factors as the choice of the host cell to be transformed, the level of expression of protein desired, etc. The expression vectors can be introduced into host cells to thereby produce proteins or peptides, including fusion proteins or peptides, encoded by nucleic acids as described herein.

Another aspect provides host cells into which a recombinant expression vector has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Preparing of Antigen Binding Proteins

Non-human antibodies that are provided can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies can be used, for instance, in in vitro cell culture and cell-culture based applications, or any other application where an immune response to the antibody does not occur or is insignificant, can be prevented, is not a concern, or is desired. In certain embodiments, the antibodies may be produced by immunizing with full-length c-fms or with the extracellular domain of c-fms. Alternatively, the certain non-human antibodies may be raised by immunizing with amino acids which are segments of c-fms that form part of the epitope to which certain antibodies provided herein bind (see infra). The antibodies may be polyclonal, monoclonal, or may be synthesized in host cells by expressing recombinant DNA.

Fully human antibodies may be prepared as described above by immunizing transgenic animals containing human immunoglobulin loci or by selecting a phage display library that is expressing a repertoire of human antibodies.

The monoclonal antibodies (mAbs) can be produced by a variety of techniques, including conventional monoclonal antibody methodology, e.g., the standard somatic cell hybridization technique of Kohler and Milstein, 1975, *Nature* 256: 495. Alternatively, other techniques for producing monoclonal antibodies can be employed, for example, the viral or oncogenic transformation of B-lymphocytes. One suitable animal system for preparing hybridomas is the murine system, which is a very well established procedure. Immunization protocols and techniques for isolation of immunized splenocytes for fusion are known in the art. For such procedures, B cells from immunized mice are fused with a suitable immortalized fusion partner, such as a murine myeloma cell line. If desired, rats or other mammals besides can be immunized instead of mice and B cells from such animals can be fused with the murine myeloma cell line to form hybridomas. Alternatively, a myeloma cell line from a source other than mouse may be used. Fusion procedures for making hybridomas also are well known.

The single chain antibodies that are provided may be formed by linking heavy and light chain variable domain (Fv region) fragments via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA.* 85:5879; Ward et al., 1989, *Nature* 334:544, de Graaf et al., 2002, *Methods Mol. Biol.* 178:379-387. Single chain antibodies derived from antibodies provided herein include, but are not limited to scFvs comprising the variable domain combinations of the heavy and light chain variable regions depicted in TABLE 2, or combinations of light and heavy chain variable domains which include CDRs depicted in TABLES 3 and 4.

Antibodies provided herein that are of one subclass can be changed to antibodies from a different subclass using subclass switching methods. Thus, IgG antibodies may be derived from an IgM antibody, for example, and vice versa. Such techniques allow the preparation of new antibodies that possess the antigen binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, *Methods Mol. Biol.* 178:303-316.

Accordingly, the antibodies that are provided include those comprising, for example, the variable domain combinations described, supra., having a desired isotype (for example, IgA, IgG1, IgG2, IgG3, IgG4, IgE, and IgD) as well as Fab or F(ab')$_2$ fragments thereof. Moreover, if an IgG4 is desired, it may also be desired to introduce a point mutation (CPSCP→CPPCP) in the hinge region as described in Bloom et al., 1997, *Protein Science* 6:407, incorporated by reference herein) to alleviate a tendency to form intra-H chain disulfide bonds that can lead to heterogeneity in the IgG4 antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, *BioTechnology* 10:779.

Conservative modifications may be made to the heavy and light chain variable regions described in TABLE 2, or the CDRs described in TABLE 3 and 4 (and corresponding modifications to the encoding nucleic acids) to produce a c-fms antigen binding protein having functional and biochemical characteristics. Methods for achieving such modifications are described above.

C-fms antigen binding proteins may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or fragment thereof. Another useful fusion partner for the antigen binding proteins or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antigen binding proteins described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a normative residue that has little or no effect on the polarity or charge of the amino acid residue at that position. See, TABLE 3, supra. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies provided herein, or to increase or decrease the affinity of these antibodies for human c-fms or for modifying the binding affinity of other antigen-binding proteins described herein.

Methods of Expressing Antigen Binding Proteins

Expression systems and constructs in the form of plasmids, expression vectors, transcription or expression cassettes that comprise at least one polynucleotide as described above are also provided herein, as well host cells comprising such expression systems or constructs.

The antigen binding proteins provided herein may be prepared by any of a number of conventional techniques. For example, c-fms antigen binding proteins may be produced by recombinant expression systems, using any technique known in the art. See, e.g. Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988).

Antigen binding proteins can be expressed in hybridoma cell lines (e.g., in particular antibodies may be expressed in hybridomas) or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. No. 4,399,216; No. 4,912,040; No. 4,740,461; No. 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a nucleic acid molecule encoding a polypeptide comprising one or more of the following: one or more CDRs provided herein; a light chain constant region; a light chain variable region; a heavy chain constant region (e.g., $C_H1$, $C_H2$ and/or $C_H3$); and/or another scaffold portion of a c-fms antigen binding protein. These nucleic acid sequences are inserted into an appropriate expression vector using standard ligation techniques. In one embodiment, the heavy or light chain constant region is appended to the C-terminus of the anti-c-fms-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences (formerly "Clontech"). Other useful vectors for cloning and expressing the antibodies and fragments include those described in Bianchi and McGrew, 2003, *Biotech. Biotechnol. Bioeng.* 84:439-44, which is hereby incorporated by reference. Additional suitable expression vectors are discussed, for example, in *Methods Enzymol.*, vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the c-fms antigen binding protein coding sequence; the oligonucleotide sequence encodes polyHis (such as hexa-His), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the c-fms antigen binding protein from the host cell. Affinity purification can be accomplished, for example, by column chromatography using antibodies against the tag as an affinity matrix. Optionally, the tag can subsequently be removed from the purified c-fms antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein that binds to c-fms polypeptide. As a result, increased quantities of a polypeptide such as an antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning will typically contain a promoter that is recognized by the host organism and operably linked to the molecule encoding c-fms antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding heavy chain or light chain comprising a c-fms antigen binding protein by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thomsen et al., 1984, *Proc. Natl. Acad. USA.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. USA.* 78:1444-1445); promoter and regulatory sequences from the metallothionine gene (Prinster et al., 1982, *Nature* 296:39-42); and prokaryotic promoters such as the beta-lactamase promoter (Villa-Kamaroff et al., 1978, *Proc. Natl. Acad. Sci. USA.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315: 115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription of DNA encoding light chain or heavy chain comprising a human c-fms antigen binding protein by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising a c-fms antigen binding sequence has been inserted into the proper site of the vector, the completed vector may be inserted into a suitable host cell for amplification and/or polypeptide expression. The transformation of an expression vector for an antigen-binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antigen binding proteins with c-fms binding properties. In another embodiment, a cell line from the B cell lineage that does not make its own antibody but has a capacity to make and secrete a heterologous antibody can be selected.

Use of Human C-fms Antigen Binding Proteins for Diagnostic and Therapeutic Purposes Antigen binding proteins are useful for detecting c-fms in biological samples and identification of cells or tissues that produce c-fms. For instance, the c-fms antigen binding proteins can be used in diagnostic assays, e.g., binding assays to detect and/or quantify c-fms expressed in a tissue or cell. Antigen binding proteins that specifically bind to c-fms can also be used in treatment of diseases related to c-fms in a patient in need thereof. In addition, c-fms antigen binding proteins can be used to inhibit c-fms from forming a complex with its ligand CSF-1, thereby modulating the biological activity of c-fms in a cell or tissue. Examples of activities that can be modulated include, but are not limited to, inhibiting autophosphorylation of c-fms, reducing monocyte chemotaxis, inhibiting monocyte migration, inhibiting the accumulation of tumor associated macrophages in a tumor or diseased tissue and/or inhibiting angiogenesis. Antigen binding proteins that bind to c-fms thus can modulate and/or block interaction with other binding compounds and as such may have therapeutic use in ameliorating diseases related to c-fms. Indications Many tumor cells secrete CSF-1 that, in turn, attracts, promotes the survival of, and activates monocyte/macrophage cells through the cognate receptor c-fms. The level of CSF-1 in human tumors has been shown to correlate positively with the number of TAMs present in those tumors (Murdoch et al., 2004, *Blood* 104:2224-2234). Several studies have linked high TAM numbers with reduced patient survival in patients with various forms of cancer. Recent studies have indicated the existence of an autocrine loop in tumor cells. Other research indicates that c-fms plays a role in various inflammatory diseases. Therefore, regulation of c-fms-CSF-1 signaling by the human c-fms antigen-binding proteins provided herein can inhibit, interfere with, or modulate at least one of the biological responses related to c-fms, and, as such, are useful for ameliorating the effects of c-fms-related diseases or conditions. C-fms binding proteins provided herein can also be used for the diagnosis, prevention or treatment of such diseases or conditions.

A disease or condition associated with human c-fms includes any disease or condition whose onset in a patient is caused by, at least in part, the interaction of c-fms with the CSF-1 ligand and/or IL-34. The severity of the disease or condition can also be increased or decreased by the interaction of c-fms with CSF-1 and/or IL-34. Examples of diseases and conditions that can be treated with the antigen binding proteins include various cancers, inflammatory diseases and bone disorders. The antigen binding proteins can also be used to treat or prevent metastasis of cancer and bone osteolysis associated with the metastasis of cancer to bone. [0325] A high level of TAMs is associated with tumor growth in a variety of cancers, including: breast (Tsutsui et al., 2005, *Oncol. Rep.* 14:425-431; Leek et al., 1999, *Br. J. Cancer* 79:991-995; Leek and Harris, 2002, *J. Mammary Gland Biol and Neoplasia* 7:177-189), prostate (Lissbrant et al. 2000, *Int. J. Oncol.* 17:445-451), endometrial (Ohno et al., 2004, *Anticancer Res.* 24:3335-3342), bladder (Hanada et al., 2000, *Int. J. Urol* 7:263-269), kidney (Hamada et al.; 2002, *Anticancer Res.* 22:4281-4284), esophageal (Lewis and Pollard, 2006, *Cancer Res.* 66(2):606-612), squamous cell (Koide et al., 2004, *Am. J. Gastroenterol.* 99:1667-1674), uveal melanoma (Makitie et al., 2001, *Invest. Opthalmol. Vis. Sci.* 42:1414-1421), follicular lymphoma (Farinha et al., 2005, *Blood* 106:2169-2174), renal and cervical (Kirma et al., 2007, *Cancer Res* 67: 1918-1926). In the cases of breast cancer, prostate cancer, endometrial cancer, bladder cancer, kidney cancer, esophageal cancer, squamous cell carcinoma, uveal melanoma, follicular lymphomas and ovarian cancer, the high levels of TAMs also indicates reduced patient survival. Therefore, the c-fms antigen binding proteins provided herein can be used to inhibit recruitment to and decrease survival and function of the TAMs in the tumor, thus negatively affecting tumor growth, and increasing patient survival.

Other cancers that can be treated include, but are not limited to, solid tumors generally, lung cancer, ovarian cancer, colorectal cancer, brain, pancreatic, head, neck, liver, leukemia, lymphoma and Hodgkin's disease, multiple myeloma (Farinha et al., 2005, *Blood* 106:2169-2174), melanoma, gastric cancer, astrocytic cancer, stomach, and pulmonary adenocarcinoma. Ishigami et al., 2003, *Anticancer Research* 23:4079-4083; Caruso et al., 1999, *Modern Pathology* 12:386-390; Witcher et al., 2004, *Research Support* 104: 3335-3342; Haran-Ghera et al. 1997, *Blood* 89:2537-2545; Hussein et al., 2006 *International Journal of Experimental Pathology* 87:163-76; Lau et al. 2006 *British Journal of Cancer.* 94:1496-1503, Leung et al. 1997, *Acta Neuropathologica.* 93:518-527, Giraudo et al., 2004, *Journal of Clinical Investigation* 114:623-633; Kirma et al., 2007, *Cancer Research* 67:1918-26, van Ravenswaay et al., 1992, *Laboratory Investigation* 67:166-174.

The antigen binding proteins can also be used to inhibit tumor growth, progression and/or metastasis. Such inhibition can be monitored using various methods. For instance, inhibition can result in reduced tumor size and/or a decrease in metabolic activity within the tumor. Both of these parameters can be measured by MRI or PET scans for example. Inhibition can also be monitored by biopsy to ascertain the level of necrosis, tumor cell death and the level of vascularity within the tumor. The extent of metastasis and bone osteolysis associated with metastasis can be monitored using known methods.

Evidence for the existence of an autocrine loop indicates that inhibition of c-fms activity can have an impact on tumor associated macrophages but also on the tumor cells. Thus, in one embodiment, tumors that have an autocrine loop are targeted as the primary target. In other embodiments, both TAMs and the tumor are targeted for a combined effect. In still other embodiments, tumors using a paracrine loop or an autocrine and paracrine loop are targeted.

The human c-fms antigen binding proteins provided herein can in certain embodiments be administered alone but can also be used in combination with one or more other cancer treatment options, such as, for example, chemotherapy, radiation therapy, or surgery. If administered with a chemotherapeutic, the antigen binding protein can be administered before or after the chemotherapeutic agent or at the same time (e.g., as part of the same composition).

Chemotherapy treatments that can be used in combination with the antigen binding proteins that are provided include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal™ (temozolamide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p-DDD) and aminoglutethimide; hormones and antagonists including adrenocorticosteroid antagonists such as prednisone and equivalents, dexamethasone and aminoglutethimide; Gemzar™ (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Therapies targeting epigenetic mechanism including, but not limited to, histone deacetylase inhibitors, demethylating agents (e.g., Vidaza) and release of transcriptional repression (ATRA) therapies can also be combined with the antigen binding proteins.

Cancer therapies, which may be administered with an antigen binding protein, also include, but are not limited to, targeted therapies. Examples of targeted therapies include, but are not limited to, use of therapeutic antibodies. Exemplary therapeutic antibodies, include, but are not limited to, mouse, mouse-human chimeric, CDR-grafted, humanized and fully human antibodies, and synthetic antibodies, including, but not limited to, those selected by screening antibody libraries. Exemplary antibodies include, but are not limited to, those which bind to cell surface proteins Her2, CDC20, CDC33, mucin-like glycoprotein, and epidermal growth factor receptor (EGFR) present on tumor cells, and optionally induce a cytostatic and/or cytotoxic effect on tumor cells displaying these proteins. Exemplary antibodies also include HERCEPTIN™ (trastuzumab), which may be used to treat breast cancer and other forms of cancer, and RITUXAN™ (rituximab), ZEVALIN™ (ibritumomab tiuxetan), GLEEVEC™, and LYMPHOCIDE™ (epratuzumab), which may be used to treat non-Hodgkin's lymphoma and other forms of cancer. Certain exemplary antibodies also include ERBITUX™ (IMC-C225); ertinolib (Iressa); BEXXAR™ (iodine 131 tositumomab); KDR (kinase domain receptor) inhibitors; anti VEGF antibodies and antagonists (e.g., Avastin™ and VEGAF-TRAP); anti VEGF receptor antibodies and antigen binding regions; anti-Ang-1 and Ang-2 antibodies and antigen binding regions; antibodies to Tie-2 and other Ang-1 and Ang-2 receptors; Tie-2 ligands; antibodies against Tie-2 kinase inhibitors; inhibitors of Hif-1a, and Campath™ (Alemtuzumab). In certain embodiments, cancer therapy agents are polypeptides which selectively induce apoptosis in tumor cells, including, but not limited to, the TNF-related polypeptide TRAIL.

Additional specific examples of chemotherapeutic agents include, taxol, taxenes (e.g., docetaxel and Taxotere), modified paclitaxel (e.g., Abraxane and Opaxio) doxorubicin, Avastin®, Sutent, Nexavar, and other multikinase inhibitors, cisplatin and carboplatin, etoposide, gemcitabine, and vinblastine. Specific inhibitors of other kinases can also be used in combination with the antigen binding proteins, including but not limited to, MAPK pathway inhibitors (e.g., inhibitors of ERK, JNK and p38), PI3kinase/AKT inhibitors and Pim inhibitors. Other inhibitors include Hsp90 inhibitors, proteasome inhibitors (e.g., Velcade) and multiple mechanism of action inhibitors such as Trisenox.

In certain embodiment, an antigen binding protein as provided herein is used in combination with one or more anti-angiogenic agents that decrease angiogenesis. Certain such agents include, but are not limited to, IL-8 antagonists; Campath, B-FGF; FGF antagonists; Tek antagonists (Cerretti et al., U.S. Publication No. 2003/0162712; Cerretti et al., U.S. Pat. No. 6,413,932, and Cerretti et al., U.S. Pat. No. 6,521, 424, each of which is incorporated herein by reference for all purposes); anti-TWEAK agents (which include, but are not limited to, antibodies and antigen binding regions); soluble TWEAK receptor antagonists (Wiley, U.S. Pat. No. 6,727, 225); an ADAM distintegrin domain to antagonize the binding of integrin to its ligands (Fanslow et al., U.S. Publication No. 2002/0042368); anti-eph receptor and anti-ephrin antibodies; antigen binding regions, or antagonists (U.S. Pat. Nos. 5,981,245; 5,728,813; 5,969,110; 6,596,852; 6,232,447; 6,057,124 and patent family members thereof); anti-VEGF agents (e.g., antibodies or antigen binding regions that specifically bind VEGF, or soluble VEGF receptors or a ligand binding regions thereof) such as Avastin™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as panitumumab, IRESSA™ (gefitinib), TARCEVA™ (erlotinib), anti-Ang-1 and anti-Ang-2 agents (e.g., antibodies or antigen binding regions specifically binding thereto or to their receptors, e.g., Tie-2/TEK), and anti-Tie-2 kinase inhibitory agents (e.g., antibodies or antigen binding regions that specifically bind and inhibit the activity of growth factors, such as antagonists of hepatocyte growth factor (HGF, also known as Scatter Factor), and antibodies or antigen binding regions that specifically bind its receptor "c-met"; anti-PDGF-BB antagonists; antibodies and antigen binding regions to PDGF-BB ligands; and PDGFR kinase inhibitors.

Other anti-angiogenic agents that can be used in combination with an antigen binding protein include agents such as MMP-2 (matrix-metalloproteinase 2) inhibitors, MMP-9 (matrix-metalloproteinase 9) inhibitors, and COX-II (cyclooxygenase II) inhibitors. Examples of useful COX-II inhibitors include CELEBREX™ (celecoxib), valdecoxib, and rofecoxib.

In certain embodiments, cancer therapy agents are angiogenesis inhibitors. Certain such inhibitors include, but are not limited to, SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); semaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin 1, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (PINN), (GlaxoSmithKline, UK); E 7820, (Eisai, Japan); CYC 381, (Harvard University, USA); AE 941, (Aetema, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); ML 993, (Novartis, Switzerland); VEGI, (Proteom Tech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); thrombospondin 1 inhibitor, (Allegheny Health, Education and Research Foundation, USA); 2-Benzenesulfonamide, 4-(5-(4-chlorophenyl)-3-(trifluoromethyl)-1H-pyrazol-1-yl)-; Arriva; and C-Met. AVE 8062 ((2S)-2-amino-3-hydroxy-N-[2-methoxy-5-[(1Z)-2-(3,4,5-tri-methoxyphenyl)ethenyl]phenyl]propanamide monohydrochloride); metelimumab (pINN)(immunoglobulin G4, anti-(human transforming growth factor .beta.1 (human monoclonal CAT 192.gamma.4-chain)), disulfide with human monoclonal CAT 192.kappa.-chain dimer); Flt3 ligand; CD40 ligand; interleukin-2; interleukin-12; 4-1BB ligand; anti-4-1BB antibodies; TNF antagonists and TNF receptor antagonists including TNFR/Fc, TWEAK antagonists and TWEAK-R antagonists including TWEAK-R/Fc; TRAIL; VEGF antagonists including anti-VEGF antibodies; VEGF receptor (including VEGF-R1 and VEGF-R2, also known as Flt1 and Flk1 or KDR) antagonists; CD148 (also referred to as DEP-1, ECRTP, and PTPRJ, see Takahashi et al., J. Am. Soc. Nephrol. 10: 213545 (1999), hereby incorporated by reference for any purpose) agonists; thrombospondin 1 inhibitor, and inhibitors of one or both of Tie-2 or Tie-2 ligands (such as Ang-2). A number of inhibitors of Ang-2 are known in the art, including anti-Ang-2 antibodies described in published U.S. Patent Application No. 20030124129 (corresponding to PCT Application No. WO03/030833), and U.S. Pat. No. 6,166,185, the contents of which are hereby incorporated by reference in their entirety. Additionally, Ang-2 peptibodies are also known in the art, and can be found in, for example, published U.S. Patent Application No. 20030229023 (corresponding to PCT Application No. WO03/057134), and published U.S. Patent Application No. 20030236193, the contents of which are hereby incorporated by reference in their entirety for all purposes.

Certain cancer therapy agents include, but are not limited to: thalidomide and thalidomide analogues (N-(2,6-dioxo-3-piperidyl)phthalimi-de); tecogalan sodium (sulfated polysaccharide peptidoglycan); TAN 1120 (8-acetyl-7,8,9,10-tetrahydro-6,8,11-trihydroxy-1-methoxy-10-[[octahydro-5-hydroxy-2-(2-hydroxypropyl)-4,10-dimethylpyrano[3,4-d]-1,3,6-dioxazocin-8-yl]oxy]-5,12-naphthacenedione); suradista (7,7'-[carbonylbis[imino(1-met-hyl-1H-pyrrole-4,2-diyl)carbonylimino(1-methyl-1H-pyrrole-4,2-diyl)carbony-limino]]bis-1,3-naphthalenedisulfonic acid tetrasodium salt); SU 302; SU 301; SU 1498 ((E)-2-cyano-3-[4-hydroxy-3,5-bis(1-methylethyl)phenyl]-N-(3-phenylpropyl)-2-propenamide); SU 1433 (4-(6,7-dimethyl-2-quinoxalinyl)-1-,2-benzenediol); ST 1514; SR 25989; soluble Tie-2; SERM derivatives, Pharmos; semaxanib (pINN)(3-[(3,5-dimethyl-1H-pyrrol-2-yl)methylene]-1,3-dihydro-2H-indol-2-one); S 836; RG 8803; RESTIN; R 440

(3-(1-methyl-1H-indol-3-yl)-4-(1-methyl-6-nitro-1H-indol-3-yl)-1H-pyrrole-2,5-dione); R 123942 (1-[6-(1,2,4-thiadiazol-5-yl)-3-pyridazinyl]-N-[3-(t-rifluoromethyl)phenyl]-4-piperidinamine); prolyl hydroxylase inhibitor; progression elevated genes; prinomastat (INN) ((S)-2,2-dimethyl-4-[[p-(4-pyridyloxy)phenyl]sulphonyl]-3-thiomorpholinecarbo-hydroxamic acid); NV 1030; NM 3 (8-hydroxy-6-methoxy-alpha-methyl-1-oxo-1H-2-benzopyran-3-acet-ic acid); NF 681; NF 050; MIG; METH 2; METH 1; manassantin B (alpha-[1-[4-[5-[4-[2-(3,4-dimethoxyphenyl)-2-hydroxy-1-methylethoxy]-3-m-ethoxyphenyl]tetrahydro-3,4-dimethyl-2-furanyl]-2-methoxyphenoxy]ethyl]-1,-3-benzodioxole-5-methanol); KDR monoclonal antibody; alpha5beta3 integrin monoclonal antibody; LY 290293 (2-amino-4-(3-pyridinyl)-4H-naphtho[1,2-b]-pyran-3-carbonitrile); KP 0201448; KM 2550; integrin-specific peptides; INGN 401; GYKI 66475; GYKI 66462; greenstatin (101-354-plasminogen (human)); gene therapy for rheumatoid arthritis, prostate cancer, ovarian cancer, glioma, endostatin, colorectal cancer, ATF BTPI, anti-angiogenesis genes, angiogenesis inhibitor, or angiogenesis; gelatinase inhibitor, FR 111142 (4,5-dihydroxy-2-hexenoic acid 5-methoxy-4-[2-methyl-3-(3-methyl-2-butenyl)oxira-nyl]-1-oxaspiro[2.5]oct-6-yl ester); forfenimex (PINN) (S)-alpha-amino-3-hydroxy-4-(hydroxymethyl)benzeneacetic acid); fibronectin antagonist (1-acetyl-L-prolyl-L-histidyl-L-seryl-L-cysteinyl-L-aspartamide); fibroblast growth factor receptor inhibitor; fibroblast growth factor antagonist; FCE 27164 (7,7'-[carbonylbis[imino(1-methyl-1H-pyrrole-4,2-diyl)carbonylimino(1-methyl-1H-pyrrole-4,2-diyl)carbon-ylimino]]bis-1,3,5-naphthalenetrisulfonic acid hexasodium salt); FCE 26752 (8,8'-[carbonylbis[imino(1-methyl-1H-pyr-role-4,2-diyl)carbonylimino(1-met-hyl-1H-pyrrole-4,2-diyl)carbonylimino]]bis-1,3,6-naphthalenetrisulfonic acid); endothelial monocyte activating polypeptide II; VEGFR anti-sense oligonucleotide; anti-angiogenic and trophic factors; ANCHOR angiostatic agent; endostatin; Del-1 angiogenic protein; CT 3577; contortrostatin; CM 101; chondroitinase AC; CDP 845; CanStatin; BST 2002; BST 2001; BLS 0597; BIBF 1000; ARRESTIN; apomigren (1304-1388-type XV collagen (human gene COL15A1 alpha1-chain precursor)); angioinhibin; aaATIII; A 36; 9alpha-fluoromedroxyprogest-erone acetate ((6-alpha)-17-(acetyloxy)-9-fluo-ro-6-methyl-pregn-4-ene-3,20-dione); 2-methyl-2-phthalimidino-glutaric acid (2-(1,3-dihydro-1-oxo-2H-isoindol-2-yl)-2-methylpen-tanedioic acid); Yttrium 90 labelled monoclonal antibody BC-1; Semaxanib (3-(4,5-Dimethylpyrrol-2-ylmethylene)indolin-2-one)(C15 H14 N2 O); PI 88 (phosphomannopen-taose sulfate); Alvocidib (4H-1-Benzopyran-4-one, 2-(2-chlorophenyl)-5,7-dihydroxy-8-(3-hydroxy-1-methyl-4-piperidinyl)-cis-1-(−)-) (C21-H20 Cl N O5); E 7820; SU 11248 (5-[3-Fluoro-2-oxo-1,2-dihydroi-ndol-(3Z)-yliden-emethyl]-2,4-dimethyl-1H-pyrrole-3-carboxylic acid (2-di-ethylaminoethyl)amide) (C22H27 F N4 O2); Squalamine (Cholestane-7,24-diol, 3-[[3-[(4-aminobutyl)aminopropyl]amino]-, 24-(hydrogen sulfate), (3.beta.,5.alpha.,7.alpha.)-) (C34 H65 N3 O.sub.5 S); Eriochrome Black T; AGM 1470 (Carbamic acid, (chloroacetyl)-, 5-methoxy-4-[2-methyl-3-(3-methyl-2-butenyl)oxiranyl]-1-oxaspiro[2,5]oct-6-yl ester, [3R-[3alpha, 4alpha(2R,3R), 5beta, 6beta]]) (C19H28Cl N O6); AZD 9935; BIBF 1000; AZD 2171; ABT 828; KS-interleukin-2; Uteroglobin; A 6; NSC 639366 (1-[3-(Diethy-lamino)-2-hydroxypropylamino]-4-(oxyran-2-ylmethy-lamino)anthraquinone fumerate) (C24 H29 N3 O4. C4 H4 O4); ISV 616; anti-ED-B fusion proteins; HUI 77; Troponin I; BC-1 monoclonal antibody; SPV 5.2; ER 68203; CKD 731 (3-(3,4,5-Trimethoxypheny-1)-2(E)-propenoic acid (3R,4S,5S,6R)-4-[2(R)-methyl-3(R)-3(R)-(3-methyl-2-butenyl)oxi-ran-2-yl]-5-methoxy-1-oxaspiro[2.5]oct-6-yl ester) (C28 H38 O8); IMC-1C11; aaATIII; SC 7; CM 101; Angiocol; Kringle 5; CKD 732 (3-[4-[2-(Dimethylamino)ethoxy]phe-nyl]-2(E)-propenoic acid) (C29 H41 N O6); U 995; Cansta-tin; SQ 885; CT 2584 (1-[11-(Dodecylamino)-10-hydrox-yun-decyl]-3,7-dimethylxanthine)(C30 H55 N5 O3); Salmosin; EMAP II; TX 1920 (1-(4-Methylpiperazino)-2-(2-nitro-1H-1-imidazoyl)-1-ethanone) (C10 H15 N5 O3); Alpha-v Beta-x inhibitor; CHIR 11509 (N-(1-Propynyl)gly-cyl-[N-(2-naphthyl)]glycyl-[N-(carbamoylmethyl)]glycine bis(4-methoxyphenyl)methylam-ide)(C36 H37 N5 O6); BST 2002; BST 2001; B 0829; FR 111142; 4,5-Dihydroxy-2(E)-hexenoic acid (3R,4S,5S,6R)-4-[1(R),2(R)-epoxy-1,5-dim-ethyl-4-hexenyl]-5-methoxy-1-oxaspiro[2.5]octan-6-yl ester (C22 H34 O7); and kinase inhibitors including, but not limited to, N-(4-chlorophenyl)-4-(4-pyridinylmethyl)-1-ph-thalazinamine; 4-[4-[[[[4-chloro-3-(trifluoromethyl)phenyl]amino]carbonyl]amino]phenoxy]-1-N-methyl-2-pyridinecarboxamide; N-[2-(diethylamino)ethyl]-5-[(5-fluoro-1,-2-dihydro-2-oxo-3H-indol-3-ylidene)methyl]-2,4-dimethyl-1H-pyrrole-3-carbo-xamide; 3-[(4-bromo-2,6-difluorophenyl)methoxy]-5-[[[[4-(1-pyrrolidinyl)bu-tyl]amino]carbonyl]amino]-4-isothiazolecarboxamide; N-(4-bromo-2-fluorophenyl)-6-methoxy-7-[(1-methyl-4-piperidinyl)methoxy]-4-quinazolinamine; 3-[5,6,7,13-tetrahydro-9-[(1-methylethoxy)methyl]-5-oxo-1-12H-indeno[2,1-a]pyrrolo[3,4-c]carbazol-12-yl]propyl ester N,N-dimethyl-glycine; N-[5-[[[5-(1,1-dimethylethyl)-2-ox-azolyl]methyl]thi-o]-2-thiazolyl]-4-piperidinecarboxamide; N-[3-chloro-4-[(3-fluorophenyl)me-thoxy]phenyl]-6-[5-[[[2-(methylsulfonyl)ethyl]amino]methyl]-2-furanyl]4-qu-inazolinamine; 4-[(4-Methyl-1-piperazinyl)methyl]-N-[4-methyl-3-[[4-(3-pyr-idinyl)-2-pyrimidinyl]amino]-phenyl]benzamide; N-(3-chloro-4-fluorophenyl)-7-methoxy-6-[3-(4-morpholinyl)propoxy]-4-quinazolinamine; N-(3-ethynylphenyl)-6,7-bis(2-methoxyethoxy)-4-quinazolinamine; N-(3-((((2R)-1-methyl-2-pyrrolidinyl)methyl)oxy)-5-(trifluoromethyl)pheny-l)-2-((3-(1,3-oxazol-5-yl)phenyl)amino)-3-pyridinecarboxamide; 2-(((4-fluorophenyl)methyl)amino)-N-(3-((((2R)-1-methyl-2-pyrrolidinyl)me-thyl)oxy)-5-(trifluoromethyl)phenyl)-3-pyridinecarboxamide; N-[3-(Azetidin-3-ylmethoxy)-5-trifluoromethyl-phenyl]-2-(4-fluoro-benzyla-mino)-nicotinamide; 6-fluoro-N-(4-(1-methylethyl)phenyl)-2-((4-pyridinylme-thyl)amino)-3-pyridinecarboxamide; 2-((4-pyridinylmethyl)amino)-N-(3-(((2S-)-2-pyrrolidinylmethyl)oxy)-5-(trifluoromethyl)phenyl)-3-pyridinecarboxami-de; N-(3-(1,1-dimethylethyl)-1H-pyrazol-5-yl)-2-((4-pyridinyl-methyl)amino)-3-pyridinecarboxamide; N-(3,3-dimethyl-2,3-dihydro-1-benzofuran-6-yl)-2-(-(4-pyridinylmethyl)amino)-3-pyridinecarboxamide; N-(3-((((2S)-1-methyl-2-p-pyrrolidinyl)methyl)oxy)-5-(trifluoromethyl)phenyl)-2-((4-pyridinylmethyl)a-mino)-3-pyridinecarboxamide; 2-((4-pyridinylmethyl)amino)-N-(3-((2-(1-pyrr-olidinyl)ethyl)oxy)-4-(trifluoromethyl)phenyl)-3-pyridinecarboxamide; N-(3,3-dimethyl-2,3-dihydro-1H-indol-6-yl)-2-((4-pyridi-nylmethyl)amino)-3-pyridinecarboxamide; N-(4-(pentafluo-roethyl)-3-(((2S)-2-pyrrolidinylmethyl-l)oxy)phenyl)-2-((4-pyridinylmethyl)amino)-3-pyridinecarboxamide; N-(3-((3-azetidinylmethyl)oxy)-5-(trifluoromethyl)phenyl)-2-((4-pyridinyl-methyl)amino)-3-pyridinecarboxamide; N-(3-(4-piperidinyloxy)-5-(trifluorom-ethyl)phenyl)-2-((2-(3-pyridinyl)ethyl)amino)-3-pyridinecarboxamide; N-(4,4-dimethyl-1,2,3,4-tetrahydroisoquinolin-7-yl)-2-(1H-indazol-6-ylami-no)-nicotinamide; 2-(1H-indazol-6-ylamino)-N-[3-(1-methylpyrrolidin-2-ylme-thoxy)-5-trifluoromethyl-phenyl]-nicotinamide; N-[1-(2- dimethylamino-acety-l)-3,3-dimethyl-2,3-dihydro-1H-indol-6-yl]-2-(1H-indazol-6-ylamino)-nicoti-namide; 2-(1H-indazol-6-ylamino)-N-[3-(pyrrolidin-2-ylmethoxy)-5-trifluoro-methyl-phenyl]-nicotinamide; N-(1-acetyl-3,3-dimethyl-2,3-dihydro-1H-indol-6-yl)-2-(1H-indazol-6-ylamino)-nicotinamide; N-(4,4-dimethyl-1-oxo-1,2,3,-4-tetrahydro-isoquinolin-7-yl)-2-(1H-indazol-6-ylamino)-nicotinamide; N-[4-(tert-butyl)-3-(3-piperidylpropyl)phenyl][2-(1H-indazol-6-ylamino)(3-pyridyl)]carboxamide; N-[5-(tert-butyl)isoxazol-3-yl][2-(1H-indazol-6-yla-mino)(3-pyridyl)]carboxamide; and N-[4-(tert-butyl)phenyl][2-(1H-indazol-6-ylamino)(3-pyridyl)]carboxamide, and kinase inhibitors disclosed in U.S. Pat. Nos. 6,258,812; 6,235,764; 6,630,500; 6,515,004; 6,713,485; 5,521,184; 5,770,599; 5,747,498; 5,990,141; U.S. Publication No. U.S. 20030105091; and Patent Cooperation Treaty publication nos. WO 01/37820; WO 01/32651; WO 02/68406; WO 02/66470; WO 02/55501; WO 04/05279; WO 04/07481; WO 04/07458; WO 04/09784; WO 02/59110; WO 99/45009; WO 98/35958; WO 00/59509; WO 99/61422; WO 00/12089; and WO 00/02871, each of which publications are hereby incorporated by reference for all purposes.

An antigen binding protein as provided herein can also be used in combination with a growth factor inhibitor. Examples of such agents, include, but are not limited to, agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in U.S. Pat. No. 5,747,498, WO 98/14451, WO 95/19970, and WO 98/02434.

Specific examples of combination therapies include, for instance, the c-fms antigen binding protein with taxol or taxanes (e.g., docetaxel or Taxotere) or a modified paclitaxel (e.g., Abraxane or Opaxio), doxorubicin and/or Avastin® for the treatment of breast cancer; the human c-fms antigen binding protein with a multi-kinase inhibitor, MKI, (Sutent, Nexavar, or 706) and/or doxorubicin for treatment of kidney cancer; the c-fms antigen binding protein with cisplatin and/or radiation for the treatment of squamous cell carcinoma; the c-fms antigen binding protein with taxol and/or carboplatin for the treatment of lung cancer.

In addition to the applications in oncology, the binding proteins provided herein can be used in the treatment or detection of inflammatory diseases. In those inflammatory diseases where macrophages contribute to the pathology of disease, the ability of the c-fms antigen binding protein to reduce levels of macrophages in other cellular compartments indicates a useful role in treating these diseases. Several studies suggest that human c-fms antigen binding protein may play a role in the modulation of inflammatory diseases, like, for example, inflammatory arthritis, atherosclerosis, and multiple sclerosis.

Additional diseases that can be treated include, but are not limited to, inflammatory bowel disease, Crohn's disease, ulcerative colitis, rheumatoid spondylitis, ankylosing spondylitis, arthritis, psoriatic arthritis, rheumatoid arthritis, osteoarthritis, eczema, contact dermatitis, psoriasis, toxic shock syndrome, sepsis, septic shock, endotoxic shock, asthma, chronic pulmonary inflammatory disease, silicosis, pulmonary sarcoidosis, osteoporosis, restenosis, cardiac and renal reperfusion injury, thrombosis, glomerularonephritis, diabetes, graft vs. host reaction, allograft rejection, multiple sclerosis, muscle degeneration, muscular dystrophy, Alzheimer's disease and stroke.

The antigen binding proteins can also be used to treat cachexia because the proinflammatory cytokines produced by macrophages are considered to be involved in cachexia pathology (Sweet et al., 2002, *J. Immunol.* 168:392-399; Boddaert et al., 2006, *Curr. Opin. Oncol.* 8:335-340 and Wang et al. 2006 *J. Endocrinology* 190:415-423).

Given the ability of the antigen binding proteins to be used to treat various inflammatory diseases, they can be used or combined with various other anti-inflammatory agents. Examples of such agents include, but are not limited to TNF-alpha inhibitors such as TNF drugs (e.g., HUMIRA™, REMICADE™) and TNF receptor immunoglobulin molecules (such as ENBREL™), IL-1 inhibitors, receptor antagonists or soluble IL-Ira (e.g. Kineret or ICE inhibitors), COX-2 inhibitors and metalloprotease inhibitors such as those described above, and alpha-2-delta ligands (e.g., PREGABALIN™ and NEUROTIN™).

In certain embodiments, antigen binding proteins can also be used to treat various bone diseases in view of the important role of c-fms in osteoclast development and activation (e.g., Rolf, F. et al. (2008) *J. Biol. Chem.* 55:340-349, and Watam, A. et al. (2006) *J. Bone Mineral Metabolism* 24:274-282). The antigen binding proteins can thus be useful for treating patients suffering from various medical disorders that involve excessive bone loss or patients who require the formation of new bone even where there may not necessarily be excessive osteoclast activity. Excessive osteoclast activity is associated with numerous osteopenic disorders that can be treated with the antigen binding proteins that are provided, including ostopenia, osteoporosis, periodontitis, Paget's disease, bone loss due to immobilization, lytic bone metastases and arthritis, including rheumatoid arthritis, psoriatic arthritis, ankylosing spondylitis and other conditions that involve bone erosion. Some cancers are known to increase osteoclast activity and induce bone resorption, such as breast and prostate cancer. Multiple myeloma, which arises in bone marrow, also is associated with bone loss.

With respect to bone metastases of cancer, inhibition of the CSF-1/c-fms axis through the use of the antigen binding proteins provided herein could be of therapeutic benefit through multiple mechanisms of action. These would include inhibition of invasion and metastasis through loss of the matrix degrading enzymes produced by TAMs, interference with tumor cell seeding within bone marrow through loss of osteoclast numbers and function, inhibition of metastatic tumor growth through previously mentioned reduction of TAMs and inhibition of bone osteolysis associated with bone metastatic lesions (Ohno, H. et al. (2008) Molecular Cancer Therapeutics. 5:2634-2643). The antigen binding proteins can also have therapeutic benefit for osteosarcoma, which is a cancer of the bone.

Various other low bone mass conditions can also be treated including a variety of forms of osteoporosis, including but not limited to, glucocorticoid induced osteoporosis, osteoporosis induced after transplantation, osteoporosis associated with chemotherapy (i.e., chemotherapy induced osteoporosis), immobilization induced osteoporosis, osteoporosis due to mechanical unloading, and osteoporosis associated with anticonvulsant use. Additional bone diseases that can be treated include bone disease associated with renal failure and nutritional, gastrointestinal and/or hepatic associated bone diseases.

Different forms of arthritis can also be treated, examples including osteoarthritis and rheumatoid arthritis. The antigen binding proteins can also be used to treat systemic bone loss associated with arthritis (e.g., rheumatoid arthritis). In treating arthritis, patients may benefit by perilesional or intralesional injections of the subject antigen binding proteins. For example, the antigen binding protein can be injected adjacent to or directly into an inflamed joint, thus stimulating repair of damaged bone at the site.

The antigen binding proteins described herein can also be used in various bone repair applications. For example, they can be useful in retarding wear debris osteolysis associated with artificial joints, accelerating the repair of bone fractures, and enhancing the incorporation of bone grafts into the surrounding living bone into which they have been engrafted.

The antigen binding proteins provided herein when used to treat bone disorders can be administered alone or in combination with other therapeutic agents, for example, in combination with cancer therapy agents, with agents that inhibit osteoclast activity or with other agents that enhance osteoblast activity. For example, the antigen binding proteins can be administered to cancer patients undergoing radiation therapy or chemotherapy. Chemotherapies used in combination with the antigen binding proteins may include anthracyclines, taxol, tamoxifene, doxorubicin, 5-fluorouracil, oxaloplatin, Velcade® ([(1R)-3-methyl-1-[[(2S)-1-oxo-3-phenyl-2-[(pyrazinylcarbonyl)amino]propyl]amino]butyl] boronic acid) and/or other small molecule drugs that are used in treating cancer.

The antigen binding proteins can be used alone for the treatment of the above referenced conditions resulting in loss of bone mass or in combination with a therapeutically effective amount of a bone growth promoting (anabolic) agent or a bone anti-resorptive agent including but not limited to: bone morphogenic factors designated BMP-1 to BMP-12; transforming growth factor-β and TGF-β family members; fibroblast growth factors FGF-1 to FGF-10; interleukin-1 inhibitors (including IL-Ira, antibodies to IL-1 and antibodies to IL-1 receptors); TNFα inhibitors (including etanercept, adalibumab and infliximab); RANK ligand inhibitors (including soluble RANK, osteoprotegerin and antagonistic antibodies that specifically bind RANK or RANK ligand), Dkk-1 inhibitors (e.g., anti-Dkk-1 antibodies) parathyroid hormone, E series prostaglandins, bisphosphonates and bone-enhancing minerals such as fluoride and calcium. Anabolic agents that can be used in combination with the antigen binding proteins and functional fragments thereof include parathyroid hormone and insulin-like growth factor (IGF), wherein the latter agent is preferably complexed with an IGF binding protein. An IL-1 receptor antagonist suitable for such combination treatment is described in WO89/11540 and a suitable soluble TNF receptor-1 is described in WO98/01555. Exemplary RANK ligand antagonists are disclosed, for example, in WO 03/086289, WO 03/002713, U.S. Pat. Nos. 6,740,511 and 6,479,635. All of the aforementioned patents and patent applications are hereby incorporated by reference.

The antigen binding proteins can also be used to inhibit angiogenesis (e.g., in tumors). For example, the antigen binding proteins can be used to decrease blood vessel formation in cases where inflammatory angiogenesis is driven primarily by FGF-2. In some embodiments, the antigen binding proteins are used to inhibit angiogenesis in tumors where VEGF levels are low and tumor vascular density is high.

Diagnostic Methods

The antigen binding proteins of the described can be used for diagnostic purposes to detect, diagnose, or monitor diseases and/or conditions associated with c-fms. The disclosed provides for the detection of the presence of c-fms in a sample using classical immunohistological methods known to those of skill in the art (e.g., Tijssen, 1993, *Practice and Theory of Enzyme Immunoassays*, Vol 15 (Eds R. H. Burdon and P. H. van Knippenberg, Elsevier, Amsterdam); Zola, 1987, *Monoclonal Anthbodies: A Manual of Techniques*, pp. 147-158 (CRC Press, Inc.); Jalkanen et al., 1985, *J. Cell. Biol.* 101: 976-985; Jalkanen et al., 1987, *J. Cell Biol.* 105:3087-3096). The detection of c-fms can be performed in vivo or in vitro.

Diagnostic applications provided herein include use of the antigen binding proteins to detect expression of c-fms and binding of the ligands to c-fms. Examples of methods useful in the detection of the presence of c-fms include immunoassays, such as the enzyme linked immunosorbent assay (ELISA) and the radioimmunoassay (RIA).

For diagnostic applications, the antigen binding protein typically will be labeled with a detectable labeling group. Suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used.

In another aspect, an antigen binding protein can be used to identify a cell or cells that express c-fms. In a specific embodiment, the antigen binding protein is labeled with a labeling group and the binding of the labeled antigen binding protein to c-fms is detected. In a further specific embodiment, the binding of the antigen binding protein to c-fms detected in vivo. In a further specific embodiment, the c-fms antigen binding protein is isolated and measured using techniques known in the art. See, for example, Harlow and Lane, 1988, *Antibodies: A Laboratory Manual*, New York: Cold Spring Harbor (ed. 1991 and periodic supplements); John E. Coligan, ed., 1993, *Current Protocols In Immunology* New York: John Wiley & Sons.

Another aspect of the disclosed provides for detecting the presence of a test molecule that competes for binding to c-fms with the antigen binding proteins provided. An example of one such assay would involve detecting the amount of free antigen binding protein in a solution containing an amount of c-fms in the presence or absence of the test molecule. An increase in the amount of free antigen binding protein (i.e., the antigen binding protein not bound to c-fms) would indicate that the test molecule is capable of competing for c-fms binding with the antigen binding protein. In one embodiment, the antigen binding protein is labeled with a labeling group. Alternatively, the test molecule is labeled and the amount of free test molecule is monitored in the presence and absence of an antigen binding protein.

Methods of Treatment: Pharmaceutical Formulations, Routes of Administration

Methods of using the antigen binding proteins are also provided. In some methods, an antigen binding protein is provided to a patient. The antigen binding protein inhibits binding of CSF-1 to human c-fms. The administration of an antigen binding protein in some methods can also inhibit autophosphorylation of human c-fms by inhibiting binding of CSF-1 to human c-fms. Further, in certain methods, monocyte chemotaxis is reduced by administering an effective amount of at least one antigen binding protein to a patient.

Monocyte migration into tumors in some methods is inhibited by administering an effective amount of an antigen binding protein. In addition, the accumulation of tumor associated macrophage in a tumor or diseased tissue can be inhibited by administering an antigen binding protein as provided herein.

Pharmaceutical compositions that comprise a therapeutically effective amount of one or a plurality of the antigen binding proteins and a pharmaceutically acceptable diluent, carrier, solubilizer, emulsifier, preservative, and/or adjuvant are also provided. In addition, methods of treating a patient by administering such pharmaceutical composition are included. The term "patient" includes human patients.

Acceptable formulation materials are nontoxic to recipients at the dosages and concentrations employed. In specific embodiments, pharmaceutical compositions comprising a therapeutically effective amount of human c-fms antigen binding proteins are provided.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins disclosed. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute. In certain embodiments, human c-fms antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the human c-fms antigen binding protein may be formulated as a lyophilizate using appropriate excipients such as sucrose.

The pharmaceutical compositions can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions may be provided in the form of a pyrogen-free, parenterally acceptable aqueous solution comprising the desired human c-fms antigen binding protein in a pharmaceutically acceptable vehicle. A particularly suitable vehicle for parenteral injection is sterile distilled water in which the human c-fms antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Certain pharmaceutical compositions are formulated for inhalation. In some embodiments, human c-fms antigen binding proteins are formulated as a dry, inhalable powder. In specific embodiments, human c-fms antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins. Some formulations can be administered orally. Human c-fms antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the human c-fms antigen binding protein. Diluents, flavorings, low melting point waxes, vegetable oils, lubricants, suspending agents, tablet disintegrating agents, and binders may also be employed.

Some pharmaceutical compositions comprise an effective quantity of one or a plurality of human c-fms antigen binding proteins in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving human c-fms antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 2:547-556), poly (2-hydroxyethyl-inethacrylate) (Langer et al., 1981, *J. Biomed. Mater. Res.* 15:167-277 and Langer, 1982, *Chem. Tech.* 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. USA.* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

In certain embodiments, cells expressing a recombinant antigen binding protein as disclosed herein is encapsulated for delivery (see, Invest. Opthalmol V is Sci 43:3292-3298, 2002 and Proc. Natl. Acad. Sciences 103:3896-3901, 2006).

In certain formulations, an antigen binding protein has a concentration of at least 10 mg/ml, 20 mg/ml, 30 mg/ml, 40 mg/ml, 50 mg/ml, 60 mg/ml, 70 mg/ml, 80 mg/ml, 90 mg/ml, 100 mg/ml or 150 mg/ml. Some formulations contain a buffer, sucrose and polysorbate. An example of a formulation is one containing 50-100 mg/ml of antigen binding protein, 5-20 mM sodium acetate, 5-10% w/v sucrose, and 0.002-0.008% w/v polysorbate. Certain, formulations, for instance, contain 65-75 mg/ml of an antigen binding protein in 9-11 mM sodium acetate buffer, 8-10% w/v sucrose, and 0.005-0.006% w/v polysorbate. The pH of certain such formulations is in the range of 4.5-6. Other formulations have a pH of 5.0-5.5 (e.g., pH of 5.0, 5.2 or 5.4).

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. Kits for producing a single-dose administration unit are also provided. Certain kits contain a first container having a dried protein and a second container having an aqueous formulation. In certain embodiments, kits containing single and multi-chambered pre-filled syringes (e.g., liquid syringes and lyosyringes) are provided. The therapeutically effective amount of a human c-fms antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the human c-fms antigen binding protein is being used, the route of administration, and the size (body weight, body surface or organ size) and/or condition (the age and general health) of the patient. In certain embodiments, the clinician may titer the dosage and modify the route of administration to obtain the optimal therapeutic effect.

A typical dosage may range from about 1 µg/kg to up to about 30 mg/kg or more, depending on the factors mentioned above. In specific embodiments, the dosage may range from 10 µg/kg up to about 30 mg/kg, optionally from 0.1 mg/kg up to about 30 mg/kg, alternatively from 0.3 mg/kg up to about 20 mg/kg. In some applications, the dosage is from 0.5 mg/kg to 20 mg/kg. In some instances, an antigen binding protein is dosed at 0.3 mg/kg, 0.5 mg/kg, 1 mg/kg, 3 mg/kg, 10 mg/kg, or 20 mg/kg. The dosage schedule in some treatment regimes is at a dose of 0.3 mg/kg qW, 0.5 mg/kg qW, 1 mg/kg qW, 3 mg/kg qW, 10 mg/kg qW, or 20 mg/kg qW.

Dosing frequency will depend upon the pharmacokinetic parameters of the particular human c-fms antigen binding protein in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Appropriate dosages may be ascertained through use of appropriate dose-response data. In certain embodiments, the antigen binding proteins can be administered to patients throughout an extended time period. Chronic administration of an antigen binding protein minimizes the adverse immune or allergic response commonly associated with antigen binding proteins that are not fully human, for example an antibody raised against a human antigen in a non-human animal, for example, a non-fully human antibody or non-human antibody produced in a non-human species.

The route of administration of the pharmaceutical composition is in accord with known methods, e.g., orally, through injection by intravenous, intraperitoneal, intracerebral (intraparenchymal), intracerebroventricular, intramuscular, intraocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use human c-fms antigen binding protein pharmaceutical compositions according to the disclosed ex vivo. In such instances, cells, tissues or organs that have been removed from the patient are exposed to human c-fms antigen binding protein pharmaceutical compositions after which the cells, tissues and/or organs are subsequently implanted back into the patient.

In particular, human c-fms antigen binding proteins can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semipermeable polymeric enclosures or membranes that allow the release of the protein product(s) but prevent the destruction of the cells by the patient's immune system or by other detrimental factors from the surrounding tissues.

The following examples, including the experiments conducted and the results achieved, are provided for illustrative purposes only and are not to be construed as limiting the scope of the appended claims.

EXAMPLES

Assays

AML-5 Assays

In order to determine whether antibodies directed against c-fms can bind and exhibit functional activity in blocking the c-fms/CSF-1 axis, a cell-based bioassay was used. This assay quantitatively measures CSF-1-driven proliferation of a growth-factor dependent human myelomonocytic cell line, AML5 (University Health Network, Toronto, Ontario). The assay therefore, measures the inhibition of this proliferation by introducing agents that block this pathway. In this assay, AML-5 cells were incubated with 10 ng/ml CSF-1 in the presence of decreasing concentrations of antibody. After 72 hours, cell proliferation was measured using Alamar Blue™ (Biosource), an indirect measure of proliferation based on metabolic activity of the cells.

Bone Marrow Assays

In a similar assay to determine whether the antibodies could cross-react with cynomolgus monkey c-fms, antibodies were tested in CSF-1-driven proliferation of the monocytic cells from primary monkey bone marrow. Similar to the AML-5 proliferation assay, cynomolgus bone marrow cells were incubated with 10 ng/ml CSF-1 in the presence of decreasing concentrations of antibody. After 72 hours, cell proliferation was measured using Alamar Blue.

Antibody Clones Used in Experiments

The following experiments include the use of three antibody clones, designated as 1.109, 1.2, 2.360, which all are tetramers including two complete heavy and two complete light chains. Clone 1.109 comprises two heavy chains H1 (SEQ ID NO:4) and two light chains L1 (SEQ ID NO:36), clone 1.2 comprises two heavy chains H8 (SEQ ID NO:11) and two light chains L8 (SEQ ID NO:43), and clone 2.360 comprises two heavy chains H24 (SEQ ID NO:27) and two light chains L22 (SEQ ID NO:57).

Example 1

Preparation of C-Fms Hybridomas

Embodiments may employ the XenoMouse® technology to develop fully human monoclonal antibodies directed against human c-fms. For immunization purposes, the c-fms-Fc, a human c-fms extracellular domain (residues 1-512, see, FIG. 8; SEQ ID: 1) with a C-terminal human Fc domain was employed. In addition, c-fms-LZ, a human c-fms extracellular domain (residues 1-512) with a C-terminal leucine zipper domain (Amgen Lot #45640-43) and 293T/c-fms cell line, a human adenovirus type 5-transformed human embryonic kidney cell line transfected with full-length human c-fms were utilized to screen the anti-c-fms antibodies.

Cohort 1 ($IgG_1$) and cohort 2 ($IgG_2$) XenoMice® were immunized/boosted with c-fms-Fc. Serum titers were measured by enzyme-linked immunoabsorbent assay (ELISA) and spleens from both cohorts 1 and 2 mice were fused to generate hybridomas. The resulting polyclonal supernatants were screened for binding to c-fms-LZ by ELISA and 293T/c-fms cells by fluorometric microvolume assay technology (FMAT). A total of 828 positive supernatants were tested for inhibition of CSF-1 binding to the c-fms/293T cells by fluorescence-activated cell sorting (FACS). The resulting 168 positive supernatants were further tested for inhibition of CSF-1-induced proliferation of acute myelogenous leukemia (AML)-5 cells. Based on the screening, 33 hybridomas were identified as antagonistic to CSF-1 activity and were selected for cloning.

Example 2

Characterization of Anti-C-fms Hybridomas

From the 33 selected hybridomas, 29 (19 IgG1 and 10 IgG2 isotypes) were successfully cloned and supernatants from these clones were tested for inhibition of CSF-1 binding to the 293T/c-fms cells and inhibition of CSF-1 induced proliferation of AML-5 cells. A low-resolution Biacore binding assay using monomeric c-fms protein indicated that the $K_D$ of these 29 anti-c-fms hybridomas was in the range of 0.1-43 nM (see TABLE 8). Anti-human IgG was immobilized on all four flow cells of a sensor chip using amine coupling. Crude hybridoma samples were diluted into halves and captured on the anti-IgG surface. Monomeric c-fms (residues 1-512)-pHis was the analyte at a concentration of 125 nM. Sequence lineage analyses were also performed on the 29 hybridomas (see, FIG. 2).

TABLE 8

Low Resolution Biacore Binding Results For Anti-C-fms Hybridomas

| mAb Clone | mAb Clone | $k_a$ (1/Ms) | $k_d$ (1/s) | $K_D$ (nM) |
|---|---|---|---|---|
| 1.109.1 | 1 | 3.85E+05 | 4.36E−05 | 0.1 |
| 2.131.2 | 2 | 4.30E+04 | 1.00E−05 | 0.2 |
| 2.508.1 | 3 | 7.49E+04 | 5.28E−05 | 0.7 |
| 1.33.1.1 | 4 | 9.89E+04 | 1.16E−04 | 1.2 |
| 1.2.1 | 5 | 8.17E+05 | 1.13E−03 | 1.4 |
| 1.42.3 | 6 | 6.60E+05 | 1.07E−03 | 1.6 |
| 1.64.1 | 7 | 2.55E+05 | 6.40E−04 | 2.5 |
| 1.30.2 | 8 | 4.06E+05 | 1.40E−03 | 3.4 |
| 1.134.1 | 9 | 1.53E+05 | 7.03E−04 | 4.6 |
| 2.475.2 | 10 | 3.00E+05 | 1.40E−03 | 4.7 |

TABLE 8-continued

Low Resolution Biacore Binding Results For Anti-C-fms Hybridomas

| mAb Clone | mAb Clone | $k_a$ (1/Ms) | $k_d$ (1/s) | $K_D$ (nM) |
|---|---|---|---|---|
| 2.103.1 | 11 | 7.51E+04 | 3.64E−04 | 4.8 |
| 1.39.3 | 12 | 1.13E+05 | 6.08E−04 | 5.4 |
| 1.72.2 | 13 | 1.03E+05 | 5.68E−04 | 5.5 |
| 2.360.3 | 14 | 6.05E+04 | 3.38E−04 | 5.6 |
| 1.13.2 | 15 | 1.20E+05 | 7.73E−04 | 6.4 |
| 2.65.2 | 16 | 1.68E+05 | 1.60E−03 | 9.5 |
| 1.143.2 | 17 | 5.50E+04 | 5.59E−04 | 10 |
| 1.90.2 | 18 | 1.93E+05 | 2.00E−03 | 10 |
| 1.144.1 | 19 | 2.30E+05 | 2.50E−03 | 11 |
| 1.26.1 | 20 | 2.39E+05 | 2.63E−03 | 11 |
| 2.369.3 | 21 | 1.00E+05 | 1.38E−03 | 14 |
| 1.16.2 | 22 | 1.29E+05 | 2.96E−03 | 23 |
| 1.66.1 | 23 | 2.39E+05 | 5.50E−03 | 23 |
| 2.550.1 | 24 | 3.00E+05 | 7.24E−03 | 24 |
| 2.291.2 | 25 | 2.86E+05 | 9.30E−03 | 33 |
| 1.27.3 | 26 | 2.99E+05 | 1.00E−02 | 33 |
| 1.34.3 | 27 | 3.65E+05 | 1.31E−02 | 36 |
| 1.131.1 | 28 | 5.31E+04 | 2.15E−03 | 41 |
| 2.534.1 | 29 | 3.45E+05 | 1.50E−02 | 43 |

Based on the binding inhibition and proliferation inhibition assays, 16 of the 29 supernatants (eleven IgG1 and five IgG2 isotypes) were selected for further characterization. Cross-reactivity to mouse and cynomolgus c-fms was tested by inhibition of CSF-1-induced proliferation of mouse DRM (a ras- and myc-immortalized monocytic cell line derived from Dexter type culture of mouse bone marrow) cells and primary cynomolgus bone marrow cells, respectively. With respect to cell proliferation, none of the supernatants inhibited the proliferation of the mouse DRM cells (data not shown) while 13 of 16 supernatants inhibited proliferation of the cynomolgus bone marrow cells. The supernatants were also tested for inhibition of CSF-1-induced proliferation of human peripheral blood-derived CD14+ monocytes and retested in the human AML-5 bioassay (see Assay section above), the results of which are shown in TABLES 9 and 10. The 2-4A5 antibody (Biosource), which is a rat anti-human c-fms antibody, was used as a positive control.

Four IgG1 isotype antibodies had <10 pM potency in the AML-5 bioassay and three of the antibodies, Clone ID Nos. 1.2.1, 1.109.3, and 1.134.1, inhibited the proliferation of cynomolgus bone marrow cells. Of the three antibodies, clones 1.2.1 and 1.109.3 had the highest affinity for c-fms in the Biacore binding assay. Two $IgG_2$ isotype antibodies, 2.103.3 and 2.360.2, showed high potency in the AML-5 and cynomolgus bone marrow bioassays and similar affinities for c-fms in the Biacore assay. The five antibodies that showed high potency in the AML-5 and cynomolgus bone marrow bioassays also showed diversity in sequence. Based on these factors of potency, affinity, and diversity, clones 1.2.1, 1.109.3, and 2.360.2 were chosen for additional development and characterization.

TABLE 9

Summary Of Bioassay Results For The Anti-C-fms Hybridoma Supernatants

| Clone ID | Cynomolgus bone marrow bioassay (mean, n = 2) $IC_{50}$ (pM) | Human CD14+ monocytes bioassay (n = 1) $IC_{50}$ (pM) | AML-5 bioassay (mean, n = 3 or 4) $IC_{50}$ (pM) |
|---|---|---|---|
| 1.2.1 | 40 | <7 | 6 |
| 1.26.1 | 33 | 13 | 27 |
| 1.27.2 | 933 | 200 | 73 |
| 1.30.3 | 267 | 67 | 40 |
| 1.39.2 | 67 | 67 | 27 |
| 1.42.3 | 200 | 67 | 20 |
| 1.64.2 | NA* | 13 | 4 |
| 1.66.2 | 47 | 67 | 27 |
| 1.109.3 | 73 | 20 | 5 |
| 1.134.1 | 40 | <7 | 7 |
| 1.143.1 | 360 | ND** | 100 |
| 2.103.3 | 27 | 133 | 53 |
| 2.360.2 | 53 | 67 | 27 |
| 2.475.2 | 167 | 67 | 40 |
| 2.508.2 | NA* | 133 | 20 |
| 2.534.2 | NA* | 47 | 20 |
| 2-4A5 | 8333 | 667 | 187 |
| c-fms-Fc | 617 | 556 | 210 |
| Anti-CSF-1 | 3333 | 667 | 20 |

*NA = No Activity, Not Cross-Reactive;
**ND = Not Done

TABLE 10

Synopsis Of Bioassay Results For Anti-c-fms Hybridoma Supernatants

Concentration of Half-Max ($IC_{50}$, ng/ml)

| Clone | Cynomolgus bone marrow bioassay (mean, n = 2) | Human CD14+ monocytes bioassay (n = 1) | AML-5 bioassay (mean, n = 3 or 4) | AML-5 × Difference |
|---|---|---|---|---|
| 1.2 | 6 | <1 | 0.9 | 4 |
| 1.26.1 | 5 | 2 | 4 | 24 |
| 1.27.2 | 140 | 30 | 11 | 44 |
| 1.30.3 | 10 | 10 | 6 | 24 |
| 1.39.2 | 30 | 10 | 4 | 24 |
| 1.42.3 | | 10 | 3 | 9 |
| 1.64.2 | NA* | 2 | 0.6 | 8 |
| 1.66.2 | 7 | 10 | 4 | 12 |
| 1.109.3 | 11 | 3 | 0.7 | 1.4 |
| 1.134.1 | 6 | <1 | 1 | 3 |
| 1.143.1 | 54 | ND** | 15 | 119 |
| 2.103.1 | 4 | 20 | 8 | 19 |
| 2.360.2 | 8 | 10 | 4 | 11 |
| 2.475.2 | 25 | 10 | 6 | 18 |
| 2.508.2 | NA* | 20 | 5 | 20 |
| 2.534.2 | NA* | 7 | 3 | 12 |
| 2-4A5 | 1250 | 100 | 28 | |
| c-fms-Fc | 100 | 90 | 34 | |
| Anti-CSF-1 | 500 | 100 | 3 (n = 1) | |

*NA = No Activity, not cross-reactive;
**ND = Not Done.

Example 3

Expression and Characterization of Antibodies

Heavy and light chain genes for antibody clones 1.2, 1.109, and 2.360 were isolated and cloned into constructs for expression as $IgG_2$ heavy chains and kappa light chains. Antibodies were expressed by transient expression in COS/PKB cells and purified by Protein A chromatography. Antibody yields were 3.6-7.4 mg/l, which is within the expected range for this expression system.

Figures 3A, 3B:
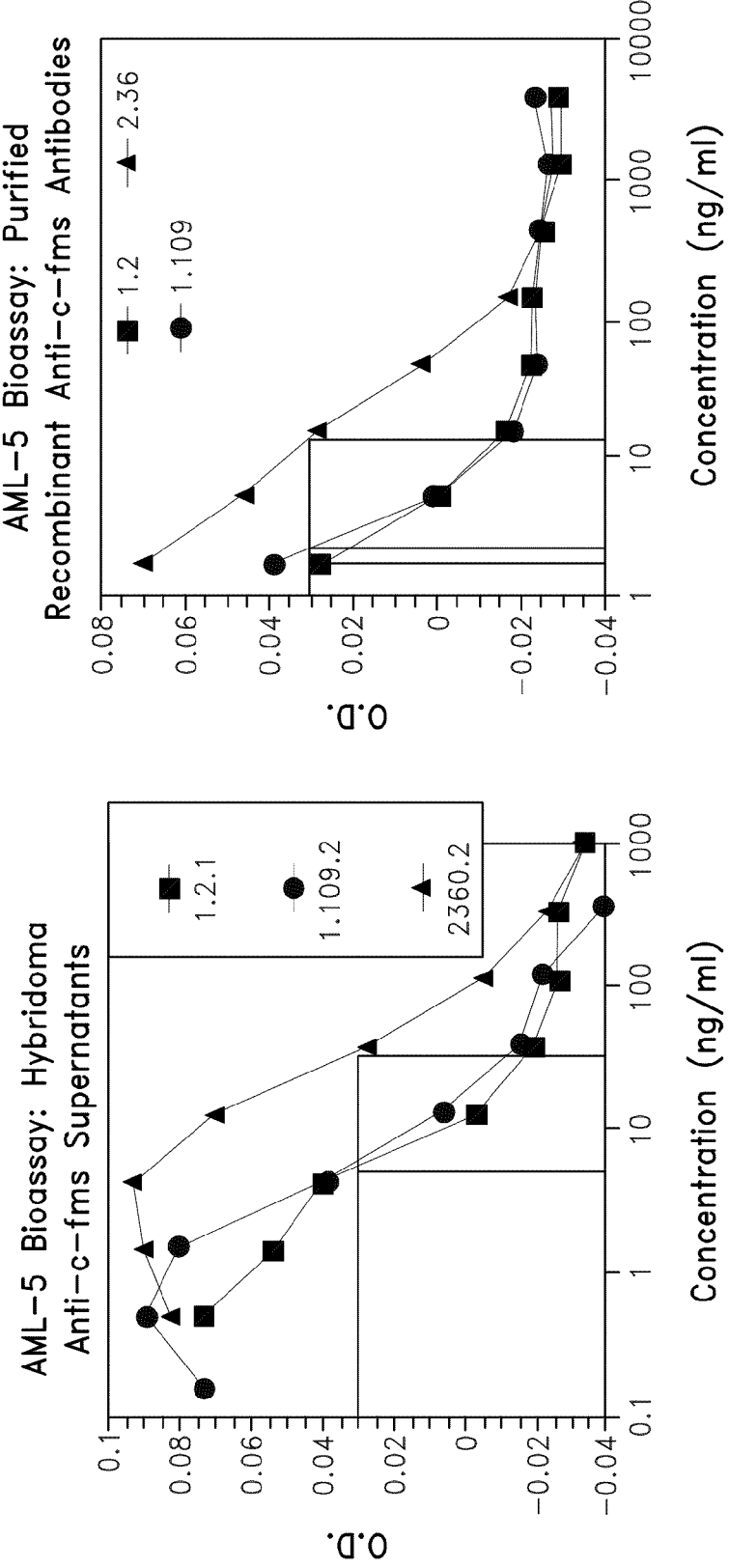
FIG. 3A shows AML-5 Bioassary with hybridoma anti-c-fms supernatans.
FIG. 3B shows AML-5 bioassay with purified recombinant anti-c-fms antibodies. AML-5 cells were incubated with 10 ng/ml CSF-1 in the presence of decreasing concentrations of antibody. After 72 hours, cell proliferation was measured using Alamar Blue.
Figure 4:
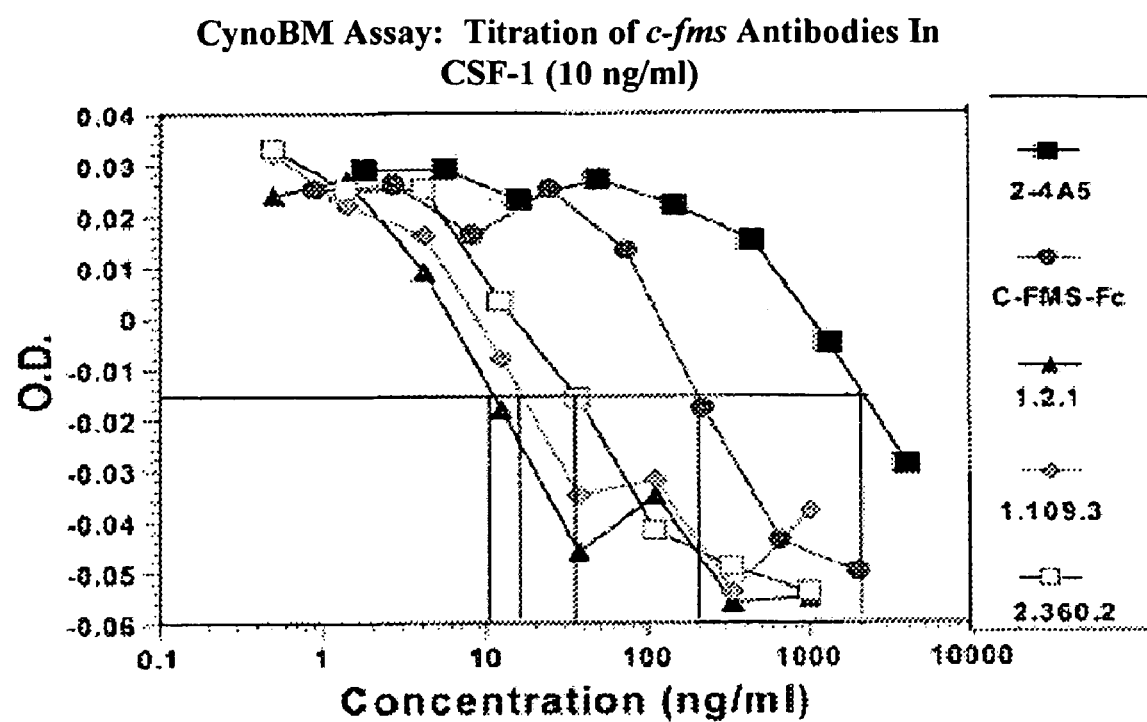
FIG. 4 shows a CynoBM assay with titration of c-fms antibodies in CSF-1. The inhibition of CSF-1-enriched cynomolgus bone marrow cell proliferation by the various hybridoma anti-c-fms supernatants is illustrated. Cynomolgus bone marrow cells were incubated with 10 ng/ml CSF-1 in the presence of decreasing concentrations of antibody. After 72 hours, cell proliferation was measured using Alamar Blue.

The activities of the cloned antibodies and the hybridoma-expressed antibodies were compared in the AML-5 proliferation assay. AML-5 cells were incubated with 10 ng/ml CSF-1 in the presence of decreasing concentrations of antibody. After 72 hours, cell proliferation was measured using Alamar Blue (see, FIG. 3). The recombinant antibodies showed similar neutralizing activity as the hybridoma supernatants, and conversion of 1.2 and 1.109 from IgG1 to IgG2 had no apparent effect. The recombinant antibodies also demonstrated good neutralizing activity in the cynomolgus proliferation assay as shown in FIG. 4. Similar to the AML-5 proliferation assay, cynomolgus bone marrow cells were incubated with 10 ng/ml CSF-1 in the presence of decreasing concentrations of antibody. After 72 hours, cell proliferation was measured using Alamar Blue.

Characterization of the purified antibodies by SDS-PAGE and size-exclusion chromatography (SEC) produced typical results, with the exception of the clone 1.109 light chain, which migrated larger than expected on SDS-PAGE. This exception was not unexpected because an N-linked glycosylation site sequence was previously noted in CDR1. The larger than expected migration suggested that this glycosylation site was occupied.

N-terminal sequencing of the antibodies confirmed that signal peptides were processed as expected and that the heavy chain N-terminal glutamine residues were likely cyclized to pyroglutamic acid as would be expected. Mass spectrometry was performed on the individual antibody chains following enzymatic deglycosylation. The masses of the heavy chains confirmed that the N-terminal glutamine residues were cyclized to pyroglutamic acid and that the C-terminal lysine residues were absent. No other post-translational modifications were noted. The masses of the clone 1.2 SM and 2.360 light chains confirmed that they were intact with no post-translational modifications. A mass was not obtained for the clone 1.109 light chain, probably because the glycosylation site was resistant to enzymatic removal and thus an accurate mass could not be obtained.

Example 4

Correction of Somatic Mutations (SMs)

Sequence comparison of IgG2 clone 1.2, 1.109 and 2.360 antibodies to known germline sequences revealed the following somatic mutations, as shown in TABLE 11, with the numbering in the table being with respect to the mature sequence as shown in FIGS. 1A and 1B.

TABLE 11

Somatic Mutations Relative To The Closest Germline Sequence

| Antibody Chain | Somatic Mutation | Germline Residue | Comments |
|---|---|---|---|
| 1.2 LC | Ser-78 in FR3 | Thr | |
| 1.2 HC | None | | |
| 1.109 LC | Asn-28 in CDR1; Asn-45 in FR2 | Asp: Lys | Asn-28 creates an N-linked glycosylation site |
| 1.109 HC | None | | |
| 2.360 LC | Gln-45 in FR2 | Lys | |
| 2.360 HC | Val-79 in FR3 | Ala | |

To test if the somatic mutations could be converted to germline residues, the relevant constructs were generated and antibodies were expressed by transient expression in COS/PKB cells and purified by Protein A chromatography. These antibodies were designated IgG$_2$ clone 1.2 SM, 1.109 SM, and 2.360 SM (SM=somatic mutation cured). For the 1.109 LC, two constructs were made. In the first construct, Asn-28 was converted to Asp-28 to eliminate the N-linked glycosylation site, and in the second construct, Asn-28 was converted to Asp-28 and Asn-45 was converted to Lys-45. Yields were 1.7-4.5 mg/l, which is within the expected range for this expression system.

Characterization of the purified antibodies by SDS-PAGE and size-exclusion chromatography (SEC) produced typical results. SDS-PAGE of the two forms of IgG$_2$ clone 1.109 SM showed that the light chain migrated faster than the parent antibody light chain, confirming that the N-linked glycosylation site was eliminated. N-terminal sequencing showed that the N-termini of the antibody chains were intact, and mass spectrometry showed that the somatic mutations had been converted to germline residues.

Example 5

Characterization of Somatic Mutation-Corrected Antibodies

Following the correction of the somatic mutations, the purified IgG$_2$ antibodies were retested in the AML-5 and cynomolgus bone marrow proliferation assays. The IC$_{50}$ in the AML-5 proliferation assay did not change for IgG$_2$ clone 1.2 SM or 1.109 SM (SM=somatic mutation cured) relative to the parent IgG$_2$ antibodies, but there was a 10-fold loss in potency for the IgG$_2$ clone 2.360 SM antibody (see, TABLE 12).

The binding affinities of the somatic mutation corrected antibodies to monomeric c-fms protein were measured by surface plasmon resonance using a Biacore 3000 instrument. The affinity of IgG$_2$ clone 1.2 SM antibody was essentially unchanged from the parent antibodies, whereas the affinities of the IgG$_2$ clone 1.109 SM and 2.360 SM antibodies were 2-fold less than the respective parent antibodies (see, TABLE 12).

The parent (PT) and SM IgG$_2$ antibodies were further tested for the ability to inhibit binding of $^{125}$I-hCSF-1 to AML-5 cells. The apparent binding affinity of $^{125}$I-hCSF-1 to AML-5 cells was first determined to be 46 pM and the K$_1$ of unlabeled hCSF-1 was 17.8 pM (see, Example 10). As shown in Table 12, the K$_1$ value for antibody 1.2 was in line with the IC$_{50}$ value in the AML-5 bioassay and 1.2 SM gave similar results. The K$_1$ value for antibody 1.109 was also in line with the IC$_{50}$ value and there was no change with the 1.109 SM antibody despite a 2-fold loss in affinity for monomeric c-fms as measured by Biacore. Antibody 2.360 did not inhibit as well as antibodies 1.2 and 1.109, and 2.360 SM inhibited less well than the parent antibody.

TABLE 12

Properties Of The Parent (PT) Versus Germlined Antibodies (SM)

| Antibody | AML-5 bioassay IC$_{50}$ (pM) | Cynomolgus bone marrow bioassay IC$_{50}$ (pM) | Inhibition (K$_I$) of $^{125}$I-CSF-1 binding to AML-5 (pM) | Binding Affinity (K$_D$) to monomeric c-fms by Biacore (pM) |
|---|---|---|---|---|
| 1.2 | 27 | 78 | 8.5 | 516 |
| 1.2 SM* | 12 | 81 | 11.5 | 548 |
| 1.109 | 27 | 16 | 13.5 | 51 |
| 1.109 SM* | | 23 | 9.7 | 102 |
| 2.360 | 60 | 67 | ~160 | 535 |
| 2.360 SM* | | | ~900 | 1200 |

*SM = somatic mutation cured

The activity of the 1.2 SM antibody was further investigated in proliferation assays using human or Cynomologous bone marrow monocytic cells. For the human assay, human cells were incubated with 11.1 ng/ml recombinant human CSF-1 in the presence of decreasing concentrations of antibody 1.2 SM. For the cynomolgus assay, cynomolgus cells were incubated with 29.63 ng/ml recombinant human CSF-1 in the presence of decreasing concentrations of antibody 1.2 SM. Human IgG2 antibody was used in control experiments. After 7 days, cell proliferation was measured using CellTiter-Glo (Promega, Madison Wis.) to determine levels of ATP. Nonlinear regression curve fit was performed to determine the $IC_{50}$ of the antibody. TABLE 13 shows the results of three sets of experiments.

TABLE 13

Activity of clone 1.2 SM antibody in cell proliferation assays

| Bone marrow monocytic cell | IC50 of 1.2 SM in the Presence of hCSF-1 (pM) | | | | |
| --- | --- | --- | --- | --- | --- |
| | Expt. 1 | Expt. 2 | Expt. 3 | Average | S.D. |
| Human | 15.5 | 20.1 | 10.9 | 15.5 | 4.6 |
| Cynomolgus | 42.55 | 26.01 | 22.90 | 32.73 | 13.89 |

Example 6

Inhibition of C-fms Tyrosine Phosphorylation

To show that anti-c-fms $IgG_2$ mAbs, 1.109, 1.2 and 2.360, are capable of complete or nearly complete inhibition of phosphotyrosine (pTyr)-response, 293T/c-fms cells were treated with these mAbs for 1 hour at various concentrations at 37° C. prior to CSF-1 stimulation.

Various concentrations of the $IgG_2$ mAbs using titration dilutions were at 1.0, 0.1, 0.01, 0.001 and 0.0001 μg/ml. As controls, a non-blocking anti-c-fms monoclonal antibody, mAb 3-4A4 (BioSource, Intl.) and a non-relevant antibody, hCD39 M105, each at 1.0 μg/ml, were used. Serum-starved 293T/c-fms cells were treated with each of the $IgG_2$ (PT) mAbs using the various concentrations as mentioned above, and each concentration varying in a ten-fold dilution prior to a five-minute CSF-1 stimulation at 50 ng/ml for 5 minutes. Following stimulation, whole-cell lysates were collected, immunoprecipitated at 4° C. overnight with an anti-c-fms C20 polyclonal antibody (Santa Cruz Biotechnology, Inc.) and examined by Western blotting wherein the blot was immunoprobed with a generic anti-pTyr antibody, 4G10 (Upstate Biotechnology), and an anti-c-fms C20 antibody for the levels of tyrosine phosphorylation of c-fms and c-fms itself, respectively.

To grow the 293T/c-fms cells on 24×10 cm dishes, at 37° C. in 5% $CO_2$, eleven T175 flasks (~50-60% confluent) were collected via 4 ml trypsin/flask (Gibco-Invitrogen) and transferred to 70 ml DMEM (Gibco)/10% FBS (JRH Biosciences). Each 10 cm dish was then given 10 ml medium and inoculated with 2 ml of the collected cells. DMEM/-FBS medium was prepared for 1 hour at 37° C. Culture medium from 10 cm dishes was removed via careful aspiration, removing as much FBS-containing medium as possible. Ten ml DMEM/-FBS was added and the mixture was incubated for 1 hour at 37° C.

After serum starvation for 1 hr at 37° C., the medium was removed. Antibody treatments and minus-Ab controls were set up with either 4.0 ml of the serially-diluted Ab-containing samples or DMEM/-FBS alone, and further incubated for another 1 hour at 37° C. to provide a total of 2 hours of serum starvation. The antibody pre-treatment and ligand stimulation is illustrated in TABLE 14.

TABLE 14

| Dish | Ab Pre-Treatment | Ligand Stimulation |
| --- | --- | --- |
| #1 | DMEM/-FBS (minus Ab) | medium alone |
| #2 | DMEM/-FBS (minus Ab) | CSF-1 |
| #3 | CLONE1.109 @ 1.0 μg/ml | medium alone |
| #4 | CLONE 1.2 @ 1.0 μg/ml | medium alone |
| #5 | CLONE 2.360 @ 1.0 μg/ml | medium alone |
| #6 | 3-4A4 @ 1.0 μg/ml | medium alone |
| #7 | M105 @ 1.0 μg/ml | medium alone |
| #8 | CLONE1.109 @ 1.0 μg/ml | CSF-1 |
| #9 | CLONE1.109 @ 0.1 μg/ml | CSF-1 |
| #10 | CLONE1.109 @ 0.01 μg/ml | CSF-1 |
| #11 | CLONE1.109 @ 0.001 μg/ml | CSF-1 |
| #12 | CLONE1.109 @ 0.0001 μg/ml | CSF-1 |
| #13 | CLONE1.2 @ 1.0 μg/ml | CSF-1 |
| #14 | CLONE1.2 @ 0.1 μg/ml | CSF-1 |
| #15 | CLONE1.2 @ 0.01 μg/ml | CSF-1 |
| #16 | CLONE1.2 @ 0.001 μg/ml | CSF-1 |
| #17 | CLONE1.2 @ 0.0001 μg/ml | CSF-1 |
| #18 | CLONE2.360 @ 1.0 μg/ml | CSF-1 |
| #19 | CLONE2.360 @ 0.1 μg/ml | CSF-1 |
| #20 | CLONE2.360 @ 0.01 μg/ml | CSF-1 |
| #21 | CLONE2.360 @ 0.001 μg/ml | CSF-1 |
| #22 | CLONE2.360 @ 0.0001 μg/ml | CSF-1 |
| #23 | 3-4A4 @ 1.0 μg/ml | CSF-1 |
| #24 | M105 @ 1.0 μg/ml | CSF-1 |

A fresh vial of CSF-1 (R&D Systems/216-MC/Lot CC093091) at 50 ng/μl (25 μg/vial) was reconstituted in 500 μl PBS (Gibco)/0.1% BSA (Sigma) and kept on ice. A 1:1000 dilution of CSF-1 stock (60 μl) was prepared into DMEM/-FBS (60 ml) approximately 5 minutes prior to the end of Ab-treatment. The 293T/c-fms cells were incubated with 50 ng/ml of CSF-1 for 5 minutes at 37° C. The supernatants were removed and 2 ml of cold lysis buffer (100 ml PBS/1% Triton, 100 μl 0.5 M EDTA, 100 μl 1.0 M NaF, 200 μl 0.5 M beta-glycerol phosphate, 500 μL sodium vanadate (100×), 10.0 μL okadaic acid (10,000×), and 4 tablets of Complete Protease Inhibitor) was added. The lysates (2.0 ml) were combined with 30 μl 50% Protein A/G Sepharose (Amersham) and incubated for 1 hour at 4° C. on a rocker platform to pre-clear non-specific binding proteins. After spinning the fractions, the supernatants were decanted onto fresh 15 ml tubes.

Whole cell lysates were immunoprecipitated with 2.5 μg/ml of anti-c-fms C20 (25 μl; at 0.2 μg/μl). The antibody-cell lysate mixtures were incubated overnight at 4° C. on the rocker platform to probe for total c-fms. Donkey anti-rabbit IgG/HRP (1:10,000 in blocking solution; Jackson) was added and further incubated for another 30 min at 4° C. The immunocomplexes were run on SDS-PAGE and immunoblotted. The Western blots were probed with either anti-pTyr 4G10 or anti-c-fms C20 for the detection of pTyr c-fms and total c-fms, respectively.

Figure 5:
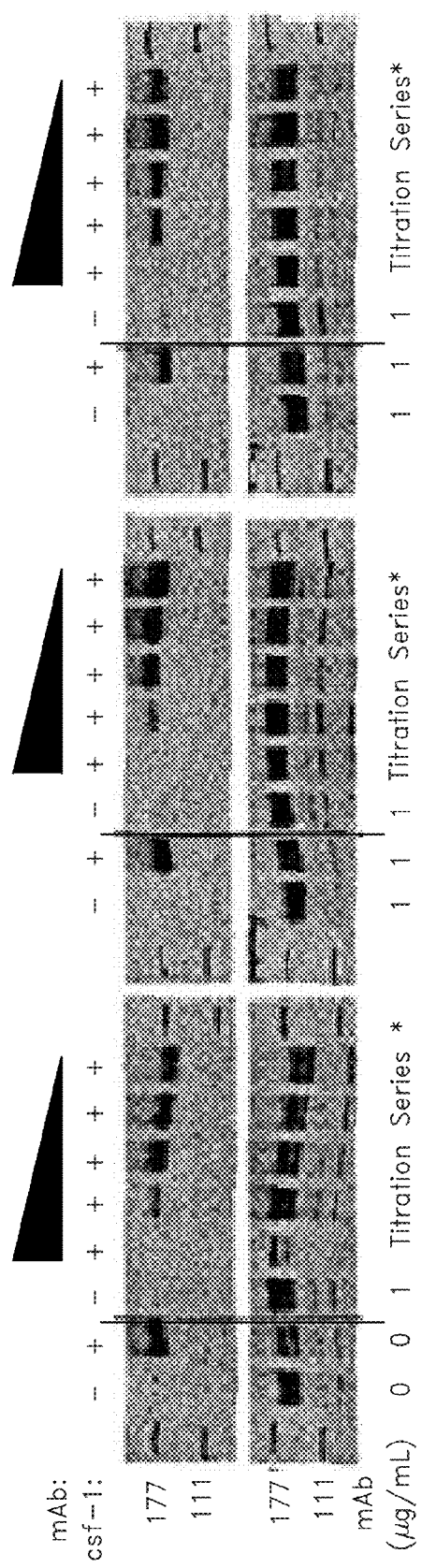
FIG. 5 shows the inhibition of ligand-induced pTyr-c-fms by the $IgG_2$ mAbs (PT, parent forms). 293T/c-fms cells were serum-starved for 1 hr and were treated with $IgG_2$ mAbs, 1.109, 1.2 or 2.360 (PT) and control mAbs anti-c-fms 3-4A4 (non-blocking) and anti-h-CD39 M105 (non-specific) in titration series (1.0 to 0.0001 µg/ml) or at 1.0 µg/ml (controls). Cells were then stimulated with 50 ng/ml CSF-1 for 5 min at 37° C. Whole cell lysates were immunoprecipitated with anti-c-fms C20 as described. Western blots were probed with either anti-pTyr 4G10 (top panel) or anti-c-fms C20 (bottom panel) for detection of pTyr/c-fms and total c-fms, respectively.

As shown in FIG. 5, $IgG_2$ clones (PT) 1.109, 1.2 and 2.360 exhibited the ability to inhibit ligand-induced pTyr/c-fms in the 293T3/c-fms assay system. Treatment with 0.1 μg/ml (8.3 nM) of $IgG_2$ clone (PT) 1.109 or 1.2 for 1 hour prior to CSF-1 stimulation reduced the phosphotyrosine signal to background levels. On the other hand, $IgG_2$ clone (PT) 2.360 produced equal inhibition at 1.0 μg/ml (83 nM). However, treatment of either antibodies at 0.01 μg/ml (0.83 nM) or less did not result in pTyr inhibition. In contrast, non-blocking anti-c-fms 3-4A4 and a non-relevant hCD39 M105 antibody, at the highest dose (1.0 μg/ml) had no effect on ligand-induced pTyr signal compared to the −mAb/+CSF-1 control. Thus, the inhibition of pTyr formation is directly linked to the blocking of CSF-1 binding.

Assuming that the 293T/c-fms transfectants used in these assays retained the previously measured cell-surface c-fms density of ~30,000 receptors/cell, ~3 million cells would bear ~90×10$^6$ c-fms, significantly less than the ~5.0×10$^{11}$ mAb in 4.0 ml pretreatment at 0.1 µg/ml. mAb present at 10,000 fold excess with respect to target makes saturation of available c-fms likely. This indicates that 8.3 nM clone (PT) 1.109 or 1.2 effectively blocked signaling of CSF-1 at 50 ng/ml or 1.0 nM, or an approximate 10:1 (mAb:c-fms) molar ratio. The threshold of effectiveness for clones (PT) 1.109 and 1.2 likely falls between 0.1 and 0.01 µg/ml (0.83-8.3 nM) in this assay system.

Treatment with 1.0 µg/ml IgG$_2$ (PT) mAbs in the absence of CSF-1 addition gave no pTyr signal above background levels. Previous experiments with all three IgG$_2$ (PT) forms used at 10 µg/ml also revealed no pTyr signal under the same conditions. There was no measured agonistic activity associated with these mAbs.

Example 7

Inhibition of Ligand-Induced pTyr/c-fms Using IgG2 PT and SM Forms

The purpose of this study was to determine if there is any functional changes in the germline-reverted (SM) forms of IgG$_2$ clones 1.109, 1.2 and 2.360, as compared with their respective parent forms (PT). To prepare the 293T/c-fms cells for this experiment, cells growing from five T175 (~80-90% confluent) were collected via 4 ml trypsin/flask and transferred to 75 ml DMEM with 10% FBS. To each 24×10 cm dish, 9 ml medium was added and inoculated with 3 ml of the collected cells. DMEM/-FBS medium was prepared, and/or warmed for 1 hour at 37° C. Culture medium was removed from 10 cm dishes via careful aspiration to remove as much FBS-containing medium as possible. DMEM/-FBS (10 ml) was added and the mixture was incubated for 1 hour at 37° C. Cold lysis buffer was prepared and kept on ice.

Monoclonal antibody titrations, as depicted in TABLE 15, were prepared and kept at room temperature.

TABLE 15

Titration of IgG$_2$ C-fms Monoclonal Antibodies

| mAb (µg/µL) | Volume Used | DMEM/-FBS |
|---|---|---|
| Clone 1.109 PT (0.41) | 14.6 µL | 6.0 ml |
| Clone 1.109 SM (G) (0.34) | 17.6 µL | 6.0 ml |
| Clone 1.109 SM (F/G) (0.58) | 10.3 µL | 6.0 ml |
| Clone 1.2 PT (1.57) | 3.8 µL | 6.0 ml |
| Clone 1.2 SM (0.35) | 17.1 µL | 6.0 ml |
| Clone 2.360 PT (0.41) | 14.6 µL | 6.0 ml |
| Clone 2.360 SM (0.55) | 10.9 µL | 6.0 ml |
| 3-4A4 (0.2) | 15 µL | 3.0 ml |

A series of serial antibody dilutions (300 µL+2.7 ml DMEM/-FBS) were tested within the range of 1.0 µg/ml to 0.1 µg/ml for each mAb. After 1 hour of serum starvation at 37° C., the medium was removed and antibody pre-treatments and minus-Ab controls were prepared similarly as described in Table 13. The antibody pretreatments and ligand stimulation is described in TABLE 16 hereinbelow:

TABLE 16

| Dish No. | Ab-pretreatment | Ligand Stimulation |
|---|---|---|
| 1 | DMEM/-FBS (minus Ab) | medium alone |
| 2 | DMEM/-FBS (minus Ab) | CSF-1 |
| 3 | 3-4A4 @ 1.0 µg/ml | CSF-1 |
| 4 | Clone 1.109 @ 1.0 µg/ml | medium alone |

TABLE 16-continued

| Dish No. | Ab-pretreatment | Ligand Stimulation |
|---|---|---|
| 5 | Clone 1.109 @ 1.0 µg/ml | CSF-1 |
| 6 | Clone 1.109 @ 0.1 µg/ml | CSF-1 |
| 7 | Clone 1.109 SM-G @ 1.0 µg/ml | medium alone |
| 8 | Clone 1.109 SM-G @ 1.0 µg/ml | CSF-1 |
| 9 | Clone 1.109 SM-G @ 0.1 µg/ml | CSF-1 |
| 10 | Clone 1.109 SM-F/G @ 1.0 µg/ml | medium alone |
| 11 | Clone 1.109 SM-F/G @ 1.0 µg/ml | CSF-1 |
| 12 | Clone 1.109 SM-F/G @ 0.1 µg/ml | CSF-1 |
| 13 | Clone 1.2 @ 1.0 µg/ml | medium alone |
| 14 | Clone 1.2 @ 1.0 µg/ml | CSF-1 |
| 15 | Clone 1.2 @ 0.1 µg/ml | CSF-1 |
| 16 | Clone 1.2 SM @ 1.0 µg/ml | medium alone |
| 17 | Clone 1.2 SM @ 1.0 µg/ml | CSF-1 |
| 18 | Clone 1.2 SM @ 0.1 µg/ml | CSF-1 |
| 19 | Clone 2.360 @ 1.0 µg/ml | medium alone |
| 20 | Clone 2.360 @ 1.0 µg/ml | CSF-1 |
| 21 | Clone 2.360 @ 0.1 µg/ml | CSF-1 |
| 22 | Clone 2.360 SM @ 1.0 µg/ml | medium alone |
| 23 | Clone 2.360 SM @ 1.0 µg/ml | CSF-1 |
| 24 | Clone 2.360 SM @ 0.1 µg/ml | CSF-1 |

Ligand-induced pTyr by anti-c-fms mAbs (SM forms) was performed as described in Example 6 for the PT forms.

Figure 6:
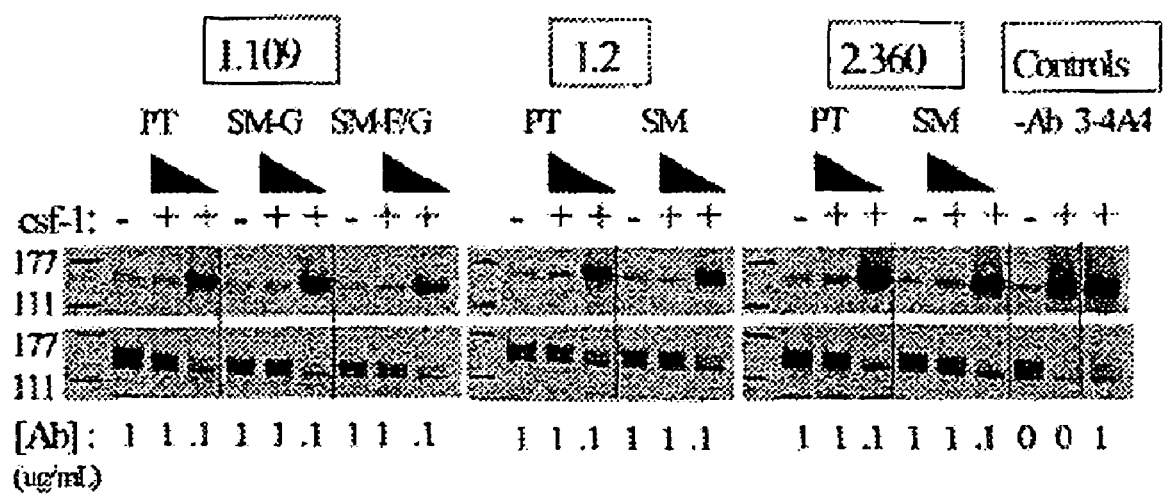
FIG. 6 compares the inhibition of ligand-induced pTyr-c-fms by $IgG_2$ mAbs (PT versus SM (somatic mutation cured) forms). 293T/c-fms cells were serum-starved for 1 hr and were treated with $IgG_2$ mAbs, 1.109, 1.2 or 2.360 (both PT or SM) and control mAbs anti-c-fms 3-4A4 (non-blocking) at 1.0 and 0.1 µg/ml. Cells were then stimulated with 50 ng/ml CSF-1 for 5 min at 37° C. and whole cell lysates were immunoprecipitated with anti-c-fms C20 as described. Western blots were probed with either anti-pTyr 4G10 (top panel) or anti-c-fms C20 (bottom panel) for detection of pTyr/c-fms and total c-fms, respectively.

Experiments using the 293T/c-fms cells to compare the effects of PT versus SM forms of the three IgG$_2$ mAbs at 1.0 and 0.1 µg/ml revealed no differences in the ability to inhibit ligand-induced pTyr/C-fms (see FIG. 6). Clones 1.109 and 1.2 (both PT and SM forms) showed inhibition at lower concentrations than with the 2.360 (PT and SM forms).

Clones 1.109 and 1.2 (PT or SM) were able to prevent ligand-induced pTyr/c-fms in vitro when 293T/c-fms cells were treated with 0.1 µg/ml (8.3 nM) or greater mAb for 1 hour at 37° C. prior to the addition of CSF-1 at 50 ng/ml (1.0 nM). The ability of these monoclonal antibodies to block the formation of pTyr/c-fms would lead to the inhibition of CSF-1 signaling, monocyte migration and, subsequently, accumulation of TAMs. No agonistic activity appeared to be associated with these mAbs, to avoid activating the receptor in a non-CSF-1 dependent manner. The mAbs showed no agonistic activity when used at a concentration of 1.0 µg/ml and as high as 10 µg/ml (data not shown).

Accordingly, the mAbs were able to prevent ligand-induced pTyr/c-fms in vitro.

Example 8

Immunoprecipitation of C-fms by Anti-c-fms mAbs

The ability of the IgG$_2$ anti-c-fms mAbs to bind and immunoprecipitate c-fms was achieved by using the stably-transfected 293T/c-fms cells as described above. Whole-cell lysates of unstimulated cells were immunoprecipitated overnight with each mAb (PT and SM) and anti-c-fms C20 antibody and examined via Western blot with C20 Ab (Santa Cruz Biotechnology, Inc.) as the probe for detection of c-fms. C-fms was immunoprecipitated by monoclonal antibodies. Lysates of stably transfected 293T/c-fms grown at 37° C./5% CO$_2$ to 75% confluency were prepared and combined with the monoclonal antibodies, as shown in TABLE 17.

TABLE 17

| Tube No. | Ab (µg/µL) | Ab (µL) |
|---|---|---|
| 1 | Clone 1.109 (0.41) | 6.1 |
| 2 | Clone 1.109 SM F/G (0.58) | 4.3 |
| 3 | Clone 1.2 (1.57) | 1.6 |
| 4 | Clone 1.2 SM (0.35) | 7.1 |
| 5 | Clone 2.360 (0.41) | 6.1 |

TABLE 17-continued

| Tube No. | Ab (µg/µL) | Ab (µL) |
|---|---|---|
| 6 | Clone 2.360 SM (0.52) | 4.8 |
| 7 | C20 (0.2) | 12.5 |
| 8 | C19 (0.2) | 12.5 |

Figure 7:
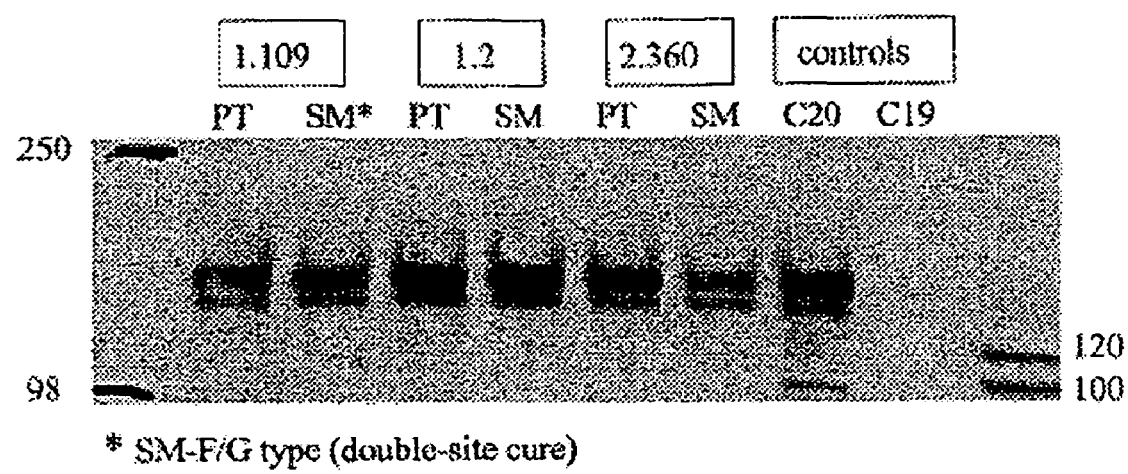
FIG. 7 shows a western blot of an immunoprecipitation of c-fms by $IgG_2$ mAbs (PT versus SM forms). Whole cell lysates of unstimulated 293T/c-fms cells were immunoprecipitated overnight at 4° C. using $IgG_2$ mAbs, 1.109, 1.2 or 2.360 (both PT or SM forms) and anti-c-fms C20 at 2.5 µg/ml. The western blot was probed with anti-c-fms C20 and anti-rabbit IgG/HRP.

Immunoprecipitation experiments using untreated whole-cell lysates of stable 293T/c-fms demonstrated comparable ability of the various mAbs (except 2.360 SM) to bind and precipitate c-fms, in comparison to the polyclonal anti-c-fms C20 control; clone 2.360-SM, however, exhibited a reduced capacity in this assay (see FIG. 7).

Example 9

Immunoprecipitation of SNP-Variants by $IgG_2$ mAbs

Single nucleotide polymorphisms or SNPs are DNA sequence variations that occur when a single nucleotide (A, G, T, or C) in the genomic sequence has been changed. SNPs may occur in both the coding and non-coding regions of the human genome. Many SNPs have no impact on cell function, but scientists consider other SNPs could predispose people to disease or have an effect in their drug response. Variations in DNA sequence can have a major influence on how a person responds to a disease, environmental insults (e.g., bacteria, viruses, toxins, and chemicals), drugs and other therapies. For this reason, SNPs are of great value to biomedical research, pharmaceutical product development and medical diagnosis. Furthermore, SNP maps will enable the scientist in the identification of multiple genes that are associated with complex diseases such as cancer, diabetes, and vascular diseases.

The extracellular region of human c-fms can be divided into five immunoglobulin (Ig)-like repeated domains (designated A through E). See, for example, Hampe, A. et al. (1989) Oncogene Res. 4:9-17 for a discussion of the human domains. See, for example, Wang, et al. (1993) Molecular and Cell Biology 13:5348-5359 for the corresponding domains in the mouse protein. Domains A-C had been shown to comprise the CSF-1 binding region, while domain D had been shown to help regulate receptor dimerization upon binding of ligand. Three naturally-occurring SNP-variants of human c-fms were prepared, namely, A245S, V279M in Ig-Domain C and H362R in Ig-Domain D (see FIG. 8 for amino acid sequence of the extracellular domain of c-fms). These SNPs are found either in or near the CSF-1 binding region and examination by Western blots probed with anti-c-fms H-300 (a rabbit polyclonal antibody raised against amino acids 11-310 mapping near the N-terminus of human c-fms/CSF-1R; Santa Cruz Biotech., Inc., Cat. No. sc-13949).

To study how human c-fms SNP variants interact with the various c-fms Abs provided herein, transiently-transfected 293T cells expressing the three types of c-fms SNP variants, as discussed above, and wildtype (WT) c-fms (as well as an irrelevant, vector-matched control) were used to assess the ability of each anti-c-fms mAb to bind SNP-variants via immunoprecipitation.

293T cells were transfected in duplicate 10-cm dishes with c-fms A245S, V279M, H362R, WT c-fms and an irrelevant control construct in the mammalian expression vector pCIneo and grown for 48 hours at 37° C./5% $CO_2$. Cell lysates were prepared as described above. Anti-c-fms mAbs and polyclonal anti-c-fms C20 or anti-c-kit C19 at 2.5 µg/ml in 1.0 ml aliquots were added to each lysate as illustrated in TABLE 18.

TABLE 18

| Tube | Transfectant | IP Ab (µg/µL) | IP Ab (µL) |
|---|---|---|---|
| 1 | c-fms | Clone 1.2 (1.57) | 1.6 |
| 2 | c-fms | Clone 1.2 SM (0.5) | 5.0 |
| 3 | c-fms | Clone 1.109 (0.41) | 6.1 |
| 4 | c-fms | Clone 1.109 SM (0.5) | 5.0 |
| 5 | c-fms | Clone 2.360 (0.41) | 6.1 |
| 6 | c-fms | Clone 2.360 SM (0.5) | 5.0 |
| 7 | c-fms | C20 (0.2) | 12.5 |
| 8 | c-fms | C19 (0.2) | 12.5 |
| 9 | A245S | Clone 1.2 (1.57) | 1.6 |
| 10 | A245S | Clone 1.2 SM (0.5) | 5.0 |
| 11 | A245S | Clone 1.109 (0.41) | 6.1 |
| 12 | A245S | Clone 1.109 SM (0.5) | 5.0 |
| 13 | A245S | Clone 2.360 (0.41) | 6.0 |
| 14 | A245S | Clone 2.360 SM (0.5) | 5.0 |
| 15 | A245S | C20 (0.2) | 12.5 |
| 16 | V279M | Clone 1.2 (1.57) | 1.6 |
| 17 | V279M | Clone 1.2 SM (0.5) | 5.0 |
| 18 | V279M | Clone 1.109 (0.41) | 6.1 |
| 19 | V279M | Clone 1.109 SM (0.5) | 5.0 |
| 20 | V279M | Clone 2.360 (0.41) | 6.1 |
| 21 | V279M | Clone 2.360 SM (0.5) | 5.0 |
| 22 | V279M | C20 (0.2) | 12.5 |
| 23 | H362R | Clone 1.2 (1.57) | 1.6 |
| 24 | H362R | Clone 1.2 SM (0.5) | 5.0 |
| 25 | H362R | Clone 1.109 (0.41) | 6.1 |
| 26 | H362R | Clone 1.109 SM (0.5) | 5.0 |
| 27 | H362R | Clone 2.360 (0.41) | 6.1 |
| 28 | H362R | Clone 2.360 SM (0.5) | 5.0 |
| 29 | H362R | C20 (0.2) | 12.5 |
| 30 | Minus control | Clone 1.2 (1.57) | 1.6 |
| 31 | Minus control | Clone 1.2 SM (0.5) | 5.0 |
| 32 | Minus control | Clone 1.109 (0.41) | 6.1 |
| 33 | Minus control | Clone 1.109 SM (0.5) | 5.0 |
| 34 | Minus control | Clone 2.360 (0.41) | 6.1 |
| 35 | Minus control | Clone 2.360 SM (0.5) | 5.0 |
| 36 | Minus control | C20 (0.2) | 12.5 |
| 37 | Minus control | C19 (0.2) | 12.5 |

The cells were incubated overnight at 4° C. on a rocker as described in Example 6.

Figure 9:
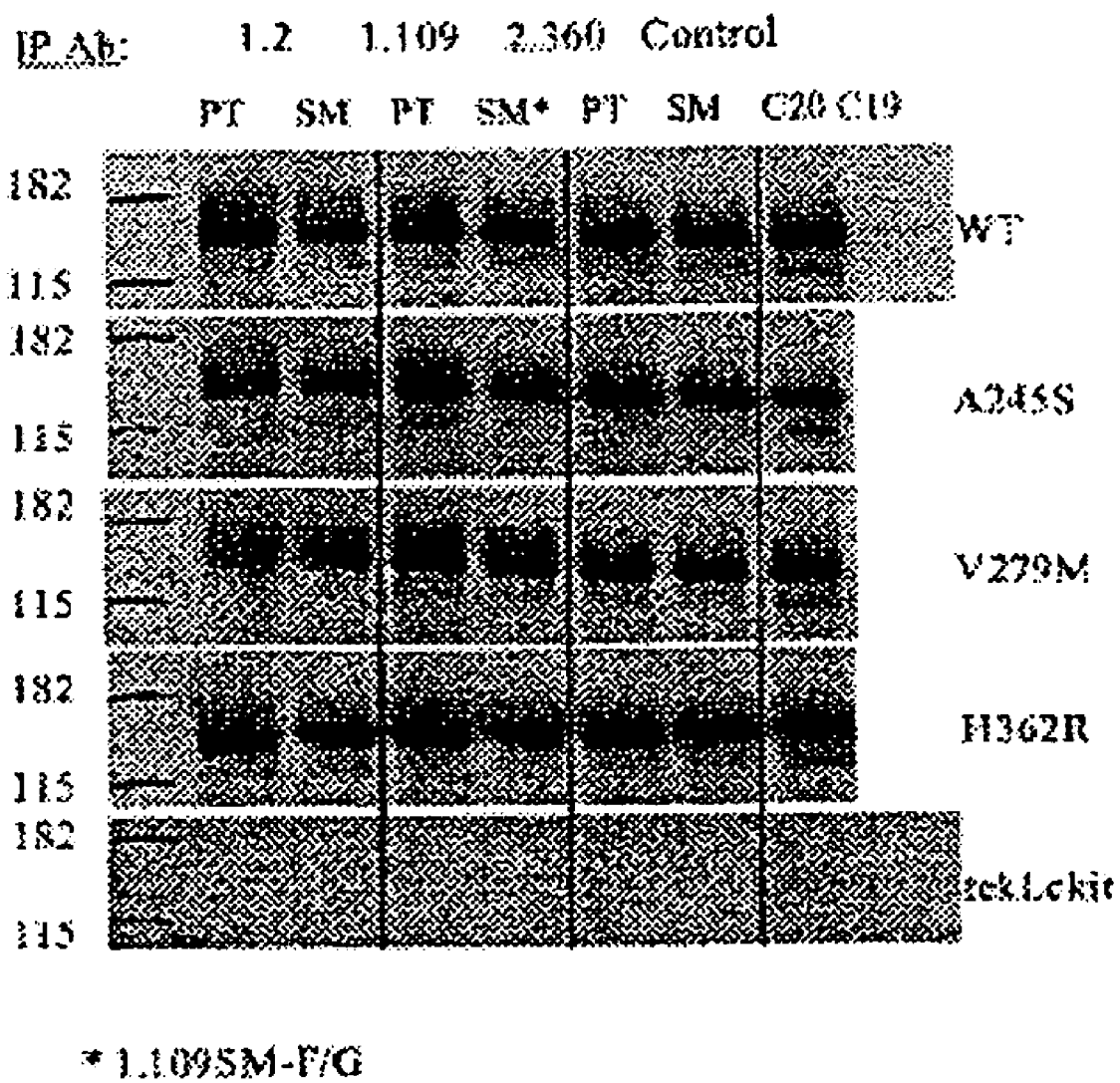
FIG. 9 shows western blots of immunoprecipitation of c-fms SNPs. Expression constructs of the indicated c-fms SNPs were constructed and transiently expressed in 293T/c-fms cells. Unstimulated whole cell lysates were then immunoprecipitated with each mAb and control Abs. Western blots were probed with c-fms H300 and anti-rabbit IgG/HRP.

The antibodies revealed no loss of ability to bind the SNP forms compared to WT control (FIG. 9). The mAbs appear to have the capability of binding to the range of naturally occurring c-fms variants.

Immunoprecipitation from untreated whole-cell lysates of stable 293T/c-fms demonstrated equal ability of all of the various mAbs (except 2.360 SM) to bind and precipitate c-fms compared to polyclonal anti-c-fms control; clone 2.360 SM exhibited a clearly reduced capacity in this assay. Examination of the ability of the various mAbs to immunoprecipitate c-fms and SNP variants from transiently-transfected 293T/c-fms cells revealed no loss of ability to bind the SNP forms. The ability of the various mAbs to bind the c-fms SNPs indicated that they recognize c-fms proteins across the spectrum of variants known to exist for humans.

Example 10

Inhibition of $^{125}I$-hCSF-1 Binding by Anti-c-fms mAbs

The affinity of anti-c-fms mAbs to cell surface expressed human c-fms was determined by measuring inhibition of $^{125}I$-hCSF-1 binding to AML-5 cells.

Recombinant hCSF-1 (Amgen) was iodinated using $^{125}I$ (Amersham) and IODO-GEN® (Pierce). Seventy-five µl PBS, 10 µg hCSF-1, and 1 mCi $^{125}I$ were added to an IODO-GEN® pre-coated iodination tube and left on ice for 15 minutes. The mixture was transferred to an equilibrated 2 ml P6 column where $^{125}I$-hCSF-1 was separated from free $^{125}I$ by gel filtration. Fractions containing iodinated hCSF-1 were pooled, then diluted to a concentration of 100 nM in binding media (RPMI-1640 with 2.5% bovine albumin Fraction V, 20 mM Hepes, and 0.2% sodium azide, pH 7.2). A specific activity of $4.8\times10^{15}$ cpm/mmol was calculated based on the initial protein concentration of hCSF-1 and a recovery of 80% from a control experiment in which an aliquot of $^{125}$I-hCSF-1 was put through the iodination protocol with omission of additional $^{125}$I.

A saturation radioligand binding experiment was performed in conjunction with each inhibition assay in order to determine both a $K_D$ and $K_I$ for hCSF-1 binding to c-fms expressed on the surface of AML-5 cells. Mixtures were set up in 96-well round-bottom microtiter plates with total volumes of 150 µl/well. All reagents were diluted in binding media containing 0.2% sodium azide and experiments were conducted at 4° C. to minimize potential receptor internalization and shedding.

For the saturation binding assay, $^{125}$I-hCSF-1 was serially diluted 2-fold, starting at a concentration of ~1.7 nM and going out 12 wells to a concentration of ~1.5 pM. Nonspecific binding was measured at a single concentration of $^{125}$I-hCSF-1 (~80 pM, in triplicate) in the presence of a 1,000-fold molar excess of unlabeled hCSF-1, and assumed to be a linear function of the concentration of radiolabeled hCSF-1 present.

For the $^{125}$I-hCSF-1 inhibition assay, unlabeled hCSF-1 was set up at a starting concentration of 5 nM. Starting concentrations for anti-c-fms 1.2, 1.109, and 2.360 (PT and SM for each) were 0.312 nM, 1.25 nM, and 20 nM, respectively. Each sample was serially diluted 2-fold out 15 wells. Triplicate wells of binding media alone and triplicate wells of 1,000-fold molar excess unlabeled hCSF-1 were set up at the beginning, middle, and end of the assay as controls to determine percent inhibition. A single concentration of $^{125}$I-hCSF-1 (~9 pM) was added to each well.

AML-5 cells were washed twice with PBS, and added to each assay plate at $1\times10^5$ cells/well just prior to incubation.

Both assays were incubated at 4° C. on a miniorbital shaker for 4 hours, the length of time needed to reach equilibrium as determined in time course experiments. Two 60 µl aliquots of each incubation mixture were transferred to chilled 400 µl polyethylene centrifuge tubes containing 200 µl phthalate oil and spun for 1.5 minutes in a 4° C. tabletop microfuge (Sorvall,) at 9615×g to separate cell associated $^{125}$I-hCSF-1 from free $^{125}$I-hCSF-1. The oil tubes were cut, and each cell pellet and supernatant collected in individual 12×75 mm glass tubes and loaded on a COBRA gamma counter (Packard Instrument Company) for cpm measurements. Cpm from duplicate aliquots taken from each well were averaged for analysis.

Saturation binding data were fit to a simple 1-site binding equation via nonlinear regression in Prism version 3.03 (GraphPad Software, Inc.) to obtain an apparent mean $K_D$ of 46 pM for $^{125}$I-hCSF-1 binding to cell surface expressed human c-fms. Inhibition data were fit to a single site competitive inhibition equation via nonlinear regression in Prism using the $K_D$ value for $^{125}$I-hCSF-1 obtained in the concurrent binding assay to generate a $K_I$ value for unlabeled hCSF-1 (apparent mean $K_I$=17.8 pM) as well as for each anti-c-fms mAb. Mean $K_I$ values from 2 experiments were reported (see, TABLE 13).

Example 11

Determination of Rate and Affinity Constants for Monomeric C-fms Binding to Anti-c-fms mAbs The affinity of human c-fms (1-512). pHIS (Amgen) for the anti-c-fms mAbs was measured by Biacore. Experiments were conducted at 25° C. using a Biacore 3000 instrument (Biacore AB) equipped with a CM4 sensor chip. Sensor chips, amine coupling reagents (EDC (1-ethyl-3(3-dimethylaminopropyl)-carbodiimide hydrochloride), NHS (N-hydroxysuccinimide), and ethanolamine-HCl, pH 8.5), 10 mM sodium acetate, pH 5.5, HBS-EP (0.01 M HEPES pH 7.4, 0.15 M NaCl, 3 mM EDTA, 0.005% v/v Surfactant P20), and 10 mM glycine-HCl, pH 1.5 were purchased from Biacore AB. Bovine serum albumin (BSA, Bovuminar Standard Powder) was purchased from Serological Corporation. AffiniPure Goat Anti-Human IgG, Fcγ Fragment Specific was purchased from Jackson ImmunoResearch Laboratories.

An anti-human IgG, Fcγ specific capture antibody was covalently immobilized to a CM4 chip using standard amine-coupling chemistry with HBS-EP as the running buffer. Briefly, each flow cell was activated for 7 minutes with a 1:1 (v/v) mixture of 0.1 M NHS and 0.4 M EDC at a flow rate of 5 µl/min. Goat anti-human IgG at 28 µg/ml in 10 mM sodium acetate, pH 5.5 was immobilized at a density of ~2700 RUs. Residual reactive surfaces were deactivated with a 7 minute injection of 1 M ethanolamine at 5 µl/min. Three 50 µl injections of 10 mM glycine HCl, pH 1.5 at 100 µl/min were used to remove any remaining noncovalently bound capture antibody and to condition each surface. The running buffer was switched to HBS-EP with 0.1 mg/ml BSA for all remaining steps.

Anti-c-fms 1.2 or 1.2 SM at 0.25 µg/ml was injected over goat anti-human IgG, Fcγ in one flow cell for 2 minutes at 10 µl/min to obtain a surface density of ~47 RUs. Another flow cell with goat anti-human IgG, Fcγ alone was used as a reference surface. Each assay started with ten cycles of buffer as the analyte to stabilize the signal. Human monomeric c-fms (1-512).pHIS samples were prepared at concentrations of 30, 10, 3.33, 1.11, 0.37, and 0.12 nM in triplicate and injected along with 6 buffer blanks in random order at 100 µl/min over both the captured anti-c-fms and reference surfaces. Each complex was allowed to associate for 2 minutes, and dissociate for 5 minutes. The surfaces were regenerated after each c-fms or buffer injection with a 30-second pulse of 10 mM glycine HCl, pH 1.5 at 100 µl/min, followed by a 30-second injection of buffer.

Other anti-c-fms antibodies were tested in a similar manner, but changes were made to the protocol to account for differences in binding characteristics. Anti-c-fms 1.109 and 1.109 SM were each injected over goat anti-human IgG at 0.5 µg/ml for 1.5 minutes at 10 µL/min to obtain surface densities of 59 and 91 RUs, respectively. Human c-fms (1-512).pHIS samples were prepared at concentrations of 10, 3.33, 1.11, 0.37, 0.12, and 0.041 nM for anti-c-fms 1.109 binding, and the same set with the exception of the 0.041 nM sample was prepared for anti-c-fms 1.109 SM binding. Human monomeric c-fms (1-512). pHIS was allowed to dissociate from anti-c-fms 1.109 for 20 mins, and 1.109 SM for 15 mins. Anti c-fms 2.360 and 2.360 SM were each injected over goat anti-human IgG, Fcγ at 1 µg/ml for 1.5 or 2 minutes, respectively, at 10 µl/min to obtain surface densities of ~100 RUs. Human c-fms (1-512)/pHIS samples were prepared at concentrations of 30, 10, 3.33, 1.11, and 0.37 nM for anti-c-fms 2.360 binding, and the same set with the addition of a 0.12 nM sample was prepared for anti-c-fms 2.360 SM binding. Human monomeric c-fms (1-512).pHIS was allowed to dissociate from anti-c-fms 2.360 for 8 mins, and 2.360 SM for 5 mins.

Data was double referenced by subtracting the reference surface responses to remove bulk refractive index changes, and then subtracting the averaged buffer blank response to remove systematic artifacts from the experimental flow cells.

The data was processed and globally fit to a 1:1 interaction model with local Rmax in BIAevaluation (version 4.1, Biacore AB) to obtain kinetic rate constants $k_a$ and $k_d$. Though data from triplicate samples at each concentration of c-fms was collected, only data from duplicate samples could be analyzed due to the parameter number restrictions inherent to BIAevaluation software. The $K_D$ was calculated from the quotient $k_d/k_a$. The results are shown in TABLE 19. Data from the various examples provided above are summarized in Table 20.

TABLE 19

Binding Affinity Of Anti-c-fms mAbs To Soluble Monomeric C-fms Protein As Measured By Biacore 3000

| Antibody | $k_a$ (1/Ms) | $k_d$ (1/s) | $K_D$ (pM) |
|---|---|---|---|
| 1.2 | $3.84 \times 10^6$ | $1.98 \times 10^{-3}$ | 516 |
| 1.2 SM* | $3.62 \times 10^6$ | $1.99 \times 10^{-3}$ | 548 |
| 1.109 | $2.54 \times 10^6$ | $1.29 \times 10^{-4}$ | 51 |
| 1.109 SM* | $2.66 \times 10^6$ | $2.71 \times 10^{-4}$ | 102 |
| 2.360 | $1.25 \times 10^6$ | $6.67 \times 10^{-4}$ | 535 |
| 2.360 SM* | $7.94 \times 10^5$ | $9.55 \times 10^{-4}$ | 1200 |

*SM = Somatic mutations removed.

TABLE 20

Summary of mAbs 1.2, 1.109, and 2.360

| Monoclonal Antibody | AML-5 proliferation $IC_{50}$ (pM)* | Cynomolgus Bone Marrow Proliferation $IC_{50}$ (pM) | Inhibition ($K_I$) of $^{125}$I-CSF-1 Binding to AML-5 Cells (pM) | Binding Affinity ($K_D$) to c-fms by Biacore (pM) | IP from 293T Cells Expressing Wt c-fms & SNPs | Inhibition on Ligand Induction of pTyr of c-fms |
|---|---|---|---|---|---|---|
| 1.2 | 27 | 78 | 8.5 | 516 | +++ | +++ |
| 1.2 SM** | 12 | 81 | 11.5 | 548 | +++ | +++ |
| 1.109 | 27 | 16 | 13.5 | 51 | +++ | +++ |
| 1.109 SM** | | 23 | 9.7 | 102 | +++ | +++ |
| 2.360 | 60 | 67 | ~160 | 535 | +++ | ++ |
| 2.360 SM** | | | ~900 | 1200 | ++ | ++ |

*Primary cell assay on human target;
**SM = Somatic mutations removed.

Example 12

Figure 10:
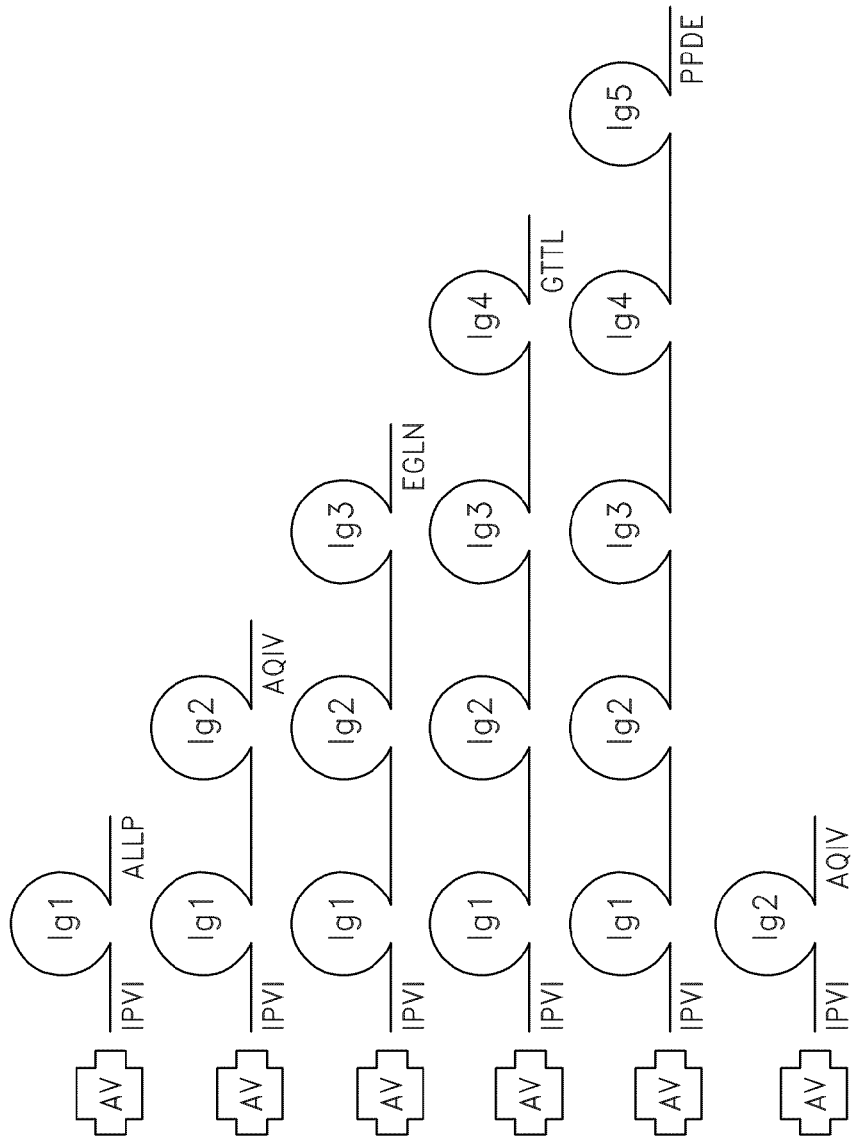
FIG. 10 shows the diagram of human c-fms ECD (extracellular domain) and truncated constructs. The avidin tag is fusioned in frame at the N terminus of c-fms. The first and last four amino acids are indicated for each c-fms constructs.

Epitope Mapping of Anti C-fms Antibodies IgG$_2$ Clones 1.109, 1.2 and 2.36 Preparation of C-fms-Avidin Fusion Constructs The c-fms avidin fusion expression constructs are shown in FIG. 10. To express each fusion protein, the coding sequence for human c-fms extracellular domain was PCR amplified and cloned into pCEP4-Avidin(N), such that the c-fms sequence was joined to the C-terminus of the chicken avidin sequence using the restriction enzyme XhoI. The signal sequence of c-fms was not included, as the signal sequence for chicken avidin was left intact in the pCEP4-avidin(N) vector.

As noted above, the extracellular domain contains five different Ig-like regions. The different domains in human c-fms are discussed, for example, in Hampe et al., 1989, *Oncogene Res.* 4:9-17. For a discussion of the corresponding domains in mouse c-fms, see, for example, Wang et al., 1993, *Molecular and Cell Biology* 13:5348-5359. The following different avidin constructs were prepared to correspond with the indicated Ig-like domain (see, FIG. 8 for the amino acid sequence of the extracellular domain; SEQ ID No 1).

Signal: amino acids 1-19
Ig-like 1 domain: amino acids 20-126
Ig-like 1-2 domain: amino acids 20-223
Ig-like 1-3 domain: amino acids 20-320
Ig-like 1-4 domain: amino acids 20-418
Ig-like 1-5 domain: amino acids 20-512
Ig-like 2 domain only: amino acids 85-223.

Thus, to create specific regions of human c-fms (truncations) for epitope mapping, PCR amplification was performed to target the following amino acids: Ig-like loop 1 (IPVI-ALLP), Ig-like loops 1 and 2 (IPVI-AQIV), Ig-like loops 1-3 (IPVI-EGLN), Ig-like loops 1-4 (IPVI-GTLL), and Ig-like loops 1-5 (IPVI-PPDE), as well as Ig-like loop 2 alone (TEPG-AQIV). The sequences identified in the parentheses indicate the starting and ending sequence respectively for each of the domains (see FIG. 8). The particular regions indicated were selected to keep the cysteine residues involved in disulfide bond formation, as these bonds are important in maintaining the native three-dimensional structure of the domains. Furthermore, the construct for the Ig-like loop 2 alone includes some sequence from the Ig-like loop 1 for the same reason. Consequently, the starting and ending amino acids of the domains that are listed differ somewhat from the domain regions specified in the articles by Hampe and Wang listed above.

Expression of Avidin Fusion Proteins

Expression of avidin fusion proteins was achieved by transient transfection of human 293T adherent cells in T75 tissue culture flasks. Cells were grown and maintained in DMEM (high glucose) with 10% dialyzed FBS and 1× Pen-strep-glutamine (growth medium), at 37° C. and 5% $CO_2$. Approximately $3 \times 10^6$ 293T cells were inoculated into T75 flasks containing 15 ml of growth medium and grown overnight for approximately 20 hours. Cells were then transfected with pCEP4-Avidin(N)-c-fms constructs. In each flask, 15 µg of DNA was mixed with 75 µl of Lipofectamine 2000 (Invitrogen) in the presence of Opti-MEM medium (Invitrogen) and the complex was incubated for 20 minutes. The transfection complex was inoculated into the corresponding flask and incubated at 37° C. for 4-5 hours in Opti-MEM media. At the end of the incubation time, the Opti-MEM medium was replaced with fresh growth medium. Approximately 48 hours post-transfection, the conditioned media was harvested and centrifuged at 2000×g for 10 minutes at 4° C. to remove cells and debris, and transferred to 50 ml tubes. A control flask was also made following the same protocol, but no DNA was used (mock transfection), yielding negative control conditioned media for binding experiments.

Detection of Fusion Proteins

The concentration of each c-fms avidin fusion protein was determined using a quantitative FACS based assay. The c-fms avidin fusion proteins were captured on 6.7 μm biotin polystyrene beads (Spherotech, Inc., Libertyville Ill.). 1× conditioned media (20 and 200 μl) were added to 5 μl (~3.5×10$^5$) beads, and incubated for 1 hr at room temperature with rotation. Conditioned media was removed by centrifugation and samples were washed with PBS containing 0.5% BSA (BPBS). The avidin beads were stained with 200 μl of a 0.5 μg/ml solution of a goat FITC-labeled anti-avidin antibody (Vector Labs, Burlingame, Calif.) in BPBS for 45 minutes at room temperature covered by foil. Following incubation, the beads were recollected by centrifugation, washed with BPBS, and resuspended for analysis in 0.5 ml BPBS. The FITC fluorescence was detected using a FACScan (Becton Dickinson Bioscience, Franklin Lakes, N.J.). The signal was converted to protein mass using a standard curve derived with rAvidin. For epitope mapping, biotin beads were loaded with ~100 ng of c-fms avidin fusion protein per 3.5×10$^5$ beads and brought up to volume with growth medium.

Antibody Binding FACS Assay

Biotin-coated polystyrene beads (Spherotech, Inc.) loaded with normalized amounts of C-FMS subdomain fusion proteins were mixed with 1 μg of FITC conjugated anti c-fms monoclonal antibody (1.109, 1.2 and 2.36) in 0.2 ml of BPBS. After incubation for 1 hr at room temperature, 3 ml washing buffer (BPBS) was added and the antibody-beads complexes were collected by centrifugation for 5 min at 750×g. The pellet was washed in 3 ml of BPBS. The antibody bound to avidin-bead complexes was detected by FACS (Becton Dickinson) analysis. The mean (X) fluorescent intensity was recorded for each sample.

Antibody Competition Assay

To prepare for labeling with fluorescein, the monoclonal antibodies were dialyzed or resuspended at a concentration of 1 mg/ml in PBS (pH 7.4). Label ([6-fluorescein-5-(and-6)-carboxamido] hexanoic acid, succinimidyl ester 5(6)-SFX) mixed isomers from Molecular Probes (F-2181) was added to the protein at a molar ratio 9.5:1 (label:protein) from a label stock of 5 mg/ml in DMSO. The mixture was incubated at room temperature for 1 hour in the dark. The labeled antibody was separated from the free label by dialysis in PBS. For each competition experiment, a binding reaction was assembled that contained a 20-fold excess (20 μg/ml) of unlabeled competitor antibody, 3.5×10$^5$ biotin beads coated with the avidin fusion protein in BPBS. The FITC-labeled antibody (1 μg/ml) was added after a 30 min pre-incubation of unlabeled competitor antibody. The process followed the one color method from this point forward.

Figure 11:
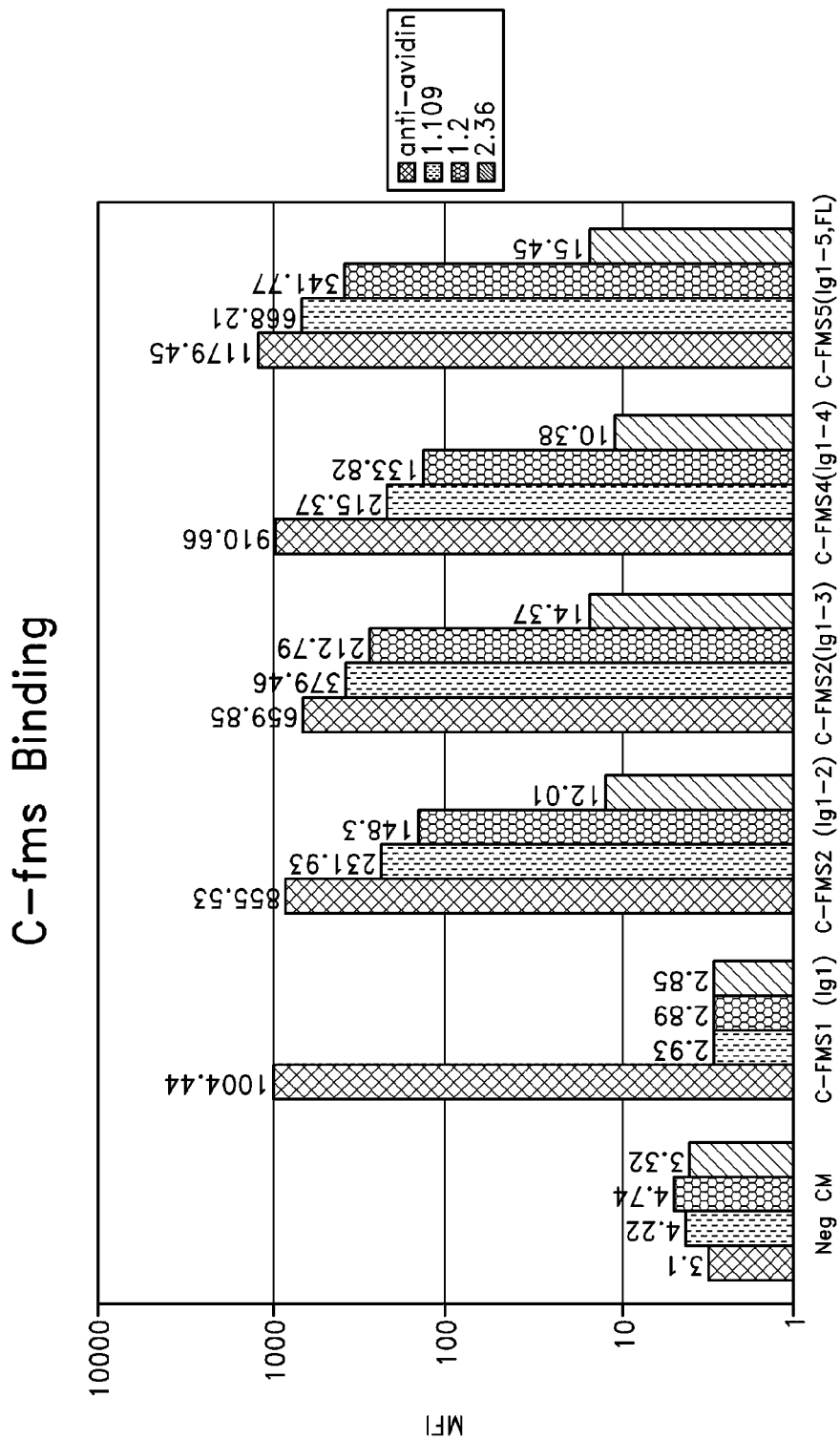
FIG. 11 demonstrates the binding of FITC labeled anti-avidin, 1.109, 1.2 and 2.360 c-fms antibodies to c-fms ECD and truncated avidin fusion protein.
Figure 12:
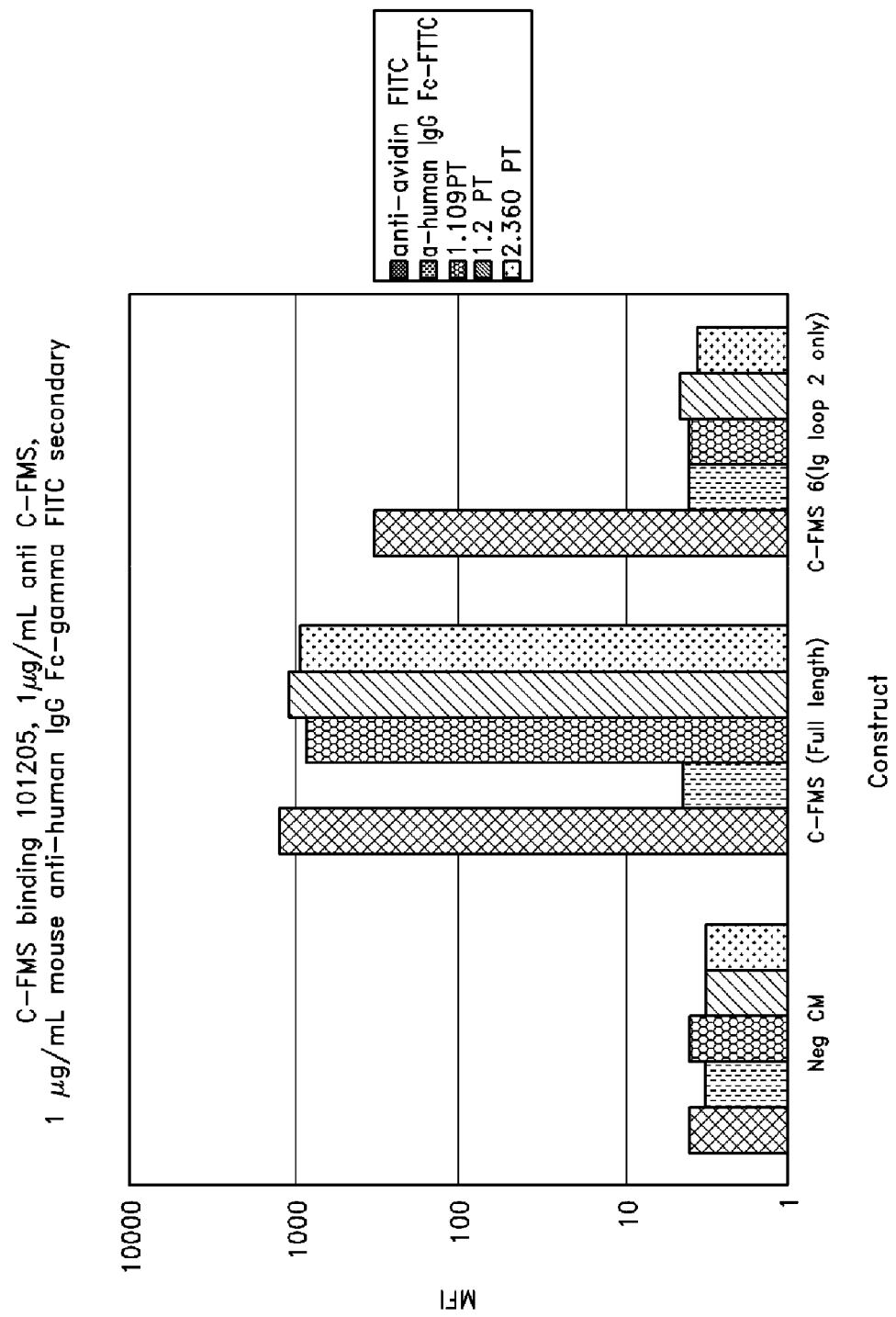
FIG. 12 shows the binding of anti-avidin FITC, control antibody and anti-c-fms antibodies (FITC labeled) to full length c-fms and Ig-like loop 2 (alone) fusion protein.

All the fusion proteins (FIG. 11) expressed in 293T cells can be detected with FITC-labeled anti-avidin antibody by FACScan. To determine which c-fms Ig-like domain is the antibody-binding site, all six fusion proteins were used in a binding assay. The antibody clones 1.109, 1.2 and 2.36 bind to the human c-fms subdomain Ig-like1-2, Ig-like1-3, Ig-like1-4 and Ig-like1-5 fusion proteins. They do not bind to the single domain c-fms Ig-like1 and Ig-like2 fusion proteins. For comparison, human c-fms ECD is used as a positive control (FIGS. 11 and 12). These results indicate that the epitopes of these three antibodies are mainly located at the N-terminus Ig-like loop 1 and Ig-like loop 2 of human c-fms, and require the presence of both the Ig-like loop 1 and the Ig-like loop 2 regions. The results also indicate that the antibody may not directly block the high-affinity binding site of the ligand which is mainly located at Ig-like loop 3. It may indirectly affect the ligand binding due to Ig-like loops 1 and 2, both of which are critical regions for ligand binding (Wang, et al., 1993, *Molecular Cell Biology* 13:5348-5359).

Figure 13:
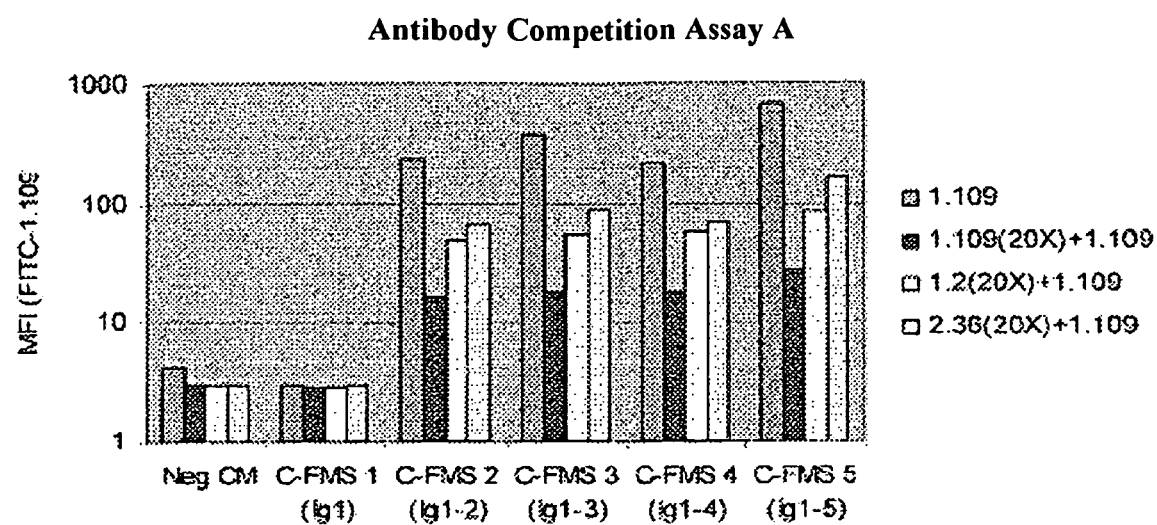
FIG. 13 exhibits the competition assay with 20× unlabeled 1.109, 1.2, and 2.360 c-fms antibodies, followed by 1 µg/ml concentration of FITC labeled 1.109.
Figure 14:
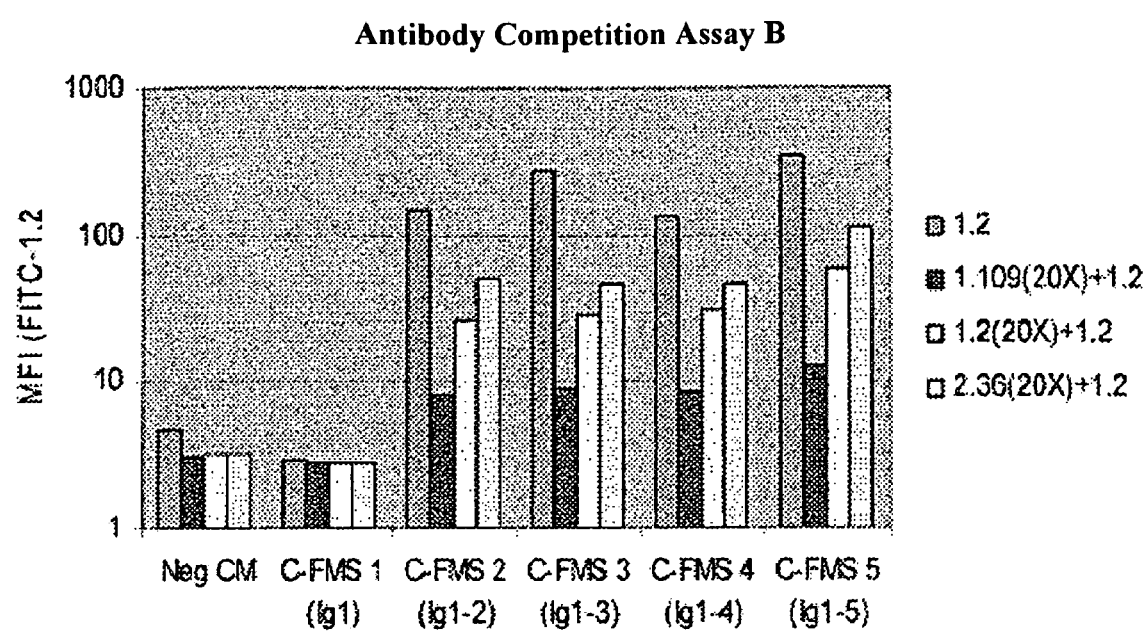
FIG. 14 shows the competition assay with 20× unlabeled 1.109, 1.2, and 2.360 c-fms antibodies, followed by 1 µg/ml concentration of FITC labeled 1.2.
Figure 15:
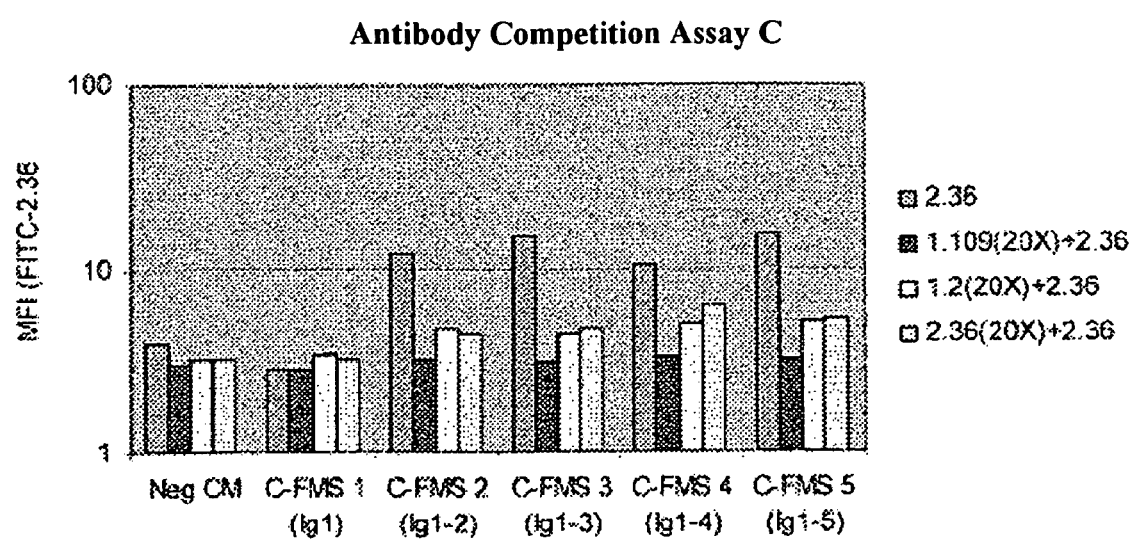
FIG. 15 shows the competition assay with 20× unlabeled 1.109, 1.2, and 2.360 c-fms antibodies, followed by 1 µg/ml concentration of FITC labeled 2.360.

Among the three antibodies, clone 1.109 has the highest binding signal compared to the other two antibodies under 1 μg/ml The competition data demonstrated that three of the antibodies can block each other with 20-fold excess unlabeled antibody (see, FIGS. 13, 14 and 15). The competition data also indicate that the epitope of these three antibodies are similar or adjacent within Ig-like loops 1 and 2.

Example 13

Epitope Mapping of Anti-c-fms Antibody 1.2 SM Versus Commercial Antibodies

This experiment was conducted to determine if certain of the human antibodies disclosed herein bound the same or a different epitope than a number of commercially-available antibodies.

Materials and Methods: Commercial C-fms Antibodies Tested

Rat and mouse antibodies tested are shown in Table 21 and Table 22.

TABLE 21

Rat antibodies

| Source | Cat. No. and Clone No. | Shorthand Designation | Binding region per manufacturer |
|---|---|---|---|
| Biosource | Cat. No. AHT1512, clone 2-4A5-2 | 2-4A5-2 | Between amino acids 349-512 |
| U.S. Biological | Cat. No. C2447-53, clone 5J15 | 5J15 | Between amino acids 349-512 |
| U.S. Biological | Cat. No. C2447-50, clone O.N. 178 | 0N178 | Not described |

TABLE 22

Mouse Antibodies

| Source | Cat. No. and Clone No. | Shorthand Designation | Binding region per manufacturer |
|---|---|---|---|
| R&D Systems | Cat. No. MAB329, clone 61708 | MAB329 | Extracellular domain used as immunogen |
| R&D Systems | Cat. No. MAB3291, clone 61701 | MAB3291 | Extracellular domain used as immunogen |
| R&D Systems | Cat. No. MAB3292, clone 61715 | MAB3292 | Extracellular domain used as immunogen |

C-fms-Avidin Fusion Constructs and Expression of Avidin Fusion Proteins

Human c-fms avidin fusion expression constructs were prepared as described in Example 12. Expression of avidin fusion proteins was achieved by transient transfection of human 293T adherent cells in 10 cm tissue culture plates. Cells were grown and maintained in DMEM (high glucose) containing 5% qualified FBS and supplemented with 1× Pen-strep-glutamine (Invitrogen), 1× non-essential amino acids (Invitrogen) and 1× sodium pyruvate (Invitrogen) (growth medium), at 37° C. and 5% $CO_2$. Approximately 2.5×10$^6$ 293T cells were inoculated into 10 cm plates containing 10 ml of growth medium and grown overnight for approximately 20 hours. Cells were then transfected with pCEP4-Avidin(N)-c-fms constructs. For each transfection, 7.5 μg of DNA was mixed with 45 μl of FuGene6 (Roche) in the presence of supplement-free DMEM medium (Invitrogen) and the complex was incubated for 20 minutes. The transfection complex was added to the corresponding plate and incubated at 37° C. overnight. The following morning, the cells were washed twice with 1× Dulbecco's Phosphate Buffered Saline (PBS) (Invitrogen) and fed with 5 ml of serum free DMEM containing the aforementioned supplements plus Insulin, Transferrin, Selenium-X (ITS-X) (Invitrogen). Approximately 48 hours post-transfection, the conditioned media was harvested and centrifuged at 2000×g for 10 minutes at 4° C. to remove cells and debris, and transferred to 15 ml tubes. A control plate was also made following the same protocol, but no DNA was used (mock transfection), yielding negative control conditioned media for binding experiments.

Detection of Fusion Proteins

The concentration of each c-fms avidin fusion protein was determined using a quantitative FACS based assay. Avidin fusion proteins were captured on 6.7 μm biotin polystyrene beads (Spherotech, Inc., Libertyville Ill.). 1× conditioned media (2, 20 and 200 μl) were added to 5 μl (~3.5×10$^5$) beads, and incubated for 1 hr at room temperature with rotation. Conditioned media was removed by centrifugation and samples were washed with PBS containing 2% FBS (FPBS). The avidin beads were stained with 500 μl of a 1.0 μg/ml solution of a FITC-labeled goat anti-avidin antibody (Vector Labs, Burlingame, Calif.) in FPBS for 30 minutes at room temperature with rotation. Following incubation, the beads were recollected by centrifugation, washed with FPBS, and resuspended for analysis in 0.5 ml FPBS. The FITC fluorescence was detected using a FACScan (Becton Dickinson Bioscience, Franklin Lakes, N.J.). The signal was converted to protein mass using a standard curve derived with rAvidin. For epitope mapping, biotin beads were loaded with ~200 ng of c-fms avidin fusion protein per 3.5×10$^5$ beads and brought up to volume with FPBS.

Antibody Binding FACS Assay

Biotin-coated polystyrene beads (Spherotech, Inc.) loaded with normalized amounts of c-fms subdomain fusion proteins were mixed with 1 μg of either human anti c-fms monoclonal antibody (1.2) mouse anti-c-fms monoclonal antibody (MAB 329, MAB 3291 and MAB3292 [R&D Systems]) or rat anti-c-fms monoclonal antibody (2-4A5-2 [Invitrogen], O.N.178 and 5J15 [U.S. Biological]) in 0.2 ml of FPBS. After incubation for 1 hr at room temperature, the antibody-bead complexes were washed three times with 1.25 ml washing buffer (FPBS) with collection by centrifugation for 1 mm at 18,000×g between washes. The antibodies were then stained a species appropriate goat secondary antibody conjugated to FITC (Southern Biotech) at 1.0 μg/ml for 30 nm. The wash steps were repeated and the antibody-bead complexes were resuspended in 0.5 ml FPBS for analysis. The antibody bound to avidin-bead complexes was detected by FACS (Becton Dickinson) analysis. The mean (X) fluorescent intensity was recorded for each sample.

Antibody Competition Assay

To prepare for labeling with fluorescein, the monoclonal antibodies were dialyzed or resuspended at a concentration of 1 mg/ml in PBS (pH 7.4). Label ([6-fluorescein-5-(and-6)-carboxamido] hexanoic acid, succinimidyl ester 5(6)-SFX]) mixed isomers from Molecular Probes (F-2181) was added to the protein at a 10:1 molar ratio (label: protein) from a stock of 10 mg/ml in DMSO. The mixture was incubated at room temperature for 1 hour in the dark. The labeled antibody was separated from the free label by NAP 5 column chromatography in PBS followed by 0.2 μm filtration. For each competition experiment, a binding reaction was assembled that contained a 25-fold excess (25 μg/ml) of unlabeled competitor antibody, 3.5×10$^5$ biotin beads coated with the avidin fusion protein in FPBS. The FITC-labeled antibody (1 μg/ml) was added after a 15 min pre-incubation. The process followed the one color method from this point forward.

Results And Discussion

All the fusion proteins expressed in 293T cells can be detected with FITC-labeled anti-avidin antibody by FACScan. As described in Example 12, several antibodies that were tested bind similar epitopes that require the presence of both Ig-like loop 1 and Ig-like loop 2 regions found in the Ig1-2 avidin fusion construct. Consequently, binding and competition experiments were done with one of the human antibodies provided herein, the commercially available anti-human c-fms antibodies and select members of the panel of avidin fusion constructs.

All of the commercial antibodies were able to successfully bind to the full length c-fms ECD Ig1-5 construct as expected. Of the six commercial antibodies, one (MAB 3291) was able to bind to the Ig1-2 construct, indicating a possible competitor for the human anti-c-fms epitopes. Further binding experiments were done using the Ig1 construct. MAB3291 was shown to bind the Ig1 construct, indicating that its epitope was located entirely within the Ig1-like domain. The slight signal seen for MAB329 in the Ig1 and Ig1-2 constructs was confirmed to be background binding of the antibody to the beads.

The competition data demonstrated that none of the commercially sourced antibodies can block the representative human antibody even at a 25 fold excess of competitor antibody.

The combined data from the binding and competition experiments demonstrate that the commercial antibodies bind to epitopes which are not utilized by the human anti-c-fms antibodies.

Example 14

Epitope Mapping of Anti C-fms Antibodies by arginine/Glutamic Acid Scanning of c-fms An arginine/glutamic acid-scanning strategy was used to map antibody binding to c-fms. The arginine and glutamic acid sidechains are charged and bulky, and may disrupt antibody binding to c-fms. This method can thus indicate residues that when mutated negatively affect the binding of the antigen binding protein to c-fms. This indicates that the corresponding residues in the unmutated antigen binding protein can be in contact with the antigen binding protein or in close proximity to the antibody such that substitution with arginine or glutamic acid is sufficient to affect binding.

Construction, Expression, and Characterization of Arginine/Glutamic Acid Mutants Ninety-five amino acids distributed throughout the first three Ig domains of c-fms were selected for mutation. The selection was biased towards charged or polar amino acids, excluding cysteine and proline in order to reduce the likelihood of the mutation resulting in a misfolded protein. Non-arginine amino acids were mutated to arginine; arginine and lysine were mutated to glutamic acid.

Sense and anti-sense oligonucleotides containing the mutated residues were synthesized in a 96-well format. Mutagenesis of the c-fms extracellular domain-Flag-His-tagged construct ("wild type") was performed using a Quikchange II kit (Stratagene, #200523). All mutant constructs of Flag-His-tagged c-fms in the pTT5 vector, were expressed in transiently transfected 293-6E suspension cells (NRCC) in 96-well plates. Expression levels and integrity of the recombinant protein in conditioned media were characterized by western blot against the His-tag followed by an anti-isotype Alexa-fluor antibody. Subsequent epitope mapping experiments were performed using protein in conditioned media.

Mutant expression was characterized by running supernatants from each well on an ePage SDS-PAGE electrophoresis apparatus (Invitrogen), blotting, and probing with an anti-His antibody (Novagen) followed by an anti-isotype Alexa-fluor antibody. Each mutant construct was expressed.

Determination of Conformational Epitopes

To determine whether anti-c-fms antibodies bound to a conformational epitope on c-fms, three anti-c-fms antibodies (1.2 SM, 1.109 SM and 2.360) and c-fms were individually run on western blots under reducing and non-reducing conditions. Antibodies 1.2 SM and 2.360 were shown to bind a conformational epitope as evidenced by the lack of bands in western blots under reducing conditions, whereas a light band was observed with antibody 1.109 SM, indicating that it can bind a linear epitope.

BioPlex Binding Assay

A bead-based multiplexed assay was used to measure antibody binding to the 95 c-fms mutants, wild type, and a negative control simultaneously. One hundred sets of color-coded strepavidin-coated LumAvidin beads (Luminex) were bound with biotinylated anti-pentaHis antibody (Qiagen, #1019225) for 1 hour at room temperature (RT) then washed. Each color-coded bead set was then allowed to bind to a c-fms mutant, wild-type, or negative control in 100 μl supernatant for 1 hour at RT and washed.

The color-coded bead sets, each associated to a specific protein, were pooled. The pooled beads were aliquoted to 96 wells of a 96-well filter plate (Millipore, #MSBVN1250). 100 μl of anti-c-fms antibodies (1.2 SM, 1.109 SM and 2.360) in 3-fold dilutions were added to three columns for triplicate points and incubated for 1 hour at RT and washed. 100 μl of 1:200 dilution phycoerythrin (PE)-conjugated anti-human IgG Fc (Jackson Immunoresearch, #109-116-170) was added to each well and incubated for 1 hour at RT and washed.

Beads were resuspended in 1% BSA in PBS, shaken for 10 minutes and read on the BioPlex instrument (Bio-Rad). The instrument identified each bead by its color-code and measured the amount of antibody bound to the beads according to the fluorescent intensity of the PE dye. Antibody binding to each mutant was compared directly to its binding to the wild type in the same pool.

Identifying Antibody Binding to Mutant c-fms

The variability of the assay system and significance of changes in binding were determined empirically. Bead-to-bead and well-to-well variability was experimentally determined by binding wild-type c-fms to all 100 sets of color-coded beads. Beads were dispensed to each well of a 96-well plate and probed with anti-c-fms antibody 1.2 SM in 3-fold dilutions down each column of the plate, across all 12 columns of the plate. EC50 were derived using curve fits from measuring the variability of maximum signals, minimum signals and slope. Variability measurements were used to determine whether a magnitude shift in EC50s was significant.

Mean fluorescence intensity (MFI) of antibody binding was graphed using a weighted 4 Parameter Logistical curve fit (4PL with VarPower in Splus). Experimental variability was determined using three wild type controls in each pool. Antibody binding to mutant antigen was compared to each wild type control. A 99% confidence interval (CI) of the EC50 fold change between mutant and each wild type control was calculated and the comparison to the wild type control giving the larger p-value was reported. Multiplicity adjustment using Benjamini-Hochberg False Discovery Rate (FDR) control was applied. Mutations whose 99% CI of the EC50 is significantly different from wild type EC50, that is having an FDR adjusted p-value of 0.02 or less, were considered important in the specific binding reaction between the protein antigen and antigen binding protein. In addition, mutations that reduced binding as evidenced by a reduction in maximum MFI signal to 30% or less of wild type were considered to significantly influence binding between the protein antigen and antigen binding protein. Table 23 summarizes the "hits" or the position of mutations that significantly reduced the ability of the 1.2 SM, 1.109, and 2.36 antibodies to bind the extracellular domain of human c-fms. The notation used in Table 23 is: (wild-type residue:position in polypeptide:mutant residue), where the numbering is as shown in SEQ ID NO:1.

TABLE 23

Summary of mutations that affect antibody binding.

Figure 16:
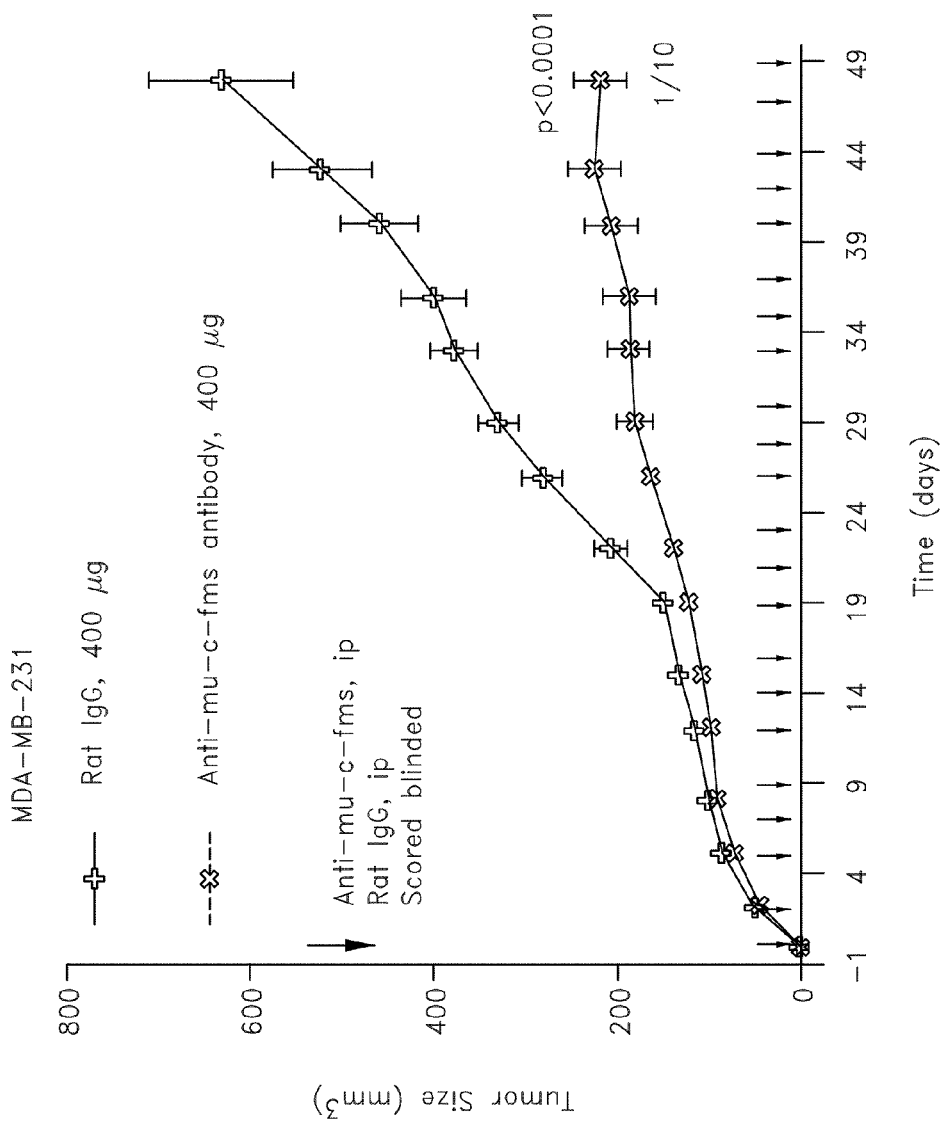
FIG. 16 shows the inhibition of the growth of MDAMB231 breast adenocarcinoma xenograft by anti-murine c-fms antibody by way of measuring tumor volume and the percent necrosis of each tumor. The percent necrosis of each tumor was then calculated from these measurements and shown in FIG. 16

| Antibody | | Hits |
|---|---|---|
| 1.2 SM | | E29R, Q121R, T152R, K185E |
| 1.109 | | E29R, Q121R, S172R, G274R, Y276R |
| 2.36 | | R106E, H151R, T152R, Y154R, S155R, W159R, Q171R, S172R, Q173R, G183R, R184E, K185E, E218R, A220R, S228R, H239R, N240R, K259E, G274R, N275R, Y276R, S277R, N282R |
| ALL | EC50 shift | K102E, R144E, R146E, D174R, A226R |
| | low/no binding | W50R, A74R, Y100R, D122R, T130R, G161R, Y175R, A179R |

Because binding of at least one antibody is maintained in the presence of the particular mutations shown in Table 23, the mutant proteins are unlikely to be grossly misfolded or aggregated due to the introduced mutation. This is also true for those mutations which caused an EC50 shift for all of the antibodies as the antibodies are still able to bind antigen. Although each of the tested antibodies bind to a similar region as shown by the binning analysis, each antibody can be distinguished by the mutations which inhibit antibody binding to mutant antigen. That some of the mutations affect multiple antibodies is consistent with the fact that the antibodies belong to similar bins.

Example 15

Inhibition of the Growth of MDAMB231 Breast Adenocarcinoma Xenograft

Because the antigen binding proteins provided herein bind human c-fms but not mouse c-fms, a series of in vivo experiments were conducted with an antibody that binds murine c-fms to demonstrate the utility of an anti-cfms antibody to treat cancer.

Athymic nude mice were subcutaneously implanted with 10 million MDAMB231 human breast adenocarcinoma cells in the presence of Matrigel (1:1). Starting within one day of tumor cell implantation, mice were injected intraperitoneally with either 400 μg of anti-murine c-fms antibody or 400 μg of control rat anti-mouse IgG in 100 μl PBS 3 times per week for the duration of the study. Tumor measurements and treatment days are shown in the FIG. 16. After 51 days mice were euthanized and tumors collected and formalin fixed. H&E stained sections and F4/80 (macrophage marker) targeted immunohistochemistry sections were evaluated. All scoring was done blinded to treatment and group. Sections from mice treated with anti-murine c-fms antibody showed significantly less staining than mice treated with the control, thus indicating a significant reduction in the number of tumor associated macrophages. To more objectively evaluate the extent of necrosis, digital images of AFOG stained sections were captured using Metavue software, the entire cross-sectional area and necrotic cross-sectional area of tumors were measured. The percent necrosis of each tumor was then calculated from these measurements and shown in FIG. 16. These results demonstrate that an anti-c-fms antibody can decrease tumor associated macrophages, increase necrosis and inhibit the growth of MDAMB231 breast adenocarcinoma xenografts.

Example 16

Inhibition of the Growth of Established NCIH1975 Lung Adenocarcinoma Xenograft

Figure 17:
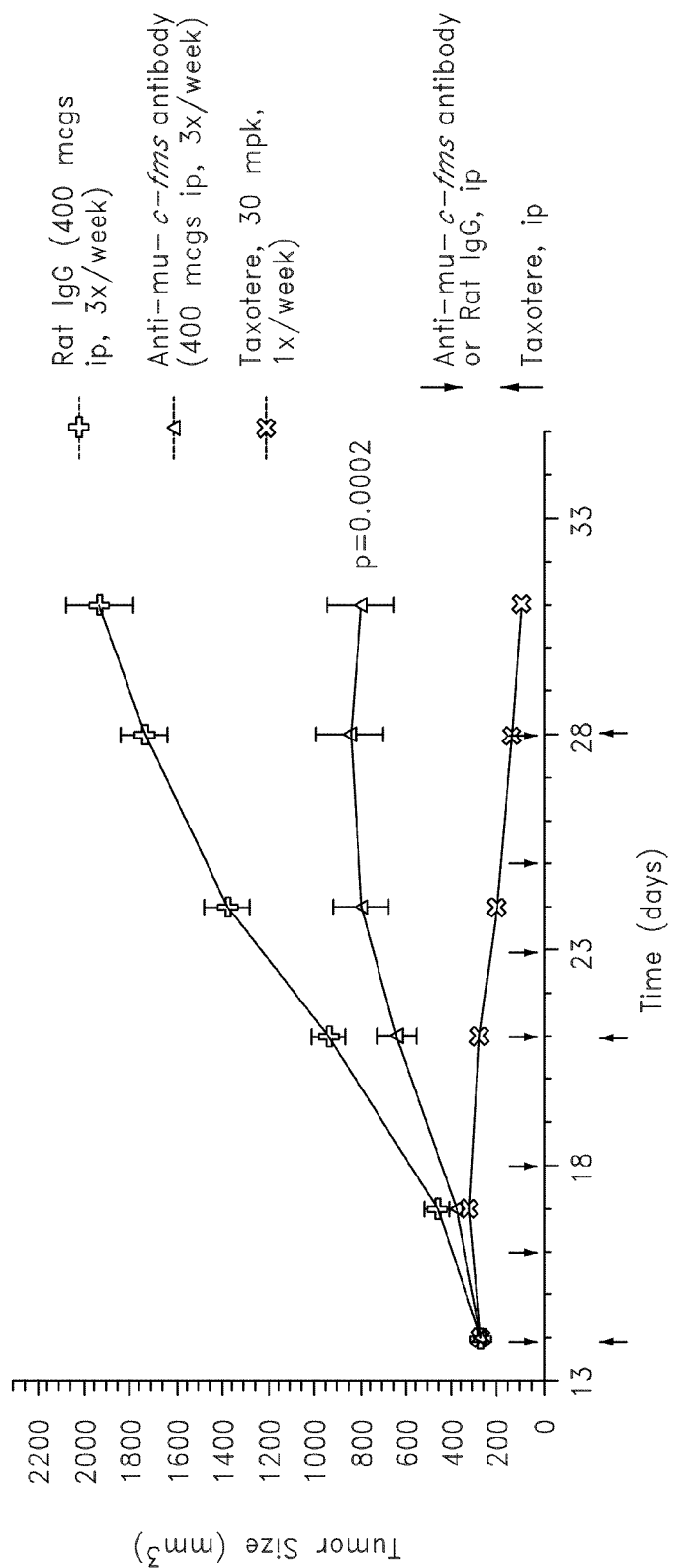
FIG. 17 shows the inhibition of the growth of established NCIH1975 lung adenocarcinoma xenografts. Tumor measurements and treatment days are shown, demonstrating that an anti-murine c-fms antibody can inhibit the growth of an established NCIH1975 lung adenocarcinoma xenograft.

Athymic nude mice were subcutaneously implanted with 10 million NCIH1975 human lung adenocarcinoma cells in the presence of Matrigel (1:1). After tumors were allowed to grow to 250-300 mm$^3$, mice were injected intraperitoneally with either 400 µg of anti-murine c-fms antibody or 400 µg of control Rat anti-mouse IgG in 100 µl PBS 3 times per week for the duration of the study. A third group of mice was treated with 30 mg/kg Taxotere (positive control) once per week. Tumor measurements and treatment days are shown in FIG. 17 which shows that an anti-cfms antibody can inhibit the growth of an established NCIH1975 lung adenocarcinoma xenograft.

The above tumor models demonstrate the utility of an anti-cfms antibody that inhibits the activity of the CSF-1/cfms axis, such as those disclosed herein, for use in the treatment of cancer. The ability of such antibodies to decrease infiltrating macrophages in diseased tissue means that the antibodies can also be used in metabolic and inflammatory diseases.

Example 17

Modulation of the CSF-1/CSF-1R Interaction to Control Angiogenesis

To test whether CSF-1 mediated recruitment, differentiation and stimulation of macrophages may be involved in promoting angiogenesis in tumors or other normal tissues, two different neutralizing rat anti-murine CSF-1R monoclonal antibodies (M279 was generated internally; the other, FS98, was obtained from Ebiosciences), were evaluated for their effect on mouse corneal angiogenesis in vivo. On day five after a single systemic dose of control mAb, M279 or AFS98, the following parameters were measured and analyzed: 1) the vascular density associated with the mouse corneal angiogenesis response, 2) circulating levels of mouse CSF-1, and 3) levels of macrophage infiltration in the cornea and other tissues.

Mouse Corneal Pocket Assay

A 4 mm PVA sponge (M-PACT Worldwide, Eudora, Kans.) was precisely cut into two equal pieces and immersed in 8 µl of PBS containing 2.4 µg of recombinant human FGF-2 or 48 µg of recombinant human VEGF (R&D Systems, Minneapolis, Minn.). The sponge was further aseptically processed into 48 similarly sized mini-sponge fragments (pellets) suitable for corneal pocket implantation. Each sponge fragment contained approximately 50 ng of recombinant human FGF-2 or 1 µg of recombinant human VEGF. Female C57 BL/6 mice (7-10 weeks of age) were anesthetized using systemic anesthesia and eyes prepared for corneal incision by placing a single drop of Proparacaine topical anesthetic in each eye. A fine slit was created in the middle of the cornea and an opening ("pocket") created in the corneal stroma that followed the curvature of the eye approximately 1 mm from the limbus. Pellets containing PBS, VEGF or FGF-2 were placed into the corneal pockets and animals treated with either rat IgG (Sigma, St. Louis, Mo.) IP at a dose of 250 µg in 200 µl pyrogen-free PBS, or with 250 µg purified rat anti-mouse CSF-1R. On day 5 post pellet implantation, mice were anesthetized with systemic anesthesia and each eye (cornea) imaged under a stereomicroscope fitted with an Insight Spot digital camera fitted with a near vertical illuminator at an incipient angle of 45 degrees from the polar axis in the meridian containing the pellet. These acquired digital images were processed by subtractive color filters (Adobe Photoshop) and analyzed using Bioquant image analysis software (Nashville, Tenn.) to determine the fraction of pixels within the total density of the corneal perimeter that exceeded a threshold matching visible capillaries. Total vascular density of the cornea was determined by using the fraction of pixels, the result of which was expressed as a ratio of blood vessel area pixel number to whole eye area pixel number.

Mouse CSF-1 ELISA

Serum levels of mouse CSF-1 were determined as a biomarker of anti CSF-1R antibody activity using the DUOSET antibody ELISA system (R&D systems) according to the manufacturer's instructions.

Immunolocalization of Macrophage and Blood Vessels in Liver and Corneal Tissues of Mice To determine the effects of anti-mouse CSF-1R antibodies on macrophage and blood vessel levels in tissue, rat anti-mouse F4/80 (a macrophage-restricted cell surface glycoprotein), conjugated with Alexa 488, clone BM8 (1:1000) was used to detect tissue macrophages. CD31, rat anti-mouse PECAM-1 IgG2a, conjugated with PE, clone 390 (use 1 µg/ml) was used to detect endothelial cells. After tissue was harvested, it was frozen in OCT for further processing. 5 micron sections of either liver or cornea were fixed with cold acetone for 15 min at room temperature and then washed twice with PBS. After washing, sections were incubated in blocking solution (BS) for 30 min at room temperature. Both F4/80-488 and CD31-PE were added at the above concentrations in BS and sections incubated 30 minutes at room temperature followed by twice washing with PBS. Slides were mounted in mounting media and fluorescent images acquired with Leica-Hamamutsu-Openlab system.

Results and Conclusion:

Rat anti-muCSF-1R neutralizing antibodies, M279 and AFS98, significantly inhibited FGF-2, but not VEGF-induced mouse corneal angiogenesis by approximately 80% (P<0.01). A single dose of 250 µg M279 or AFS98, significantly increased muCSF-1 serum levels compared to levels observed in rat IgG-treated mice (45-83 fold increase). Immunofluorescent staining/localization (IMF) results in mouse corneal sections showed that FGF-2 and VEGF pellet implantation increases macrophage infiltration in the cornea compared to surgery/PBS pellet implantation alone. M279 treatment robustly diminished stimulus-induced (both FGF-2 and VEGF) corneal macrophage infiltration compared to control rat IgG treatment by approximately 85 to 96 percent. The IMF results in mouse liver sections also showed that the single treatment with M279 or AFS98 significantly decreased the number of F4/80 positive macrophages by approximately 60% in the mouse liver while not appreciably altering vascular density as assessed by CD31 IMF (P<0.01). Macrophages follow the blood vessel network but do not generally co-localize with microvessels in the vascularized mouse cornea.

When evaluating both angiogenic stimuli (FGF-2 and VEGF), blocking the CSF-1/CSF-1R interaction decreased macrophage infilitration to the tissue while it only inhibited FGF-2 angiogenesis based on corneal vessel density imaging. Based on these results, it appears that the inflammatory environment dictates when CSF-1 responsive tissue macrophages can facilitate/promote angiogenesis, while at the same time illustrating that tissue macrophages at multiple inflammatory sites require ongoing CSF-1/CSF-1R interaction to maintain their presence at the inflammatory lesion. The results indicate that in cases where inflammatory angiogenesis is driven primarily by FGF-2 that inhibiting the CSF-1/CSF-1R interaction can be beneficial in decreasing new blood vessel formation, especially in tumors where VEGF levels are not high but tumor vascular density is.

Example 18

Toxicology Studies in Cynomolgus Monkeys

Cynomolgus monkeys were administered the 1.2 SM antibody and pharmocodynamic markers were measured. The cohort used to study the effects of a c-fms antigen binding protein is shown in TABLE 24. Antibody 1.2 SM was administered weekly by intravenous injection to Cynomolgus monkeys for 4 weeks followed by an 11-week recovery period, with terminal necropsy on day 29 and recovery necropsy at 3 months. Pharmocodynamic markers including serum CSF-1 levels, Tartrate-resistant acid phosphatase 5b (Trap5b) concentrations and the quantity of colon macrophages were measured. As described in greater detail below, the measurement of each of these markers demonstrated the ability of the antibody to bind c-fms and inhibit the c-fms/CSF-1 axis. The level of the markers also correlated with the level of antibody in the blood.

TABLE 24

Cohort for toxicology study

| Group | Dose (mg/kg) | No. Males/ Females | No. M/F Terminal Necropsy | No. M/F Recovery Necropsy |
|---|---|---|---|---|
| 1 | 0 | 5/5 | 3/3 | 2/2 |
| 2 | 20 | 5/5 | 3/3 | 2/2 |
| 3 | 100 | 5/5 | 3/3 | 2/2 |
| 4 | 300 | 5/5 | 3/3 | 2/2 |

Response of Serum CSF-1 Levels to Treatment with Antibody 1.2 SM

Serum CSF-1 levels provide a biomarker for the presence and activity of anti-c-fms antibody. This is evidenced by the selective degradation by macrophage of $^{125}$I-labeled CSF-1 in mice (Tushinski R J et al. *Cell* (1982) 28:71-81); observations that CSF-1 is elevated in serum of the c-fms knock out mice (Dai X M et al. *Blood* (2002) 99:111-120); and demonstrations that serum CSF-1 levels are elevated in mice treated with an anti-mouse c-fms antibody.

Relative concentrations of Cynomolgus CSF-1 were determined for serum specimens collected at −7, 8, 29, 57, 85, and 99 days. Samples were analyzed using an enzyme-linked immunosorbent assay (ELISA) following the protocol provided by the assay manufacturer (R&D Systems Human CSF-1 DuoSet ELISA kit; Minneapolis, Minn.). Cynomolgus CSF-1 concentrations were determined by comparison to a human CSF-1 standard curve.

To measure the concentration of serum antibody 1.2 SM, a mouse anti-1.2 SM antibody was passively adsorbed to Maxisorp microplate wells (Nunc). The microplate wells were blocked with SuperBlock® T20 (Pierce, Rockford, Ill.) after removing excess mouse anti-1.2 SM antibody. Standards and quality controls (QCs) were prepared by spiking antibody 1.2 SM into 100% Cynomolgus monkey serum pool. The microplate wells were washed following blocking. The standards, matrix blank (NSB), QCs, and study samples were thawed at ambient room temperature then loaded into the microplate wells after pretreating ⅕₀ with SuperBlock®T20. The antibody 1.2 SM in the samples was captured by the immobilized mouse anti-1.2 SM antibody. Unbound antibody 1.2 SM was removed by washing the microplate wells. Following washing, a second horseradish peroxidase (HRP) conjugated mouse anti-1.2 SM antibody was added to the microplate wells to bind the captured antibody 1.2 SM. Unbound HRP conjugated antibody was removed by washing. A 2-component 3,3',5,5'-Tetramethylbenzidine (TMB) substrate solution was added to the wells. The TMB substrate solution reacted with peroxide, and in the presence of HRP created a colorimetric signal that was proportional to the amount of antibody 1.2 SM bound by the capture reagent in the initial step. The color development was stopped and the intensity of the color (optical density, OD) was measured at 450 nm to 650 nm. Data was reduced using Watson version 7.0.0.01 reduction package using a Logistic (auto-estimate) (4 parameter logistic; 4-PL) regression model with a weighting factor of 1/Y.

Treatment of monkeys with antibody 1.2 SM resulted in a significant increase in serum CSF-1 levels and this correlated with the antibody serum concentration. Thus, CSF-1 serum levels were found to increase after administration of antibody and its accumulation in the serum and then to decrease after administration was completed and the serum antibody levels decreased. These observations are consistent with the antibody acting on the c-fms/CSF-1 axis.

Response of Trap5b Levels to Treatment with Antibody 1.2 SM

Trap5b levels provide a marker for anti-c-fms antibodies. Trap5b is specifically expressed by osteoclasts and is an indicator of osteoclast number. Osteoclasts, which are derived from the myeloid lineage of hematopoietic cells express c-fms and utilize CSF-1. Consistent with this is the observation that loss of CSF-1 results in decreased osteolasts and levels of Trap5b in CSF-1 knock out (op/op) mice (Dai X M et al., *Blood* (2002) 99:111-120).

The BoneTRAP® assay (Immunodiagnostic Systems Limited, Fountain Hills, Ariz.) was used to quantitate TRAP5b in subjects. Antibody 1.2 SM serum concentrations were determined as described above. Levels of TRAP5b and antibody 1.2 SM in serum were determined for serum specimens collected at −7, 8, 29, 57, 85, and 99 days.

At day 29 of the dosing phase, all subjects treated with 1.2 SM antibody had decreased Trap5b. Subsequent to treatment with antibody 1.2 SM, serum Trap5b concentrations increased as serum antibody concentrations decreased. Treatment with antibody 1.2 SM correlated with a decreased serum Trap5b concentration.

Response of Macrophage to Treatment with Antibody 1.2 SM

As an additional indicator of the activity of antibody 1.2 SM in Cynomolgus monkeys, the number of macrophages present in colon tissue was quantitated by laser scanning cytometry (LSC) of CD-68-stained tissue. Colon samples were collected from 3 animals/sex/group at the day 29 necropsy and 2 animals/sex/group at the day 100 necropsy. A sample of each tissue was collected in OCT (Optimal Cutting Temperature) media (Sakura Finetek, Torrance, Calif.) and frozen in a dry ice/butane bath. Macrophages were stained using conventional immunohistochemistry with anti-CD68 or an isotype antibody. Diaminobenzidine (DAB) positive events were enumerated using laser scanning cytometry (LSC). A 2 scan method was used in which laser light absorption was quantified by the photodiode detector above the stage. The first low resolution pass identified the position of the section on the slide and the subsequent high resolution pass acquired field images. Quantitative analysis of DAB staining was performed using the LSC-associated iCyte software.

TABLE 25 summarizes the changes in the number of colon macrophage immediately after treatment (Day 29) and subsequent to a recovery period where antibody 1.2 SM was no longer administered (Day 99). As can be seen from this table, administration of antibody 1.2 SM reduced the number of colony macrophage, whereas the number of macrophage increased after treatment was discontinued, thus demonstrating the activity of the antibody.

TABLE 25

Effect of Antibody 1.2 SM on Macrophage Population

| | | | Group Comparison | | |
|---|---|---|---|---|---|
| ANOVA | | Dose | Group | % decrease | p-values |
| Day | Effect | p-value | (mg/kg) | mean | (vs. Control) | (vs. Control) |
| 29 | gender | 0.4461 | 0 | 11.05 | | |
| | dose | 0.0005 | 20 | 1.75 | 84.16% | 0.0013 |
| | | | 100 | 2.36 | 78.64% | 0.0037 |
| | | | 300 | 1.94 | 82.44% | 0.0003 |
| 99 | gender | 0.8172 | 0 | 10.62 | | |
| | dose | 0.1043 | 20 | 12.12 | −14.12% | 0.9953 |
| | | | 100 | 9.23 | 13.09% | 0.8493 |
| | | | 300 | 2.67 | 74.86% | 0.0975 |

Example 19

Treatment of a Tumor in a Patient Using a c-fms Binding Protein

A human patient is diagnosed with a malignant tumor. The patient is treated with an effective amount of a c-fms binding protein described herein. Subsequent to administration of the c-fms binding protein, the size and/or metabolic activity of the tumor is measured (e.g., by MRI or PET scans). Significant reductions in the size and/or metabolic activity or other indicators of tumor growth, viability, metastasis are found in response to administration of the c-fms binding protein.

Example 20

Reduction of TAMs in a Patient with a Malignant Tumor Using a c-fms Binding Protein A human patient is diagnosed with a malignant tumor. The patient is treated with an effective amount of a c-fms binding protein described herein. Subsequent to administration of the c-fms binding protein, the number of TAMs is measured. Significant reductions in the number of TAMs are found in response to administration of the c-fms binding protein.

Example 21

Treatment of Cachexia Using a c-fms Binding Protein

A human patient is diagnosed with cancer. The patient is treated with an effective amount of a c-fms binding protein described herein. Subsequent to administration of the c-fms binding protein, the level of cachexia is assessed. A significant reduction in the level of cachexia is found in response to administration of the c-fms binding protein.

Example 22

Reduction of Vascularization Using a c-fms Binding Protein

A human patient is diagnosed with a malignant tumor. The patient is treated with an effective amount of a c-fms binding protein described herein. Subsequent to administration of the c-fms binding protein, a biopsy of the tumor is taken and the level of vascularization is assessed. A significant reduction in the level and/or function of tumor vascularization is found in response to administration of the c-fms binding protein.

Example 23

Treatment of Inflammatory Arthritis Using a c-fms Binding Protein

A human patient is diagnosed with inflammatory arthritis. The patient is treated with an effective amount of a c-fms binding protein described herein. Subsequent to administration of the c-fms binding protein, the level of inflammation and/or bone density is assessed. A significant reduction in the level of inflammation and/or bone osteolysis is found in response to administration of the c-fms binding protein.

All patents and other publications identified are expressly incorporated herein by reference for the purpose of describing and disclosing, for example, the methodologies described in such publications that might be used in connection with the described. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An isolated antibody or fragment thereof that binds human c-fms, wherein the antibody or fragment comprises:
  (A) a heavy chain variable domain comprising a CDRH1, a CDRH2 and a CDRH3, wherein the CDRH1 comprises the amino acid sequence of SEQ ID NO:147, the CDRH2 comprises the amino acid sequence of SEQ ID NO:163, and the CDRH3 comprises the amino acid sequence of SEQ ID NO:186; and
  (B) a light chain variable domain comprising a CDRL1, a CDRL2 and a CDRL3, wherein the CDRL1 comprises the amino acid sequence of SEQ ID NO:193; the CDRL2 comprises the amino acid sequence of SEQ ID NO:214 and the CDRL3 comprises the amino acid sequence of SEQ ID NO:228.

2. The antibody or fragment of claim 1 that has one or more of the following characteristics:
  (A) is a monoclonal antibody;
  (B) is a chimeric, a humanized or a fully human antibody;
  (C) is an antibody of the IgG1-, IgG2-, IgG3- or IgG4-type;
  (D) is a Fab fragment, a Fab' fragment, an F(ab')2 fragment, or an Fv fragment;
  (E) is labeled.

3. An isolated antibody or fragment thereof that binds human c-fms, wherein the antibody or fragment comprises:
  (A) a heavy chain variable domain comprising the amino sequence of SEQ ID NO:77; and
  (B) a light chain variable domain comprising the amino acid sequence of SEQ ID NO:110.

4. The antibody or fragment thereof of claim 3 that has one or more of the following characteristics:
  (A) is a monoclonal antibody;
  (B) is a chimeric, a humanized or a fully human antibody;
  (C) is an antibody of the IgG1-, IgG2-, IgG3- or IgG4-type;
  (D) is a Fab fragment, a Fab' fragment, an F(ab')2 fragment, or an Fv fragment;
  (E) is labeled.

5. An isolated, fully human, monoclonal antibody comprising a heavy chain and a light chain, wherein the heavy chain comprises the amino acid sequence of SEQ ID NO:11 and the light chain comprises the amino acid sequence of SEQ ID NO:44.

6. An isolated antibody or antibody fragment that competes with the antibody or fragment of claim 3 for binding to the extracellular domain of human c-fms of SEQ ID NO:1.

7. A composition comprising the antibody or fragment of claim 1 and a pharmaceutically acceptable diluent or carrier.

8. A composition comprising the antibody or fragment of claim 3 and a pharmaceutically acceptable diluent or carrier.

9. A composition comprising the antibody of claim 5 and a pharmaceutically acceptable diluent or carrier.

10. A composition comprising the antibody or fragment of claim 6 and a pharmaceutically acceptable diluent or carrier.

* * * * *